(12) United States Patent
Witschel et al.

(10) Patent No.: US 8,877,683 B2
(45) Date of Patent: Nov. 4, 2014

(54) SUBSTITUTED PYRIDINES HAVING HERBICIDAL ACTIVITY

(75) Inventors: Matthias Witschel, Bad Duerkheim (DE); William Karl Moberg, Neustadt (DE); Liliana Parra Rapado, Offenburg (DE); Gilbert Besong, Bad Duerkheim (DE); Michael Rack, Eppelheim (DE); Andree Van Der Kloet, Heidelberg (DE); Thomas Seitz, Viernheim (DE); Ruediger Reingruber, Ludwigshafen (DE); Helmut Kraus, Wissembourg (FR); Johannes Hutzler, Waldsee (DE); Trevor William Newton, Neustadt (DE); Jens Lerchl, Golm (DE); Klaus Kreuz, Denzlingen (DE); Klaus Grossmann, Neuhofen (DE); Richard Roger Evans, Limburgerhof (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/995,975

(22) PCT Filed: Dec. 19, 2011

(86) PCT No.: PCT/EP2011/073157
§ 371 (c)(1),
(2), (4) Date: Jun. 20, 2013

(87) PCT Pub. No.: WO2012/084755
PCT Pub. Date: Jun. 28, 2012

(65) Prior Publication Data
US 2013/0288899 A1     Oct. 31, 2013

Related U.S. Application Data

(60) Provisional application No. 61/426,523, filed on Dec. 23, 2010.

(30) Foreign Application Priority Data

Dec. 23, 2010  (EP) .................................... 10196742

(51) Int. Cl.
*C07D 495/04*     (2006.01)
*A01N 43/90*     (2006.01)

(52) U.S. Cl.
CPC .............. *A01N 43/90* (2013.01); *C07D 495/04* (2013.01)
USPC ........... 504/246; 514/301; 546/114; 546/122; 549/23; 549/28

(58) Field of Classification Search
CPC ............................. A01N 43/90; C07D 495/04
USPC .................. 504/246; 514/301; 546/114, 122; 549/23, 28
See application file for complete search history.

(56) References Cited

U.S. PATENT DOCUMENTS 5,756,515 A * 5/1998 Urbahns et al. ............... 514/301
6,265,417 B1 * 7/2001 Carroll et al. ................. 514/301

FOREIGN PATENT DOCUMENTS

| WO | WO 2009/063180 | 5/2009 |
| WO | WO 2010/029311 | 3/2010 |
| WO | WO 2010/130970 | 11/2010 |
| WO | WO2010/130970 A1 * 11/2010 ........... C07D 495/04 |

OTHER PUBLICATIONS

International Search Report, PCT/EP2011/073157, filed Dec. 19, 2011, search completed Feb. 24, 2012.
International Preliminary Report on Patentability, PCT/EP2011/073157, filed Dec. 19, 2011, report issued Jun. 25, 2013.

* cited by examiner

*Primary Examiner* — Jane C Oswecki
(74) *Attorney, Agent, or Firm* — Brinks Gilson & Lione

(57) ABSTRACT

The present invention provides substituted pyridine compounds of the formula I

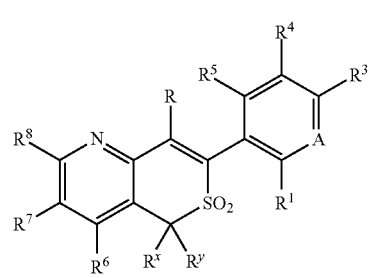

or N-oxides or agriculturally suitable salts thereof, wherein the variables in the formula I are defined as in the description. Substituted pyridines of formula I are useful as herbicides.

20 Claims, No Drawings

SUBSTITUTED PYRIDINES HAVING HERBICIDAL ACTIVITY

This application is a National Stage application of International Application No. PCT/EP2011/073157, filed Dec. 19, 2011, which claims the benefit of U.S. Provisional Application No. 61/426,523, filed Dec. 23, 2010, the entire contents of which are hereby incorporated herein by reference. This application also claims priority under 35 U.S.C. §119 to European Patent Application No. 10196742.0, filed Dec. 23, 2010, the entire contents of which is hereby incorporated herein by reference.

The present invention relates to substituted pyridines of the general formula I defined below and to their use as herbicides. Moreover, the invention relates to compositions for crop protection and to a method for controlling unwanted vegetation.

WO 2009/063180 and WO 2010/029311 describe certain herbicidal pyridopyrazines.

WO 2010/130970 describes certain 6,6-dioxo-6-thia-1,4-diaza-naphthalene derivatives having herbicidal activity.

However, the herbicidal properties of these known compounds with regard to the harmful plants are not always entirely satisfactory.

It is therefore an object of the present invention to provide compounds having improved herbicidal activity. To be provided are in particular compounds which have high herbicidal activity, in particular even at low application rates, and which are sufficiently compatible with crop plants for commercial utilization.

These and further objects are achieved by the substituted pyridine compound of the formula I, defined below, and by their agriculturally suitable salts.

Accordingly, the present invention provides a substituted pyridine compound of formula I

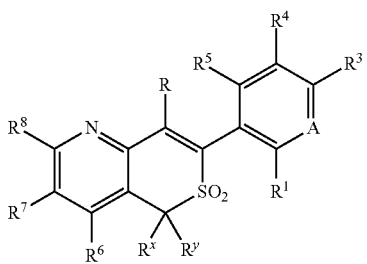

wherein the variables have the following meaning:

R is O—$R^A$, S(O)$_n$—$R^A$ or O—S(O)$_n$—$R^A$;

$R^A$ is hydrogen, $C_1$-$C_4$-alkyl, Z—$C_3$-$C_6$-cycloalkyl, $C_1$-$C_4$-haloalkyl, $C_2$-$C_6$-alkenyl, Z—$C_3$-$C_6$-cycloalkenyl, $C_2$-$C_6$-alkynyl, Z—C(=O)—$R^a$, Z—$NR^i$—C(O)—$NR^iR^{ii}$, Z—P(=O)($R^a$)$_2$, $NR^iR^{ii}$ or a 3- to 7-membered monocyclic or 9- or 10-membered bicyclic saturated, unsaturated or aromatic heterocycle which contains 1, 2, 3 or 4 heteroatoms selected from the group consisting of O, N and S and which may be partially or fully substituted by groups $R^a$ and/or $R^b$, $R^a$ is independently hydrogen, OH, $C_1$-$C_8$-alkyl, $C_1$-$C_4$-haloalkyl, Z—$C_3$-$C_6$-cycloalkyl, $C_2$-$C_8$-alkenyl, Z—$C_5$-$C_6$-cycloalkenyl, $C_2$-$C_8$-alkynyl, Z—$C_1$-$C_6$-alkoxy, Z—$C_1$-$C_4$-haloalkoxy, Z—$C_3$-$C_8$-alkenyloxy, Z—$C_3$-$C_8$-alkynyloxy, $NR^iR^{ii}$, $C_1$-$C_6$-alkylsulfonyl, Z-(tri-$C_1$-$C_4$-alkyl)silyl, Z-phenyl, Z-phenoxy, Z-phenylamino or a 5- or 6-membered monocyclic or 9- or 10-membered bicyclic heterocycle which contains 1, 2, 3 or 4 heteroatoms selected from the group consisting of O, N and S, where the cyclic groups are unsubstituted or substituted by 1, 2, 3 or 4 groups $R^b$;

$R^i$, $R^{ii}$ independently of one another are hydrogen, $C_1$-$C_8$-alkyl, $C_1$-$C_4$-haloalkyl, $C_3$-$C_8$-alkenyl, $C_3$-$C_8$-alkynyl, Z—$C_3$-$C_6$-cycloalkyl, Z—$C_1$-$C_8$-alkoxy, Z—$C_1$-$C_8$-haloalkoxy, Z—C(=O)—$R^a$, Z-phenyl, a 3- to 7-membered monocyclic or 9- or 10-membered bicyclic saturated, unsaturated or aromatic heterocycle which contains 1, 2, 3 or 4 heteroatoms selected from the group consisting of O, N and S and which is attached via Z;

$R^i$ and $R^{ii}$ together with the nitrogen atom to which they are attached may also form a 5- or 6-membered monocyclic or 9- or 10-membered bicyclic heterocycle which contains 1, 2, 3 or 4 heteroatoms selected from the group consisting of O, N and S;

$R^b$ independently of one another are Z—CN, Z—OH, Z—NO$_2$, Z-halogen, oxo(=O), =N—$R^a$, $C_1$-$C_8$-alkyl, $C_1$-$C_4$-haloalkyl, $C_2$-$C_8$-alkenyl, $C_2$-$C_8$-alkynyl, Z—$C_1$-$C_8$-alkoxy, Z—$C_1$-$C_8$-halo-alkoxy, Z—$C_3$-$C_{10}$-cycloalkyl, O—Z—$C_3$-$C_{10}$-cycloalkyl, Z—C(=O)—$R^a$, $NR^iR^{ii}$, Z-(tri-$C_1$-$C_4$-alkyl)silyl, Z-phenyl or S(O)$_n$$R^{bb}$; or two groups $R^b$ may together form a ring which has 3 to 6 ring members and, in addition to carbon atoms, may contain heteroatoms selected from the group consisting of O, N and S and may be unsubstituted or substituted by further groups $R^b$;

$R^{bb}$ is $C_1$-$C_8$-alkyl, $C_2$-$C_6$-alkenyl, $C_2$-$C_6$-alkynyl, $C_2$-$C_6$-haloalkenyl, $C_2$-$C_6$-haloalkynyl or $C_1$-$C_6$-haloalkyl;

Z is a covalent bond or $C_1$-$C_4$-alkylene;

n is 0, 1 or 2;

$R^1$ is cyano, halogen, nitro, $C_1$-$C_6$-alkyl, $C_2$-$C_6$-alkenyl, $C_2$-$C_6$-alkynyl, $C_1$-$C_6$-haloalkyl, Z—$C_1$-$C_6$-alkoxy, Z—$C_1$-$C_4$-alkoxy-$C_1$-$C_4$-alkoxy, Z—$C_1$-$C_4$-alkylthio, Z—$C_1$-$C_4$-alkylthio-$C_1$-$C_4$-alkylthio, $C_2$-$C_6$-alkenyloxy, $C_2$-$C_6$-alkynyloxy, $C_1$-$C_6$-haloalkoxy, $C_1$-$C_4$-haloalkoxy-$C_1$-$C_4$-alkoxy, S(O)$_n$$R^{bb}$, Z-phenoxy or Z-heterocyclyloxy, where heterocyclyl is a 5- or 6-membered monocyclic or 9- or 10-membered bicyclic saturated, partially unsaturated or aromatic heterocycle which contains 1, 2, 3 or 4 heteroatoms selected from the group consisting of O, N and S, where cyclic groups are unsubstituted or partially or fully substituted by $R^b$;

A is N or C—$R^2$;

$R^2$, $R^3$, $R^4$, $R^5$ independently of one another are hydrogen, Z-halogen, Z—CN, Z—OH, Z—NO$_2$, $C_1$-$C_8$-alkyl, $C_1$-$C_4$-haloalkyl, $C_2$-$C_8$-alkenyl, $C_2$-$C_8$-alkynyl, $C_2$-$C_8$-haloalkenyl, $C_2$-$C_8$-haloalkynyl, Z—$C_1$-$C_8$-alkoxy, Z—$C_1$-$C_8$-haloalkoxy, Z—$C_1$-$C_4$-alkoxy-$C_1$-$C_4$-alkoxy, Z—$C_1$-$C_4$-alkylthio, Z—$C_1$-$C_6$-haloalkylthio, $C_2$-$C_6$-alkenyloxy, $C_2$-$C_6$-alkynyloxy, $C_1$-$C_6$-haloalkoxy, haloalkoxy-$C_1$-$C_4$-alkoxy, Z—$C_3$-$C_{10}$-cycloalkyl, O—Z—$C_3$-$C_{10}$-cycloalkyl, Z—C(=O)—$R^a$, $NR^iR^{ii}$, Z-(tri-$C_1$-$C_4$-alkyl)silyl, S(O)$_n$$R^{bb}$, Z-phenyl, $Z^1$-phenyl, Z-heterocyclyl or $Z^1$-heterocyclyl, where heterocyclyl is a 5- or 6-membered monocyclic or 9- or 10-membered bicyclic saturated, partially unsaturated or aromatic heterocycle which contains 1, 2, 3 or 4 heteroatoms selected from the group consisting of O, N and S, where cyclic groups are unsubstituted or partially or fully substituted by $R^b$;

$R^2$ together with the group attached to the adjacent carbon atom may also form a 5- to 10-membered saturated or partially or fully unsaturated mono- or bicyclic ring which, in addition to carbon atoms, may contain 1, 2 or 3 heteroatoms selected from the group consisting of O, N and S and may be substituted by further groups $R^b$;

$Z^1$ is a covalent bond, $C_1$-$C_4$-alkyleneoxy, $C_1$-$C_4$-oxyalkylene or $C_1$-$C_4$-alkyleneoxy-$C_1$-$C_4$-alkylene;

$R^6$ is hydrogen, $C_1$-$C_4$-alkyl, $C_1$-$C_4$-haloalkyl, $C_1$-$C_4$-alkoxy, $C_1$-$C_4$-haloalkoxy or $C_1$-$C_4$-haloalkylthio;

$R^7$, $R^8$ independently of one another are hydrogen, halogen or $C_1$-$C_4$-alkyl;

$R^x$, $R^y$ independently of one another are hydrogen, $C_1$-$C_5$-alkyl, $C_2$-$C_5$-alkenyl, $C_2$-$C_5$-alkynyl, $C_1$-$C_5$-haloalkyl, $C_1$-$C_2$-alkoxy-$C_1$-$C_2$-alkyl or halogen; or $R^x$ and $R^y$ are together a $C_2$-$C_5$-alkylene or $C_2$-$C_5$-alkenylene chain and form a 3-, 4-, 5- or 6-membered saturated, partially unsaturated or fully unsaturated monocyclic ring together with the carbon atom they are bonded to, wherein 1 or 2 of any of the $CH_2$ or CH groups in the $C_2$-$C_5$-alkylene or $C_2$-$C_5$-alkenylene chain may be replaced by 1 or 2 heteroatoms independently selected from O or S;

where in the groups $R^A$, and $R^1$, $R^2$, $R^3$, $R^4$ and $R^5$ and their substituents, the carbon chains and/or the cyclic groups may be partially or fully substituted by groups $R^b$, or an N-oxide or an agriculturally suitable salt thereof.

The present invention also provides herbicidally active compositions comprising at least one substituted pyridine compound of formula I and at least one further compound selected from herbicidal active compounds B and safeners C.

The present invention also provides the use of a substituted pyridine compound of the general formula I as herbicides, i.e. for controlling harmful plants.

The present invention also provides compositions comprising at least one substituted pyridine compound of the formula I and auxiliaries customary for formulating crop protection agents.

The present invention furthermore provides a method for controlling unwanted vegetation where a herbicidal effective amount of at least one substituted pyridine compound of the formula I is allowed to act on plants, their seeds and/or their habitat. Application can be done before, during and/or after, preferably during and/or after, the emergence of the undesirable plants.

Moreover, the invention relates to processes and intermediates for preparing substituted pyridine compounds of the formula I.

Further embodiments of the present invention are evident from the claims, the description and the examples. It is to be understood that the features mentioned above and still to be illustrated below of the subject matter of the invention can be applied not only in the combination given in each particular case but also in other combinations, without leaving the scope of the invention.

As used herein, the terms "controlling" and "combating" are synonyms. As used herein, the terms "undesirable vegetation" and "harmful plants" are synonyms.

If the compounds of formula I as described herein are capable of forming geometrical isomers, for example E/Z isomers, it is possible to use both, the pure isomers and mixtures thereof, in the compositions according to the invention.

If the compounds of formula I as described herein have one or more centers of chirality and, as a consequence, are present as enantiomers or diastereomers, it is possible to use both, the pure enantiomers and diastereomers and their mixtures, in the compositions according to the invention.

If the compounds of formula I as described herein have ionizable functional groups, they can also be employed in the form of their agriculturally acceptable salts. Suitable are, in general, the salts of those cations and the acid addition salts of those acids whose cations and anions, respectively, have no adverse effect on the activity of the active compounds.

Preferred cations are the ions of the alkali metals, preferably of lithium, sodium and potassium, of the alkaline earth metals, preferably of calcium and magnesium, and of the transition metals, preferably of manganese, copper, zinc and iron, further ammonium and substituted ammonium in which one to four hydrogen atoms are replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl or benzyl, preferably ammonium, methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyeth-1-oxy)eth-1-ylammonium, di(2-hydroxyeth-1-yl)ammonium, benzyltrimethylammonium, benzyltriethylammonium, furthermore phosphonium ions, sulfonium ions, preferably tri($C_1$-$C_4$-alkyl)sulfonium, such as trimethylsulfonium, and sulfoxonium ions, preferably tri ($C_1$-$C_4$-alkyl)sulfoxonium.

Anions of useful acid addition salts are primarily chloride, bromide, fluoride, iodide, hydrogensulfate, methylsulfate, sulfate, dihydrogenphosphate, hydrogenphosphate, nitrate, bicarbonate, carbonate, hexafluorosilicate, hexafluorophosphate, benzoate and also the anions of $C_1$-$C_4$-alkanoic acids, preferably formate, acetate, propionate and butyrate.

Compounds of formula I as described herein having a carboxyl group can be employed in the form of the acid, in the form of an agriculturally suitable salt or else in the form of an agriculturally acceptable derivative, for example as amides, such as mono- and di-$C_1$-$C_6$-alkylamides or arylamides, as esters, for example as allyl esters, propargyl esters, $C_1$-$C_{10}$-alkyl esters, alkoxyalkyl esters and also as thioesters, for example as $C_1$-$C_{10}$-alkylthio esters. Preferred mono- and di-$C_1$-$C_6$-alkylamides are the methyl and the dimethylamides. Preferred arylamides are, for example, the anilides and the 2-chloroanilides. Preferred alkyl esters are, for example, the methyl, ethyl, propyl, isopropyl, butyl, isobutyl, pentyl, mexyl(1-methylhexyl) or isooctyl(2-ethylhexyl)esters. Preferred $C_1$-$C_4$-alkoxy-$C_1$-$C_4$-alkyl esters are the straight-chain or branched $C_1$-$C_4$-alkoxy ethyl esters, for example the methoxyethyl, ethoxyethyl or butoxyethyl ester. An example of a straight-chain or branched $C_1$-$C_{10}$-alkylthio ester is the ethylthio ester.

The organic moieties mentioned in the definition of the variables R, $R^1$, $R^2$, $R^3$, $R^4$, $R^5$, $R^6$, $R^7$, $R^8$, $R^x$, $R^y$, $R^A$, $R^aR^b$, $R^{bb}$, $R^i$, $R^{ii}$, Z and $Z^1$ are—like the term halogen—collective terms for individual enumerations of the individual group members. The term halogen denotes in each case fluorine, chlorine, bromine or iodine. All hydrocarbon chains, i.e. all alkyl, can be straight-chain or branched, the prefix $C_n$-$C_m$ denoting in each case the possible number of carbon atoms in the group.

Examples of such meanings are:

$C_1$-$C_2$-alkyl and also the $C_1$-$C_2$-alkyl moieties of $C_1$-$C_2$-alkoxy-$C_1$-$C_2$-alkyl includes $CH_3$ and $C_2H_5$;

$C_1$-$C_4$-alkyl and also the $C_1$-$C_4$-alkyl moieties of Z-(tri-$C_1$-$C_4$-alkyl)silyl and $C_3$-$C_6$-cycloalkyl-$C_1$-$C_4$-alkyl: $C_1$-$C_2$-alkyl as mentioned above, and also, for example, n-propyl, $CH(CH_3)_2$, n-butyl, $CH(CH_3)$—$C_2H_5$, $CH_2$—$CH(CH_3)_2$ and $C(CH_3)_3$;

$C_1$-$C_5$-alkyl: $C_1$-$C_4$-alkyl as mentioned above, and also, for example, n-pentyl, 1-methylbutyl, 2-methylbutyl, 3-methylbutyl, 2,2-dimethylpropyl, 1,1-dimethylpropyl, 1,2-dimethylpropyl, and 1-ethylpropyl;

$C_1$-$C_6$-alkyl and also the $C_1$-$C_6$-alkyl moieties of $C_1$-$C_6$-alkylsulfonyl and $C_1$-$C_6$-alkyoxy-$C_1$-$C_6$-alkyl: $C_1$-$C_5$-alkyl as mentioned above, and also, for example, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably methyl, ethyl, n-propyl, 1-methylethyl, n-butyl, 1,1-dimethylethyl, n-pentyl or n-hexyl;

$C_1$-$C_8$-alkyl: $C_1$-$C_6$-alkyl as mentioned above, and also, for example, n-heptyl, n-octyl or 2-ethylhexyl;

$C_1$-$C_4$-haloalkyl: a $C_1$-$C_4$-alkyl radical as mentioned above which is partially or fully substituted by fluorine, chlorine, bromine and/or iodine, for example, chloromethyl, dichloromethyl, trichloromethyl, fluoromethyl, difluoromethyl, trifluoromethyl, chlorofluoromethyl, dichlorofluoromethyl, chlorodifluoromethyl, bromomethyl, iodomethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl, nonafluorobutyl, 1,1,2,2,-tetrafluoroethyl and 1-trifluoromethyl-1,2,2,2-tetrafluoroethyl;

$C_1$-$C_5$-haloalkyl: $C_1$-$C_4$-haloalkyl as mentioned above, and also, for example, 5-fluoropentyl, 5-chloropentyl, 5-bromopentyl, 5-iodopentyl and undecafluoropentyl;

$C_1$-$C_6$-haloalkyl: $C_1$-$C_5$-haloalkyl as mentioned above, and also, for example, 6-fluorohexyl, 6-chlorohexyl, 6-bromohexyl, 6-iodohexyl and dodecafluorohexyl;

$C_3$-$C_6$-cycloalkyl and also the cycloalkyl moieties of Z—$C_3$-$C_6$-cycloalkyl and $C_3$-$C_6$-cycloalkyl-$C_1$-$C_4$-alkyl: monocyclic saturated hydrocarbons having 3 to 6 ring members, such as cyclopropyl, cyclobutyl, cyclopentyl and cyclohexyl;

$C_3$-$C_{10}$-cycloalkyl and also the cycloalkyl moieties of Z—$C_3$-$C_{10}$-cycloalkyl and O—Z—$C_3$-$C_{10}$-cycloalkyl: $C_3$-$C_6$-cycloalkyl as mentioned above, and also, for example, cyclo-heptyl, cyclooctyl, cyclononyl and cyclodecyl;

$C_2$-$C_5$-alkenyl: for example ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl and 1-ethyl-2-propenyl;

$C_2$-$C_6$-alkenyl and also the alkenyl moieties of $C_2$-$C_6$-alkenyloxy: $C_2$-$C_5$-alkenyl as mentioned above, and also, for example, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

$C_2$-$C_8$-alkenyl: $C_2$-$C_6$-alkenyl as mentioned above, and also, for example 1-heptenyl, 2-heptenyl, 3-heptenyl, 1-octenyl, 2-octenyl, 3-octenyl and 4-octenyl.

$C_3$-$C_8$-alkenyl and also the alkenyl moieties of Z—$C_3$-$C_8$-alkenyloxy: $C_2$-$C_8$-alkenyl as mentioned above, with the exception of ethenyl;

$C_3$-$C_6$-cycloalkenyl and also the cycloalkenyl moieties of Z—$C_3$-$C_6$-cycloalkenyl: for example cyclopropenyl, cyclobutenyl, cyclopentenyl and cyclohexenyl;

$C_5$-$C_6$-cycloalkenyl and also the cycloalkenyl moieties of Z—$C_5$-$C_6$-cycloalkenyl: for example cyclopentenyl and cyclohexenyl;

$C_2$-$C_6$-haloalkenyl: a $C_2$-$C_6$-alkenyl radical as mentioned above which is partially or fully substituted by fluorine, chlorine, bromine and/or iodine, for example 2-dibromoethenyl, 2-fluoro-2-bromoethenyl, 2-chloroprop-2-en-1-yl, 3-chloroprop-2-en-1-yl, 2,3-dichloroprop-2-en-1-yl, 3,3-dichloroprop-2-en-1-yl, 2,3,3-trichloro-2-en-1-yl, 2,3-dichlorobut-2-en-1-yl, 2-bromoprop-2-en-1-yl, 3-bromoprop-2-en-1-yl, 2,3-dibromoprop-2-en-1-yl, 3,3-dibromoprop-2-en-1-yl, 2,3,3-tribromo-2-en-1-yl or 2,3-dibromobut-2-en-1-yl;

$C_3$-$C_6$-haloalkenyl: $C_2$-$C_6$-haloalkenyl as mentioned above with the exception of $C_2$-haloalkenyl radicals;

$C_2$-$C_8$-haloalkenyl: $C_2$-$C_6$-haloalkenyl as mentioned above, and also, for example, 3-fluoro-n-heptenyl-1,1, 3,3,-trichloro-n-heptenyl-5 and 1,3,5-trichloro-n-octenyl-6;

$C_2$-$C_5$-alkynyl: for example ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl and 1-ethyl-2-propynyl;

$C_2$-$C_6$-alkynyl and also the alkynyl moieties of $C_2$-$C_6$-alkynyloxy: $C_2$-$C_5$-alkynyl as mentioned above, and also, for example, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

$C_2$-$C_8$-alkynyl: $C_2$-$C_6$-alkynyl as mentioned above, and also, for example, 1-heptynyl, 2-heptynyl, 1-octynyl and 2-octynyl;

$C_3$-$C_8$-alkynyl and also the alkynyl moieties of Z—$C_3$-$C_8$-alkynyloxy: a $C_2$-$C_8$-alkynyl radical as mentioned above with the exception of $C_2$-alkynyl radicals;

$C_2$-$C_6$-haloalkynyl: a $C_2$-$C_6$-alkynyl radical as mentioned above which is partially or fully substituted by fluorine, chlorine, bromine and/or iodine, for example 1,1-difluoroprop-2-yn-1-yl, 3-chloroprop-2-yn-1-yl, 3-bromoprop-2-yn-1-yl, 3-iodoprop-2-yn-1-yl, 4-fluorobut-2-yn-1-yl, 4-chlorobut-2-yn-1-yl, 1,1-difluorobut-2-yn-1-yl, 4-iodobut-3-yn-1-yl, 5-fluoropent-3-yn-1-yl, 5-iodopent-4-yn-1-yl, 6-fluorohex-4-yn-1-yl or 6-iodohex-5-yn-1-yl;

$C_3$-$C_6$-haloalkynyl: a $C_2$-$C_6$-haloalkynyl as mentioned above with the exception of $C_2$-haloalkynyl radicals;

$C_2$-$C_8$-haloalkynyl: $C_2$-$C_6$-haloalkynyl as mentioned above, and also, for example, 1-chloro-2-heptynyl and 1-chloro-2-octynyl;

$C_1$-$C_2$-alkoxy and also the $C_1$-$C_2$-alkoxy moieties of $C_1$-$C_2$-alkoxy-$C_1$-$C_2$-alkyl: for example methoxy and ethoxy;

$C_1$-$C_4$-alkoxy and also the $C_1$-$C_4$-alkoxy moieties of Z—$C_1$-$C_4$-alkoxy-$C_1$-$C_4$-alkoxy, $C_1$-$C_4$-haloalkoxy-$C_1$-$C_4$-alkoxy, hydroxycarbonyl-$C_1$-$C_4$-alkoxy and $C_1$-$C_6$-alkoxycarbonyl-$C_1$-$C_4$-alkoxy: $C_1$-$C_2$-alkoxy as mentioned above, and also, for example, propoxy, 1-methylethoxy butoxy, 1-methylpropoxy, 2-methylpropoxy and 1,1-dimethylethoxy;

$C_1$-$C_6$-alkoxy and also the $C_1$-$C_6$-alkoxy moieties of Z—$C_1$-$C_6$-alkoxy and $C_1$-$C_6$-alkoxycarbonyl-$C_1$-$C_4$-alkoxy: $C_1$-$C_4$-alkoxy as mentioned above, and also, for example, pentoxy, 1-methylbutoxy, 2-methylbutoxy, 3-methoxybutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy;

$C_1$-$C_8$-alkoxy and also the $C_1$-$C_8$-alkoxy moieties of Z—$C_1$-$C_8$-alkoxy: $C_1$-$C_6$-alkoxy as mentioned above, and also, for example, heptoxy, octoxy, 1,1,3,3-tetramethylbutoxy and 2-ethylhexoxy;

$C_1$-$C_4$-haloalkoxy and also the $C_1$-$C_4$-haloalkoxy moieties of Z—$C_1$-$C_4$-haloalkoxy and $C_1$-$C_4$-haloalkoxy-$C_1$-$C_4$-alkoxy: for example $OCH_2F$, $OCHF_2$, $OCF_3$, $OCH_2Cl$, $OCHCl_2$, $OCCl_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or $OC_2F_5$. $C_1$-$C_4$-haloalkoxy is additionally, for example, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, $OCH_2$—$C_2F_5$, $OCF_2$—$C_2F_5$, 1-($CH_2F$)-2-fluoroethoxy, 1-($CH_2Cl$)-2-chloroethoxy, 1-($CH_2Br$)-2-bromoethoxy, 4-fluorobutoxy, 4-chlorobutoxy, 4-bromobutoxy or nonafluorobutoxy;

$C_1$-$C_6$-haloalkoxy: $C_1$-$C_4$-haloalkoxy as mentioned above, and also, for example, 5-fluoropentoxy, 5-chloropentoxy, 5-brompentoxy, 5-iodopentoxy, undecafluoropentoxy, 6-fluorohexoxy, 6-chlorohexoxy, 6-bromohexoxy, 6-iodohexoxy or dodecafluorohexoxy;

$C_1$-$C_8$-haloalkoxy and also the $C_1$-$C_8$-haloalkoxy moieties of Z—$C_1$-$C_8$-haloalkoxy: $C_1$-$C_6$-haloalkoxy as mentioned above, and also, for example, 7-fluoroheptoxy, 7-chloroheptoxy, 7-bromoheptoxy, 7-iodoheptoxy, perfluoroheptoxy, 8-fluorooctoxy, 8-chlorooctoxy, 8-bromooctoxy, 8-iodooctoxy and octadecafluorooctoxy;

$C_1$-$C_4$-alkylthio also the $C_1$-$C_4$-alkylthio moieties of Z—$C_1$-$C_4$-alkylthio, Z—$C_1$-$C_4$-alkylthio-$C_1$-$C_4$-alkylthio: for example methylthio, ethylthio, propylthio, 1-methylethylthio, butylthio, 1-methylpropylthio, 2-methylpropylthio and 1,1-dimethylethylthio;

$C_1$-$C_4$-haloalkylthio: for example $SCH_2F$, $SCHF_2$, $SCF_3$, $SCH_2Cl$, $SCHCl_2$, $SCCl_3$, chlorofluoromethylthio, dichlorofluoromethylthio, chlorodifluoromethylthio, 2-fluoroethylthio, 2-chloroethylthio, 2-bromoethylthio, 2-iodoethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or $SC_2F_5$. $C_1$-$C_4$-haloalkylthio is additionally, for example, 2-fluoropropylthio, 3-fluoropropylthio, 2,2-difluoropropylthio, 2,3-difluoropropylthio, 2-chloropropylthio, 3-chloropropylthio, 2,3-dichloropropylthio, 2-bromopropylthio, 3-bromopropylthio, 3,3,3-trifluoropropylthio, 3,3,3-trichloropropylthio, $SCH_2$—$C_2F_5$, $SCF_2$—$C_2F_5$, 1-($CH_2F$)-2-fluoroethylthio, 1-($CH_2Cl$)-2-chloroethylthio, 1-($CH_2Br$)-2-bromoethylthio, 4-fluorobutylthio, 4-chlorobutylthio, 4-bromobutylthio or nonafluorobutylthio;

$C_1$-$C_6$-haloalkylthio and also the $C_1$-$C_6$-alkylthio moieties of Z—$C_1$-$C_6$-haloalkylthio: $C_1$-$C_4$-haloalkylthio as mentioned above, and also, for example, 5-fluoropentylthio, 5-chloropentylthio, 5-brompentylthio, 5-iodopentylthio, undecafluoropentylthio, 6-fluorohexylthio, 6-chlorohexylthio, 6-bromohexylthio, 6-iodohexylthio or dodecafluorohexylthio;

$C_1$-$C_4$-alkylene and also the $C_1$-$C_4$-alkylene moieties in $C_1$-$C_4$-alkyleneoxy, $C_1$-$C_4$-oxyalkylene and $C_1$-$C_4$-alkyleneoxy-$C_1$-$C_4$-alkylene: a straight carbon chain having from 1 to 4 carbon atoms and having only carbon-carbon single bonds, for example meth-ylene ($CH_2$), ethylene ($CH_2CH_2$), n-propylene ($CH_2CH_2CH_2$) and n-butylene ($CH_2CH_2CH_2CH_2$).

$C_2$-$C_5$-alkylene: $C_1$-$C_4$-alkylene as mentioned above, and also n-pentylene ($CH_2CH_2CH_2CH_2CH_2$);

$C_2$-$C_5$-alkenylene chain: a straight carbon chain having from 2 to 5 carbon atoms and at least one carbon-carbon double bond and no carbon-carbon triple bond, for example, CH=CH, CH=CH—$CH_2$, CH=CH—$CH_2CH_2$, CH=CH—CH=$CH_2$ and CH=CH—$CH_2CH_2CH_2$;

a 3- to 7-membered monocyclic or 9- or 10-membered bicyclic saturated, unsaturated or aromatic heterocycle which contains 1, 2, 3 or 4 heteroatoms selected from the group consisting of O, N and S means, for example, pyridazin-3-yl, pyridazin-4-yl, pyrimidin-2-yl, pyrimidin-4-yl, pyrimidin-5-yl, pyrazin-2-yl, 2-furyl, 3-furyl, 2-thienyl, 3-thienyl, pyrazol-1-yl, pyrazol-3-yl, pyrazol-4-yl, isoxazol-3-yl, isoxazol-4-yl, isoxazol-5-yl, isothiazol-3-yl, isothiazol-4-yl, isothiazol-5-yl, imidazol-1-yl, imidazol-2-yl, imidazol-4-yl, oxazol-2-yl, oxazol-4-yl, oxazol-5-yl, thiazol-2-yl, thiazol-4-yl, thiazol-5-yl, pyrazol-3-yl, imidazol-5-yl, oxazol-2-yl, thiazol-2-yl, thiazol-4-yl, thiazol-5-yl, pyridin-2-yl, pyridin-3-yl, pyridin-4-yl, pyrimidin-2-yl, pyrimidin-4-yl, pyrimidin-5-yl, pyridazin-4-yl, pyrazin-2-yl, [1H]-tetrazol-5-yl; [2H]-tetrazol-5-yl, 2-tetrahydrofuryl, 3-tetrahydrofuryl, 2-oxetanyl and 3-oxetanyl;

a 5- or 6-membered monocyclic or 9- or 10-membered bicyclic heterocycle which contains 1, 2, 3 or 4 heteroatoms selected from the group consisting of O, N and S means, for example: pyridazin-3-yl, pyridazin-4-yl, pyrimidin-2-yl, pyrimidin-4-yl, pyrimidin-5-yl, pyrazin-2-yl, 2-furyl, 3-furyl, 2-thienyl, 3-thienyl, pyrazol-1-yl, pyrazol-3-yl, pyrazol-4-yl, isoxazol-3-yl, isoxazol-4-yl, isoxazol-5-yl, isothiazol-3-yl, isothiazol-4-yl, isothiazol-5-yl, imidazol-1-yl, imidazol-2-yl, imidazol-4-yl, oxazol-2-yl, oxazol-4-yl, oxazol-5-yl, thiazol-2-yl, thiazol-4-yl and thiazol-5-yl, pyrazol-3-yl, imidazol-5-yl, oxazol-2-yl, thiazol-2-yl, thiazol-4-yl, thiazol-5-yl, pyridin-2-yl, pyridin-3-yl, pyridin-4-yl, pyrimidin-2-yl, pyrimidin-4-yl, pyrimidin-5-yl, pyridazin-4-yl, pyrazin-2-yl, [1H]-tetrazol-5-yl and [2H]-tetrazol-5-yl, 2-tetrahydrofuryl and 3-tetrahydrofuryl;

a 5- to 10-membered saturated or partially or fully unsaturated mono- or bicyclic ring which, in addition to carbon atoms, may contain 1, 2 or 3 heteroatoms selected from the group consisting of O, N and S means, for example: pyridazin-3-yl, pyridazin-4-yl, pyrimidin-2-yl, pyrimidin-4-yl, pyrimidin-5-yl, pyrazin-2-yl, 2-furyl, 3-furyl, 2-thienyl, 3-thienyl, pyrazol-1-yl, pyrazol-3-yl, pyrazol-4-yl, isoxazol-3-yl, isoxazol-4-yl, isoxazol-5-yl, isothiazol-3-yl, isothiazol-4-yl, isothiazol-5-yl, imidazol-1-yl, imidazol-2-yl, imidazol-4-yl, oxazol-2-yl, oxazol-4-yl, oxazol-5-yl, thiazol-2-yl, thiazol-4-yl and thiazol-5-yl, pyrazol-3-yl, imidazol-5-yl, oxazol-2-yl, thiazol-2-yl, thiazol-4-yl, thiazol-5-yl, pyridin-2-yl, pyridin-3-yl, pyridin-4-yl, pyrimidin-2-yl, pyrimidin-4-yl, pyrimidin-5-yl, pyridazin-4-yl, pyrazin-2-yl, [1H]-tetrazol-5-yl and [2H]-tetrazol-5-yl, cyclopentyl, cyclohexyl, 2-tetrahydrofuryl and 3-tetrahydrofuryl.

According to a preferred embodiment of the invention preference is also given to those compounds of formula I, wherein the variables, either independently of one another or in combination with one another, have the following meanings:

In one preferred embodiment of the compounds of the formula I, R is O—$R^A$, in which $R^A$ is H, $C_3$-$C_8$-alkenyl, $C_3$-$C_8$-haloalkenyl, $C_3$-$C_8$-alkynyl, $C_3$-$C_8$-haloalkynyl, $C_1$-$C_6$-alkylcarbonyl, such as $C(O)CH_3$, $C(O)CH_2CH_3$, $C(O)CH(CH_3)_2$ or $C(O)C(CH_3)_3$; $C_1$-$C_6$-cycloalkylcarbonyl, such as cyclopropylcarbonyl, cyclopentylcarbonyl or cyclohexylcarbonyl; $C_2$-$C_6$-alkenylcarbonyl, such as $C(O)CH=CH_2$ or $C(O)CH_2CH=CH_2$, optionally subst. benzoyl, such as $C(O)C_6H_5$, $C(O)[2$-$CH_3$—$C_6H_4]$, $C(O)[4$-$CH_3$—$C_6H_4]$, $C(O)[2$-F—$C_6H_4]$, $C(O)[4$-F—$C_6H_4]$, or optionally substituted heteroaryl, such as pyridyl, which is attached via a carbonyl group. Particularly preferably, $R^A$ is H, $C_3$-$C_4$-alkenyl, $C_3$-$C_4$-alkynyl or $C_1$-$C_6$-alkylcarbonyl. Especially preferably, $R^A$ is selected from the group consisting of H, $CH_2CH=CH_2$, $CH_2C\equiv CH$, $CH_3$, $C(O)CH_3$, $C(O)CH_2CH_3$, $C(O)CH(CH_3)_2$, $C(O)C(CH_3)_3$, $C(O)$-c-$C_3H_5$, $C(O)$—$C_6H_5$, $C(O)$—$CH_2C_6H_5$, $C(O)CH_2Cl$, $C(O)CF_3$, $C(O)CH_2OCH_3$, $C(O)N(CH_3)_2$ and $C(O)OCH_2CH_3$.

In a further preferred embodiment of the compounds of the formula I, R is $OS(O)_n$—$R^A$ where n is preferably 0 or 2, in particular 2, such as, for example, $OS(O)_2$—$CH_3$, $OS(O)_2$—$C_2H_5$, $OS(O)_2$—$C_3H_7$, $OS(O)_2$—$C_6H_5$ or $OS(O)_2$-(4-$CH_3$—$C_6H_4$).

In a further preferred embodiment, R is O—$S(O)_n$—$NR^iR^{ii}$, in particular with the groups $NR^iR^{ii}$ mentioned below as preferred.

$R^i$ and $R^{ii}$ are preferably $C_1$-$C_8$-alkyl, $C_1$-$C_4$-haloalkyl, Z—$C_3$-$C_6$-cycloalkyl, Z—$C_1$-$C_8$-alkoxy, Z—$C_1$-$C_8$-haloalkoxy, Z-phenyl, Z—$C(=O)$—$R^a$ or Z-hetaryl. Preference is given here to $CH_3$, $C_2H_5$, n-propyl, $CH(CH_3)_2$, butyl, 2-choroethyl, cyclopentyl, cyclohexyl, 2-ethoxymethyl, 2-chloroethoxy, phenyl, pyrimidines or triazines, which rings are unsubstituted or substituted. Preferred substituents are $C_1$-$C_4$-alkylcarbonyl or $C_1$-$C_4$-haloalkylcarbonyl, in particular $C(=O)$—$CH_3$, $C(=O)$—$C_2H_5$, $C(=O)$—$C_3H_7$, $C(=O)$—$CH(CH_3)_2$, butylcarbonyl and $C(=O)$—$CH_2Cl$. Particularly preferred aspects of group $NR^iR^{ii}$ are $N(di$-$C_1$-$C_4$-alkyl), in particular $N(CH_3)$—$C_1$-$C_4$-alkyl, such as $N(CH_3)_2$, $N(CH_3)CH_2CH_3$, $N(CH_3)C_3H_7$ and $N(CH_3)CH(CH_3)_2$.

Further particularly preferred aspects of $NR^iR^{ii}$ are NH-aryl, where aryl is preferably phenyl which is substituted—in particular in the 2- and 6-position—by one to three identical or different groups from the group consisting of halogen, $CH_3$, halo-$C_1$-$C_2$-alkyl, halo-$C_1$-$C_2$-alkoxy and carboxyl, such as 2-Cl, 6-COOH—$C_6H_3$, 2,6-$Cl_2$-$C_6H_3$, 2,6-$F_2$-$C_6H_3$, 2,6-$Cl_2$ 3-$C_6H_2$, 2-$CF_3$, 6-$CH_2CHF_2$—$C_6H_3$, 2-$CF_3$, 6-$OCF_3$—$C_6H_3$ and 2-$CF_3$, 6-$CH_2CHF_2$—$C_6H_3$.

In a further preferred embodiment of the invention, $R^A$ is a 5- or 6-membered heterocycle optionally substituted by $R^b$ as defined above, which preferably has either 1, 2, 3 or 4 N or 1 O or 1 S atom and if appropriate 1 or 2 N atoms as ring members and which is unsubstituted or may have 1 or 2 substituents selected from $R^b$. Preference is given to saturated or unsaturated groups attached via nitrogen, such as, for example:

Heteroaromatic groups: pyridazin-3-yl, pyridazin-4-yl, pyrimidin-2-yl, pyrimidin-4-yl, pyrimidin-5-yl, pyrazin-2-yl, 2-furyl, 3-furyl, 2-thienyl, 3-thienyl, pyrazol-1-yl, pyrazol-3-yl, pyrazol-4-yl, isoxazol-3-yl, isoxazol-4-yl, isoxazol-5-yl, isothiazol-3-yl, isothiazol-4-yl, isothiazol-5-yl, imidazol-1-yl, imidazol-2-yl, imidazol-4-yl, oxazol-2-yl, oxazol-4-yl, oxazol-5-yl, thiazol-2-yl, thiazol-4-yl and thiazol-5-yl.

In another aspect, $R^A$ is a heteroaromatic group attached via carbon, such as pyrazol-3-yl, imidazol-5-yl, oxazol-2-yl, thiazol-2-yl, thiazol-4-yl, thiazol-5-yl, pyridin-2-yl, pyridin-3-yl, pyridin-4-yl, pyrimidin-2-yl, pyrimidin-4-yl, pyrimidin-5-yl, pyridazin-4-yl, pyrazin-2-yl, [1H]-tetrazol-5-yl and [2H]-tetrazol-5-yl, where each of the heterocycles mentioned here in an exemplary manner may have 1 or 2 substituents selected from $R^b$. Preferred groups $R^b$ are in this case in particular F, Cl, CN, $NO_2$, $CH_3$, $C_2H_5$, $OCH_3$, $OC_2H_5$, $OCHF_2$, $OCF_3$ and $CF_3$.

In particularly preferred embodiments of the compounds of the formula I, R is selected from the group consisting of OH, $OCH_2CH=CH_2$, $OCH_2C\equiv CH$, $OCH_3$, $OC(O)CH_3$, $OC(O)CH_2CH_3$, $OC(O)CH(CH_3)_2$, $OC(O)C(CH_3)_3$, $OC(O)$-c-$C_3H_5$, $OC(O)$—$C_6H_5$, $OC(O)$—$CH_2C_6H_5$, $OC(O)CH_2Cl$, $OC(O)$—$CF_3$, $OC(O)$—$CH_2OCH_3$, $OC(O)$—$N(CH_3)_2$ and $OC(O)$—$OCH_2CH_3$.

Groups $R^a$ preferred for the compounds of the formula I are selected from the group consisting of OH, $C_1$-$C_8$-alkyl, $C_1$-$C_4$-haloalkyl, $C_3$-$C_8$-alkenyl, $C_3$-$C_8$-alkynyl, Z—$C_1$-$C_6$-alkoxy, Z—$C_1$-$C_4$-haloalkoxy, Z—$C_3$-$C_8$-alkenyloxy, Z—$C_3$-$C_8$-alkynyloxy and $NR^iR^{ii}$.

For the compounds of the formula I, the groups $R^b$ are preferably selected from the group consisting of halogen, oxo(=O), =N—$R^a$, $C_1$-$C_4$-alkyl, $C_1$-$C_4$-haloalkyl, $C_2$-$C_6$-alkenyl, $C_2$-$C_6$-alkynyl, Z—$C_1$-$C_4$-haloalkoxy, $C_1$-$C_4$-alkoxy-$C_1$-$C_4$-alkyl, $C_1$-$C_4$-alkylthio-$C_1$-$C_4$-alkyl, $C_1$-$C_4$-alkoxy-$C_1$-$C_4$-alkoxy-$C_1$-$C_4$-alkyl, $C_1$-$C_4$-alkylthio-$C_1$-$C_4$-alkylthio-$C_1$-$C_4$-alkyl, Z—$C(=O)$—$R^a$ and $S(O)_nR^{bb}$, where $R^{bb}$ is preferably $C_1$-$C_4$-alkyl or $C_1$-$C_4$-haloalkyl and n is 0, 1 or 2.

Particularly preferably, $R^b$ is a group selected from the group consisting of halogen, $C_1$-$C_4$-alkyl, $C_1$-$C_4$-haloalkyl, $C_1$-$C_4$-alkoxy, $C_1$-$C_4$-alkylthio, $C_1$-$C_4$-alkoxy-$C_1$-$C_4$-alkyl, $C_1$-$C_4$-alkylthio-$C_1$-$C_4$-alkyl, $C_1$-$C_4$-alkoxy-$C_1$-$C_4$-alkoxy-$C_1$-$C_4$-alkyl, $C_1$-$C_4$-haloalkoxy, $C_1$-$C_4$-haloalkylthio, $C_3$-$C_4$-alkenyl, $C_3$-$C_4$-alkynyl and =N—$C_1$-$C_4$-alkoxy.

Two groups $R^b$ together may form a ring which preferably has three to seven ring members and, in addition to carbon atoms, may also contain heteroatoms from the group consisting of O, N and S and which may be unsubstituted or substituted by further groups $R^b$. These substituents $R^b$ are preferably selected from the group consisting of halogen, $C_1$-$C_4$-alkyl, $C_1$-$C_4$-alkoxy and $C_1$-$C_4$-haloalkyl.

Groups $R^a$ and $R^b$ are selected independently of one another if a plurality of such groups is present.

In a preferred embodiment of the compounds of the formula I, $R^1$ is cyano, halogen, nitro, $C_1$-$C_6$-alkyl, $C_2$-$C_6$-alkenyl, $C_2$-$C_6$-alkynyl, $C_1$-$C_6$-haloalkyl, Z—$C_1$-$C_6$-alkoxy, Z—$C_1$-$C_4$-alkoxy-$C_1$-$C_4$-alkoxy, Z—$C_1$-$C_4$-alkylthio, Z—$C_1$-$C_4$-alkylthio-$C_1$-$C_4$-alkylthio, $C_2$-$C_6$-alkenyloxy, $C_2$-$C_6$-alkynyloxy, $C_1$-$C_6$-haloalkoxy, $C_1$-$C_4$-haloalkoxy-$C_1$-$C_4$-alkoxy, $S(O)_n R^{bb}$, Z-phenoxy, Z-heterocyclyloxy, where heterocyclyl is a 5- or 6-membered monocyclic or 9- or 10-membered bicyclic saturated, partially unsaturated or aromatic heterocycle which contains 1, 2, 3 or 4 heteroatoms selected from the group consisting of O, N and S, cyclic groups being unsubstituted or partially or fully substituted by $R^b$.

In a particularly preferred embodiment of the compounds of the formula I, $R^1$ is halogen, CN, $NO_2$, $C_1$-$C_4$-alkyl, $C_1$-$C_4$-haloalkyl, $C_1$-$C_4$-alkoxy-$C_1$-$C_4$-alkyl, $C_1$-$C_4$-alkoxy-$C_1$-$C_4$-alkoxy-$C_1$-$C_4$-alkyl, $C_1$-$C_4$-alkylthio-$C_1$-$C_4$-alkyl, $C_1$-$C_4$-alkylthio-$C_1$-$C_4$-alkylthio-$C_1$-$C_4$-alkyl, $C_1$-$C_4$-alkoxy, $C_1$-$C_4$-haloalkoxy, $C_3$-$C_4$-alkenyloxy, $C_3$-$C_4$-alkynyloxy, $C_1$-$C_4$-alkoxy-$C_1$-$C_4$-alkoxy, $C_1$-$C_4$-haloalkoxy-$C_1$-$C_4$-alkoxy, $S(O)_n$—$C_1$-$C_4$-alkyl and $S(O)_n$—$C_1$-$C_4$-haloalkyl. Particularly preferably, $R^1$ is selected from the group consisting of F, Cl, Br, $NO_2$, $CH_3$, $CHF_2$, $CF_3$, $OCH_3$, $OCF_3$, $SCF_3$, $SO_2CH_3$, $OCH_2CH_2OCH_3$, $CH_2OCH_2CH_2OCH_3$ and $CH_2OCH_2CF_3$. Particularly preferably, $R^1$ is selected from the group consisting of F, Cl, Br, $NO_2$, $CH_3$, $CF_3$, $OCH_3$, $OCF_3$, $SCF_3$, $SO_2CH_3$, $OCH_2CH_2OCH_3$, $CH_2OCH_2CH_2OCH_3$ and $CH_2OCH_2CF_3$.

In a further preferred embodiment of the compounds of the formula I, A is C—$R^2$. These compounds correspond to the formula I.1

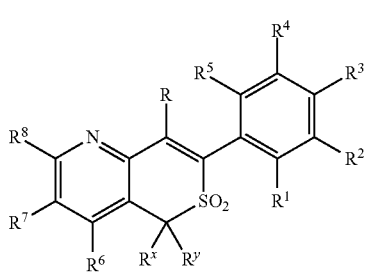

I.1 where the variables have the meanings defined at the outset and preferably the meanings mentioned as preferred.

More preferably, in the compounds of the formula I.1, the group
$R^1$ is halogen, $C_1$-$C_4$-alkyl, $C_1$-$C_4$-haloalkyl, $C_1$-$C_4$-alkoxy-$C_1$-$C_4$-alkyl, $C_1$-$C_4$-alkoxy-$C_1$-$C_4$-alkoxy-$C_1$-$C_4$-alkyl, $C_1$-$C_4$-alkoxy, $C_1$-$C_4$-haloalkoxy, $C_1$-$C_4$-alkylthio, $C_1$-$C_4$-haloalkylthio or $C_1$-$C_4$-alkylsulfonyl, in particular F, Cl, Br, I, $NO_2$, $CH_3$, $CF_3$, $OCH_3$, $OCF_3$, $OCHF_2$, $SCF_3$, $SCHF_2$, $SO_2CH_3$, $CH_2OCH_2CH_2OCH_3$;
$R^3$ is H, halogen, CN, $NO_2$, $C_1$-$C_4$-alkyl, $C_1$-$C_4$-haloalkyl, $C_1$-$C_4$-alkoxy, $C_1$-$C_4$-alkylthio, $C_1$-$C_4$-alkylsulfonyl, in particular H, F, Cl, Br, CN, $NO_2$, $CH_3$, $CH_2CH_3$, $CF_3$, $CHF_2$, $OCH_3$, $OCF_3$, $OCHF_2$, $SCH_3$, $SO_2CH_3$ or $SO_2CH_2CH_3$;
$R^4$, $R^5$ are H.

Particularly preferably, in the compounds of the formula I.1, the group
$R^1$ is halogen, $C_1$-$C_4$-alkyl, $C_1$-$C_4$-haloalkyl, $C_1$-$C_4$-alkoxy-$C_1$-$C_4$-alkyl, $C_1$-$C_4$-alkoxy-$C_1$-$C_4$-alkoxy-$C_1$-$C_4$-alkyl, $C_1$-$C_4$-alkoxy, $C_1$-$C_4$-haloalkoxy, $C_1$-$C_4$-alkylthio, $C_1$-$C_4$-haloalkylthio or $C_1$-$C_4$-alkylsulfonyl, in particular F, Cl, Br, $NO_2$, $CH_3$, $CF_3$, $OCH_3$, $OCF_3$, $OCHF_2$, $SCF_3$, $SCHF_2$, $SO_2CH_3$, $CH_2OCH_2CH_2OCH_3$;
$R^3$ is H, halogen, CN, $NO_2$, $C_1$-$C_4$-alkyl, $C_1$-$C_4$-haloalkyl, $C_1$-$C_4$-alkoxy, $C_1$-$C_4$-alkylthio, $C_1$-$C_4$-alkylsulfonyl, in particular H, F, Cl, Br, CN, $NO_2$, $CH_3$, $CH_2CH_3$, $CF_3$, $CHF_2$, $OCH_3$, $OCF_3$, $OCHF_2$, $SCH_3$, $SO_2CH_3$ or $SO_2CH_2CH_3$;
$R^4$ is H
$R^5$ is H, F or Cl, in particular H.

In a preferred embodiment of the compounds of the formula I.1, $R^2$ is $Z^1$-heterocyclyl where heterocyclyl is a 5- or 6-membered monocyclic or 9- or 10-membered bicyclic, saturated, partially unsaturated or aromatic heterocycle which contains 1, 2, 3 or 4 heteroatoms selected from the group consisting of O, N and S, cyclic groups being unsubstituted or partially or fully substituted by $R^b$.

$R^2$ is in this case preferably a 3- to 7-membered monocyclic or 9- or 10-membered bicyclic saturated, partially unsaturated or aromatic heterocycle which is attached via $Z^1$ and contains 1, 2, 3 or 4 heteroatoms selected from the group consisting of O, N and S, where the cyclic groups are unsubstituted or partially or fully substituted by groups $R^b$.

In a further preferred aspect of the compounds of the formula I.1, $R^2$ is a 3- to 7-membered monocyclic or 9- or 10-membered bicyclic saturated, partially unsaturated or aromatic heterocycle which is attached directly or via $C_1$-$C_4$-alkyleneoxy, $C_1$-$C_4$-oxyalkylene or $C_1$-$C_4$-alkyleneoxy-$C_1$-$C_4$-alkylene, which contains 1, 2, 3 or 4 heteroatoms selected from the group consisting of O, N and S and which may be substituted as defined at the outset.

A preferred aspect of group $R^2$ relates to five- or six-membered saturated or partially unsaturated heterocycles, such as, for example, isoxazoline, tetrazolone, 1,2-dihydrotetrazolone, 1,4-dihydrotetrazolone, tetrahydrofuran, dioxolane, piperidine, morpholine and piperazine. Particular preference is given to 3-isoxazoline, 5-isoxazoline, 1-tetrazolone, 2-tetrazolone, [1,3]dioxolane-2 and N-morpholine. Especially preferred are: 4,5-dihydroisoxazole-3, unsubstituted or substituted by 5-$CH_3$, 5-$CH_2F$ or 5-$CHF_2$; 4,5-dihydroisoxazole-5, unsubstituted or substituted by 3-$CH_3$, 3-$OCH_3$, 3-$CH_2OCH_3$, 3-$CH_2SCH_3$; 1-methyl-5-oxo-1,5-dihydrotetrazole-2; 4-methyl-5-oxo-4,5-dihydro-tetrazole-1 and N-morpholine.

A further preferred aspect of group $R^2$ relates to five- or six-membered aromatic heterocycles, such as, for example, isoxazole, pyrazole, thiazole, furyl, pyridine, pyrimidine and pyrazine. Particular preference is given to 3-isoxazole, 5-isoxazole, 3-pyrazole, 5-pyrazole, 2-thiazole, 2-oxazole, 2-furyl. Especially preferred are: 3-isoxazole, 5-methyl-3-isoxazole, 5-isoxazole, 3-methyl-5-isoxazole, 1-methyl-1H-pyrazole-3,2-methyl-2H-pyrazole-3 and thiazole-2.

In a preferred aspect of the compounds of the formula I, the groups $R^b$ independently of one another are Z—CN, Z—OH, Z—NO$_2$, Z-halogen, oxo(=O), =N—R$^a$, C$_1$-C$_8$-alkyl, C$_1$-C$_4$-haloalkyl, C$_2$-C$_8$-alkenyl, C$_2$-C$_8$-alkynyl, Z—C$_1$-C$_8$-alkoxy, Z—C$_1$-C$_8$-haloalkoxy, Z—C$_3$-C$_{10}$-cycloalkyl, O—Z—C$_3$-C$_{10}$-cycloalkyl, Z—C(=O)—R$^a$, NR$'$R$''$, Z-(tri-C$_1$-C$_4$-alkyl)silyl, Z-phenyl or S(O)$_n$R$^{bb}$.

In a preferred aspect of heterocyclic groups R$^2$, the groups R$^b$ independently of one another are preferably C$_1$-C$_4$-alkyl, C$_1$-C$_4$-haloalkyl, C$_1$-C$_4$-alkoxy, C$_1$-C$_4$-alkoxy-C$_1$-C$_4$-alkyl, C$_1$-C$_4$-alkylthio-C$_1$-C$_4$-alkyl, C$_1$-C$_4$-alkylthio or C$_1$-C$_4$-alkylsulfonyl. Especially preferred are CH$_3$, C$_2$H$_5$, CH$_2$F, CF$_2$H, CF$_3$, OCH$_3$, CH$_2$OCH$_3$, CH$_2$SCH$_3$, SCH$_3$ and SO$_2$CH$_3$.

The group R$^{bb}$ is preferably C$_1$-C$_8$-alkyl.

In a preferred aspect, the group Z$^1$ is a covalent bond.

In a further preferred aspect, the group Z$^1$ is C$_1$-C$_4$-alkyleneoxy, in particular OCH$_2$ or OCH$_2$CH$_2$.

In a further preferred aspect, the group Z$^1$ is C$_1$-C$_4$-oxyalkylene, in particular CH$_2$O or CH$_2$CH$_2$O.

In a further preferred aspect, the group Z$^1$ is C$_1$-C$_4$-alkyleneoxy-C$_1$-C$_4$-alkylene, in particular OCH$_2$OCH$_2$ or OCH$_2$CH$_2$OCH$_2$.

Particularly preferred aspects of heterocycles attached via Z$^1$ include tetrahydrofuran-2-ylmethoxymethyl and [1,3]dioxolan-2-ylmethoxy.

In a further preferred embodiment of the compounds of the formula I.1, R$^2$ is phenyl which is attached via Z$^1$ or oxygen and is unsubstituted or substituted by C$_1$-C$_4$-alkyl, C$_1$-C$_4$-alkoxy, C$_1$-C$_4$-haloalkyl, C$_1$-C$_4$-alkoxy-C$_1$-C$_4$-alkyl or C$_1$-C$_4$-alkoxy-C$_1$-C$_4$-alkoxy. Particular preference is given in this case to a phenyl group which may be partially or fully substituted—preferably mono-, di- or trisubstituted, in particular monosubstituted—by groups R$^b$. Groups R$^b$ preferred for this aspect include: C$_1$-C$_2$-alkyl, C$_1$-C$_4$-alkoxy, C$_1$-C$_2$-haloalkyl, C$_1$-C$_2$-alkoxy-C$_1$-C$_2$-alkyl or C$_1$-C$_2$-alkoxy-C$_1$-C$_2$-alkoxy. Particular preference is given to CH$_3$, C$_2$H$_5$, OCH$_3$, OC$_2$H$_5$, CHF$_2$, CF$_3$, OCHF$_2$, OCF$_3$, OCH$_2$OCH$_3$ and OCH$_2$CH$_2$OCH$_3$. Special preference is given to alkoxy, such as OCH$_3$ or OC$_2$H$_5$. A group R$^b$ is preferably in position 4. A particularly preferred phenyl group R$^2$ is a group P:

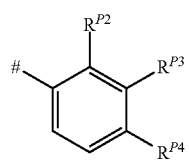

in which # denotes the bond via which the group R$^2$ is attached and the substituents are selected from R$^b$ and are in particular:

R$^{P2}$ H or F;
R$^{P3}$ H, F, Cl or OCH$_3$; and
R$^{P4}$ H, F, Cl, CH$_3$, CF$_3$, OCH$_3$, OCH$_2$OCH$_3$ or OCH$_2$CH$_2$OCH$_3$.

In a further preferred embodiment of the compounds of the formula I.1, R$^2$ is an aliphatic group selected from the group consisting of C$_1$-C$_8$-alkyl, C$_2$-C$_6$-haloalkyl, C$_1$-C$_4$-alkoxy-C$_1$-C$_4$-alkyl, C$_2$-C$_8$-alkenyl, C$_2$-C$_8$-alkynyl, C$_2$-C$_8$-haloalkenyl, C$_2$-C$_8$-haloalkynyl, C$_1$-C$_6$-alkoxy, Z—C$_1$-C$_4$-alkoxy-C$_1$-C$_4$-alkoxy, Z—C$_1$-C$_4$-haloalkoxy-C$_1$-C$_4$-alkoxy, Z—C$_1$-C$_6$-haloalkoxy, C$_2$-C$_8$-alkenyloxy, C$_2$-C$_8$-alkynyloxy, Z—C$_1$-C$_4$-alkylthio, Z—C$_1$-C$_6$-haloalkylthio, Z—C(=O)—R$^a$ or S(O)$_n$R$^{bb}$.

In a particularly preferred aspect of these compounds of the formula I.1, R$^2$ is an aliphatic group selected from the group consisting of C$_1$-C$_6$-alkyl, C$_1$-C$_4$-alkoxy-C$_1$-C$_4$-alkyl, C$_1$-C$_4$-haloalkoxy-C$_1$-C$_4$-alkyl, C$_2$-C$_6$-alkenyl, C$_2$-C$_6$-alkynyl, C$_2$-C$_4$-alkoxy, C$_1$-C$_4$-haloalkoxy, C$_3$-C$_6$-alkenyloxy, C$_3$-C$_6$-alkynyloxy, C$_3$-C$_6$-haloalkenyloxy, C$_3$-C$_6$-haloalkynyloxy, C$_1$-C$_4$-alkoxycarbonyl, S(O)$_2$—C$_1$-C$_4$-alkyl and S(O)$_2$—C$_1$-C$_6$-halo-alkyl.

Particularly preferred aliphatic groups R$^2$ include C$_2$-C$_4$-alkenyl, C$_2$-C$_4$-alkynyl, C$_1$-C$_2$-haloalkoxy-C$_1$-C$_2$-alkyl, C$_3$-C$_4$-alkenyloxy, C$_3$-C$_4$-alkynyloxy, C$_1$-C$_4$-alkylsulfonyl, C$_1$-C$_4$-alkoxy, C$_1$-C$_4$-alkoxycarbonyl and S(O)$_2$—C$_1$-C$_4$-alkyl. Special preference is given to CH=CH$_2$, CH=CHCH$_3$, CH$_2$OCH$_2$CF$_3$, OC$_2$H$_5$, OCH$_2$CH=CH$_2$, OCH$_2$C≡CH, OCH$_2$CH$_2$OCH$_3$, COOCH$_3$, COOC$_2$H$_5$ and SO$_2$CH$_3$, SO$_2$C$_2$H$_5$ and SO$_2$CH(CH$_3$)$_2$.

In a further preferred aspect, R$^2$ together with the group attached to the adjacent carbon atom forms a five- to ten-membered saturated, partially or fully unsaturated mono- or bicyclic ring which, in addition to carbon atoms, may contain 1, 2 or 3 heteroatoms selected from the group consisting of O, N and S and which may be substituted by further groups R$^b$.

In a particularly preferred aspect, R$^2$ together with R$^1$ or R$^3$ forms a five- to ten-membered mono- or bicyclic, saturated or partially unsaturated ring which contains 1, 2, 3 or 4 heteroatoms selected from the group consisting of O, N and S and which may be partially or fully substituted by groups R$^b$. Together with the phenyl group which carries the groups R$^1$ to R$^5$, a nine- to fifteen-membered bi- or tricyclic, optionally heterocyclic, ring system results. Suitable are, for example, the following: 2,3-dihydrobenzo[b]thiophene 1,1-dioxide, thiochroman 1,1-dioxide, 2,3-dihydrobenzo[1,4]dithiin 1,1, 4,4-tetraoxide, 3H-benzothiazol-2-one, quinoline and saccharin.

Preferably, R$^2$ together with R$^1$ or R$^3$ forms a five- or six-membered monocyclic, saturated or partially unsaturated ring.

Preferred bicyclic ring systems comprising the phenyl group attached to the dioxodihydrothiatriazanaphthalene skeleton and R$^1$ and R$^2$ are, for example, groups A to D:

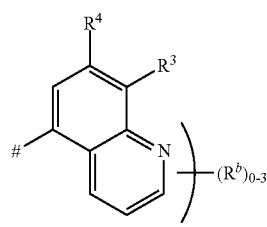

A

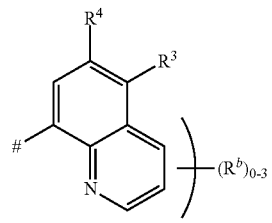

B

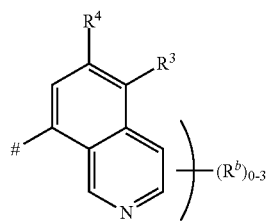
C

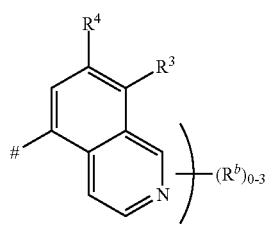
D denotes the bond to the skeleton.

Preferred bi- and tricyclic ring systems comprising the phenyl group attached to the dioxodihydrothiatriazanaphthalene skeleton and $R^2$ and $R^3$ contain one or two sulfur atoms and optionally one nitrogen atom. Preferred are groups E to L:

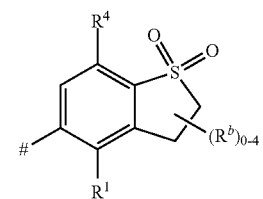
E

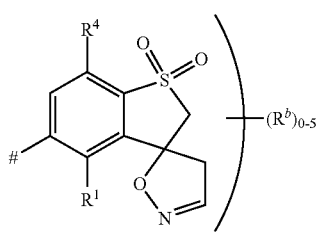
F

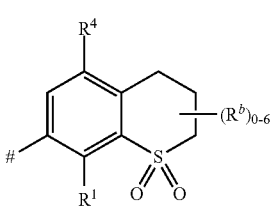
G

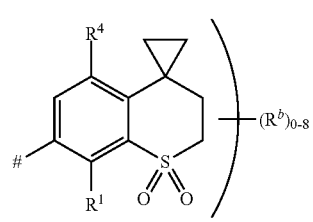
H

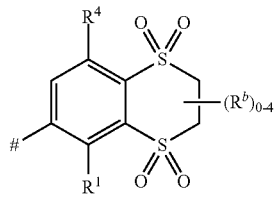
I

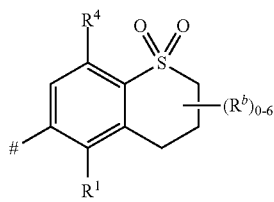
J

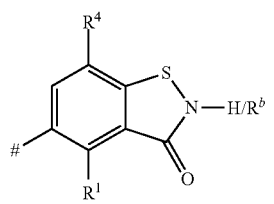
K

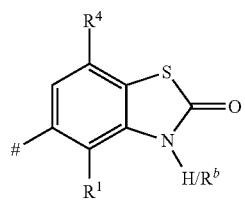
L

In groups A to L, the groups $R^b$ independently of one another are preferably halogen, $C_1$-$C_4$-alkyl, $C_1$-$C_4$-alkoxy, $C_1$-$C_4$-alkoxy-$C_1$-$C_4$-alkyl, $C_1$-$C_4$-alkoxy-$C_1$-$C_4$-alkoxy-$C_1$-$C_4$-alkyl, $C_1$-$C_4$-alkylthio, $C_1$-$C_4$-haloalkyl, $C_1$-$C_4$-haloalkoxy, $C_1$-$C_4$-haloalkylthio, $C_3$-$C_4$-alkenyl, $C_3$-$C_4$-alkynyl, =N—$C_1$-$C_4$-alkoxy.

The compounds of the formula I in which $R^2$ is one of groups A to L correspond to the formulae I.A to I.L.

In the formulae I.A to I.L, $R^b$ is preferably halogen, $C_1$-$C_4$-alkyl, $C_1$-$C_4$-alkoxy or $C_1$-$C_4$-haloalkyl.

The following examples represent particularly preferred groups A to L:

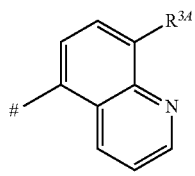
A.1

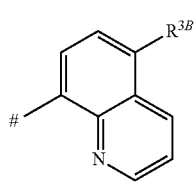
B.1

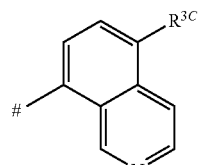
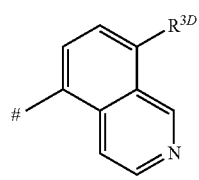
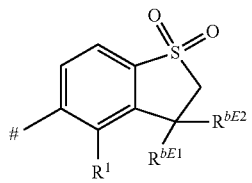
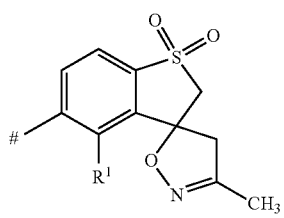
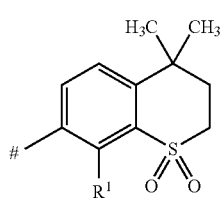
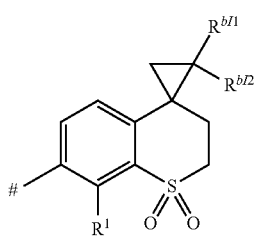
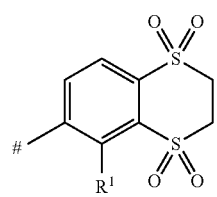
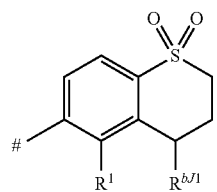

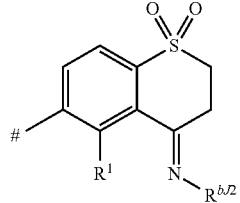
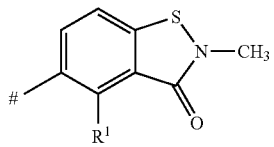
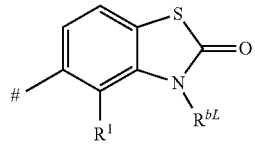

$R^{3A}$, $R^{3B}$, $R^{3C}$ and $R^{3D}$ are preferably halogen, $C_1$-$C_4$-alkyl, $C_1$-$C_4$-haloalkyl, $C_1$-$C_4$-alkoxy, in particular F, Cl, Br, $CH_3$, $CF_3$ or $OCH_3$.

$R^{bE1}$, $R^{bE2}$ are preferably H, $C_1$-$C_4$-alkyl or $C_1$-$C_4$-alkoxy, in particular $R^{bE1}$ is H or $CH_3$; $R^{bE2}$ is H, $CH_3$ or $OCH_3$.

$R^{bJ1}$ is preferably $C_1$-$C_4$-haloalkoxy, in particular $OCH_2CH_2F$.

$R^{bJ2}$ is preferably $C_1$-$C_4$-alkoxy, in particular $OCH_3$ or $OCH_2CH_3$.

$R^{bL}$ is preferably $C_1$-$C_4$-Alkyl or $C_3$-$C_4$-Alkenyl, in particular $CH_3$, $CH_2CH_3$, $CH_2CH_2CH_3$, $CH(CH_3)_2$ or $CH_2CH=CH_2$.

In a further preferred embodiment of the compounds of the formula I, in particular of the formula I.1, $R^3$ is hydrogen, cyano, halogen, nitro, $C_1$-$C_4$-alkyl, $C_1$-$C_4$-haloalkyl, $C_1$-$C_4$-alkoxy, $C_1$-$C_4$-haloalkoxy, $C_2$-$C_4$-alkenyl, $C_2$-$C_4$-alkynyl, $C_2$-$C_4$-alkenyloxy, $C_2$-$C_4$-alkynyloxy or $S(O)_n R^{bb}$.

In a particularly preferred embodiment of the compounds of the formula I, in particular of the formula I.1, $R^3$ is hydrogen, halogen, CN, $NO_2$, $C_1$-$C_4$-alkyl, $C_1$-$C_4$-haloalkyl, $C_1$-$C_4$-alkoxy, $C_1$-$C_4$-haloalkoxy, $S(O)_n$—$C_1$-$C_4$-alkyl and $S(O)_n$—$C_1$-$C_4$-haloalkyl, where n is preferably 0 or 2. Particularly preferably, $R^3$ is selected from the group consisting of H, F, Cl, Br, CN, $NO_2$, $CH_3$, $CF_3$, $CHF_2$, $OCH_3$, $OCF_3$, $OCHF_2$, $SCH_3$, $SCF_3$, $SCHF_2$, $SO_2CH_3$ and $SO_2CH_2CH_3$.

In further preferred aspects of the formula I.1, the groups $R^1$, $R^2$, $R^3$, $R^4$ and $R^5$ together form the following substitution patterns: 2-Br, 2-Cl, 2,4-$Cl_2$, 2-Cl-4-F, 2-Cl-5-F, 2-Cl-6-F, 2-Cl-4-$CF_3$, 2-Cl-5-$CF_3$, 2-Cl-6-$CF_3$, 2-Cl-3,6-$F_2$, 2-F, 2,4-$F_2$, 2,5-$F_2$, 2,6-$F_2$, 2-F-4-$CF_3$, 2-F-5-$CF_3$, 2-F-6-$CF_3$, 2,3,6-$F_3$, 2-$NO_2$, 2-$NO_2$-4-F, 2-$NO_2$-5-F, 2-$NO_2$-6-F, 2-$NO_2$-4-$CF_3$, 2-$NO_2$-5-$CF_3$, 2-$NO_2$-6-$CF_3$, 2-$NO_2$-3,6-$F_2$, 2-CN, 2-$CH_3$, 2-$CH_3$-4-F, 2-$CH_3$-5-F, 2-$CH_3$-6-F, 2-$CH_3$-4-$CF_3$, 2-$CH_3$-5-$CF_3$, 2-$CH_3$-6-$CF_3$, 2-$CH_3$-3,6-$F_2$, 2-$OCH_3$, 2-$OCH_3$-4-F, 2-$OCH_3$-5-F, 2-$OCH_3$-6-F, 2-$OCH_3$-4-$CF_3$, 2-$OCH_3$-5-$CF_3$, 2-$OCH_3$-6-$CF_3$, 2-$OCH_3$-3,6-$F_2$, 2-$CHF_2$, 2-$CHF_2$-4-F, 2-$CHF_2$-5-F, 2-$CHF_2$-6-F, 2-$CHF_2$-4-$CF_3$, 2-$CHF_2$-5-$CF_3$, 2-$CHF_2$-6-$CF_3$, 2-$CHF_2$-3,6-$F_2$, 2-$CF_3$, 2-$CF_3$-4-F, 2-$CF_3$-5-F, 2-$CF_3$-6-F, 2-$CF_3$-4-$CF_3$, 2-$CF_3$-5-$CF_3$, 2-$CF_3$-6-$CF_3$, 2-$CF_3$-3,6-$F_2$, 2-$OCHF_2$, 2-$OCHF_2$-4-F, 2-$OCHF_2$-5-F, 2-$OCHF_2$-6-F, 2-$OCHF_2$-4-$CF_3$, 2-$OCHF_2$-5-$CF_3$, 2-$OCHF_2$-6-$CF_3$, 2-$OCHF_2$-3,6-$F_2$, 2-$OCF_3$, 2-$OCF_3$-4-F, 2-$OCF_3$-5-F, 2-$OCF_3$-6-F, 2-$OCF_3$-4-$CF_3$, 2-$OCF_3$-5-$CF_3$, 2-$OCF_3$-6-$CF_3$, 2-$OCF_3$-3,6-$F_2$, 2-Cl-3-Br-6-F, 2-Cl-5-

$CF_3$, 2,5,6-$Cl_3$, 2-$CF_3$-5-Cl, 2,6-$Cl_2$, 2-Br-4-F, 2,4,6-$Cl_3$, 2-Br-4-F-6-Cl, 2-Br-4,6-$Cl_2$, 2-Br-4,6-$F_2$, 2,4-$Cl_2$-6-F, 2-$CF_3$-4,6-$Cl_2$, 2-$CF_3$-4-F-6-Cl, 2-$CF_3$-4,6-$F_2$, 2,6-$Cl_2$, 2-Br-4-F, 2,4,6-$Cl_3$, 2-Br-4-F-6-Cl, 2-Br-4,6-$Cl_2$, 2-Br-4,6-$F_2$, 2,4-$Cl_2$-6-F, 2-$CF_3$-4,6-$Cl_2$, 2-$CF_3$-4-F-6-Cl, 2-$CF_3$-4,6-$F_2$, 2-Cl-4-$SO_2CH_3$ or 2-$CF_3$-4-$SO_2CH_3$

In further preferred aspects of the formula I.1, the groups $R^1$, $R^2$, $R^3$, $R^4$ and $R^5$ together form the following substitution patterns: 2-Br, 2-Cl, 2,4-$Cl_2$, 2-Cl-4-F, 2-Cl-5-F, 2-Cl-6-F, 2-Cl-4-$CF_3$, 2-Cl-5-$CF_3$, 2-Cl-6-$CF_3$, 2-Cl-3,6-$F_2$, 2-F, 2,4-$F_2$, 2,5-$F_2$, 2,6-$F_2$, 2-F-4-$CF_3$, 2-F-5-$CF_3$, 2-F-6-$CF_3$, 2,3,6-$F_3$, 2-$NO_2$, 2-$NO_2$-4-F, 2-$NO_2$-5-F, 2-$NO_2$-6-F, 2-$NO_2$-4-$CF_3$, 2-$NO_2$-5-$CF_3$, 2-$NO_2$-6-$CF_3$, 2-$NO_2$-3,6-$F_2$, 2-CN, 2-$CH_3$, 2-$CH_3$-4-F, 2-$CH_3$-5-F, 2-$CH_3$-6-F, 2-$CH_3$-4-$CF_3$, 2-$CH_3$-5-$CF_3$, 2-$CH_3$-6-$CF_3$, 2-$CH_3$-3,6-$F_2$, 2-$OCH_3$, 2-$OCH_3$-4-F, 2-$OCH_3$-5-F, 2-$OCH_3$-6-F, 2-$OCH_3$-4-$CF_3$, 2-$OCH_3$-5-$CF_3$, 2-$OCH_3$-6-$CF_3$, 2-$OCH_3$-3,6-$F_2$, 2-$CHF_2$, 2-$CHF_2$-4-F, 2-$CHF_2$-5-F, 2-$CHF_2$-6-F, 2-$CHF_2$-4-$CF_3$, 2-$CHF_2$-5-$CF_3$, 2-$CHF_2$-6-$CF_3$, 2-$CHF_2$-3,6-$F_2$, 2-$CF_3$, 2-$CF_3$-4-F, 2-$CF_3$-5-F, 2-$CF_3$-6-F, 2-$CF_3$-4-$CF_3$, 2-$CF_3$-5-$CF_3$, 2-$CF_3$-6-$CF_3$, 2-$CF_3$-3,6-$F_2$, 2-$OCHF_2$, 2-$OCHF_2$-4-F, 2-$OCHF_2$-5-F, 2-$OCHF_2$-6-F, 2-$OCHF_2$-4-$CF_3$, 2-$OCHF_2$-5-$CF_3$, 2-$OCHF_2$-6-$CF_3$, 2-$OCHF_2$-3,6-$F_2$, 2-$OCF_3$, 2-$OCF_3$-4-F, 2-$OCF_3$-5-F, 2-$OCF_3$-6-F, 2-$OCF_3$-4-$CF_3$, 2-$OCF_3$-5-$CF_3$, 2-$OCF_3$-6-$CF_3$, 2-$OCF_3$-3,6-$F_2$, 2-Cl-3-Br-6-F, 2-Cl-5-$CF_3$, 2,5,6-$Cl_3$, 2-$CF_3$-5-Cl, 2,6-$Cl_2$, 2-Br-4-F, 2,4,6-$Cl_3$, 2-Br-4-F-6-Cl, 2-Br-4,6-$Cl_2$, 2-Br-4,6-$F_2$, 2,4-$Cl_2$-6-F, 2-$CF_3$-4,6-$Cl_2$, 2-$CF_3$-4-F-6-Cl, 2-$CF_3$-4,6-$F_2$, 2,6-$Cl_2$, 2-Br-4-F, 2,4,6-$Cl_3$, 2-Br-4-F-6-Cl, 2-Br-4,6-$Cl_2$, 2-Br-4,6-$F_2$, 2,4-$Cl_2$-6-F, 2-$CF_3$-4,6-$Cl_2$, 2-$CF_3$-4-F-6-Cl or 2-$CF_3$-4,6-$F_2$.

In further preferred aspects of the formula I.1, the groups $R^1$, $R^2$, $R^3$, $R^4$ and $R^5$ together form the following substitution patterns: 2-Br, 2-Cl, 2,4-$Cl_2$, 2-Cl-4-F, 2-Cl-5-F, 2-Cl-6-F, 2-Cl-4-$CF_3$, 2-Cl-5-$CF_3$, 2-Cl-6-$CF_3$, 2-Cl-3,6-$F_2$, 2-F, 2,4-$F_2$, 2,5-$F_2$, 2,6-$F_2$, 2-F-4-$CF_3$, 2-F-5-$CF_3$, 2-F-6-$CF_3$, 2,3,6-$F_3$, 2-$NO_2$, 2-$NO_2$-4-F, 2-$NO_2$-5-F, 2-$NO_2$-6-F, 2-$NO_2$-4-$CF_3$, 2-$NO_2$-5-$CF_3$, 2-$NO_2$-6-$CF_3$, 2-$NO_2$-3,6-$F_2$, 2-CN, 2-$CH_3$, 2-$CH_3$-4-F, 2-$CH_3$-5-F, 2-$CH_3$-6-F, 2-$CH_3$-4-$CF_3$, 2-$CH_3$-5-$CF_3$, 2-$CH_3$-6-$CF_3$, 2-$CH_3$-3,6-$F_2$, 2-$OCH_3$, 2-$OCH_3$-4-F, 2-$OCH_3$-5-F, 2-$OCH_3$-6-F, 2-$OCH_3$-4-$CF_3$, 2-$OCH_3$-5-$CF_3$, 2-$OCH_3$-6-$CF_3$, 2-$OCH_3$-3,6-$F_2$, 2-$CHF_2$, 2-$CHF_2$-4-F, 2-$CHF_2$-5-F, 2-$CHF_2$-6-F, 2-$CHF_2$-4-$CF_3$, 2-$CHF_2$-5-$CF_3$, 2-$CHF_2$-6-$CF_3$, 2-$CHF_2$-3,6-$F_2$, 2-$CF_3$, 2-$CF_3$-4-F, 2-$CF_3$-5-F, 2-$CF_3$-6-F, 2-$CF_3$-4-$CF_3$, 2-$CF_3$-5-$CF_3$, 2-$CF_3$-6-$CF_3$, 2-$CF_3$-3,6-$F_2$, 2-$OCHF_2$, 2-$OCHF_2$-4-F, 2-$OCHF_2$-5-F, 2-$OCHF_2$-6-F, 2-$OCHF_2$-4-$CF_3$, 2-$OCHF_2$-5-$CF_3$, 2-$OCHF_2$-6-$CF_3$, 2-$OCHF_2$-3,6-$F_2$, 2-$OCF_3$, 2-$OCF_3$-4-F, 2-$OCF_3$-5-F, 2-$OCF_3$-6-F, 2-$OCF_3$-4-$CF_3$, 2-$OCF_3$-5-$CF_3$, 2-$OCF_3$-6-$CF_3$, 2-$OCF_3$-3,6-$F_2$, 2-Cl-3-Br-6-F, 2-Cl-5-$CF_3$, 2,5,6-$Cl_3$, 2,6-$Cl_2$, 2-$CF_3$-4,6-$Cl_2$, 2,4,5-$Cl_3$, 2,4,6-$Cl_3$ or 2-$CF_3$-5-Cl.

In a further preferred embodiment of the compounds of the formula I, A is N. These compounds correspond to formula I.2,

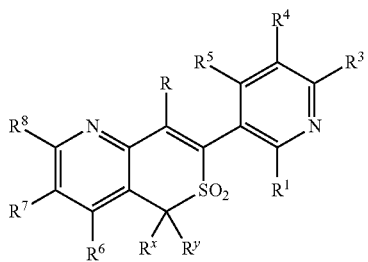

I.2 in which the variables have the meanings defined at the outset and preferably those mentioned above. In one embodiment, $R^1$ and $R^3$ are not halogen. Especially preferably, in compounds of the formula I.2 the group $R^1$ is nitro, $C_1$-$C_4$-alkyl, $C_1$-$C_4$-haloalkyl, $C_1$-$C_4$-alkoxy-$C_1$-$C_4$-alkyl, $C_1$-$C_4$-alkoxy-$C_1$-$C_4$-alkoxy-$C_1$-$C_4$-alkyl, $C_1$-$C_4$-alkoxy, $C_1$-$C_4$-haloalkoxy, $C_1$-$C_4$-alkylthio, $C_1$-$C_4$-haloalkylthio or $C_1$-$C_4$-alkylsulfonyl, in particular $NO_2$, $CH_3$, $CF_3$, $CH_2OCH_2CH_2OCH_3$, $OCH_3$, $OCF_3$, $OCHF_2$, $SCF_3$, $SCHF_2$, $SO_2CH_3$;

$R^3$ is H, CN, $NO_2$, $C_1$-$C_4$-alkyl, $C_1$-$C_4$-haloalkyl, $C_1$-$C_4$-alkoxy, $C_1$-$C_4$-alkylthio, $C_1$-$C_4$-alkylsulfonyl, in particular H, CN, $NO_2$, $CH_3$, $CH_2CH_3$, $CF_3$, $CHF_2$, $OCH_3$, $OCF_3$, $OCHF_2$, $SCH_3$, $SO_2CH_3$ or $SO_2CH_2CH_3$;

$R^4$, $R^5$ are H.

In a further preferred embodiment of the compounds of the formula I, $R^4$ is hydrogen, halogen or $C_1$-$C_4$-haloalkyl, in particular H.

In a further preferred embodiment of the compounds of the formula I, $R^5$ is hydrogen or halogen, particularly preferably H, F or Cl, in particular H.

In a further preferred embodiment of the compounds of the formula I, one of the groups $R^4$ and $R^5$ is halogen, such as Cl or F.

In a further preferred embodiment of the compounds of the formula I, $R^6$ is hydrogen, $C_1$-$C_4$-alkyl, $C_1$-$C_4$-haloalkyl, $C_1$-$C_4$-alkoxy, $C_1$-$C_4$-alkylthio, $C_1$-$C_4$-haloalkoxy or $C_1$-$C_4$-haloalkylthio, particularly preferably H, $CH_3$, $CF_3$, $CHF_2$, $OCH_3$, $OCF_3$, $OCHF_2$, $SCH_3$, $SCF_3$, $SCHF_2$, in particular H.

In further preferred embodiments:

$R^7$ is H, OH, CN, halogen, alkyl, alkoxy, haloalkyl, in particular H; and $R^8$ is H, OH, CN, halogen, alkyl, alkoxy, haloalkyl, in particular H.

In a further preferred embodiment of the compounds of the formula I, at least one of the groups $R^7$ and $R^8$, preferably both groups, is/are hydrogen.

$R^x$ and $R^y$, independently of one another, are preferably H, $C_1$-$C_5$-alkyl, such as $CH_3$, $C_2H_5$, n-$C_3H_7$, $CH(CH_3)_2$, n-$C_3H_9$, or $C(CH_3)_3$; $C_3$-$C_5$-alkenyl, $C_3$-$C_5$-alkynyl, such as $CH_2CH=CH_2$, $CH_2C(CH_3)=CH_2$, $CH_2CH_2H=CH_2$, $CH_2CH_2C(CH_3)=CH_2$, $CH_2CH_2CH=CH_2$, $CH_2C=CH$, or $C_1$-$C_8$-haloalkyl, such as $CH_2CF_3$, $CH_2CHF_2$. Particularly preferably, $R^x$ and $R^y$ are, independently of one another, H, $C_1$-$C_4$-alkyl or $C_1$-$C_4$-haloalkyl.

In a further preferred embodiment of the compounds of the formula I, $R^6$, $R^7$ and $R^8$ are all hydrogen. These compounds correspond to formula I.A

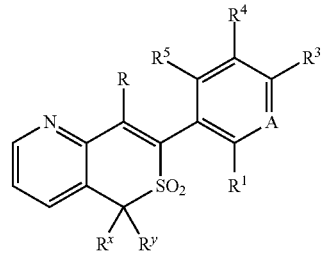

I.A in which the variables have the meanings defined at the outset and preferably those mentioned above. Especially preferably, in compounds of the formula I.A the group R is O—$R^A$ wherein $R^A$ is hydrogen or $C_1$-$C_6$-alkylcarbonyl, in particular hydrogen $C(O)CH_3$, $C(O)CH_2CH_3$, $C(O)CH(CH_3)_2$, $C(O)C(CH_3)_3$ or $C(O)OCH_2CH_3$ $R^1$ is halogen, $C_1$-$C_4$-haloalkyl or —$SO_2$—$C_1$-$C_4$-alkyl, in particular halogen or $C_1$-$C_4$-haloalkyl;

A is N or C—$R^2$;

$R^2$ is hydrogen or halogen;

$R^3$ is hydrogen, halogen or cyano, in particular halogen or cyano $R^4$ is hydrogen or halogen, in particular hydrogen;

$R^5$ is hydrogen or halogen, in particular hydrogen;

$R^x$ is hydrogen, $C_1$-$C_4$-alkyl or $C_1$-$C_4$-haloalkyl, preferably hydrogen or $C_1$-$C_4$-alkyl and in particular $C_1$-$C_4$-alkyl; and $R^y$ is hydrogen, $C_1$-$C_4$-alkyl or $C_1$-$C_4$-haloalkyl, preferably hydrogen or $C_1$-$C_4$-alkyl and in particular $C_1$-$C_4$-alkyl.

A further embodiment relates to the N-oxides of the compounds of the formula I. A further embodiment relates to salts of the compounds of the formula I, in particular those which are obtainable by quaternization of a pyridazine nitrogen atom, which may preferably take place by alkylation or arylation of the compounds of the formula I. Preferred salts of the compounds are thus the N-alkyl salts, in particular the N-methyl salts, and the N-phenyl salts.

In particular with a view to their use, preference is given to the compounds of the formula I compiled in the tables below, which compounds correspond to the formulae I.1A and I.2A. The groups mentioned for a substituent in the tables are furthermore per se, independently of the combination in which they are mentioned, a particularly preferred aspect of the substituent in question.

Table 1
Compounds of the formula I, in which $R^x$ is H, $R^y$ is H, R is OH and the combination of $R^1$ to $R^5$ for a compound corresponds in each case to one row of table A Table 2
Compounds of the formula I, in which $R^x$ is H, $R^y$ is H, R is $OC(O)C(CH_3)_3$ and the combination of $R^1$ to $R^5$ for a compound corresponds in each case to one row of table A Table 3
Compounds of the formula I, in which $R^x$ is H, $R^y$ is H, R is $OC(O)CH(CH_3)_2$ and the combination of $R^1$ to $R^5$ for a compound corresponds in each case to one row of table A Table 4
Compounds of the formula I, in which $R^x$ is H, $R^y$ is $CH_3$, R is OH and the combination of $R^1$ to $R^5$ for a compound corresponds in each case to one row of table A Table 5
Compounds of the formula I, in which $R^x$ is H, $R^y$ is $CH_3$, R is $OC(O)C(CH_3)_3$ and the combination of $R^1$ to $R^5$ for a compound corresponds in each case to one row of table A Table 6
Compounds of the formula I, in which $R^x$ is H, $R^y$ is $CH_3$, R is $OC(O)CH(CH_3)_2$ and the combination of $R^1$ to $R^5$ for a compound corresponds in each case to one row of table A Table 7
Compounds of the formula I, in which $R^x$ is $CH_3$, $R^y$ is H, R is OH and the combination of $R^1$ to $R^5$ for a compound corresponds in each case to one row of table A Table 8
Compounds of the formula I, in which $R^x$ is $CH_3$, $R^y$ is H, R is $OC(O)C(CH_3)_3$ and the combination of $R^1$ to $R^5$ for a compound corresponds in each case to one row of table A Table 9
Compounds of the formula I, in which $R^x$ is $CH_3$, $R^y$ is H, R is $OC(O)CH(CH_3)_2$ and the combination of $R^1$ to $R^5$ for a compound corresponds in each case to one row of table A Table 10
Compounds of the formula I, in which $R^x$ is $CH_3$, $R^y$ is $CH_3$, R is OH and the combination of $R^1$ to $R^5$ for a compound corresponds in each case to one row of table A Table 11
Compounds of the formula I, in which $R^x$ is $CH_3$, $R^y$ is $CH_3$, R is $OC(O)C(CH_3)_3$ and the combination of $R^1$ to $R^5$ for a compound corresponds in each case to one row of table A Table 12
Compounds of the formula I, in which $R^x$ is $CH_3$, $R^y$ is $CH_3$, R is $OC(O)CH(CH_3)_2$ and the combination of $R^1$ to $R^5$ for a compound corresponds in each case to one row of table A Table 13
Compounds of the formula I, in which $R^x$ is $C_2H_5$, $R^y$ is H, R is OH and the combination of $R^1$ to $R^5$ for a compound corresponds in each case to one row of table A Table 14
Compounds of the formula I, in which $R^x$ is $C_2H_5$, $R^y$ is H, R is $OC(O)C(CH_3)_3$ and the combination of $R^1$ to $R^5$ for a compound corresponds in each case to one row of table A Table 15
Compounds of the formula I, in which $R^x$ is $C_2H_5$, $R^y$ is H, R is $OC(O)CH(CH_3)_2$ and the combination of $R^1$ to $R^5$ for a compound corresponds in each case to one row of table A Table 16
Compounds of the formula I, in which $R^x$ is $C_2H_5$, $R^y$ is $CH_3$, R is OH and the combination of $R^1$ to $R^5$ for a compound corresponds in each case to one row of table A Table 17
Compounds of the formula I, in which $R^x$ is $C_2H_5$, $R^y$ is $CH_3$, R is $OC(O)C(CH_3)_3$ and the combination of $R^1$ to $R^5$ for a compound corresponds in each case to one row of table A Table 18
Compounds of the formula I, in which $R^x$ is $C_2H_5$, $R^y$ is $CH_3$, R is $OC(O)CH(CH_3)_2$ and the combination of $R^1$ to $R^5$ for a compound corresponds in each case to one row of table A Table 19
Compounds of the formula I, in which $R^x$ is $CH_2CHF_2$, $R^y$ is H, R is OH and the combination of $R^1$ to $R^5$ for a compound corresponds in each case to one row of table A Table 20
Compounds of the formula I, in which $R^x$ is $CH_2CHF_2$, $R^y$ is H, R is $OC(O)C(CH_3)_3$ and the combination of $R^1$ to $R^5$ for a compound corresponds in each case to one row of table A Table 21
Compounds of the formula I, in which $R^x$ is $CH_2CHF_2$, $R^y$ is H, R is $OC(O)CH(CH_3)_2$ and the combination of $R^1$ to $R^5$ for a compound corresponds in each case to one row of table A Table 22
Compounds of the formula I, in which $R^x$ is $CH_2CHF_2$, $R^y$ is $CH_3$, R is OH and the combination of $R^1$ to $R^5$ for a compound corresponds in each case to one row of table A Table 23
Compounds of the formula I, in which $R^x$ is $CH_2CHF_2$, $R^y$ is $CH_3$, R is $OC(O)C(CH_3)_3$ and the combination of $R^1$ to $R^5$ for a compound corresponds in each case to one row of table A Table 24
Compounds of the formula I, in which $R^x$ is $CH_2CHF_2$, $R^y$ is $CH_3$, R is $OC(O)CH(CH_3)_2$ and the combination of $R^1$ to $R^5$ for a compound corresponds in each case to one row of table A Table 25
Compounds of the formula I, in which $R^x$ is $CH_2CF_3$, $R^y$ is H, R is OH and the combination of $R^1$ to $R^5$ for a compound corresponds in each case to one row of table A Table 26

Compounds of the formula I, in which $R^x$ is $CH_2CF_3$, $R^y$ is H, R is $OC(O)C(CH_3)_3$ and the combination of $R^1$ to $R^5$ for a compound corresponds in each case to one row of table A Table 27

Compounds of the formula I, in which $R^x$ is $CH_2CF_3$, $R^y$ is H, R is $OC(O)CH(CH_3)_2$ and the combination of $R^1$ to $R^5$ for a compound corresponds in each case to one row of table A Table 28

Compounds of the formula I, in which $R^x$ is $CH_2CF_3$, $R^y$ is $CH_3$, R is OH and the combination of $R^1$ to $R^5$ for a compound corresponds in each case to one row of table A Table 29

Compounds of the formula I, in which $R^x$ is $CH_2CF_3$, $R^y$ is $CH_3$, R is $OC(O)C(CH_3)_3$ and the combination of $R^1$ to $R^5$ for a compound corresponds in each case to one row of table A Table 30

Compounds of the formula I, in which $R^x$ is $CH_2CF_3$, $R^y$ is $CH_3$, R is $OC(O)CH(CH_3)_2$ and the combination of $R^1$ to $R^5$ for a compound corresponds in each case to one row of table A

TABLE A

Compounds of the formula I which correspond to the formulae I.1A and I.2A

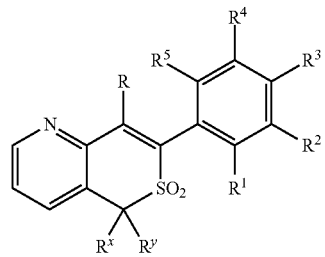

I.1A

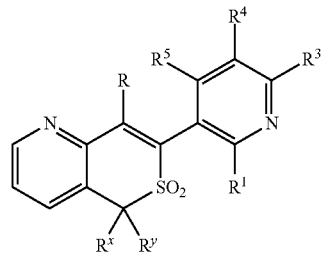

I.2A

| No. | Formula | $R^1$ | $R^2$ | $R^3$ | $R^4$ | $R^5$ |
|---|---|---|---|---|---|---|
| A-1 | I.1A | Cl | H | H | H | H |
| A-2 | I.1A | Br | H | H | H | H |
| A-3 | I.1A | $CH_3$ | H | H | H | H |
| A-4 | I.1A | $CF_3$ | H | H | H | H |
| A-5 | I.1A | $OCF_3$ | H | H | H | H |
| A-6 | I.1A | $SCF_3$ | H | H | H | H |
| A-7 | I.1A | Cl | Cl | H | H | H |
| A-8 | I.1A | Br | Cl | H | H | H |
| A-9 | I.1A | $CH_3$ | Cl | H | H | H |
| A-10 | I.1A | $CF_3$ | Cl | H | H | H |
| A-11 | I.1A | $OCF_3$ | Cl | H | H | H |
| A-12 | I.1A | $SCF_3$ | Cl | H | H | H |
| A-13 | I.1A | Cl | F | H | H | H |
| A-14 | I.1A | Br | F | H | H | H |
| A-15 | I.1A | $CH_3$ | F | H | H | H |
| A-16 | I.1A | $CF_3$ | F | H | H | H |
| A-17 | I.1A | $OCF_3$ | F | H | H | H |
| A-18 | I.1A | $SCF_3$ | F | H | H | H |
| A-19 | I.1A | Cl | H | Cl | H | H |
| A-20 | I.1A | Br | H | Cl | H | H |
| A-21 | I.1A | $CH_3$ | H | Cl | H | H |
| A-22 | I.1A | $CF_3$ | H | Cl | H | H |
| A-23 | I.1A | $OCF_3$ | H | Cl | H | H |
| A-24 | I.1A | $SCF_3$ | H | Cl | H | H |
| A-25 | I.1A | Cl | H | F | H | H |
| A-26 | I.1A | Br | H | F | H | H |
| A-27 | I.1A | $CH_3$ | H | F | H | H |
| A-28 | I.1A | $CF_3$ | H | F | H | H |
| A-29 | I.1A | $OCF_3$ | H | F | H | H |
| A-30 | I.1A | $SCF_3$ | H | F | H | H |
| A-31 | I.1A | Cl | H | $CF_3$ | H | H |
| A-32 | I.1A | Br | H | $CF_3$ | H | H |

TABLE A-continued

Compounds of the formula I which correspond to the formulae I.1A and I.2A

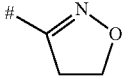

| No. | Formula | R¹ | R² | R³ | R⁴ | R⁵ |
|---|---|---|---|---|---|---|
| A-33 | I.1A | Cl | H | CF₃ | H | H |
| A-34 | I.1A | CF₃ | H | CF₃ | H | H |
| A-35 | I.1A | OCF₃ | H | CF₃ | H | H |
| A-36 | I.1A | SCF₃ | H | CF₃ | H | H |
| A-37 | I.1A | Cl | H | H | Cl | H |
| A-38 | I.1A | Br | H | H | Cl | H |
| A-39 | I.1A | CH₃ | H | H | Cl | H |
| A-40 | I.1A | CF₃ | H | H | Cl | H |
| A-41 | I.1A | OCF₃ | H | H | Cl | H |
| A-42 | I.1A | SCF₃ | H | H | Cl | H |
| A-43 | I.1A | Cl | H | H | F | H |
| A-44 | I.1A | Br | H | H | F | H |
| A-45 | I.1A | CH₃ | H | H | F | H |
| A-46 | I.1A | CF₃ | H | H | F | H |
| A-47 | I.1A | OCF₃ | H | H | F | H |
| A-48 | I.1A | SCF₃ | H | H | F | H |
| A-49 | I.1A | Cl | H | H | CF₃ | H |
| A-50 | I.1A | Br | H | H | CF₃ | H |
| A-51 | I.1A | CH₃ | H | H | CF₃ | H |
| A-52 | I.1A | CF₃ | H | H | CF₃ | H |
| A-53 | I.1A | OCF₃ | H | H | CF₃ | H |
| A-54 | I.1A | SCF₃ | H | H | CF₃ | H |
| A-55 | I.1A | Cl | H | H | H | Cl |
| A-56 | I.1A | Br | H | H | H | Cl |
| A-57 | I.1A | CH₃ | H | H | H | Cl |
| A-58 | I.1A | CF₃ | H | H | H | Cl |
| A-59 | I.1A | OCF₃ | H | H | H | Cl |
| A-60 | I.1A | SCF₃ | H | H | H | Cl |
| A-61 | I.1A | Cl | H | H | H | F |
| A-62 | I.1A | Br | H | H | H | F |
| A-63 | I.1A | CH₃ | H | H | H | F |
| A-64 | I.1A | CF₃ | H | H | H | F |
| A-65 | I.1A | OCF₃ | H | H | H | F |
| A-66 | I.1A | SCF₃ | H | H | H | F |
| A-67 | I.1A | Cl | F | H | H | F |
| A-68 | I.1A | Br | F | H | H | F |
| A-69 | I.1A | CH₃ | F | H | H | F |
| A-70 | I.1A | CF₃ | F | H | H | F |
| A-71 | I.1A | OCF₃ | F | H | H | F |
| A-72 | I.1A | SCF₃ | F | H | H | F |
| A-73 | I.1A | Cl | ![isoxazoline] | H | H | H |

TABLE A-continued
Compounds of the formula I which correspond to the formulae I.1A and I.2A
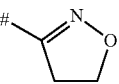
I.1A
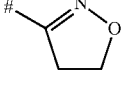
I.2A
| No. | Formula | R¹ | R² | R³ | R⁴ | R⁵ |
|---|---|---|---|---|---|---|
| A-74 | I.1A | Cl | 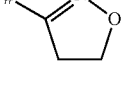 | Cl | H | H |
| A-75 | I.1A | Cl | 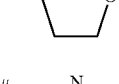 | $CF_3$ | H | H |
| A-76 | I.1A | Cl | 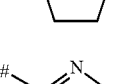 | $CHF_2$ | H | H |
| A-77 | I.1A | Cl | 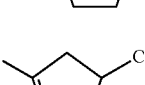 | F | H | H |
| A-78 | I.1A | Cl | 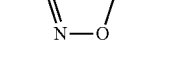 | $OCHF_2$ | H | H |
| A-79 | I.1A | Cl | 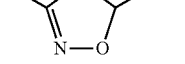 | $SO_2CH_3$ | H | H |
| A-80 | I.1A | Cl | 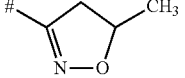 | H | H | H |
| A-81 | I.1A | Cl | | Cl | H | H |
| A-82 | I.1A | Cl | | $CF_3$ | H | H |

TABLE A-continued
Compounds of the formula I which correspond to the formulae I.1A and I.2A
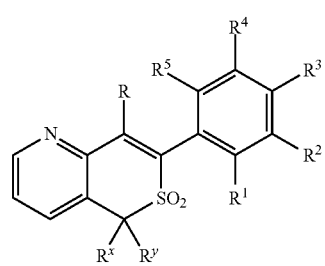
I.1A
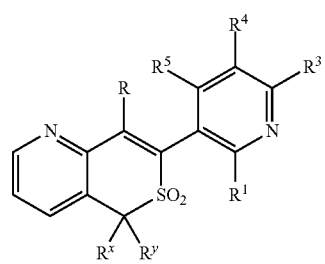
I.2A
| No. | Formula | R¹ | R² | R³ | R⁴ | R⁵ |
|---|---|---|---|---|---|---|
| A-83 | I.1A | Cl | # isoxazoline-CH₃ | CHF₂ | H | H |
| A-84 | I.1A | Cl | # isoxazoline-CH₃ | F | H | H |
| A-85 | I.1A | Cl | # isoxazoline-CH₃ | OCHF₂ | H | H |
| A-86 | I.1A | Cl | # isoxazoline-CH₃ | SO₂CH₃ | H | H |
| A-87 | I.1A | Cl | # isoxazole | H | H | H |
| A-88 | I.1A | Cl | # isoxazole | Cl | H | H |
| A-89 | I.1A | Cl | # isoxazole | CF₃ | H | H |
| A-90 | I.1A | Cl | # isoxazole | CHF₂ | H | H |

TABLE A-continued

Compounds of the formula I which correspond to the formulae I.1A and I.2A

I.1A

I.2A

| No. | Formula | R¹ | R² | R³ | R⁴ | R⁵ |
|---|---|---|---|---|---|---|
| A-91 | I.1A | Cl | 3-isoxazolyl | F | H | H |
| A-92 | I.1A | Cl | 3-isoxazolyl | OCHF$_2$ | H | H |
| A-93 | I.1A | Cl | 3-isoxazolyl | SO$_2$CH$_3$ | H | H |
| A-94 | I.1A | Cl | 5-methyl-3-isoxazolyl | H | H | H |
| A-95 | I.1A | Cl | 5-methyl-3-isoxazolyl | Cl | H | H |
| A-96 | I.1A | Cl | 5-methyl-3-isoxazolyl | CF$_3$ | H | H |
| A-97 | I.1A | Cl | 5-methyl-3-isoxazolyl | CHF$_2$ | H | H |
| A-98 | I.1A | Cl | 5-methyl-3-isoxazolyl | F | H | H |

TABLE A-continued
Compounds of the formula I which correspond to the formulae I.1A and I.2A
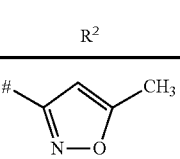
I.1A
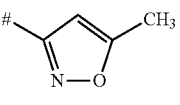
I.2A
| No. | Formula | R¹ | R² | R³ | R⁴ | R⁵ |
|---|---|---|---|---|---|---|
| A-99 | I.1A | Cl | 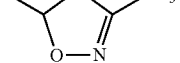 | OCHF$_2$ | H | H |
| A-100 | I.1A | Cl | 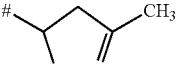 | SO$_2$CH$_3$ | H | H |
| A-101 | I.1A | Cl | 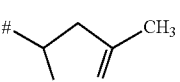 | H | H | H |
| A-102 | I.1A | Cl | 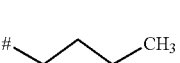 | Cl | H | H |
| A-103 | I.1A | Cl | 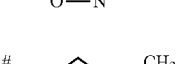 | CF$_3$ | H | H |
| A-104 | I.1A | Cl | 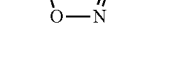 | CHF$_2$ | H | H |
| A-105 | I.1A | Cl |  | F | H | H |
| A-106 | I.1A | Cl |  | OCHF$_2$ | H | H |

TABLE A-continued
Compounds of the formula I which correspond to the formulae I.1A and I.2A
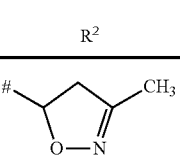
I.1A
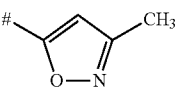
I.2A
| No. | Formula | R¹ | R² | R³ | R⁴ | R⁵ |
|---|---|---|---|---|---|---|
| A-107 | I.1A | Cl | 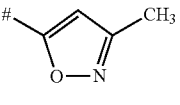 | SO₂CH₃ | H | H |
| A-108 | I.1A | Cl | 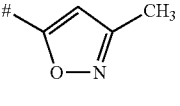 | H | H | H |
| A-109 | I.1A | Cl | 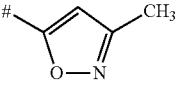 | Cl | H | H |
| A-110 | I.1A | Cl | 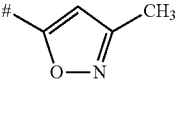 | CF₃ | H | H |
| A-111 | I.1A | Cl | 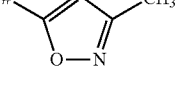 | CHF₂ | H | H |
| A-112 | I.1A | Cl | 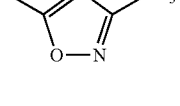 | F | H | H |
| A-113 | I.1A | Cl |  | OCHF₂ | H | H |
| A-114 | I.1A | Cl |  | SO₂CH₃ | H | H |

TABLE A-continued
Compounds of the formula I which correspond to the formulae I.1A and I.2A
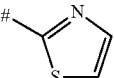
I.1A
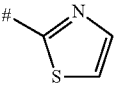
I.2A
| No. | Formula | R¹ | R² | R³ | R⁴ | R⁵ |
|---|---|---|---|---|---|---|
| A-115 | I.1A | Cl | 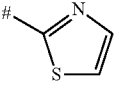 | H | H | H |
| A-116 | I.1A | Cl | 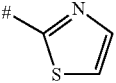 | Cl | H | H |
| A-117 | I.1A | Cl | 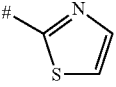 | CF₃ | H | H |
| A-118 | I.1A | Cl | 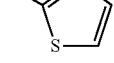 | CHF₂ | H | H |
| A-119 | I.1A | Cl | 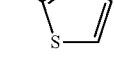 | F | H | H |
| A-120 | I.1A | Cl | (thiazole) | OCHF₂ | H | H |
| A-121 | I.1A | Cl | (thiazole) | SO₂CH₃ | H | H |
| A-122 | I.1A | Cl | 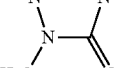 | H | H | H |

TABLE A-continued
Compounds of the formula I which correspond to the formulae I.1A and I.2A
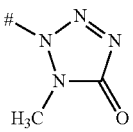
I.1A
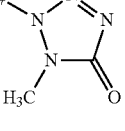
I.2A
| No. | Formula | R¹ | R² | R³ | R⁴ | R⁵ |
|---|---|---|---|---|---|---|
| A-123 | I.1A | Cl | 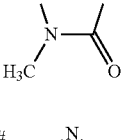 | Cl | H | H |
| A-124 | I.1A | Cl | 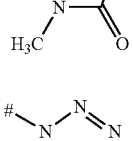 | $CF_3$ | H | H |
| A-125 | I.1A | Cl | 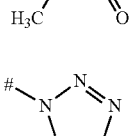 | $CHF_2$ | H | H |
| A-126 | I.1A | Cl |  | F | H | H |
| A-127 | I.1A | Cl | 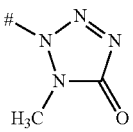 | $OCHF_2$ | H | H |
| A-128 | I.1A | Cl | 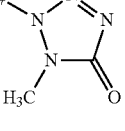 | $SO_2CH_3$ | H | H |

TABLE A-continued
Compounds of the formula I which correspond to the formulae I.1A and I.2A
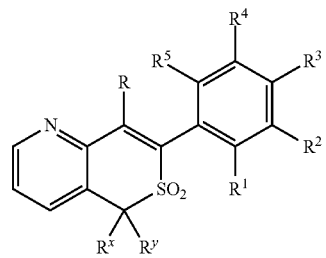
I.1A
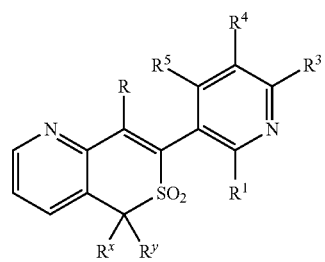
I.2A
| No. | Formula | R¹ | R² | R³ | R⁴ | R⁵ |
|---|---|---|---|---|---|---|
| A-129 | I.1A | Cl | (1-methyl-5-oxo-tetrazol-4-yl) | H | H | H |
| A-130 | I.1A | Cl | (1-methyl-5-oxo-tetrazol-4-yl) | Cl | H | H |
| A-131 | I.1A | Cl | (1-methyl-5-oxo-tetrazol-4-yl) | $CF_3$ | H | H |
| A-132 | I.1A | Cl | (1-methyl-5-oxo-tetrazol-4-yl) | $CHF_2$ | H | H |
| A-133 | I.1A | Cl | (1-methyl-5-oxo-tetrazol-4-yl) | F | H | H |

TABLE A-continued

Compounds of the formula I which correspond to the formulae I.1A and I.2A

I.1A

I.2A

| No. | Formula | R¹ | R² | R³ | R⁴ | R⁵ |
|---|---|---|---|---|---|---|
| A-134 | I.1A | Cl | #-N(tetrazolinone-N-CH₃) | OCHF₂ | H | H |
| A-135 | I.1A | Cl | #-N(tetrazolinone-N-CH₃) | SO₂CH₃ | H | H |
| A-136 | I.1A | Cl | #-morpholino | H | H | H |
| A-137 | I.1A | Cl | #-morpholino | Cl | H | H |
| A-138 | I.1A | Cl | #-morpholino | CF₃ | H | H |
| A-139 | I.1A | Cl | #-morpholino | CHF₂ | H | H |
| A-140 | I.1A | Cl | #-morpholino | F | H | H |

TABLE A-continued

Compounds of the formula I which correspond to the formulae I.1A and I.2A

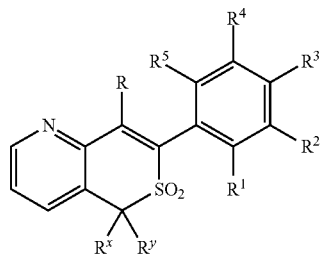

I.1A

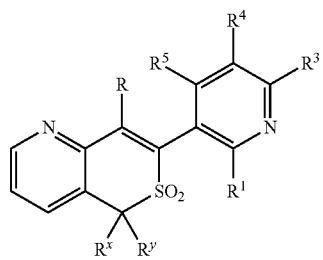

I.2A

| No. | Formula | R¹ | R² | R³ | R⁴ | R⁵ |
|---|---|---|---|---|---|---|
| A-141 | I.1A | Cl | #–N(morpholine) | OCHF₂ | H | H |
| A-142 | I.1A | Cl | #–N(morpholine) | SO₂CH₃ | H | H |
| A-143 | I.1A | Cl | C₆H₅ | H | H | H |
| A-144 | I.1A | Cl | C₆H₅ | Cl | H | H |
| A-145 | I.1A | Cl | C₆H₅ | CF₃ | H | H |
| A-146 | I.1A | Cl | C₆H₅ | CHF₂ | H | H |
| A-147 | I.1A | Cl | C₆H₅ | F | H | H |
| A-148 | I.1A | Cl | C₆H₅ | OCHF₂ | H | H |
| A-149 | I.1A | Cl | C₆H₅ | SO₂CH₃ | H | H |
| A-150 | I.1A | Cl | 4-OCH₃—C₆H₄ | H | H | H |
| A-151 | I.1A | Cl | 4-OCH₃—C₆H₄ | Cl | H | H |
| A-152 | I.1A | Cl | 4-OCH₃—C₆H₄ | CF₃ | H | H |
| A-153 | I.1A | Cl | 4-OCH₃—C₆H₄ | CHF₂ | H | H |
| A-154 | I.1A | Cl | 4-OCH₃—C₆H₄ | F | H | H |
| A-155 | I.1A | Cl | 4-OCH₃—C₆H₄ | OCHF₂ | H | H |
| A-156 | I.1A | Cl | 4-OCH₃—C₆H₄ | SO₂CH₃ | H | H |
| A-157 | I.1A | Cl | CH=CH₂ | H | H | H |
| A-158 | I.1A | Cl | CH=CH₂ | Cl | H | H |
| A-159 | I.1A | Cl | CH=CH₂ | CF₃ | H | H |
| A-160 | I.1A | Cl | CH=CH₂ | CHF₂ | H | H |
| A-161 | I.1A | Cl | CH=CH₂ | F | H | H |
| A-162 | I.1A | Cl | CH=CH₂ | OCHF₂ | H | H |
| A-163 | I.1A | Cl | CH=CH₂ | SO₂CH₃ | H | H |
| A-164 | I.1A | Cl | CH=CH—CH₃ | H | H | H |
| A-165 | I.1A | Cl | CH=CH—CH₃ | Cl | H | H |
| A-166 | I.1A | Cl | CH=CH—CH₃ | CF₃ | H | H |
| A-167 | I.1A | Cl | CH=CH—CH₃ | CHF₂ | H | H |
| A-168 | I.1A | Cl | CH=CH—CH₃ | F | H | H |
| A-169 | I.1A | Cl | CH=CH—CH₃ | OCHF₂ | H | H |
| A-170 | I.1A | Cl | CH=CH—CH₃ | SO₂CH₃ | H | H |
| A-171 | I.1A | Cl | CH₂CH=CH₂ | H | H | H |
| A-172 | I.1A | Cl | CH₂CH=CH₂ | Cl | H | H |
| A-173 | I.1A | Cl | CH₂CH=CH₂ | CF₃ | H | H |
| A-174 | I.1A | Cl | CH₂CH=CH₂ | CHF₂ | H | H |
| A-175 | I.1A | Cl | CH₂CH=CH₂ | F | H | H |
| A-176 | I.1A | Cl | CH₂CH=CH₂ | OCHF₂ | H | H |

TABLE A-continued

Compounds of the formula I which correspond to the formulae I.1A and I.2A

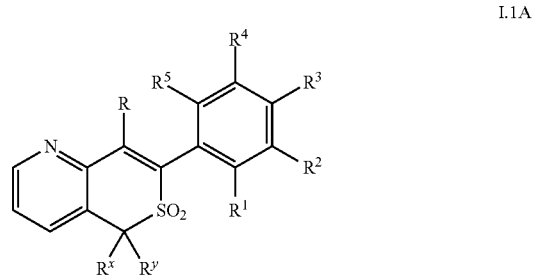

I.1A

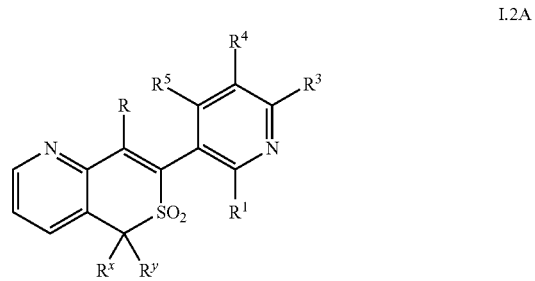

I.2A

| No. | Formula | R¹ | R² | R³ | R⁴ | R⁵ |
|---|---|---|---|---|---|---|
| A-177 | I.1A | Cl | $CH_2CH{=}CH_2$ | $SO_2CH_3$ | H | H |
| A-178 | I.1A | Cl | $CH_2C{\equiv}CH$ | H | H | H |
| A-179 | I.1A | Cl | $CH_2C{\equiv}CH$ | Cl | H | H |
| A-180 | I.1A | Cl | $CH_2C{\equiv}CH$ | $CF_3$ | H | H |
| A-181 | I.1A | Cl | $CH_2C{\equiv}CH$ | $CHF_2$ | H | H |
| A-182 | I.1A | Cl | $CH_2C{\equiv}CH$ | F | H | H |
| A-183 | I.1A | Cl | $CH_2C{\equiv}CH$ | $OCHF_2$ | H | H |
| A-184 | I.1A | Cl | $CH_2C{\equiv}CH$ | $SO_2CH_3$ | H | H |
| A-185 | I.1A | Cl | $CH_2OCH_2CF_3$ | H | H | H |
| A-186 | I.1A | Cl | $CH_2OCH_2CF_3$ | Cl | H | H |
| A-187 | I.1A | Cl | $CH_2OCH_2CF_3$ | $CF_3$ | H | H |
| A-188 | I.1A | Cl | $CH_2OCH_2CF_3$ | $CHF_2$ | H | H |
| A-189 | I.1A | Cl | $CH_2OCH_2CF_3$ | F | H | H |
| A-190 | I.1A | Cl | $CH_2OCH_2CF_3$ | $OCHF_2$ | H | H |
| A-191 | I.1A | Cl | $CH_2OCH_2CF_3$ | $SO_2CH_3$ | H | H |
| A-192 | I.1A | Cl | (tetrahydrofuran-2-ylmethoxymethyl) | H | H | H |
| A-193 | I.1A | Cl | (tetrahydrofuran-2-ylmethoxymethyl) | Cl | H | H |
| A-194 | I.1A | Cl | (tetrahydrofuran-2-ylmethoxymethyl) | $CF_3$ | H | H |
| A-195 | I.1A | Cl | (tetrahydrofuran-2-ylmethoxymethyl) | $CHF_2$ | H | H |
| A-196 | I.1A | Cl | (tetrahydrofuran-2-ylmethoxymethyl) | F | H | H |
| A-197 | I.1A | Cl | (tetrahydrofuran-2-ylmethoxymethyl) | $OCHF_2$ | H | H |

TABLE A-continued

Compounds of the formula I which correspond to the formulae I.1A and I.2A

I.1A

I.2A

| No. | Formula | R¹ | R² | R³ | R⁴ | R⁵ |
| --- | --- | --- | --- | --- | --- | --- |
| A-198 | I.1A | Cl | (tetrahydrofuran-2-ylmethoxymethyl, # attached) | SO₂CH₃ | H | H |
| A-199 | I.1A | Cl | OCH₂CH₃ | H | H | H |
| A-200 | I.1A | Cl | OCH₂CH₃ | Cl | H | H |
| A-201 | I.1A | Cl | OCH₂CH₃ | CF₃ | H | H |
| A-202 | I.1A | Cl | OCH₂CH₃ | CHF₂ | H | H |
| A-203 | I.1A | Cl | OCH₂CH₃ | F | H | H |
| A-204 | I.1A | Cl | OCH₂CH₃ | OCHF₂ | H | H |
| A-205 | I.1A | Cl | OCH₂CH₃ | SO₂CH₃ | H | H |
| A-206 | I.1A | Cl | OCH₂CH₂OCH₃ | H | H | H |
| A-207 | I.1A | Cl | OCH₂CH₂OCH₃ | Cl | H | H |
| A-208 | I.1A | Cl | OCH₂CH₂OCH₃ | CF₃ | H | H |
| A-209 | I.1A | Cl | OCH₂CH₂OCH₃ | CHF₂ | H | H |
| A-210 | I.1A | Cl | OCH₂CH₂OCH₃ | F | H | H |
| A-211 | I.1A | Cl | OCH₂CH₂OCH₃ | OCHF₂ | H | H |
| A-212 | I.1A | Cl | OCH₂CH₂OCH₃ | SO₂CH₃ | H | H |
| A-213 | I.1A | Cl | SO₂CH₃ | H | H | H |
| A-214 | I.1A | Cl | SO₂CH₃ | Cl | H | H |
| A-215 | I.1A | Cl | SO₂CH₃ | CF₃ | H | H |
| A-216 | I.1A | Cl | SO₂CH₃ | CHF₂ | H | H |
| A-217 | I.1A | Cl | SO₂CH₃ | F | H | H |
| A-218 | I.1A | Cl | SO₂CH₃ | OCHF₂ | H | H |
| A-219 | I.1A | Cl | SO₂CH₃ | SO₂CH₃ | H | H |
| A-220 | I.1A | Cl | SO₂CH₂CH₃ | H | H | H |
| A-221 | I.1A | Cl | SO₂CH₂CH₃ | Cl | H | H |
| A-222 | I.1A | Cl | SO₂CH₂CH₃ | CF₃ | H | H |
| A-223 | I.1A | Cl | SO₂CH₂CH₃ | CHF₂ | H | H |
| A-224 | I.1A | Cl | SO₂CH₂CH₃ | F | H | H |
| A-225 | I.1A | Cl | SO₂CH₂CH₃ | OCHF₂ | H | H |
| A-226 | I.1A | Cl | SO₂CH₂CH₃ | SO₂CH₃ | H | H |
| A-227 | I.1A | Cl | SO₂CH(CH₃)₂ | H | H | H |
| A-228 | I.1A | Cl | SO₂CH(CH₃)₂ | Cl | H | H |
| A-229 | I.1A | Cl | SO₂CH(CH₃)₂ | CF₃ | H | H |
| A-230 | I.1A | Cl | SO₂CH(CH₃)₂ | CHF₂ | H | H |
| A-231 | I.1A | Cl | SO₂CH(CH₃)₂ | OCH₃ | H | H |
| A-232 | I.1A | Cl | SO₂CH(CH₃)₂ | OCHF₂ | H | H |
| A-233 | I.1A | Cl | SO₂CH(CH₃)₂ | SO₂CH₃ | H | H |
| A-234 | I.1A | Cl | COOCH₃ | H | H | H |
| A-235 | I.1A | Cl | COOCH₃ | Cl | H | H |
| A-236 | I.1A | Cl | COOCH₃ | CF₃ | H | H |
| A-237 | I.1A | Cl | COOCH₃ | CHF₂ | H | H |
| A-238 | I.1A | Cl | COOCH₃ | F | H | H |
| A-239 | I.1A | Cl | COOCH₃ | OCHF₂ | H | H |

TABLE A-continued

Compounds of the formula I which correspond to the formulae I.1A and I.2A

I.1A

I.2A

| No. | Formula | R¹ | R² | R³ | R⁴ | R⁵ |
|---|---|---|---|---|---|---|
| A-240 | I.1A | Cl | COOCH$_3$ | SO$_2$CH$_3$ | H | H |
| A-241 | I.1A | Cl | COOCH$_2$CH$_3$ | H | H | H |
| A-242 | I.1A | Cl | COOCH$_2$CH$_3$ | Cl | H | H |
| A-243 | I.1A | Cl | COOCH$_2$CH$_3$ | CF$_3$ | H | H |
| A-244 | I.1A | Cl | COOCH$_2$CH$_3$ | CHF$_2$ | H | H |
| A-245 | I.1A | Cl | COOCH$_2$CH$_3$ | F | H | H |
| A-246 | I.1A | Cl | COOCH$_2$CH$_3$ | OCHF$_2$ | H | H |
| A-247 | I.1A | Cl | COOCH$_2$CH$_3$ | SO$_2$CH$_3$ | H | H |
| A-248 | I.1A | Cl | #²—CH$_2$CH$_2$SO$_2$—#³ | | H | H |
| A-249 | I.1A | Cl | #²—CH(CH$_3$)CH$_2$SO$_2$—#³ | | H | H |
| A-250 | I.1A | Cl | #²—C(CH$_3$)$_2$CH$_2$SO$_2$—#³ | | H | H |
| A-251 | I.1A | Cl | #²—SO$_2$CH$_2$CH$_2$SO$_2$—#³ | | H | H |
| A-252 | I.1A | Cl | #²—CH(OCH$_2$CH$_2$F)CH$_2$SO$_2$—#³ | | H | H |
| A-253 | I.1A | Cl | #²—C(=NOCH$_3$)CH$_2$SO$_2$—#³ | | H | H |
| A-254 | I.1A | Cl | #²—SO$_2$CH$_2$CH$_2$C(CH$_3$)$_2$—#³ | | H | H |
| A-255 | I.1A | Cl | #²—N(CH$_3$)C(=O)S—#³ | | H | H |
| A-256 | I.1A | Cl | #²—C(=O)N(CH$_3$)SO$_2$—#³ | | H | H |
| A-257 | I.1A | Br | 4,5-dihydroisoxazol-3-yl | H | H | H |
| A-258 | I.1A | Br | 4,5-dihydroisoxazol-3-yl | Cl | H | H |
| A-259 | I.1A | Br | 4,5-dihydroisoxazol-3-yl | CF$_3$ | H | H |
| A-260 | I.1A | Br | 4,5-dihydroisoxazol-3-yl | CHF$_2$ | H | H |
| A-261 | I.1A | Br | 4,5-dihydroisoxazol-3-yl | F | H | H |

TABLE A-continued
Compounds of the formula I which correspond to the formulae I.1A and I.2A
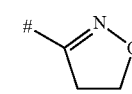
I.1A
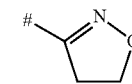
I.2A
| No. | Formula | R¹ | R² | R³ | R⁴ | R⁵ |
|---|---|---|---|---|---|---|
| A-262 | I.1A | Br | 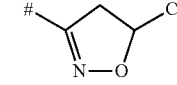 | OCHF$_2$ | H | H |
| A-263 | I.1A | Br | 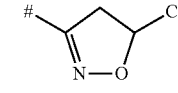 | SO$_2$CH$_3$ | H | H |
| A-264 | I.1A | Br | 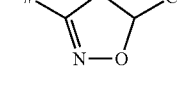 | H | H | H |
| A-265 | I.1A | Br | 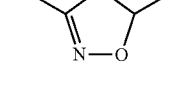 | Cl | H | H |
| A-266 | I.1A | Br | 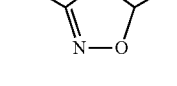 | CF$_3$ | H | H |
| A-267 | I.1A | Br | 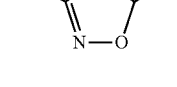 | CHF$_2$ | H | H |
| A-268 | I.1A | Br | 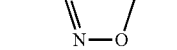 | F | H | H |
| A-269 | I.1A | Br | (isoxazoline-CH$_3$) | OCHF$_2$ | H | H |
| A-270 | I.1A | Br | (isoxazoline-CH$_3$) | SO$_2$CH$_3$ | H | H |

TABLE A-continued
Compounds of the formula I which correspond to the formulae I.1A and I.2A
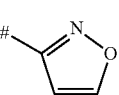
I.1A
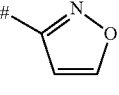
I.2A
| No. | Formula | R¹ | R² | R³ | R⁴ | R⁵ |
|---|---|---|---|---|---|---|
| A-271 | I.1A | Br | 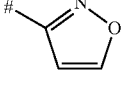 | H | H | H |
| A-272 | I.1A | Br | 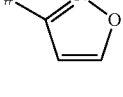 | Cl | H | H |
| A-273 | I.1A | Br | 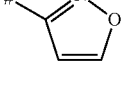 | CF$_3$ | H | H |
| A-274 | I.1A | Br | 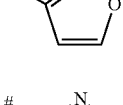 | CHF$_2$ | H | H |
| A-275 | I.1A | Br | 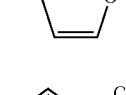 | F | H | H |
| A-276 | I.1A | Br | 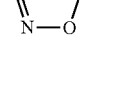 | OCHF$_2$ | H | H |
| A-277 | I.1A | Br |  | SO$_2$CH$_3$ | H | H |
| A-278 | I.1A | Br |  | H | H | H |

TABLE A-continued
Compounds of the formula I which correspond to the formulae I.1A and I.2A
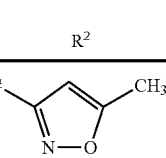
I.1A
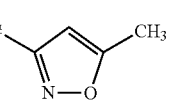
I.2A
| No. | Formula | R¹ | R² | R³ | R⁴ | R⁵ |
|---|---|---|---|---|---|---|
| A-279 | I.1A | Br | 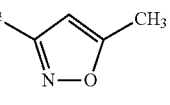 | Cl | H | H |
| A-280 | I.1A | Br | 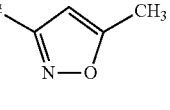 | $CF_3$ | H | H |
| A-281 | I.1A | Br | 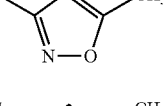 | $CHF_2$ | H | H |
| A-282 | I.1A | Br | 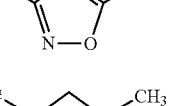 | F | H | H |
| A-283 | I.1A | Br | 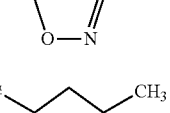 | $OCHF_2$ | H | H |
| A-284 | I.1A | Br | 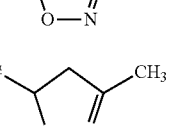 | $SO_2CH_3$ | H | H |
| A-285 | I.1A | Br | 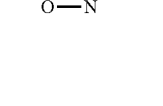 | H | H | H |
| A-286 | I.1A | Br | 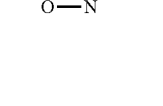 | Cl | H | H |
| A-287 | I.1A | Br | 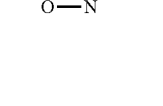 | $CF_3$ | H | H |

TABLE A-continued

Compounds of the formula I which correspond to the formulae I.1A and I.2A

I.1A

I.2A

| No. | Formula | R¹ | R² | R³ | R⁴ | R⁵ |
|---|---|---|---|---|---|---|
| A-288 | I.1A | Br | # 5-(3-methyl-4,5-dihydroisoxazolyl) | CHF₂ | H | H |
| A-289 | I.1A | Br | # 5-(3-methyl-4,5-dihydroisoxazolyl) | F | H | H |
| A-290 | I.1A | Br | # 5-(3-methyl-4,5-dihydroisoxazolyl) | OCHF₂ | H | H |
| A-291 | I.1A | Br | # 5-(3-methyl-4,5-dihydroisoxazolyl) | SO₂CH₃ | H | H |
| A-292 | I.1A | Br | # 5-(3-methylisoxazolyl) | H | H | H |
| A-293 | I.1A | Br | # 5-(3-methylisoxazolyl) | Cl | H | H |
| A-294 | I.1A | Br | # 5-(3-methylisoxazolyl) | CF₃ | H | H |
| A-295 | I.1A | Br | # 5-(3-methylisoxazolyl) | CHF₂ | H | H |

TABLE A-continued
Compounds of the formula I which correspond to the formulae I.1A and I.2A
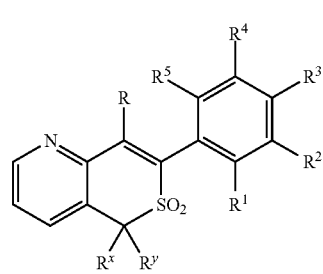
I.1A
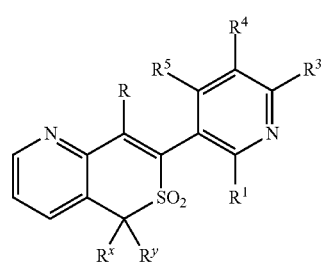
I.2A
| No. | Formula | R¹ | R² | R³ | R⁴ | R⁵ |
|---|---|---|---|---|---|---|
| A-296 | I.1A | Br | 5-(3-methylisoxazolyl) | F | H | H |
| A-297 | I.1A | Br | 5-(3-methylisoxazolyl) | OCHF$_2$ | H | H |
| A-298 | I.1A | Br | 5-(3-methylisoxazolyl) | SO$_2$CH$_3$ | H | H |
| A-299 | I.1A | Br | 2-thiazolyl | H | H | H |
| A-300 | I.1A | Br | 2-thiazolyl | Cl | H | H |
| A-301 | I.1A | Br | 2-thiazolyl | CF$_3$ | H | H |
| A-302 | I.1A | Br | 2-thiazolyl | CHF$_2$ | H | H |
| A-303 | I.1A | Br | 2-thiazolyl | F | H | H |

TABLE A-continued
Compounds of the formula I which correspond to the formulae I.1A and I.2A
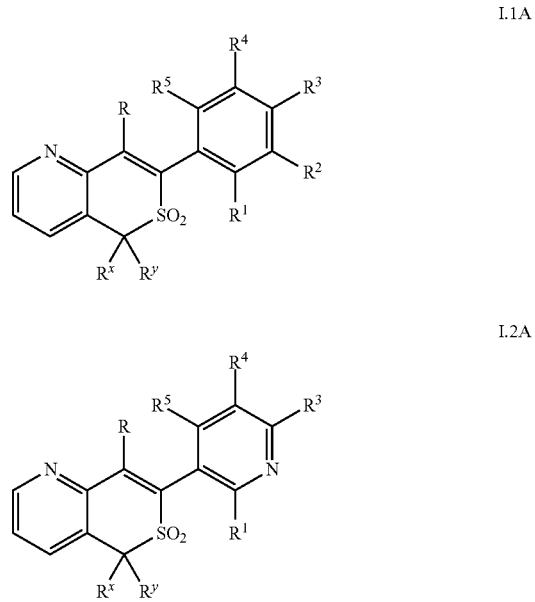
| No. | Formula | R¹ | R² | R³ | R⁴ | R⁵ |
|---|---|---|---|---|---|---|
| A-304 | I.1A | Br | 2-thiazolyl | OCHF$_2$ | H | H |
| A-305 | I.1A | Br | 2-thiazolyl | SO$_2$CH$_3$ | H | H |
| A-306 | I.1A | Br | 4-methyl-5-oxo-tetrazolyl | H | H | H |
| A-307 | I.1A | Br | 4-methyl-5-oxo-tetrazolyl | Cl | H | H |
| A-308 | I.1A | Br | 4-methyl-5-oxo-tetrazolyl | CF$_3$ | H | H |
| A-309 | I.1A | Br | 4-methyl-5-oxo-tetrazolyl | CHF$_2$ | H | H |

TABLE A-continued
Compounds of the formula I which correspond to the formulae I.1A and I.2A
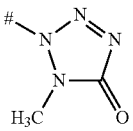
I.1A
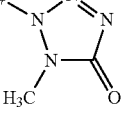
I.2A
| No. | Formula | R¹ | R² | R³ | R⁴ | R⁵ |
|---|---|---|---|---|---|---|
| A-310 | I.1A | Br | 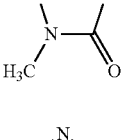 | F | H | H |
| A-311 | I.1A | Br | 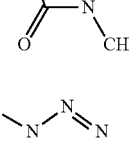 | OCHF$_2$ | H | H |
| A-312 | I.1A | Br | 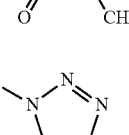 | SO$_2$CH$_3$ | H | H |
| A-313 | I.1A | Br |  | H | H | H |
| A-314 | I.1A | Br |  | Cl | H | H |
| A-315 | I.1A | Br |  | CF$_3$ | H | H |

TABLE A-continued
Compounds of the formula I which correspond to the formulae I.1A and I.2A
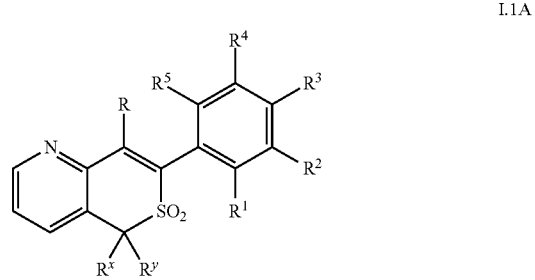
I.1A
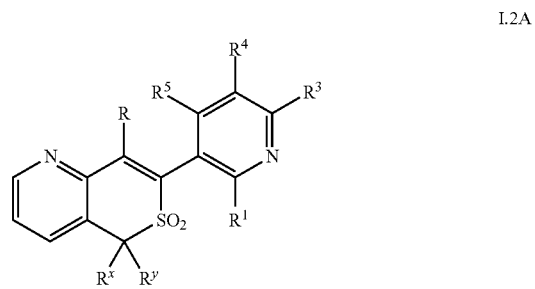
I.2A
| No. | Formula | R¹ | R² | R³ | R⁴ | R⁵ |
|---|---|---|---|---|---|---|
| A-316 | I.1A | Br | 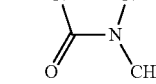 | CHF$_2$ | H | H |
| A-317 | I.1A | Br | 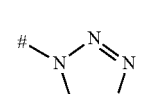 | F | H | H |
| A-318 | I.1A | Br | 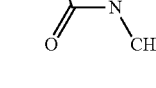 | OCHF$_2$ | H | H |
| A-319 | I.1A | Br | 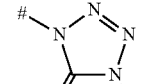 | SO$_2$CH$_3$ | H | H |
| A-320 | I.1A | Br | 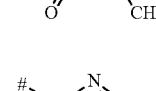 | H | H | H |
| A-321 | I.1A | Br | 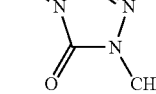 | Cl | H | H |

TABLE A-continued

Compounds of the formula I which correspond to the formulae I.1A and I.2A

I.1A

I.2A

| No. | Formula | R¹ | R² | R³ | R⁴ | R⁵ |
|---|---|---|---|---|---|---|
| A-322 | I.1A | Br | #-morpholin-4-yl | $CF_3$ | H | H |
| A-323 | I.1A | Br | #-morpholin-4-yl | $CHF_2$ | H | H |
| A-324 | I.1A | Br | #-morpholin-4-yl | F | H | H |
| A-325 | I.1A | Br | #-morpholin-4-yl | $OCHF_2$ | H | H |
| A-326 | I.1A | Br | #-morpholin-4-yl | $SO_2CH_3$ | H | H |
| A-327 | I.1A | Br | $C_6H_5$ | H | H | H |
| A-328 | I.1A | Br | $C_6H_5$ | Cl | H | H |
| A-329 | I.1A | Br | $C_6H_5$ | $CF_3$ | H | H |
| A-330 | I.1A | Br | $C_6H_5$ | $CHF_2$ | H | H |
| A-331 | I.1A | Br | $C_6H_5$ | F | H | H |
| A-332 | I.1A | Br | $C_6H_5$ | $OCHF_2$ | H | H |
| A-333 | I.1A | Br | $C_6H_5$ | $SO_2CH_3$ | H | H |
| A-334 | I.1A | Br | 4-$OCH_3$—$C_6H_4$ | H | H | H |
| A-335 | I.1A | Br | 4-$OCH_3$—$C_6H_4$ | Cl | H | H |
| A-336 | I.1A | Br | 4-$OCH_3$—$C_6H_4$ | $CF_3$ | H | H |
| A-337 | I.1A | Br | 4-$OCH_3$—$C_6H_4$ | $CHF_2$ | H | H |
| A-338 | I.1A | Br | 4-$OCH_3$—$C_6H_4$ | F | H | H |
| A-339 | I.1A | Br | 4-$OCH_3$—$C_6H_4$ | $OCHF_2$ | H | H |
| A-340 | I.1A | Br | 4-$OCH_3$—$C_6H_4$ | $SO_2CH_3$ | H | H |
| A-341 | I.1A | Br | $CH=CH_2$ | H | H | H |
| A-342 | I.1A | Br | $CH=CH_2$ | Cl | H | H |

TABLE A-continued

Compounds of the formula I which correspond to the formulae I.1A and I.2A

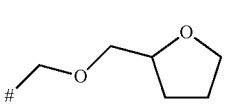

| No. | Formula | R¹ | R² | R³ | R⁴ | R⁵ |
|---|---|---|---|---|---|---|
| A-343 | I.1A | Br | CH=CH$_2$ | CF$_3$ | H | H |
| A-344 | I.1A | Br | CH=CH$_2$ | CHF$_2$ | H | H |
| A-345 | I.1A | Br | CH=CH$_2$ | F | H | H |
| A-346 | I.1A | Br | CH=CH$_2$ | OCHF$_2$ | H | H |
| A-347 | I.1A | Br | CH=CH$_2$ | SO$_2$CH$_3$ | H | H |
| A-348 | I.1A | Br | CH=CH—CH$_3$ | H | H | H |
| A-349 | I.1A | Br | CH=CH—CH$_3$ | Cl | H | H |
| A-350 | I.1A | Br | CH=CH—CH$_3$ | CF$_3$ | H | H |
| A-351 | I.1A | Br | CH=CH—CH$_3$ | CHF$_2$ | H | H |
| A-352 | I.1A | Br | CH=CH—CH$_3$ | F | H | H |
| A-353 | I.1A | Br | CH=CH—CH$_3$ | OCHF$_2$ | H | H |
| A-354 | I.1A | Br | CH=CH—CH$_3$ | SO$_2$CH$_3$ | H | H |
| A-355 | I.1A | Br | CH$_2$CH=CH$_2$ | H | H | H |
| A-356 | I.1A | Br | CH$_2$CH=CH$_2$ | Cl | H | H |
| A-357 | I.1A | Br | CH$_2$CH=CH$_2$ | CF$_3$ | H | H |
| A-358 | I.1A | Br | CH$_2$CH=CH$_2$ | CHF$_2$ | H | H |
| A-359 | I.1A | Br | CH$_2$CH=CH$_2$ | F | H | H |
| A-360 | I.1A | Br | CH$_2$CH=CH$_2$ | OCHF$_2$ | H | H |
| A-361 | I.1A | Br | CH$_2$CH=CH$_2$ | SO$_2$CH$_3$ | H | H |
| A-362 | I.1A | Br | CH$_2$C≡CH | H | H | H |
| A-363 | I.1A | Br | CH$_2$C≡CH | Cl | H | H |
| A-364 | I.1A | Br | CH$_2$C≡CH | CF$_3$ | H | H |
| A-365 | I.1A | Br | CH$_2$C≡CH | CHF$_2$ | H | H |
| A-366 | I.1A | Br | CH$_2$C≡CH | F | H | H |
| A-367 | I.1A | Br | CH$_2$C≡CH | OCHF$_2$ | H | H |
| A-368 | I.1A | Br | CH$_2$C≡CH | SO$_2$CH$_3$ | H | H |
| A-369 | I.1A | Br | CH$_2$OCH$_2$CF$_3$ | H | H | H |
| A-370 | I.1A | Br | CH$_2$OCH$_2$CF$_3$ | Cl | H | H |
| A-371 | I.1A | Br | CH$_2$OCH$_2$CF$_3$ | CF$_3$ | H | H |
| A-372 | I.1A | Br | CH$_2$OCH$_2$CF$_3$ | CHF$_2$ | H | H |
| A-373 | I.1A | Br | CH$_2$OCH$_2$CF$_3$ | F | H | H |
| A-374 | I.1A | Br | CH$_2$OCH$_2$CF$_3$ | OCHF$_2$ | H | H |
| A-375 | I.1A | Br | CH$_2$OCH$_2$CF$_3$ | SO$_2$CH$_3$ | H | H |
| A-376 | I.1A | Br | 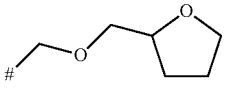 | H | H | H |
| A-377 | I.1A | Br | 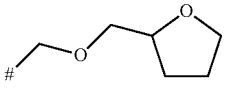 | Cl | H | H |

TABLE A-continued

Compounds of the formula I which correspond to the formulae I.1A and I.2A

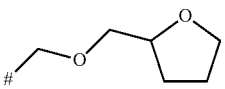

I.1A

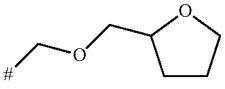

I.2A

| No. | Formula | R¹ | R² | R³ | R⁴ | R⁵ |
|---|---|---|---|---|---|---|
| A-378 | I.1A | Br | 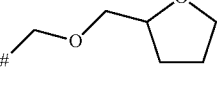 | $CF_3$ | H | H |
| A-379 | I.1A | Br | 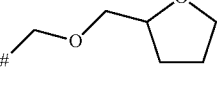 | $CHF_2$ | H | H |
| A-380 | I.1A | Br | 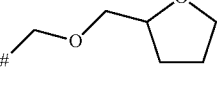 | F | H | H |
| A-381 | I.1A | Br | 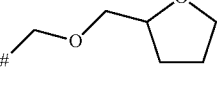 | $OCHF_2$ | H | H |
| A-382 | I.1A | Br | 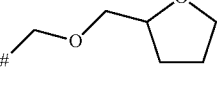 | $SO_2CH_3$ | H | H |
| A-383 | I.1A | Br | $OCH_2CH_3$ | H | H | H |
| A-384 | I.1A | Br | $OCH_2CH_3$ | Cl | H | H |
| A-385 | I.1A | Br | $OCH_2CH_3$ | $CF_3$ | H | H |
| A-386 | I.1A | Br | $OCH_2CH_3$ | $CHF_2$ | H | H |
| A-387 | I.1A | Br | $OCH_2CH_3$ | F | H | H |
| A-388 | I.1A | Br | $OCH_2CH_3$ | $OCHF_2$ | H | H |
| A-389 | I.1A | Br | $OCH_2CH_3$ | $SO_2CH_3$ | H | H |
| A-390 | I.1A | Br | $OCH_2CH_2OCH_3$ | H | H | H |
| A-391 | I.1A | Br | $OCH_2CH_2OCH_3$ | Cl | H | H |
| A-392 | I.1A | Br | $OCH_2CH_2OCH_3$ | $CF_3$ | H | H |
| A-393 | I.1A | Br | $OCH_2CH_2OCH_3$ | $CHF_2$ | H | H |
| A-394 | I.1A | Br | $OCH_2CH_2OCH_3$ | F | H | H |
| A-395 | I.1A | Br | $OCH_2CH_2OCH_3$ | $OCHF_2$ | H | H |
| A-396 | I.1A | Br | $OCH_2CH_2OCH_3$ | $SO_2CH_3$ | H | H |
| A-397 | I.1A | Br | $SO_2CH_3$ | H | H | H |
| A-398 | I.1A | Br | $SO_2CH_3$ | Cl | H | H |
| A-399 | I.1A | Br | $SO_2CH_3$ | $CF_3$ | H | H |
| A-400 | I.1A | Br | $SO_2CH_3$ | $CHF_2$ | H | H |
| A-401 | I.1A | Br | $SO_2CH_3$ | F | H | H |
| A-402 | I.1A | Br | $SO_2CH_3$ | $OCHF_2$ | H | H |

TABLE A-continued

Compounds of the formula I which correspond to the formulae I.1A and I.2A

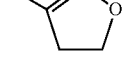

| No. | Formula | $R^1$ | $R^2$ | $R^3$ | $R^4$ | $R^5$ |
|---|---|---|---|---|---|---|
| A-403 | I.1A | Br | $SO_2CH_3$ | $SO_2CH_3$ | H | H |
| A-404 | I.1A | Br | $SO_2CH_2CH_3$ | H | H | H |
| A-405 | I.1A | Br | $SO_2CH_2CH_3$ | Cl | H | H |
| A-406 | I.1A | Br | $SO_2CH_2CH_3$ | $CF_3$ | H | H |
| A-407 | I.1A | Br | $SO_2CH_2CH_3$ | $CHF_2$ | H | H |
| A-408 | I.1A | Br | $SO_2CH_2CH_3$ | F | H | H |
| A-409 | I.1A | Br | $SO_2CH_2CH_3$ | $OCHF_2$ | H | H |
| A-410 | I.1A | Br | $SO_2CH_2CH_3$ | $SO_2CH_3$ | H | H |
| A-411 | I.1A | Br | $SO_2CH(CH_3)_2$ | H | H | H |
| A-412 | I.1A | Br | $SO_2CH(CH_3)_2$ | Cl | H | H |
| A-413 | I.1A | Br | $SO_2CH(CH_3)_2$ | $CF_3$ | H | H |
| A-414 | I.1A | Br | $SO_2CH(CH_3)_2$ | $CHF_2$ | H | H |
| A-415 | I.1A | Br | $SO_2CH(CH_3)_2$ | F | H | H |
| A-416 | I.1A | Br | $SO_2CH(CH_3)_2$ | $OCHF_2$ | H | H |
| A-417 | I.1A | Br | $SO_2CH(CH_3)_2$ | $SO_2CH_3$ | H | H |
| A-418 | I.1A | Br | $COOCH_3$ | H | H | H |
| A-419 | I.1A | Br | $COOCH_3$ | Cl | H | H |
| A-420 | I.1A | Br | $COOCH_3$ | $CF_3$ | H | H |
| A-421 | I.1A | Br | $COOCH_3$ | $CHF_2$ | H | H |
| A-422 | I.1A | Br | $COOCH_3$ | F | H | H |
| A-423 | I.1A | Br | $COOCH_3$ | $OCHF_2$ | H | H |
| A-424 | I.1A | Br | $COOCH_3$ | $SO_2CH_3$ | H | H |
| A-425 | I.1A | Br | $COOCH_2CH_3$ | H | H | H |
| A-426 | I.1A | Br | $COOCH_2CH_3$ | Cl | H | H |
| A-427 | I.1A | Br | $COOCH_2CH_3$ | $CF_3$ | H | H |
| A-428 | I.1A | Br | $COOCH_2CH_3$ | $CHF_2$ | H | H |
| A-429 | I.1A | Br | $COOCH_2CH_3$ | F | H | H |
| A-430 | I.1A | Br | $COOCH_2CH_3$ | $OCHF_2$ | H | H |
| A-431 | I.1A | Br | $COOCH_2CH_3$ | $SO_2CH_3$ | H | H |
| A-432 | I.1A | Br | $\#^2$—$CH_2CH_2SO_2$—$\#^3$ | | H | H |
| A-433 | I.1A | Br | $\#^2$—$CH(CH_3)CH_2SO_2$—$\#^3$ | | H | H |
| A-434 | I.1A | Br | $\#^2$—$C(CH_3)_2CH_2SO_2$—$\#^3$ | | H | H |
| A-435 | I.1A | Br | $\#^2$—$SO_2CH_2CH_2SO_2$—$\#^3$ | | H | H |
| A-436 | I.1A | Br | $\#^2$—$CH(OCH_2CH_2F)CH_2CH_2SO_2$—$\#^3$ | | H | H |
| A-437 | I.1A | Br | $\#^2$—$C(=NOCH_3)CH_2CH_2SO_2$—$\#^3$ | | H | H |
| A-438 | I.1A | Br | $\#^2$—$SO_2CH_2CH_2C(CH_3)_2$—$\#^3$ | | H | H |
| A-439 | I.1A | Br | $\#^2$—$N(CH_3)C(=O)S$—$\#^3$ | | H | H |
| A-440 | I.1A | Br | $\#^2$—$C(=O)N(CH_3)SO_2$—$\#^3$ | | H | H |
| A-441 | I.1A | $CH_3$ | ![3-(4,5-dihydroisoxazol-3-yl)] | H | H | H |

TABLE A-continued

Compounds of the formula I which correspond to the formulae I.1A and I.2A

I.1A

I.2A

| No. | Formula | R¹ | R² | R³ | R⁴ | R⁵ |
|---|---|---|---|---|---|---|
| A-442 | I.1A | CH₃ | 3-(4,5-dihydroisoxazolyl) | Cl | H | H |
| A-443 | I.1A | CH₃ | 3-(4,5-dihydroisoxazolyl) | CF₃ | H | H |
| A-444 | I.1A | CH₃ | 3-(4,5-dihydroisoxazolyl) | CHF₂ | H | H |
| A-445 | I.1A | CH₃ | 3-(4,5-dihydroisoxazolyl) | F | H | H |
| A-446 | I.1A | CH₃ | 3-(4,5-dihydroisoxazolyl) | OCHF₂ | H | H |
| A-447 | I.1A | CH₃ | 3-(4,5-dihydroisoxazolyl) | SO₂CH₃ | H | H |
| A-448 | I.1A | CH₃ | 3-(5-methyl-4,5-dihydroisoxazolyl) | H | H | H |
| A-449 | I.1A | CH₃ | 3-(5-methyl-4,5-dihydroisoxazolyl) | Cl | H | H |
| A-450 | I.1A | CH₃ | 3-(5-methyl-4,5-dihydroisoxazolyl) | CF₃ | H | H |

TABLE A-continued
Compounds of the formula I which correspond to the formulae I.1A and I.2A
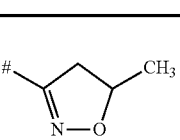
I.1A
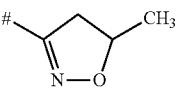
I.2A
| No. | Formula | R¹ | R² | R³ | R⁴ | R⁵ |
|---|---|---|---|---|---|---|
| A-451 | I.1A | $CH_3$ | 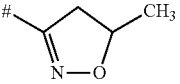 | $CHF_2$ | H | H |
| A-452 | I.1A | $CH_3$ | 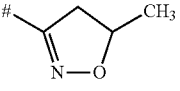 | F | H | H |
| A-453 | I.1A | $CH_3$ | 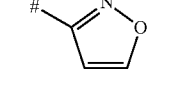 | $OCHF_2$ | H | H |
| A-454 | I.1A | $CH_3$ | 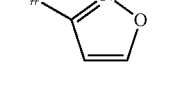 | $SO_2CH_3$ | H | H |
| A-455 | I.1A | $CH_3$ | 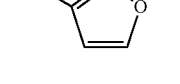 | H | H | H |
| A-456 | I.1A | $CH_3$ |  | Cl | H | H |
| A-457 | I.1A | $CH_3$ |  | $CF_3$ | H | H |
| A-458 | I.1A | $CH_3$ |  | $CHF_2$ | H | H |

TABLE A-continued
Compounds of the formula I which correspond to the formulae I.1A and I.2A
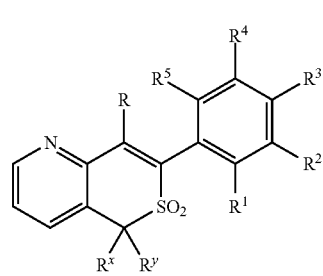
I.1A
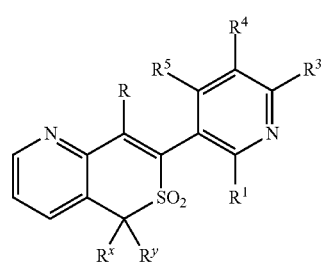
I.2A
| No. | Formula | R¹ | R² | R³ | R⁴ | R⁵ |
|---|---|---|---|---|---|---|
| A-459 | I.1A | CH₃ | isoxazol-3-yl | F | H | H |
| A-460 | I.1A | CH₃ | isoxazol-3-yl | OCHF₂ | H | H |
| A-461 | I.1A | CH₃ | isoxazol-3-yl | SO₂CH₃ | H | H |
| A-462 | I.1A | CH₃ | 5-methylisoxazol-3-yl | H | H | H |
| A-463 | I.1A | CH₃ | 5-methylisoxazol-3-yl | Cl | H | H |
| A-464 | I.1A | CH₃ | 5-methylisoxazol-3-yl | CF₃ | H | H |
| A-465 | I.1A | CH₃ | 5-methylisoxazol-3-yl | CHF₂ | H | H |
| A-466 | I.1A | CH₃ | 5-methylisoxazol-3-yl | F | H | H |

TABLE A-continued

Compounds of the formula I which correspond to the formulae I.1A and I.2A

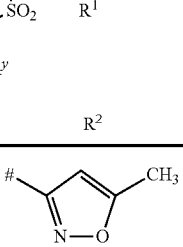

I.1A

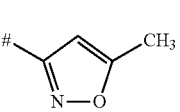

I.2A

| No. | Formula | R¹ | R² | R³ | R⁴ | R⁵ |
|---|---|---|---|---|---|---|
| A-467 | I.1A | CH₃ | 3-methyl-isoxazol-5-yl (N—O, CH₃) | OCHF₂ | H | H |
| A-468 | I.1A | CH₃ | 3-methyl-isoxazol-5-yl (N—O, CH₃) | SO₂CH₃ | H | H |
| A-469 | I.1A | CH₃ | 3-methyl-4,5-dihydroisoxazol-5-yl | H | H | H |
| A-470 | I.1A | CH₃ | 3-methyl-4,5-dihydroisoxazol-5-yl | Cl | H | H |
| A-471 | I.1A | CH₃ | 3-methyl-4,5-dihydroisoxazol-5-yl | CF₃ | H | H |
| A-472 | I.1A | CH₃ | 3-methyl-4,5-dihydroisoxazol-5-yl | CHF₂ | H | H |
| A-473 | I.1A | CH₃ | 3-methyl-4,5-dihydroisoxazol-5-yl | F | H | H |
| A-474 | I.1A | CH₃ | 3-methyl-4,5-dihydroisoxazol-5-yl | OCHF₂ | H | H |

TABLE A-continued

Compounds of the formula I which correspond to the formulae I.1A and I.2A

I.1A

I.2A

| No. | Formula | R¹ | R² | R³ | R⁴ | R⁵ |
|---|---|---|---|---|---|---|
| A-475 | I.1A | $CH_3$ | 3-methyl-4,5-dihydroisoxazol-5-yl | $SO_2CH_3$ | H | H |
| A-476 | I.1A | $CH_3$ | 3-methylisoxazol-5-yl | H | H | H |
| A-477 | I.1A | $CH_3$ | 3-methylisoxazol-5-yl | Cl | H | H |
| A-478 | I.1A | $CH_3$ | 3-methylisoxazol-5-yl | $CF_3$ | H | H |
| A-479 | I.1A | $CH_3$ | 3-methylisoxazol-5-yl | $CHF_2$ | H | H |
| A-480 | I.1A | $CH_3$ | 3-methylisoxazol-5-yl | F | H | H |
| A-481 | I.1A | $CH_3$ | 3-methylisoxazol-5-yl | $OCHF_2$ | H | H |
| A-482 | I.1A | $CH_3$ | 3-methylisoxazol-5-yl | $SO_2CH_3$ | H | H |

TABLE A-continued
Compounds of the formula I which correspond to the formulae I.1A and I.2A
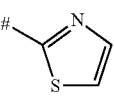
I.1A
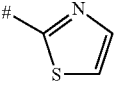
I.2A
| No. | Formula | R¹ | R² | R³ | R⁴ | R⁵ |
|---|---|---|---|---|---|---|
| A-483 | I.1A | CH₃ | 2-thiazolyl | H | H | H |
| A-484 | I.1A | CH₃ | 2-thiazolyl | Cl | H | H |
| A-485 | I.1A | CH₃ | 2-thiazolyl | CF₃ | H | H |
| A-486 | I.1A | CH₃ | 2-thiazolyl | CHF₂ | H | H |
| A-487 | I.1A | CH₃ | 2-thiazolyl | F | H | H |
| A-488 | I.1A | CH₃ | 2-thiazolyl | OCHF₂ | H | H |
| A-489 | I.1A | CH₃ | 2-thiazolyl | SO₂CH₃ | H | H |
| A-490 | I.1A | CH₃ | (1-methyl-5-oxo-tetrazol-4-yl) | H | H | H |

TABLE A-continued
Compounds of the formula I which correspond to the formulae I.1A and I.2A
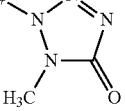
I.1A
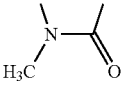
I.2A
| No. | Formula | R¹ | R² | R³ | R⁴ | R⁵ |
|---|---|---|---|---|---|---|
| A-491 | I.1A | $CH_3$ | (N-methyl-tetrazolone) | Cl | H | H |
| A-492 | I.1A | $CH_3$ | (N-methyl-tetrazolone) | $CF_3$ | H | H |
| A-493 | I.1A | $CH_3$ | (N-methyl-tetrazolone) | $CHF_2$ | H | H |
| A-494 | I.1A | $CH_3$ | (N-methyl-tetrazolone) | F | H | H |
| A-495 | I.1A | $CH_3$ | (N-methyl-tetrazolone) | $OCHF_2$ | H | H |
| A-496 | I.1A | $CH_3$ | (N-methyl-tetrazolone) | $SO_2CH_3$ | H | H |

TABLE A-continued
Compounds of the formula I which correspond to the formulae I.1A and I.2A
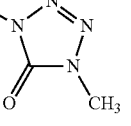
I.1A
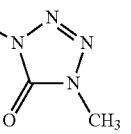
I.2A
| No. | Formula | R¹ | R² | R³ | R⁴ | R⁵ |
|---|---|---|---|---|---|---|
| A-497 | I.1A | $CH_3$ | 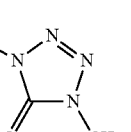 | H | H | H |
| A-498 | I.1A | $CH_3$ | 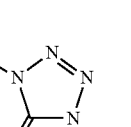 | Cl | H | H |
| A-499 | I.1A | $CH_3$ | 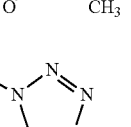 | $CF_3$ | H | H |
| A-500 | I.1A | $CH_3$ | 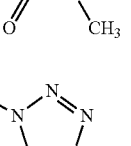 | $CHF_2$ | H | H |
| A-501 | I.1A | $CH_3$ | | F | H | H |
| A-502 | I.1A | $CH_3$ | | $OCHF_2$ | H | H |

TABLE A-continued

Compounds of the formula I which correspond to the formulae I.1A and I.2A

I.1A

I.2A

| No. | Formula | R¹ | R² | R³ | R⁴ | R⁵ |
|---|---|---|---|---|---|---|
| A-503 | I.1A | CH₃ | 1-(4-methyl-5-oxo-4,5-dihydro-1H-tetrazol-1-yl) | SO₂CH₃ | H | H |
| A-504 | I.1A | CH₃ | morpholin-4-yl | H | H | H |
| A-505 | I.1A | CH₃ | morpholin-4-yl | Cl | H | H |
| A-506 | I.1A | CH₃ | morpholin-4-yl | CF₃ | H | H |
| A-507 | I.1A | CH₃ | morpholin-4-yl | CHF₂ | H | H |
| A-508 | I.1A | CH₃ | morpholin-4-yl | F | H | H |
| A-509 | I.1A | CH₃ | morpholin-4-yl | OCHF₂ | H | H |

TABLE A-continued

Compounds of the formula I which correspond to the formulae I.1A and I.2A

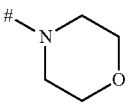

| No. | Formula | R¹ | R² | R³ | R⁴ | R⁵ |
|---|---|---|---|---|---|---|
| A-510 | I.1A | $CH_3$ | #-N(morpholine) | $SO_2CH_3$ | H | H |
| A-511 | I.1A | $CH_3$ | $C_6H_5$ | H | H | H |
| A-512 | I.1A | $CH_3$ | $C_6H_5$ | Cl | H | H |
| A-513 | I.1A | $CH_3$ | $C_6H_5$ | $CF_3$ | H | H |
| A-514 | I.1A | $CH_3$ | $C_6H_5$ | $CHF_2$ | H | H |
| A-515 | I.1A | $CH_3$ | $C_6H_5$ | F | H | H |
| A-516 | I.1A | $CH_3$ | $C_6H_5$ | $OCHF_2$ | H | H |
| A-517 | I.1A | $CH_3$ | $C_6H_5$ | $SO_2CH_3$ | H | H |
| A-518 | I.1A | $CH_3$ | 4-$OCH_3$—$C_6H_4$ | H | H | H |
| A-519 | I.1A | $CH_3$ | 4-$OCH_3$—$C_6H_4$ | Cl | H | H |
| A-520 | I.1A | $CH_3$ | 4-$OCH_3$—$C_6H_4$ | $CF_3$ | H | H |
| A-521 | I.1A | $CH_3$ | 4-$OCH_3$—$C_6H_4$ | $CHF_2$ | H | H |
| A-522 | I.1A | $CH_3$ | 4-$OCH_3$—$C_6H_4$ | F | H | H |
| A-523 | I.1A | $CH_3$ | 4-$OCH_3$—$C_6H_4$ | $OCHF_2$ | H | H |
| A-524 | I.1A | $CH_3$ | 4-$OCH_3$—$C_6H_4$ | $SO_2CH_3$ | H | H |
| A-525 | I.1A | $CH_3$ | $CH=CH_2$ | H | H | H |
| A-526 | I.1A | $CH_3$ | $CH=CH_2$ | Cl | H | H |
| A-527 | I.1A | $CH_3$ | $CH=CH_2$ | $CF_3$ | H | H |
| A-528 | I.1A | $CH_3$ | $CH=CH_2$ | $CHF_2$ | H | H |
| A-529 | I.1A | $CH_3$ | $CH=CH_2$ | F | H | H |
| A-530 | I.1A | $CH_3$ | $CH=CH_2$ | $OCHF_2$ | H | H |
| A-531 | I.1A | $CH_3$ | $CH=CH_2$ | $SO_2CH_3$ | H | H |
| A-532 | I.1A | $CH_3$ | $CH=CH—CH_3$ | H | H | H |
| A-533 | I.1A | $CH_3$ | $CH=CH—CH_3$ | Cl | H | H |
| A-534 | I.1A | $CH_3$ | $CH=CH—CH_3$ | $CF_3$ | H | H |
| A-535 | I.1A | $CH_3$ | $CH=CH—CH_3$ | $CHF_2$ | H | H |
| A-536 | I.1A | $CH_3$ | $CH=CH—CH_3$ | F | H | H |
| A-537 | I.1A | $CH_3$ | $CH=CH—CH_3$ | $OCHF_2$ | H | H |
| A-538 | I.1A | $CH_3$ | $CH=CH—CH_3$ | $SO_2CH_3$ | H | H |
| A-539 | I.1A | $CH_3$ | $CH_2CH=CH_2$ | H | H | H |
| A-540 | I.1A | $CH_3$ | $CH_2CH=CH_2$ | Cl | H | H |
| A-541 | I.1A | $CH_3$ | $CH_2CH=CH_2$ | $CF_3$ | H | H |
| A-542 | I.1A | $CH_3$ | $CH_2CH=CH_2$ | $CHF_2$ | H | H |
| A-543 | I.1A | $CH_3$ | $CH_2CH=CH_2$ | F | H | H |
| A-544 | I.1A | $CH_3$ | $CH_2CH=CH_2$ | $OCHF_2$ | H | H |
| A-545 | I.1A | $CH_3$ | $CH_2CH=CH_2$ | $SO_2CH_3$ | H | H |
| A-546 | I.1A | $CH_3$ | $CH_2C\equiv CH$ | H | H | H |
| A-547 | I.1A | $CH_3$ | $CH_2C\equiv CH$ | Cl | H | H |
| A-548 | I.1A | $CH_3$ | $CH_2C\equiv CH$ | $CF_3$ | H | H |
| A-549 | I.1A | $CH_3$ | $CH_2C\equiv CH$ | $CHF_2$ | H | H |
| A-550 | I.1A | $CH_3$ | $CH_2C\equiv CH$ | F | H | H |
| A-551 | I.1A | $CH_3$ | $CH_2C\equiv CH$ | $OCHF_2$ | H | H |

TABLE A-continued

Compounds of the formula I which correspond to the formulae I.1A and I.2A

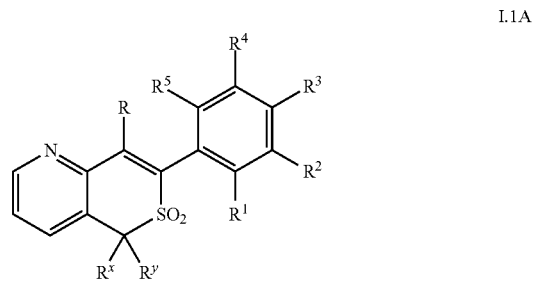

I.1A

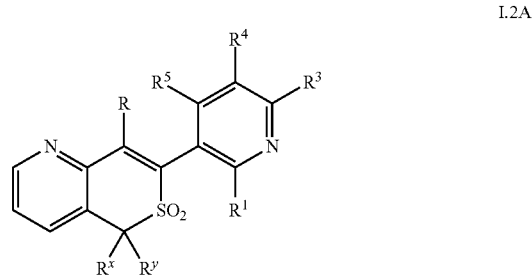

I.2A

| No. | Formula | $R^1$ | $R^2$ | $R^3$ | $R^4$ | $R^5$ |
|---|---|---|---|---|---|---|
| A-552 | I.1A | $CH_3$ | $CH_2C{\equiv}CH$ | $SO_2CH_3$ | H | H |
| A-553 | I.1A | $CH_3$ | $CH_2OCH_2CF_3$ | H | H | H |
| A-554 | I.1A | $CH_3$ | $CH_2OCH_2CF_3$ | Cl | H | H |
| A-555 | I.1A | $CH_3$ | $CH_2OCH_2CF_3$ | $CF_3$ | H | H |
| A-556 | I.1A | $CH_3$ | $CH_2OCH_2CF_3$ | $CHF_2$ | H | H |
| A-557 | I.1A | $CH_3$ | $CH_2OCH_2CF_3$ | F | H | H |
| A-558 | I.1A | $CH_3$ | $CH_2OCH_2CF_3$ | $OCHF_2$ | H | H |
| A-559 | I.1A | $CH_3$ | $CH_2OCH_2CF_3$ | $SO_2CH_3$ | H | H |
| A-560 | I.1A | $CH_3$ | (tetrahydrofuranylmethoxymethyl) | H | H | H |
| A-561 | I.1A | $CH_3$ | (tetrahydrofuranylmethoxymethyl) | Cl | H | H |
| A-562 | I.1A | $CH_3$ | (tetrahydrofuranylmethoxymethyl) | $CF_3$ | H | H |
| A-563 | I.1A | $CH_3$ | (tetrahydrofuranylmethoxymethyl) | $CHF_2$ | H | H |
| A-564 | I.1A | $CH_3$ | (tetrahydrofuranylmethoxymethyl) | F | H | H |
| A-565 | I.1A | $CH_3$ | (tetrahydrofuranylmethoxymethyl) | $OCHF_2$ | H | H |
| A-566 | I.1A | $CH_3$ | (tetrahydrofuranylmethoxymethyl) | $SO_2CH_3$ | H | H |

TABLE A-continued

Compounds of the formula I which correspond to the formulae I.1A and I.2A

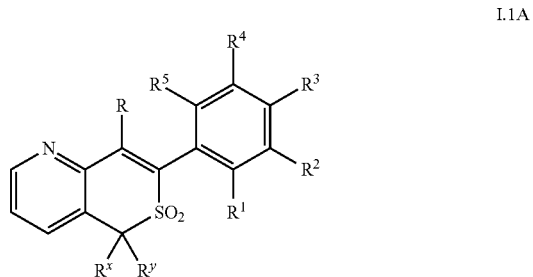

I.1A

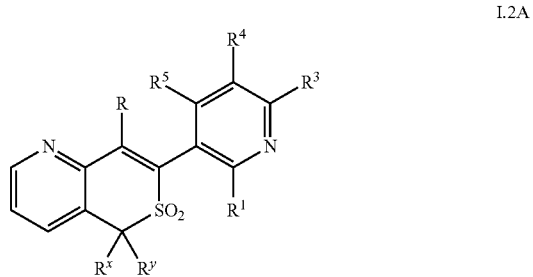

I.2A

| No. | Formula | R¹ | R² | R³ | R⁴ | R⁵ |
|---|---|---|---|---|---|---|
| A-567 | I.1A | CH₃ | OCH₂CH₃ | H | H | H |
| A-568 | I.1A | CH₃ | OCH₂CH₃ | Cl | H | H |
| A-569 | I.1A | CH₃ | OCH₂CH₃ | CF₃ | H | H |
| A-570 | I.1A | CH₃ | OCH₂CH₃ | CHF₂ | H | H |
| A-571 | I.1A | CH₃ | OCH₂CH₃ | F | H | H |
| A-572 | I.1A | CH₃ | OCH₂CH₃ | OCHF₂ | H | H |
| A-573 | I.1A | CH₃ | OCH₂CH₃ | SO₂CH₃ | H | H |
| A-574 | I.1A | CH₃ | OCH₂CH₂OCH₃ | H | H | H |
| A-575 | I.1A | CH₃ | OCH₂CH₂OCH₃ | Cl | H | H |
| A-576 | I.1A | CH₃ | OCH₂CH₂OCH₃ | CF₃ | H | H |
| A-577 | I.1A | CH₃ | OCH₂CH₂OCH₃ | CHF₂ | H | H |
| A-578 | I.1A | CH₃ | OCH₂CH₂OCH₃ | F | H | H |
| A-579 | I.1A | CH₃ | OCH₂CH₂OCH₃ | OCHF₂ | H | H |
| A-580 | I.1A | CH₃ | OCH₂CH₂OCH₃ | SO₂CH₃ | H | H |
| A-581 | I.1A | CH₃ | SO₂CH₃ | H | H | H |
| A-582 | I.1A | CH₃ | SO₂CH₃ | Cl | H | H |
| A-583 | I.1A | CH₃ | SO₂CH₃ | CF₃ | H | H |
| A-584 | I.1A | CH₃ | SO₂CH₃ | CHF₂ | H | H |
| A-585 | I.1A | CH₃ | SO₂CH₃ | F | H | H |
| A-586 | I.1A | CH₃ | SO₂CH₃ | OCHF₂ | H | H |
| A-587 | I.1A | CH₃ | SO₂CH₃ | SO₂CH₃ | H | H |
| A-588 | I.1A | CH₃ | SO₂CH₂CH₃ | H | H | H |
| A-589 | I.1A | CH₃ | SO₂CH₂CH₃ | Cl | H | H |
| A-590 | I.1A | CH₃ | SO₂CH₂CH₃ | CF₃ | H | H |
| A-591 | I.1A | CH₃ | SO₂CH₂CH₃ | CHF₂ | H | H |
| A-592 | I.1A | CH₃ | SO₂CH₂CH₃ | F | H | H |
| A-593 | I.1A | CH₃ | SO₂CH₂CH₃ | OCHF₂ | H | H |
| A-594 | I.1A | CH₃ | SO₂CH₂CH₃ | SO₂CH₃ | H | H |
| A-595 | I.1A | CH₃ | SO₂CH(CH₃)₂ | H | H | H |
| A-596 | I.1A | CH₃ | SO₂CH(CH₃)₂ | Cl | H | H |
| A-597 | I.1A | CH₃ | SO₂CH(CH₃)₂ | CF₃ | H | H |
| A-598 | I.1A | CH₃ | SO₂CH(CH₃)₂ | CHF₂ | H | H |
| A-599 | I.1A | CH₃ | SO₂CH(CH₃)₂ | F | H | H |
| A-600 | I.1A | CH₃ | SO₂CH(CH₃)₂ | OCHF₂ | H | H |
| A-601 | I.1A | CH₃ | SO₂CH(CH₃)₂ | SO₂CH₃ | H | H |
| A-602 | I.1A | CH₃ | COOCH₃ | H | H | H |
| A-603 | I.1A | CH₃ | COOCH₃ | Cl | H | H |
| A-604 | I.1A | CH₃ | COOCH₃ | CF₃ | H | H |
| A-605 | I.1A | CH₃ | COOCH₃ | CHF₂ | H | H |
| A-606 | I.1A | CH₃ | COOCH₃ | F | H | H |
| A-607 | I.1A | CH₃ | COOCH₃ | OCHF₂ | H | H |
| A-608 | I.1A | CH₃ | COOCH₃ | SO₂CH₃ | H | H |
| A-609 | I.1A | CH₃ | COOCH₂CH₃ | H | H | H |
| A-610 | I.1A | CH₃ | COOCH₂CH₃ | Cl | H | H |
| A-611 | I.1A | CH₃ | COOCH₂CH₃ | CF₃ | H | H |
| A-612 | I.1A | CH₃ | COOCH₂CH₃ | CHF₂ | H | H |

TABLE A-continued

Compounds of the formula I which correspond to the formulae I.1A and I.2A

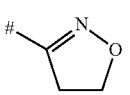

I.1A

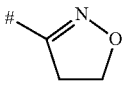

I.2A

| No. | Formula | $R^1$ | $R^2$ | $R^3$ | $R^4$ | $R^5$ |
|---|---|---|---|---|---|---|
| A-613 | I.1A | $CH_3$ | $COOCH_2CH_3$ | F | H | H |
| A-614 | I.1A | $CH_3$ | $COOCH_2CH_3$ | $OCHF_2$ | H | H |
| A-615 | I.1A | $CH_3$ | $COOCH_2CH_3$ | $SO_2CH_3$ | H | H |
| A-616 | I.1A | $CH_3$ | $\#^2$—$CH_2CH_2SO_2$—$\#^3$ | | H | H |
| A-617 | I.1A | $CH_3$ | $\#^2$—$CH(CH_3)CH_2SO_2$—$\#^3$ | | H | H |
| A-618 | I.1A | $CH_3$ | $\#^2$—$C(CH_3)_2CH_2SO_2$—$\#^3$ | | H | H |
| A-619 | I.1A | $CH_3$ | $\#^2$—$SO_2CH_2CH_2SO_2$—$\#^3$ | | H | H |
| A-620 | I.1A | $CH_3$ | $\#^2$—$CH(OCH_2CH_2F)CH_2CH_2SO_2$—$\#^3$ | | H | H |
| A-621 | I.1A | $CH_3$ | $\#^2$—$C(=NOCH_3)CH_2CH_2SO_2$—$\#^3$ | | H | H |
| A-622 | I.1A | $CH_3$ | $\#^2$—$SO_2CH_2CH_2C(CH_3)_2$—$\#^3$ | | H | H |
| A-623 | I.1A | $CH_3$ | $\#^2$—$N(CH_3)C(=O)S$—$\#^3$ | | H | H |
| A-624 | I.1A | $CH_3$ | $\#^2$—$C(=O)N(CH_3)SO_2$—$\#^3$ | | H | H |
| A-625 | I.1A | $CF_3$ | 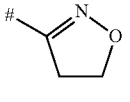 | H | H | H |
| A-626 | I.1A | $CF_3$ | 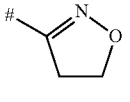 | Cl | H | H |
| A-627 | I.1A | $CF_3$ | 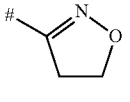 | $CF_3$ | H | H |
| A-628 | I.1A | $CF_3$ | 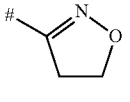 | $CHF_2$ | H | H |
| A-629 | I.1A | $CF_3$ | 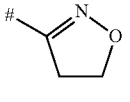 | F | H | H |
| A-630 | I.1A | $CF_3$ | 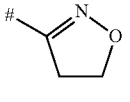 | $OCHF_2$ | H | H |

TABLE A-continued
Compounds of the formula I which correspond to the formulae I.1A and I.2A
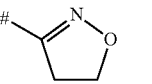
I.1A
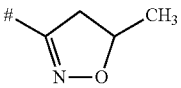
I.2A
| No. | Formula | R¹ | R² | R³ | R⁴ | R⁵ |
|-----|---------|-----|-----|-----|-----|-----|
| A-631 | I.1A | $CF_3$ | 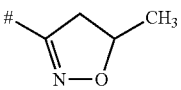 | $SO_2CH_3$ | H | H |
| A-632 | I.1A | $CF_3$ | 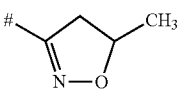 | H | H | H |
| A-633 | I.1A | $CF_3$ | 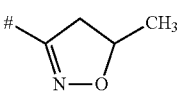 | Cl | H | H |
| A-634 | I.1A | $CF_3$ | 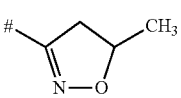 | $CF_3$ | H | H |
| A-635 | I.1A | $CF_3$ | 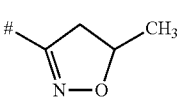 | $CHF_2$ | H | H |
| A-636 | I.1A | $CF_3$ | (same isoxazoline with CH₃) | F | H | H |
| A-637 | I.1A | $CF_3$ | (same isoxazoline with CH₃) | $OCHF_2$ | H | H |
| A-638 | I.1A | $CF_3$ | 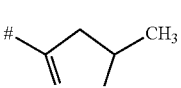 | $SO_2CH_3$ | H | H |
| A-639 | I.1A | $CF_3$ | 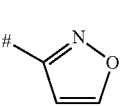 | H | H | H |

TABLE A-continued

Compounds of the formula I which correspond to the formulae I.1A and I.2A

I.1A

I.2A

| No. | Formula | R¹ | R² | R³ | R⁴ | R⁵ |
|---|---|---|---|---|---|---|
| A-640 | I.1A | $CF_3$ | #-isoxazol-3-yl | Cl | H | H |
| A-641 | I.1A | $CF_3$ | #-isoxazol-3-yl | $CF_3$ | H | H |
| A-642 | I.1A | $CF_3$ | #-isoxazol-3-yl | $CHF_2$ | H | H |
| A-643 | I.1A | $CF_3$ | #-isoxazol-3-yl | F | H | H |
| A-644 | I.1A | $CF_3$ | #-isoxazol-3-yl | $OCHF_2$ | H | H |
| A-645 | I.1A | $CF_3$ | #-isoxazol-3-yl | $SO_2CH_3$ | H | H |
| A-646 | I.1A | $CF_3$ | #-(5-methyl-isoxazol-3-yl) | H | H | H |
| A-647 | I.1A | $CF_3$ | #-(5-methyl-isoxazol-3-yl) | Cl | H | H |

TABLE A-continued

Compounds of the formula I which correspond to the formulae I.1A and I.2A

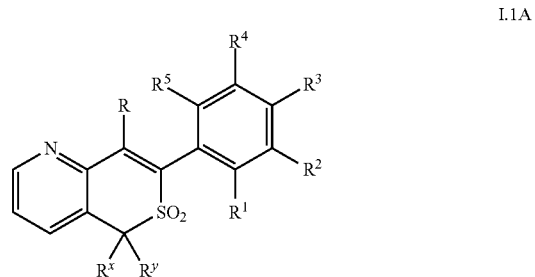
I.1A

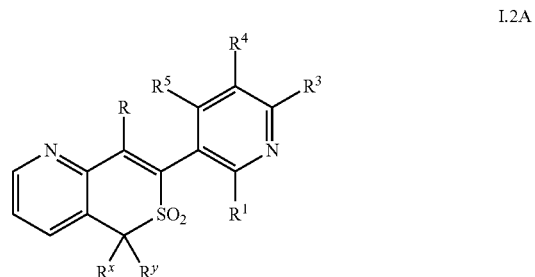
I.2A

| No. | Formula | R¹ | R² | R³ | R⁴ | R⁵ |
|---|---|---|---|---|---|---|
| A-648 | I.1A | $CF_3$ | 3-methyl-5-yl isoxazole (#-C=N-O-C(CH_3)) | $CF_3$ | H | H |
| A-649 | I.1A | $CF_3$ | 3-methyl-5-yl isoxazole | $CHF_2$ | H | H |
| A-650 | I.1A | $CF_3$ | 3-methyl-5-yl isoxazole | F | H | H |
| A-651 | I.1A | $CF_3$ | 3-methyl-5-yl isoxazole | $OCHF_2$ | H | H |
| A-652 | I.1A | $CF_3$ | 3-methyl-5-yl isoxazole | $SO_2CH_3$ | H | H |
| A-653 | I.1A | $CF_3$ | 3-methyl-4,5-dihydroisoxazol-5-yl | H | H | H |
| A-654 | I.1A | $CF_3$ | 3-methyl-4,5-dihydroisoxazol-5-yl | Cl | H | H |
| A-655 | I.1A | $CF_3$ | 3-methyl-4,5-dihydroisoxazol-5-yl | $CF_3$ | H | H |
| A-656 | I.1A | $CF_3$ | 3-methyl-4,5-dihydroisoxazol-5-yl | $CHF_2$ | H | H |

TABLE A-continued

Compounds of the formula I which correspond to the formulae I.1A and I.2A

I.1A

I.2A

| No. | Formula | R¹ | R² | R³ | R⁴ | R⁵ |
|---|---|---|---|---|---|---|
| A-657 | I.1A | $CF_3$ | #―[4,5-dihydro-3-methylisoxazol-5-yl] | F | H | H |
| A-658 | I.1A | $CF_3$ | #―[4,5-dihydro-3-methylisoxazol-5-yl] | $OCHF_2$ | H | H |
| A-659 | I.1A | $CF_3$ | #―[4,5-dihydro-3-methylisoxazol-5-yl] | $SO_2CH_3$ | H | H |
| A-660 | I.1A | $CF_3$ | #―[3-methylisoxazol-5-yl] | H | H | H |
| A-661 | I.1A | $CF_3$ | #―[3-methylisoxazol-5-yl] | Cl | H | H |
| A-662 | I.1A | $CF_3$ | #―[3-methylisoxazol-5-yl] | $CF_3$ | H | H |
| A-663 | I.1A | $CF_3$ | #―[3-methylisoxazol-5-yl] | $CHF_2$ | H | H |
| A-664 | I.1A | $CF_3$ | #―[3-methylisoxazol-5-yl] | F | H | H |

TABLE A-continued
Compounds of the formula I which correspond to the formulae I.1A and I.2A
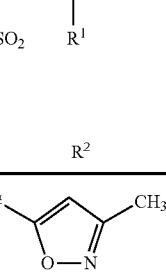
I.1A
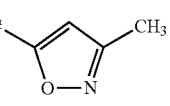
I.2A
| No. | Formula | R¹ | R² | R³ | R⁴ | R⁵ |
|---|---|---|---|---|---|---|
| A-665 | I.1A | $CF_3$ | #-(5-yl-3-methylisoxazole) | $OCHF_2$ | H | H |
| A-666 | I.1A | $CF_3$ | #-(5-yl-3-methylisoxazole) | $SO_2CH_3$ | H | H |
| A-667 | I.1A | $CF_3$ | #-(2-yl-thiazole) | H | H | H |
| A-668 | I.1A | $CF_3$ | #-(2-yl-thiazole) | Cl | H | H |
| A-669 | I.1A | $CF_3$ | #-(2-yl-thiazole) | $CF_3$ | H | H |
| A-670 | I.1A | $CF_3$ | #-(2-yl-thiazole) | $CHF_2$ | H | H |
| A-671 | I.1A | $CF_3$ | #-(2-yl-thiazole) | F | H | H |
| A-672 | I.1A | $CF_3$ | #-(2-yl-thiazole) | $OCHF_2$ | H | H |

TABLE A-continued
Compounds of the formula I which correspond to the formulae I.1A and I.2A
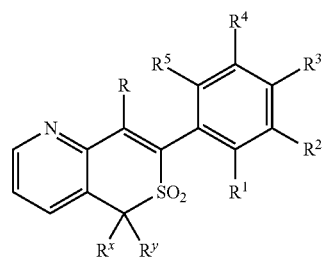
I.1A
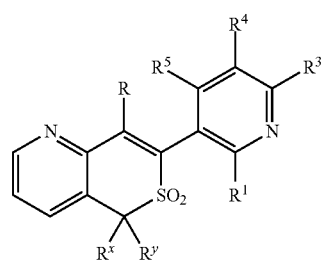
I.2A
| No. | Formula | R¹ | R² | R³ | R⁴ | R⁵ |
|---|---|---|---|---|---|---|
| A-673 | I.1A | $CF_3$ | 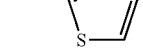 | $SO_2CH_3$ | H | H |
| A-674 | I.1A | $CF_3$ |  | H | H | H |
| A-675 | I.1A | $CF_3$ |  | Cl | H | H |
| A-676 | I.1A | $CF_3$ | 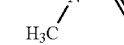 | $CF_3$ | H | H |
| A-677 | I.1A | $CF_3$ |  | $CHF_2$ | H | H |
| A-678 | I.1A | $CF_3$ |  | F | H | H |

TABLE A-continued
Compounds of the formula I which correspond to the formulae I.1A and I.2A
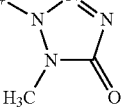
I.1A
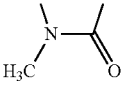
I.2A
| No. | Formula | R¹ | R² | R³ | R⁴ | R⁵ |
|---|---|---|---|---|---|---|
| A-679 | I.1A | $CF_3$ | 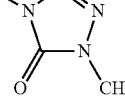 | $OCHF_2$ | H | H |
| A-680 | I.1A | $CF_3$ | 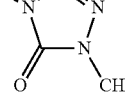 | $SO_2CH_3$ | H | H |
| A-681 | I.1A | $CF_3$ | 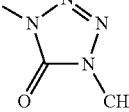 | H | H | H |
| A-682 | I.1A | $CF_3$ | 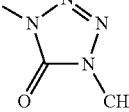 | Cl | H | H |
| A-683 | I.1A | $CF_3$ | 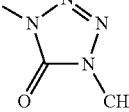 | $CF_3$ | H | H |
| A-684 | I.1A | $CF_3$ | 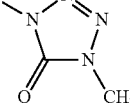 | $CHF_2$ | H | H |

TABLE A-continued

Compounds of the formula I which correspond to the formulae I.1A and I.2A

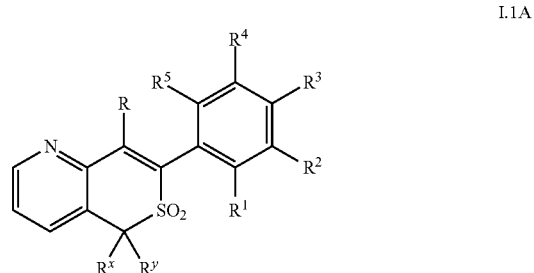

I.1A

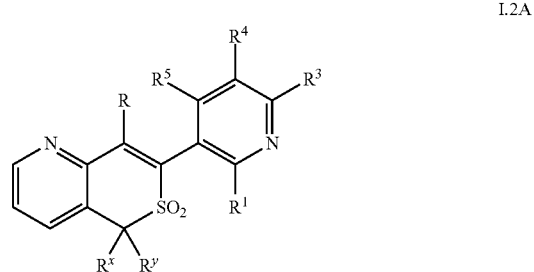

I.2A

| No. | Formula | R¹ | R² | R³ | R⁴ | R⁵ |
|---|---|---|---|---|---|---|
| A-685 | I.1A | $CF_3$ | # -N-N=N-N(CH₃)-C(=O)- (1-tetrazol-5(4H)-one, 4-methyl) | F | H | H |
| A-686 | I.1A | $CF_3$ | # -N-N=N-N(CH₃)-C(=O)- (1-tetrazol-5(4H)-one, 4-methyl) | $OCHF_2$ | H | H |
| A-687 | I.1A | $CF_3$ | # -N-N=N-N(CH₃)-C(=O)- (1-tetrazol-5(4H)-one, 4-methyl) | $SO_2CH_3$ | H | H |
| A-688 | I.1A | $CF_3$ | # -morpholin-4-yl | H | H | H |
| A-689 | I.1A | $CF_3$ | # -morpholin-4-yl | Cl | H | H |
| A-690 | I.1A | $CF_3$ | # -morpholin-4-yl | $CF_3$ | H | H |
| A-691 | I.1A | $CF_3$ | # -morpholin-4-yl | $CHF_2$ | H | H |

TABLE A-continued

Compounds of the formula I which correspond to the formulae I.1A and I.2A

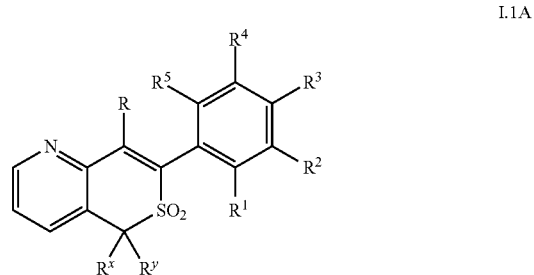

I.1A

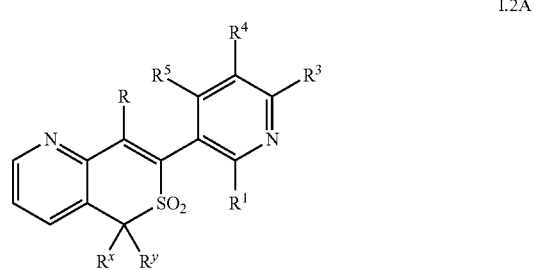

I.2A

| No. | Formula | R¹ | R² | R³ | R⁴ | R⁵ |
|---|---|---|---|---|---|---|
| A-692 | I.1A | $CF_3$ | #-N-morpholine | F | H | H |
| A-693 | I.1A | $CF_3$ | #-N-morpholine | $OCHF_2$ | H | H |
| A-694 | I.1A | $CF_3$ | #-N-morpholine | $SO_2CH_3$ | H | H |
| A-695 | I.1A | $CF_3$ | $C_6H_5$ | H | H | H |
| A-696 | I.1A | $CF_3$ | $C_6H_5$ | Cl | H | H |
| A-697 | I.1A | $CF_3$ | $C_6H_5$ | $CF_3$ | H | H |
| A-698 | I.1A | $CF_3$ | $C_6H_5$ | $CHF_2$ | H | H |
| A-699 | I.1A | $CF_3$ | $C_6H_5$ | F | H | H |
| A-700 | I.1A | $CF_3$ | $C_6H_5$ | $OCHF_2$ | H | H |
| A-701 | I.1A | $CF_3$ | $C_6H_5$ | $SO_2CH_3$ | H | H |
| A-702 | I.1A | $CF_3$ | 4-$OCH_3$—$C_6H_4$ | H | H | H |
| A-703 | I.1A | $CF_3$ | 4-$OCH_3$—$C_6H_4$ | Cl | H | H |
| A-704 | I.1A | $CF_3$ | 4-$OCH_3$—$C_6H_4$ | $CF_3$ | H | H |
| A-705 | I.1A | $CF_3$ | 4-$OCH_3$—$C_6H_4$ | $CHF_2$ | H | H |
| A-706 | I.1A | $CF_3$ | 4-$OCH_3$—$C_6H_4$ | F | H | H |
| A-707 | I.1A | $CF_3$ | 4-$OCH_3$—$C_6H_4$ | $OCHF_2$ | H | H |
| A-708 | I.1A | $CF_3$ | 4-$OCH_3$—$C_6H_4$ | $SO_2CH_3$ | H | H |
| A-709 | I.1A | $CF_3$ | $CH=CH_2$ | H | H | H |
| A-710 | I.1A | $CF_3$ | $CH=CH_2$ | Cl | H | H |
| A-711 | I.1A | $CF_3$ | $CH=CH_2$ | $CF_3$ | H | H |
| A-712 | I.1A | $CF_3$ | $CH=CH_2$ | $CHF_2$ | H | H |
| A-713 | I.1A | $CF_3$ | $CH=CH_2$ | F | H | H |
| A-714 | I.1A | $CF_3$ | $CH=CH_2$ | $OCHF_2$ | H | H |
| A-715 | I.1A | $CF_3$ | $CH=CH_2$ | $SO_2CH_3$ | H | H |
| A-716 | I.1A | $CF_3$ | $CH=CH$—$CH_3$ | H | H | H |
| A-717 | I.1A | $CF_3$ | $CH=CH$—$CH_3$ | Cl | H | H |
| A-718 | I.1A | $CF_3$ | $CH=CH$—$CH_3$ | $CF_3$ | H | H |
| A-719 | I.1A | $CF_3$ | $CH=CH$—$CH_3$ | $CHF_2$ | H | H |
| A-720 | I.1A | $CF_3$ | $CH=CH$—$CH_3$ | F | H | H |
| A-721 | I.1A | $CF_3$ | $CH=CH$—$CH_3$ | $OCHF_2$ | H | H |
| A-722 | I.1A | $CF_3$ | $CH=CH$—$CH_3$ | $SO_2CH_3$ | H | H |
| A-723 | I.1A | $CF_3$ | $CH_2CH=CH_2$ | H | H | H |

TABLE A-continued

Compounds of the formula I which correspond to the formulae I.1A and I.2A

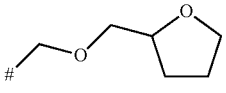

I.1A

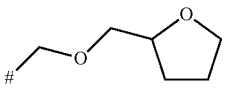

I.2A

| No. | Formula | R¹ | R² | R³ | R⁴ | R⁵ |
|---|---|---|---|---|---|---|
| A-724 | I.1A | $CF_3$ | $CH_2CH=CH_2$ | Cl | H | H |
| A-725 | I.1A | $CF_3$ | $CH_2CH=CH_2$ | $CF_3$ | H | H |
| A-726 | I.1A | $CF_3$ | $CH_2CH=CH_2$ | $CHF_2$ | H | H |
| A-727 | I.1A | $CF_3$ | $CH_2CH=CH_2$ | F | H | H |
| A-728 | I.1A | $CF_3$ | $CH_2CH=CH_2$ | $OCHF_2$ | H | H |
| A-729 | I.1A | $CF_3$ | $CH_2CH=CH_2$ | $SO_2CH_3$ | H | H |
| A-730 | I.1A | $CF_3$ | $CH_2C\equiv CH$ | H | H | H |
| A-731 | I.1A | $CF_3$ | $CH_2C\equiv CH$ | Cl | H | H |
| A-732 | I.1A | $CF_3$ | $CH_2CH=CH$ | $CF_3$ | H | H |
| A-733 | I.1A | $CF_3$ | $CH_2C\equiv CH$ | $CHF_2$ | H | H |
| A-734 | I.1A | $CF_3$ | $CH_2C\equiv CH$ | F | H | H |
| A-735 | I.1A | $CF_3$ | $CH_2C\equiv CH$ | $OCHF_2$ | H | H |
| A-736 | I.1A | $CF_3$ | $CH_2C\equiv CH$ | $SO_2CH_3$ | H | H |
| A-737 | I.1A | $CF_3$ | $CH_2OCH_2CF_3$ | H | H | H |
| A-738 | I.1A | $CF_3$ | $CH_2OCH_2CF_3$ | Cl | H | H |
| A-739 | I.1A | $CF_3$ | $CH_2OCH_2CF_3$ | $CF_3$ | H | H |
| A-740 | I.1A | $CF_3$ | $CH_2OCH_2CF_3$ | $CHF_2$ | H | H |
| A-741 | I.1A | $CF_3$ | $CH_2OCH_2CF_3$ | F | H | H |
| A-742 | I.1A | $CF_3$ | $CH_2OCH_2CF_3$ | $OCHF_2$ | H | H |
| A-743 | I.1A | $CF_3$ | $CH_2OCH_2CF_3$ | $SO_2CH_3$ | H | H |
| A-744 | I.1A | $CF_3$ | 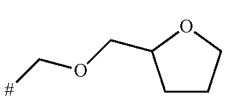 | H | H | H |
| A-745 | I.1A | $CF_3$ | 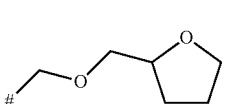 | Cl | H | H |
| A-746 | I.1A | $CF_3$ | 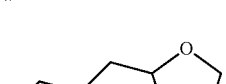 | $CF_3$ | H | H |
| A-747 | I.1A | $CF_3$ | | $CHF_2$ | H | H |
| A-748 | I.1A | $CF_3$ | | F | H | H |

TABLE A-continued

Compounds of the formula I which correspond to the formulae I.1A and I.2A

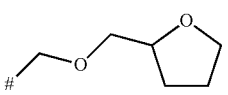

I.1A

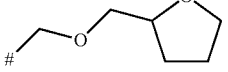

I.2A

| No. | Formula | R¹ | R² | R³ | R⁴ | R⁵ |
|---|---|---|---|---|---|---|
| A-749 | I.1A | $CF_3$ | #-CH$_2$-O-CH$_2$-(tetrahydrofuran-2-yl) | $OCHF_2$ | H | H |
| A-750 | I.1A | $CF_3$ | #-CH$_2$-O-CH$_2$-(tetrahydrofuran-2-yl) | $SO_2CH_3$ | H | H |
| A-751 | I.1A | $CF_3$ | $OCH_2CH_3$ | H | H | H |
| A-752 | I.1A | $CF_3$ | $OCH_2CH_3$ | Cl | H | H |
| A-753 | I.1A | $CF_3$ | $OCH_2CH_3$ | $CF_3$ | H | H |
| A-754 | I.1A | $CF_3$ | $OCH_2CH_3$ | $CHF_2$ | H | H |
| A-755 | I.1A | $CF_3$ | $OCH_2CH_3$ | F | H | H |
| A-756 | I.1A | $CF_3$ | $OCH_2CH_3$ | $OCHF_2$ | H | H |
| A-757 | I.1A | $CF_3$ | $OCH_2CH_3$ | $SO_2CH_3$ | H | H |
| A-758 | I.1A | $CF_3$ | $OCH_2CH_2OCH_3$ | H | H | H |
| A-759 | I.1A | $CF_3$ | $OCH_2CH_2OCH_3$ | Cl | H | H |
| A-760 | I.1A | $CF_3$ | $OCH_2CH_2OCH_3$ | $CF_3$ | H | H |
| A-761 | I.1A | $CF_3$ | $OCH_2CH_2OCH_3$ | $CHF_2$ | H | H |
| A-762 | I.1A | $CF_3$ | $OCH_2CH_2OCH_3$ | F | H | H |
| A-763 | I.1A | $CF_3$ | $OCH_2CH_2OCH_3$ | $OCHF_2$ | H | H |
| A-764 | I.1A | $CF_3$ | $OCH_2CH_2OCH_3$ | $SO_2CH_3$ | H | H |
| A-765 | I.1A | $CF_3$ | $SO_2CH_3$ | H | H | H |
| A-766 | I.1A | $CF_3$ | $SO_2CH_3$ | Cl | H | H |
| A-767 | I.1A | $CF_3$ | $SO_2CH_3$ | $CF_3$ | H | H |
| A-768 | I.1A | $CF_3$ | $SO_2CH_3$ | $CHF_2$ | H | H |
| A-769 | I.1A | $CF_3$ | $SO_2CH_3$ | F | H | H |
| A-770 | I.1A | $CF_3$ | $SO_2CH_3$ | $OCHF_2$ | H | H |
| A-771 | I.1A | $CF_3$ | $SO_2CH_3$ | $SO_2CH_3$ | H | H |
| A-772 | I.1A | $CF_3$ | $SO_2CH_2CH_3$ | H | H | H |
| A-773 | I.1A | $CF_3$ | $SO_2CH_2CH_3$ | Cl | H | H |
| A-774 | I.1A | $CF_3$ | $SO_2CH_2CH_3$ | $CF_3$ | H | H |
| A-775 | I.1A | $CF_3$ | $SO_2CH_2CH_3$ | $CHF_2$ | H | H |
| A-776 | I.1A | $CF_3$ | $SO_2CH_2CH_3$ | F | H | H |
| A-777 | I.1A | $CF_3$ | $SO_2CH_2CH_3$ | $OCHF_2$ | H | H |
| A-778 | I.1A | $CF_3$ | $SO_2CH_2CH_3$ | $SO_2CH_3$ | H | H |
| A-779 | I.1A | $CF_3$ | $SO_2CH(CH_3)_2$ | H | H | H |
| A-780 | I.1A | $CF_3$ | $SO_2CH(CH_3)_2$ | Cl | H | H |
| A-781 | I.1A | $CF_3$ | $SO_2CH(CH_3)_2$ | $CF_3$ | H | H |
| A-782 | I.1A | $CF_3$ | $SO_2CH(CH_3)_2$ | $CHF_2$ | H | H |
| A-783 | I.1A | $CF_3$ | $SO_2CH(CH_3)_2$ | F | H | H |
| A-784 | I.1A | $CF_3$ | $SO_2CH(CH_3)_2$ | $OCHF_2$ | H | H |
| A-785 | I.1A | $CF_3$ | $SO_2CH(CH_3)_2$ | $SO_2CH_3$ | H | H |

TABLE A-continued

Compounds of the formula I which correspond to the formulae I.1A and I.2A

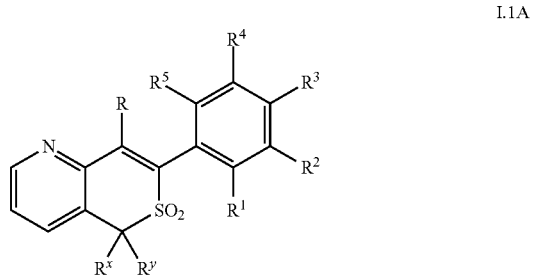
I.1A

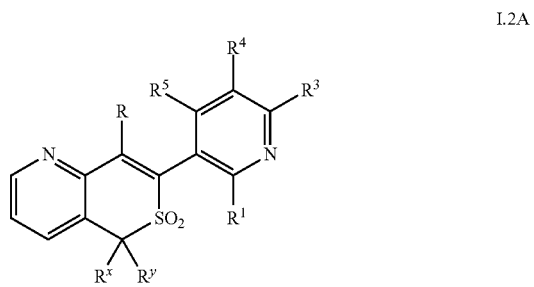
I.2A

| No. | Formula | R$^1$ | R$^2$ | R$^3$ | R$^4$ | R$^5$ |
|---|---|---|---|---|---|---|
| A-786 | I.1A | CF$_3$ | COOCH$_3$ | H | H | H |
| A-787 | I.1A | CF$_3$ | COOCH$_3$ | Cl | H | H |
| A-788 | I.1A | CF$_3$ | COOCH$_3$ | CF$_3$ | H | H |
| A-789 | I.1A | CF$_3$ | COOCH$_3$ | CHF$_2$ | H | H |
| A-790 | I.1A | CF$_3$ | COOCH$_3$ | F | H | H |
| A-791 | I.1A | CF$_3$ | COOCH$_3$ | OCHF$_2$ | H | H |
| A-792 | I.1A | CF$_3$ | COOCH$_3$ | SO$_2$CH$_3$ | H | H |
| A-793 | I.1A | CF$_3$ | COOCH$_2$CH$_3$ | H | H | H |
| A-794 | I.1A | CF$_3$ | COOCH$_2$CH$_3$ | Cl | H | H |
| A-795 | I.1A | CF$_3$ | COOCH$_2$CH$_3$ | CF$_3$ | H | H |
| A-796 | I.1A | CF$_3$ | COOCH$_2$CH$_3$ | CHF$_2$ | H | H |
| A-797 | I.1A | CF$_3$ | COOCH$_2$CH$_3$ | F | H | H |
| A-798 | I.1A | CF$_3$ | COOCH$_2$CH$_3$ | OCHF$_2$ | H | H |
| A-799 | I.1A | CF$_3$ | COOCH$_2$CH$_3$ | SO$_2$CH$_3$ | H | H |
| A-800 | I.1A | CF$_3$ | #$^2$—CH$_2$CH$_2$SO$_2$—#$^3$ | | H | H |
| A-801 | I.1A | CF$_3$ | #$^2$—CH(CH$_3$)CH$_2$SO$_2$—#$^3$ | | H | H |
| A-802 | I.1A | CF$_3$ | #$^2$—C(CH$_3$)$_2$CH$_2$SO$_2$—#$^3$ | | H | H |
| A-803 | I.1A | CF$_3$ | #$^2$—SO$_2$CH$_2$CH$_2$SO$_2$—#$^3$ | | H | H |
| A-804 | I.1A | CF$_3$ | #$^2$—CH(OCH$_2$CH$_2$F)CH$_2$CH$_2$SO$_2$—#$^3$ | | H | H |
| A-805 | I.1A | CF$_3$ | #$^2$—C(=NOCH$_3$)CH$_2$CH$_2$SO$_2$—#$^3$ | | H | H |
| A-806 | I.1A | CF$_3$ | #$^2$—SO$_2$CH$_2$CH$_2$C(CH$_3$)$_2$—#$^3$ | | H | H |
| A-807 | I.1A | CF$_3$ | #$^2$—N(CH$_3$)C(=O)S—#$^3$ | | H | H |
| A-808 | I.1A | CF$_3$ | #$^2$—C(=O)N(CH$_3$)SO$_2$—#$^3$ | | H | H |
| A-809 | I.1A | OCF$_3$ | (3-isoxazolinyl) | H | H | H |
| A-810 | I.1A | OCF$_3$ | (3-isoxazolinyl) | Cl | H | H |
| A-811 | I.1A | OCF$_3$ | (3-isoxazolinyl) | CF$_3$ | H | H |
| A-812 | I.1A | OCF$_3$ | (3-isoxazolinyl) | CHF$_2$ | H | H |

TABLE A-continued

Compounds of the formula I which correspond to the formulae I.1A and I.2A

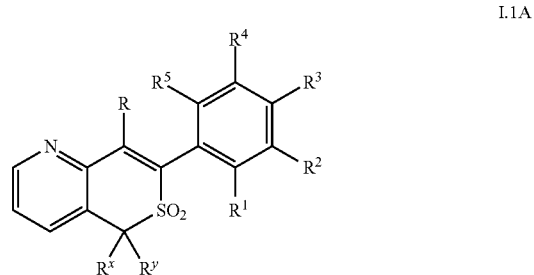
I.1A

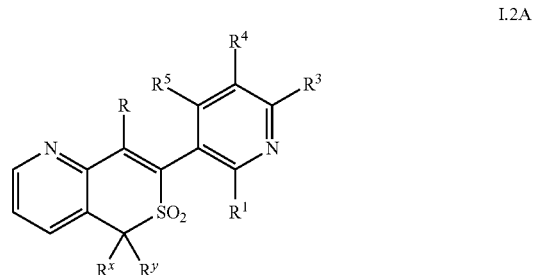
I.2A

| No. | Formula | R¹ | R² | R³ | R⁴ | R⁵ |
|---|---|---|---|---|---|---|
| A-813 | I.1A | $OCF_3$ | # 3-(4,5-dihydroisoxazol) | F | H | H |
| A-814 | I.1A | $OCF_3$ | # 3-(4,5-dihydroisoxazol) | $OCHF_2$ | H | H |
| A-815 | I.1A | $OCF_3$ | # 3-(4,5-dihydroisoxazol) | $SO_2CH_3$ | H | H |
| A-816 | I.1A | $OCF_3$ | # 3-(5-methyl-4,5-dihydroisoxazol) | H | H | H |
| A-817 | I.1A | $OCF_3$ | # 3-(5-methyl-4,5-dihydroisoxazol) | Cl | H | H |
| A-818 | I.1A | $OCF_3$ | # 3-(5-methyl-4,5-dihydroisoxazol) | $CF_3$ | H | H |
| A-819 | I.1A | $OCF_3$ | # 3-(5-methyl-4,5-dihydroisoxazol) | $CHF_2$ | H | H |
| A-820 | I.1A | $OCF_3$ | # 3-(5-methyl-4,5-dihydroisoxazol) | F | H | H |
| A-821 | I.1A | $OCF_3$ | # 3-(5-methyl-4,5-dihydroisoxazol) | $OCHF_2$ | H | H |

TABLE A-continued
Compounds of the formula I which correspond to the formulae I.1A and I.2A
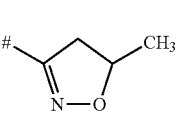
I.1A
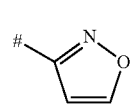
I.2A
| No. | Formula | R¹ | R² | R³ | R⁴ | R⁵ |
|---|---|---|---|---|---|---|
| A-822 | I.1A | OCF$_3$ | 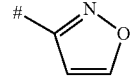 | SO$_2$CH$_3$ | H | H |
| A-823 | I.1A | OCF$_3$ | 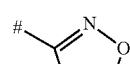 | H | H | H |
| A-824 | I.1A | OCF$_3$ | 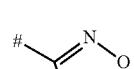 | Cl | H | H |
| A-825 | I.1A | OCF$_3$ | 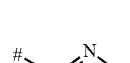 | CF$_3$ | H | H |
| A-826 | I.1A | OCF$_3$ | 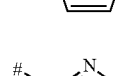 | CHF$_2$ | H | H |
| A-827 | I.1A | OCF$_3$ | 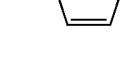 | F | H | H |
| A-828 | I.1A | OCF$_3$ | 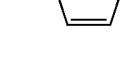 | OCHF$_2$ | H | H |
| A-829 | I.1A | OCF$_3$ | 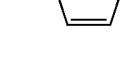 | SO$_2$CH$_3$ | H | H |

TABLE A-continued

Compounds of the formula I which correspond to the formulae I.1A and I.2A

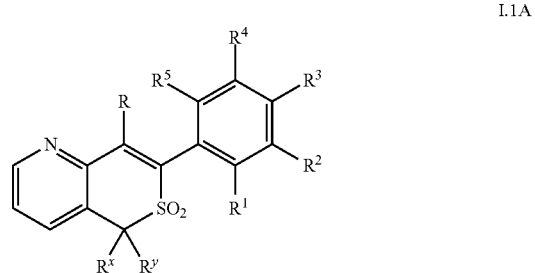

I.1A

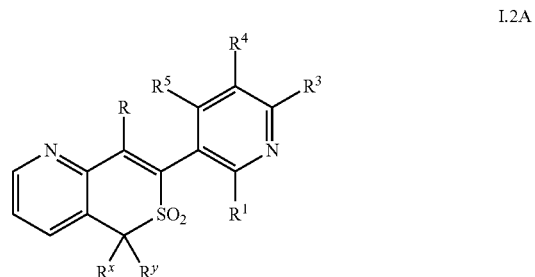

I.2A

| No. | Formula | R¹ | R² | R³ | R⁴ | R⁵ |
|---|---|---|---|---|---|---|
| A-830 | I.1A | OCF$_3$ | 3-CH$_3$-isoxazol-5-yl (3-yl attach, 5-CH$_3$) | H | H | H |
| A-831 | I.1A | OCF$_3$ | 3-CH$_3$-isoxazol-5-yl (3-yl attach, 5-CH$_3$) | Cl | H | H |
| A-832 | I.1A | OCF$_3$ | 3-CH$_3$-isoxazol-5-yl (3-yl attach, 5-CH$_3$) | CF$_3$ | H | H |
| A-833 | I.1A | OCF$_3$ | 3-CH$_3$-isoxazol-5-yl (3-yl attach, 5-CH$_3$) | CHF$_2$ | H | H |
| A-834 | I.1A | OCF$_3$ | 3-CH$_3$-isoxazol-5-yl (3-yl attach, 5-CH$_3$) | F | H | H |
| A-835 | I.1A | OCF$_3$ | 3-CH$_3$-isoxazol-5-yl (3-yl attach, 5-CH$_3$) | OCHF$_2$ | H | H |
| A-836 | I.1A | OCF$_3$ | 3-CH$_3$-isoxazol-5-yl (3-yl attach, 5-CH$_3$) | SO$_2$CH$_3$ | H | H |
| A-837 | I.1A | OCF$_3$ | 3-methyl-4,5-dihydroisoxazol-5-yl | H | H | H |
| A-838 | I.1A | OCF$_3$ | 3-methyl-4,5-dihydroisoxazol-5-yl | Cl | H | H |

TABLE A-continued

Compounds of the formula I which correspond to the formulae I.1A and I.2A

I.1A

I.2A

| No. | Formula | R¹ | R² | R³ | R⁴ | R⁵ |
|---|---|---|---|---|---|---|
| A-839 | I.1A | $OCF_3$ | #-(4,5-dihydro-3-methylisoxazol-5-yl) | $CF_3$ | H | H |
| A-840 | I.1A | $OCF_3$ | #-(4,5-dihydro-3-methylisoxazol-5-yl) | $CHF_2$ | H | H |
| A-841 | I.1A | $OCF_3$ | #-(4,5-dihydro-3-methylisoxazol-5-yl) | F | H | H |
| A-842 | I.1A | $OCF_3$ | #-(4,5-dihydro-3-methylisoxazol-5-yl) | $OCHF_2$ | H | H |
| A-843 | I.1A | $OCF_3$ | #-(4,5-dihydro-3-methylisoxazol-5-yl) | $SO_2CH_3$ | H | H |
| A-844 | I.1A | $OCF_3$ | #-(3-methylisoxazol-5-yl) | H | H | H |
| A-845 | I.1A | $OCF_3$ | #-(3-methylisoxazol-5-yl) | Cl | H | H |
| A-846 | I.1A | $OCF_3$ | #-(3-methylisoxazol-5-yl) | $CF_3$ | H | H |

TABLE A-continued

Compounds of the formula I which correspond to the formulae I.1A and I.2A

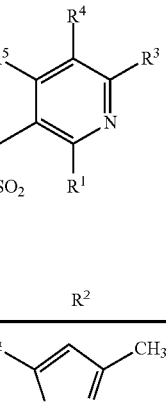

I.1A

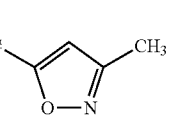

I.2A

| No. | Formula | R¹ | R² | R³ | R⁴ | R⁵ |
|---|---|---|---|---|---|---|
| A-847 | I.1A | OCF$_3$ | 5-methyl-3-methylisoxazol-5-yl | CHF$_2$ | H | H |
| A-848 | I.1A | OCF$_3$ | 5-methyl-3-methylisoxazol-5-yl | F | H | H |
| A-849 | I.1A | OCF$_3$ | 5-methyl-3-methylisoxazol-5-yl | OCHF$_2$ | H | H |
| A-850 | I.1A | OCF$_3$ | 5-methyl-3-methylisoxazol-5-yl | SO$_2$CH$_3$ | H | H |
| A-851 | I.1A | OCF$_3$ | thiazol-2-yl | H | H | H |
| A-852 | I.1A | OCF$_3$ | thiazol-2-yl | Cl | H | H |
| A-853 | I.1A | OCF$_3$ | thiazol-2-yl | CF$_3$ | H | H |
| A-854 | I.1A | OCF$_3$ | thiazol-2-yl | CHF$_2$ | H | H |

TABLE A-continued
Compounds of the formula I which correspond to the formulae I.1A and I.2A
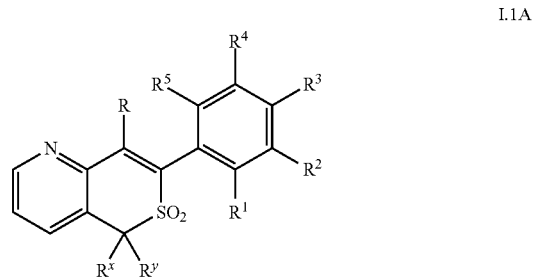
I.1A
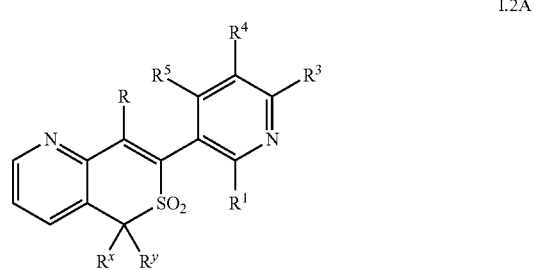
I.2A
| No. | Formula | R¹ | R² | R³ | R⁴ | R⁵ |
|---|---|---|---|---|---|---|
| A-855 | I.1A | OCF$_3$ | 2-thiazolyl | F | H | H |
| A-856 | I.1A | OCF$_3$ | 2-thiazolyl | OCHF$_2$ | H | H |
| A-857 | I.1A | OCF$_3$ | 2-thiazolyl | SO$_2$CH$_3$ | H | H |
| A-858 | I.1A | OCF$_3$ | 4-methyl-5-oxo-tetrazolyl | H | H | H |
| A-859 | I.1A | OCF$_3$ | 4-methyl-5-oxo-tetrazolyl | Cl | H | H |
| A-860 | I.1A | OCF$_3$ | 4-methyl-5-oxo-tetrazolyl | CF$_3$ | H | H |
| A-861 | I.1A | OCF$_3$ | 4-methyl-5-oxo-tetrazolyl | CHF$_2$ | H | H |

TABLE A-continued
Compounds of the formula I which correspond to the formulae I.1A and I.2A
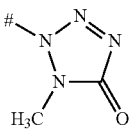
I.1A
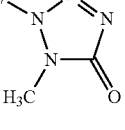
I.2A
| No. | Formula | R¹ | R² | R³ | R⁴ | R⁵ |
|---|---|---|---|---|---|---|
| A-862 | I.1A | OCF₃ | 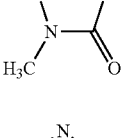 | F | H | H |
| A-863 | I.1A | OCF₃ | 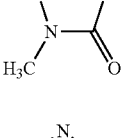 | OCHF₂ | H | H |
| A-864 | I.1A | OCF₃ | 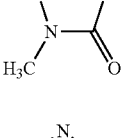 | SO₂CH₃ | H | H |
| A-865 | I.1A | OCF₃ | 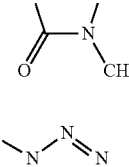 | H | H | H |
| A-866 | I.1A | OCF₃ | 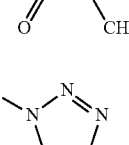 | Cl | H | H |
| A-867 | I.1A | OCF₃ |  | CF₃ | H | H |

TABLE A-continued

Compounds of the formula I which correspond to the formulae I.1A and I.2A

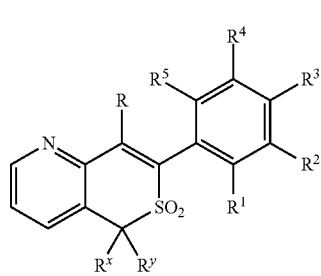
I.1A

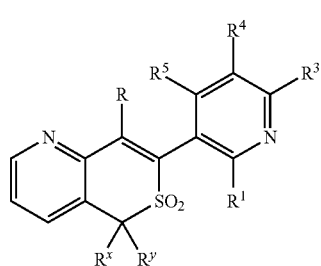
I.2A

| No. | Formula | R¹ | R² | R³ | R⁴ | R⁵ |
|---|---|---|---|---|---|---|
| A-868 | I.1A | OCF$_3$ | #-N(N=N-N)C(=O)-N-CH$_3$ tetrazolinone | CHF$_2$ | H | H |
| A-869 | I.1A | OCF$_3$ | #-N(N=N-N)C(=O)-N-CH$_3$ tetrazolinone | F | H | H |
| A-870 | I.1A | OCF$_3$ | #-N(N=N-N)C(=O)-N-CH$_3$ tetrazolinone | OCHF$_2$ | H | H |
| A-871 | I.1A | OCF$_3$ | #-N(N=N-N)C(=O)-N-CH$_3$ tetrazolinone | SO$_2$CH$_3$ | H | H |
| A-872 | I.1A | OCF$_3$ | #-morpholinyl | H | H | H |
| A-873 | I.1A | OCF$_3$ | #-morpholinyl | Cl | H | H |

TABLE A-continued

Compounds of the formula I which correspond to the formulae I.1A and I.2A

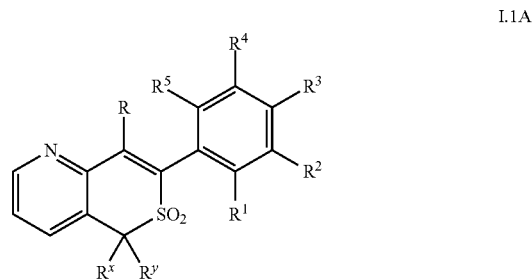
I.1A

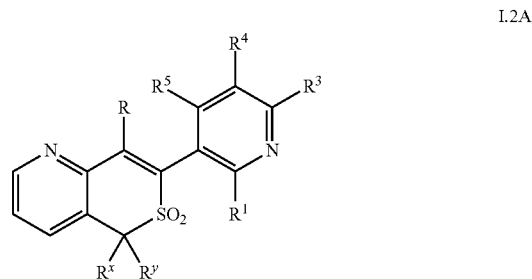
I.2A

| No. | Formula | R¹ | R² | R³ | R⁴ | R⁵ |
|---|---|---|---|---|---|---|
| A-874 | I.1A | OCF$_3$ | #-N(morpholine) | CF$_3$ | H | H |
| A-875 | I.1A | OCF$_3$ | #-N(morpholine) | CHF$_2$ | H | H |
| A-876 | I.1A | OCF$_3$ | #-N(morpholine) | F | H | H |
| A-877 | I.1A | OCF$_3$ | #-N(morpholine) | OCHF$_2$ | H | H |
| A-878 | I.1A | OCF$_3$ | #-N(morpholine) | SO$_2$CH$_3$ | H | H |
| A-879 | I.1A | OCF$_3$ | C$_6$H$_5$ | H | H | H |
| A-880 | I.1A | OCF$_3$ | C$_6$H$_5$ | Cl | H | H |
| A-881 | I.1A | OCF$_3$ | C$_6$H$_5$ | CF$_3$ | H | H |
| A-882 | I.1A | OCF$_3$ | C$_6$H$_5$ | CHF$_2$ | H | H |
| A-883 | I.1A | OCF$_3$ | C$_6$H$_5$ | F | H | H |
| A-884 | I.1A | OCF$_3$ | C$_6$H$_5$ | OCHF$_2$ | H | H |
| A-885 | I.1A | OCF$_3$ | C$_6$H$_5$ | SO$_2$CH$_3$ | H | H |
| A-886 | I.1A | OCF$_3$ | 4-OCH$_3$—C$_6$H$_4$ | H | H | H |
| A-887 | I.1A | OCF$_3$ | 4-OCH$_3$—C$_6$H$_4$ | Cl | H | H |
| A-888 | I.1A | OCF$_3$ | 4-OCH$_3$—C$_6$H$_4$ | CF$_3$ | H | H |
| A-889 | I.1A | OCF$_3$ | 4-OCH$_3$—C$_6$H$_4$ | CHF$_2$ | H | H |
| A-890 | I.1A | OCF$_3$ | 4-OCH$_3$—C$_6$H$_4$ | F | H | H |
| A-891 | I.1A | OCF$_3$ | 4-OCH$_3$—C$_6$H$_4$ | OCHF$_2$ | H | H |
| A-892 | I.1A | OCF$_3$ | 4-OCH$_3$—C$_6$H$_4$ | SO$_2$CH$_3$ | H | H |
| A-893 | I.1A | OCF$_3$ | CH=CH$_2$ | H | H | H |
| A-894 | I.1A | OCF$_3$ | CH=CH$_2$ | Cl | H | H |

TABLE A-continued

Compounds of the formula I which correspond to the formulae I.1A and I.2A

I.1A

I.2A

| No. | Formula | R¹ | R² | R³ | R⁴ | R⁵ |
|---|---|---|---|---|---|---|
| A-895 | I.1A | OCF$_3$ | CH=CH$_2$ | CF$_3$ | H | H |
| A-896 | I.1A | OCF$_3$ | CH=CH$_2$ | CHF$_2$ | H | H |
| A-897 | I.1A | OCF$_3$ | CH=CH$_2$ | F | H | H |
| A-898 | I.1A | OCF$_3$ | CH=CH$_2$ | OCHF$_2$ | H | H |
| A-899 | I.1A | OCF$_3$ | CH=CH$_2$ | SO$_2$CH$_3$ | H | H |
| A-900 | I.1A | OCF$_3$ | CH=CH—CH$_3$ | H | H | H |
| A-901 | I.1A | OCF$_3$ | CH=CH—CH$_3$ | Cl | H | H |
| A-902 | I.1A | OCF$_3$ | CH=CH—CH$_3$ | CF$_3$ | H | H |
| A-903 | I.1A | OCF$_3$ | CH=CH—CH$_3$ | CHF$_2$ | H | H |
| A-904 | I.1A | OCF$_3$ | CH=CH—CH$_3$ | F | H | H |
| A-905 | I.1A | OCF$_3$ | CH=CH—CH$_3$ | OCHF$_2$ | H | H |
| A-906 | I.1A | OCF$_3$ | CH=CH—CH$_3$ | SO$_2$CH$_3$ | H | H |
| A-907 | I.1A | OCF$_3$ | CH$_2$CH=CH$_2$ | H | H | H |
| A-908 | I.1A | OCF$_3$ | CH$_2$CH=CH$_2$ | Cl | H | H |
| A-909 | I.1A | OCF$_3$ | CH$_2$CH=CH$_2$ | CF$_3$ | H | H |
| A-910 | I.1A | OCF$_3$ | CH$_2$CH=CH$_2$ | CHF$_2$ | H | H |
| A-911 | I.1A | OCF$_3$ | CH$_2$CH=CH$_2$ | F | H | H |
| A-912 | I.1A | OCF$_3$ | CH$_2$CH=CH$_2$ | OCHF$_2$ | H | H |
| A-913 | I.1A | OCF$_3$ | CH$_2$CH=CH$_2$ | SO$_2$CH$_3$ | H | H |
| A-914 | I.1A | OCF$_3$ | CH$_2$C≡CH | H | H | H |
| A-915 | I.1A | OCF$_3$ | CH$_2$C≡CH | Cl | H | H |
| A-916 | I.1A | OCF$_3$ | CH$_2$C≡CH | CF$_3$ | H | H |
| A-917 | I.1A | OCF$_3$ | CH$_2$C≡CH | CHF$_2$ | H | H |
| A-918 | I.1A | OCF$_3$ | CH$_2$C≡CH | F | H | H |
| A-919 | I.1A | OCF$_3$ | CH$_2$C≡CH | OCHF$_2$ | H | H |
| A-920 | I.1A | OCF$_3$ | CH$_2$C≡CH | SO$_2$CH$_3$ | H | H |
| A-921 | I.1A | OCF$_3$ | CH$_2$OCH$_2$CF$_3$ | H | H | H |
| A-922 | I.1A | OCF$_3$ | CH$_2$OCH$_2$CF$_3$ | Cl | H | H |
| A-923 | I.1A | OCF$_3$ | CH$_2$OCH$_2$CF$_3$ | CF$_3$ | H | H |
| A-924 | I.1A | OCF$_3$ | CH$_2$OCH$_2$CF$_3$ | CHF$_2$ | H | H |
| A-925 | I.1A | OCF$_3$ | CH$_2$OCH$_2$CF$_3$ | F | H | H |
| A-926 | I.1A | OCF$_3$ | CH$_2$OCH$_2$CF$_3$ | OCHF$_2$ | H | H |
| A-927 | I.1A | OCF$_3$ | CH$_2$OCH$_2$CF$_3$ | SO$_2$CH$_3$ | H | H |
| A-928 | I.1A | OCF$_3$ | #-CH$_2$-O-CH$_2$-(tetrahydrofuran-2-yl) | H | H | H |
| A-929 | I.1A | OCF$_3$ | #-CH$_2$-O-CH$_2$-(tetrahydrofuran-2-yl) | Cl | H | H |

TABLE A-continued

Compounds of the formula I which correspond to the formulae I.1A and I.2A

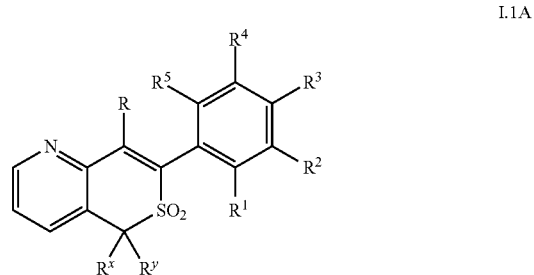

I.1A

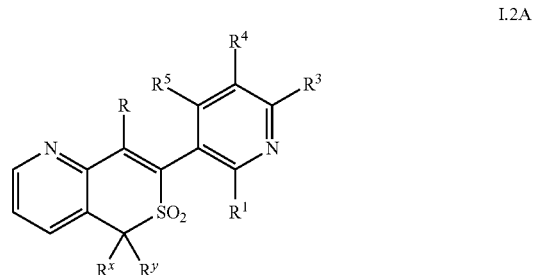

I.2A

| No. | Formula | R¹ | R² | R³ | R⁴ | R⁵ |
| --- | --- | --- | --- | --- | --- | --- |
| A-930 | I.1A | $OCF_3$ | #-CH₂-O-CH₂-(tetrahydrofuran-2-yl) | $CF_3$ | H | H |
| A-931 | I.1A | $OCF_3$ | #-CH₂-O-CH₂-(tetrahydrofuran-2-yl) | $CHF_2$ | H | H |
| A-932 | I.1A | $OCF_3$ | #-CH₂-O-CH₂-(tetrahydrofuran-2-yl) | F | H | H |
| A-933 | I.1A | $OCF_3$ | #-CH₂-O-CH₂-(tetrahydrofuran-2-yl) | $OCHF_2$ | H | H |
| A-934 | I.1A | $OCF_3$ | #-CH₂-O-CH₂-(tetrahydrofuran-2-yl) | $SO_2CH_3$ | H | H |
| A-935 | I.1A | $OCF_3$ | $OCH_2CH_3$ | H | H | H |
| A-936 | I.1A | $OCF_3$ | $OCH_2CH_3$ | Cl | H | H |
| A-937 | I.1A | $OCF_3$ | $OCH_2CH_3$ | $CF_3$ | H | H |
| A-938 | I.1A | $OCF_3$ | $OCH_2CH_3$ | $CHF_2$ | H | H |
| A-939 | I.1A | $OCF_3$ | $OCH_2CH_3$ | F | H | H |
| A-940 | I.1A | $OCF_3$ | $OCH_2CH_3$ | $OCHF_2$ | H | H |
| A-941 | I.1A | $OCF_3$ | $OCH_2CH_3$ | $SO_2CH_3$ | H | H |
| A-942 | I.1A | $OCF_3$ | $OCH_2CH_2OCH_3$ | H | H | H |
| A-943 | I.1A | $OCF_3$ | $OCH_2CH_2OCH_3$ | Cl | H | H |
| A-944 | I.1A | $OCF_3$ | $OCH_2CH_2OCH_3$ | $CF_3$ | H | H |
| A-945 | I.1A | $OCF_3$ | $OCH_2CH_2OCH_3$ | $CHF_2$ | H | H |
| A-946 | I.1A | $OCF_3$ | $OCH_2CH_2OCH_3$ | F | H | H |
| A-947 | I.1A | $OCF_3$ | $OCH_2CH_2OCH_3$ | $OCHF_2$ | H | H |
| A-948 | I.1A | $OCF_3$ | $OCH_2CH_2OCH_3$ | $SO_2CH_3$ | H | H |
| A-949 | I.1A | $OCF_3$ | $SO_2CH_3$ | H | H | H |
| A-950 | I.1A | $OCF_3$ | $SO_2CH_3$ | Cl | H | H |
| A-951 | I.1A | $OCF_3$ | $SO_2CH_3$ | $CF_3$ | H | H |
| A-952 | I.1A | $OCF_3$ | $SO_2CH_3$ | $CHF_2$ | H | H |
| A-953 | I.1A | $OCF_3$ | $SO_2CH_3$ | F | H | H |

TABLE A-continued

Compounds of the formula I which correspond to the formulae I.1A and I.2A

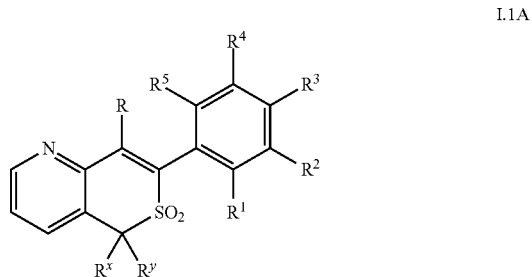
I.1A

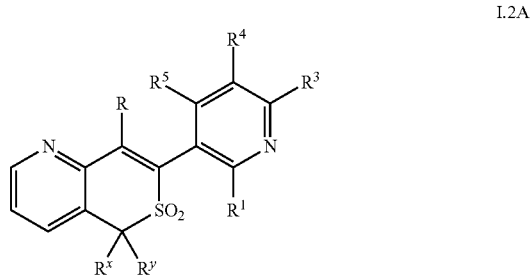
I.2A

| No. | Formula | $R^1$ | $R^2$ | $R^3$ | $R^4$ | $R^5$ |
|---|---|---|---|---|---|---|
| A-954 | I.1A | $OCF_3$ | $SO_2CH_3$ | $OCHF_2$ | H | H |
| A-955 | I.1A | $OCF_3$ | $SO_2CH_3$ | $SO_2CH_3$ | H | H |
| A-956 | I.1A | $OCF_3$ | $SO_2CH_2CH_3$ | H | H | H |
| A-957 | I.1A | $OCF_3$ | $SO_2CH_2CH_3$ | Cl | H | H |
| A-958 | I.1A | $OCF_3$ | $SO_2CH_2CH_3$ | CF3 | H | H |
| A-959 | I.1A | $OCF_3$ | $SO_2CH_2CH_3$ | $CHF_2$ | H | H |
| A-960 | I.1A | $OCF_3$ | $SO_2CH_2CH_3$ | F | H | H |
| A-961 | I.1A | $OCF_3$ | $SO_2CH_2CH_3$ | $OCHF_2$ | H | H |
| A-962 | I.1A | $OCF_3$ | $SO_2CH_2CH_3$ | $SO_2CH_3$ | H | H |
| A-963 | I.1A | $OCF_3$ | $SO_2CH(CH_3)_2$ | H | H | H |
| A-964 | I.1A | $OCF_3$ | $SO_2CH(CH_3)_2$ | Cl | H | H |
| A-965 | I.1A | $OCF_3$ | $SO_2CH(CH_3)_2$ | $CF_3$ | H | H |
| A-966 | I.1A | $OCF_3$ | $SO_2CH(CH_3)_2$ | $CHF_2$ | H | H |
| A-967 | I.1A | $OCF_3$ | $SO_2CH(CH_3)_2$ | F | H | H |
| A-968 | I.1A | $OCF_3$ | $SO_2CH(CH_3)_2$ | $OCHF_2$ | H | H |
| A-969 | I.1A | $OCF_3$ | $SO_2CH(CH_3)_2$ | $SO_2CH_3$ | H | H |
| A-970 | I.1A | $OCF_3$ | $COOCH_3$ | H | H | H |
| A-971 | I.1A | $OCF_3$ | $COOCH_3$ | Cl | H | H |
| A-972 | I.1A | $OCF_3$ | $COOCH_3$ | $CF_3$ | H | H |
| A-973 | I.1A | $OCF_3$ | $COOCH_3$ | $CHF_2$ | H | H |
| A-974 | I.1A | $OCF_3$ | $COOCH_3$ | F | H | H |
| A-975 | I.1A | $OCF_3$ | $COOCH_3$ | $OCHF_2$ | H | H |
| A-976 | I.1A | $OCF_3$ | $COOCH_3$ | $SO_2CH_3$ | H | H |
| A-977 | I.1A | $OCF_3$ | $COOCH_2CH_3$ | H | H | H |
| A-978 | I.1A | $OCF_3$ | $COOCH_2CH_3$ | Cl | H | H |
| A-979 | I.1A | $OCF_3$ | $COOCH_2CH_3$ | $CF_3$ | H | H |
| A-980 | I.1A | $OCF_3$ | $COOCH_2CH_3$ | $CHF_2$ | H | H |
| A-981 | I.1A | $OCF_3$ | $COOCH_2CH_3$ | F | H | H |
| A-982 | I.1A | $OCF_3$ | $COOCH_2CH_3$ | $OCHF_2$ | H | H |
| A-983 | I.1A | $OCF_3$ | $COOCH_2CH_3$ | $SO_2CH_3$ | H | H |
| A-984 | I.1A | $OCF_3$ | $\#^2{-}CH_2CH_2SO_2{-}\#^3$ | | H | H |
| A-985 | I.1A | $OCF_3$ | $\#^2{-}CH(CH_3)CH_2SO_2{-}\#^3$ | | H | H |
| A-986 | I.1A | $OCF_3$ | $\#^2{-}C(CH_3)_2CH_2SO_2{-}\#^3$ | | H | H |
| A-987 | I.1A | $OCF_3$ | $\#^2{-}SO_2CH_2CH_2SO_2{-}\#^3$ | | H | H |
| A-988 | I.1A | $OCF_3$ | $\#^2{-}CH(OCH_2CH_2F)CH_2CH_2SO_2{-}\#^3$ | | H | H |
| A-989 | I.1A | $OCF_3$ | $\#^2{-}C({=}NOCH_3)CH_2CH_2SO_2{-}\#^3$ | | H | H |
| A-990 | I.1A | $OCF_3$ | $\#^2{-}SO_2CH_2CH_2C(CH_3)_2{-}\#^3$ | | H | H |
| A-991 | I.1A | $OCF_3$ | $\#^2{-}N(CH_3)C({=}O)S{-}\#^3$ | | H | H |
| A-992 | I.1A | $OCF_3$ | $\#^2{-}C({=}O)N(CH_3)SO_2{-}\#^3$ | | H | H |
| A-993 | I.1A | $SCF_3$ | ![isoxazoline] | H | H | H |

TABLE A-continued

Compounds of the formula I which correspond to the formulae I.1A and I.2A

I.1A

I.2A

| No. | Formula | R¹ | R² | R³ | R⁴ | R⁵ |
|---|---|---|---|---|---|---|
| A-994 | I.1A | SCF$_3$ | 3-(4,5-dihydroisoxazolyl) | Cl | H | H |
| A-995 | I.1A | SCF$_3$ | 3-(4,5-dihydroisoxazolyl) | CF$_3$ | H | H |
| A-996 | I.1A | SCF$_3$ | 3-(4,5-dihydroisoxazolyl) | CHF$_2$ | H | H |
| A-997 | I.1A | SCF$_3$ | 3-(4,5-dihydroisoxazolyl) | F | H | H |
| A-998 | I.1A | SCF$_3$ | 3-(4,5-dihydroisoxazolyl) | OCHF$_2$ | H | H |
| A-999 | I.1A | SCF$_3$ | 3-(4,5-dihydroisoxazolyl) | SO$_2$CH$_3$ | H | H |
| A-1000 | I.1A | SCF$_3$ | 5-methyl-4,5-dihydroisoxazol-3-yl | H | H | H |
| A-1001 | I.1A | SCF$_3$ | 5-methyl-4,5-dihydroisoxazol-3-yl | Cl | H | H |
| A-1002 | I.1A | SCF$_3$ | 5-methyl-4,5-dihydroisoxazol-3-yl | CF$_3$ | H | H |

TABLE A-continued

Compounds of the formula I which correspond to the formulae I.1A and I.2A

I.1A

I.2A

| No. | Formula | R¹ | R² | R³ | R⁴ | R⁵ |
|---|---|---|---|---|---|---|
| A-1003 | I.1A | $SCF_3$ | # 5-methyl-4,5-dihydroisoxazol-3-yl | $CHF_2$ | H | H |
| A-1004 | I.1A | $SCF_3$ | # 5-methyl-4,5-dihydroisoxazol-3-yl | F | H | H |
| A-1005 | I.1A | $SCF_3$ | # 5-methyl-4,5-dihydroisoxazol-3-yl | $OCHF_2$ | H | H |
| A-1006 | I.1A | $SCF_3$ | # 5-methyl-4,5-dihydroisoxazol-3-yl | $SO_2CH_3$ | H | H |
| A-1007 | I.1A | $SCF_3$ | # isoxazol-3-yl | H | H | H |
| A-1008 | I.1A | $SCF_3$ | # isoxazol-3-yl | Cl | H | H |
| A-1009 | I.1A | $SCF_3$ | # isoxazol-3-yl | $CF_3$ | H | H |
| A-1010 | I.1A | $SCF_3$ | # isoxazol-3-yl | $CHF_2$ | H | H |

TABLE A-continued

Compounds of the formula I which correspond to the formulae I.1A and I.2A

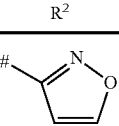

I.1A

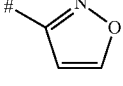

I.2A

| No. | Formula | R¹ | R² | R³ | R⁴ | R⁵ |
|---|---|---|---|---|---|---|
| A-1011 | I.1A | SCF$_3$ | 3-isoxazolyl | F | H | H |
| A-1012 | I.1A | SCF$_3$ | 3-isoxazolyl | OCHF$_2$ | H | H |
| A-1013 | I.1A | SCF$_3$ | 3-isoxazolyl | SO$_2$CH$_3$ | H | H |
| A-1014 | I.1A | SCF$_3$ | 5-methyl-3-isoxazolyl | H | H | H |
| A-1015 | I.1A | SCF$_3$ | 5-methyl-3-isoxazolyl | Cl | H | H |
| A-1016 | I.1A | SCF$_3$ | 5-methyl-3-isoxazolyl | CF$_3$ | H | H |
| A-1017 | I.1A | SCF$_3$ | 5-methyl-3-isoxazolyl | CHF$_2$ | H | H |
| A-1018 | I.1A | SCF$_3$ | 5-methyl-3-isoxazolyl | F | H | H |
| A-1019 | I.1A | SCF$_3$ | 5-methyl-3-isoxazolyl | OCHF$_2$ | H | H |

TABLE A-continued
Compounds of the formula I which correspond to the formulae I.1A and I.2A
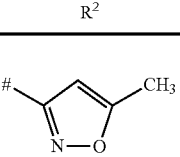
I.1A
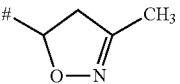
I.2A
| No. | Formula | R¹ | R² | R³ | R⁴ | R⁵ |
|---|---|---|---|---|---|---|
| A-1020 | I.1A | $SCF_3$ | 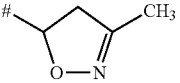 | $SO_2CH_3$ | H | H |
| A-1021 | I.1A | $SCF_3$ | 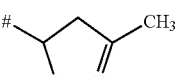 | H | H | H |
| A-1022 | I.1A | $SCF_3$ | 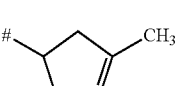 | Cl | H | H |
| A-1023 | I.1A | $SCF_3$ | 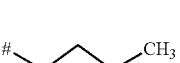 | $CF_3$ | H | H |
| A-1024 | I.1A | $SCF_3$ | 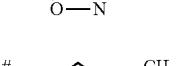 | $CHF_2$ | H | H |
| A-1025 | I.1A | $SCF_3$ | 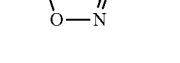 | F | H | H |
| A-1026 | I.1A | $SCF_3$ |  | $OCHF_2$ | H | H |
| A-1027 | I.1A | $SCF_3$ |  | $SO_2CH_3$ | H | H |

TABLE A-continued
Compounds of the formula I which correspond to the formulae I.1A and I.2A
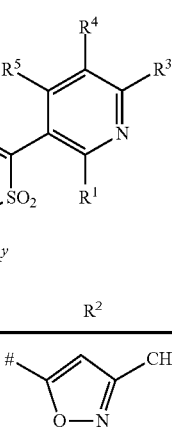
I.1A
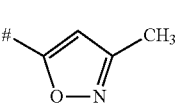
I.2A
| No. | Formula | R¹ | R² | R³ | R⁴ | R⁵ |
|---|---|---|---|---|---|---|
| A-1028 | I.1A | SCF$_3$ | 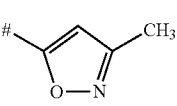 | H | H | H |
| A-1029 | I.1A | SCF$_3$ | 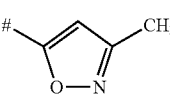 | Cl | H | H |
| A-1030 | I.1A | SCF$_3$ | 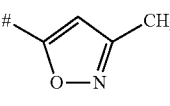 | CF$_3$ | H | H |
| A-1031 | I.1A | SCF$_3$ | 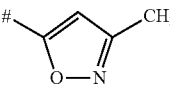 | CHF$_2$ | H | H |
| A-1032 | I.1A | SCF$_3$ | 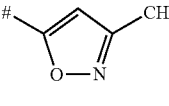 | F | H | H |
| A-1033 | I.1A | SCF$_3$ | 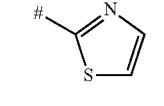 | OCHF$_2$ | H | H |
| A-1034 | I.1A | SCF$_3$ | 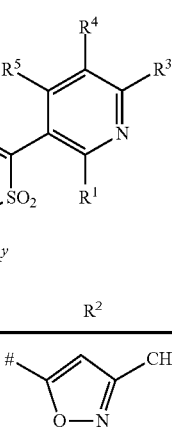 | SO$_2$CH$_3$ | H | H |
| A-1035 | I.1A | SCF$_3$ | 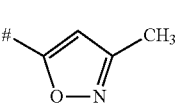 | H | H | H |

TABLE A-continued

Compounds of the formula I which correspond to the formulae I.1A and I.2A

I.1A

I.2A

| No. | Formula | $R^1$ | $R^2$ | $R^3$ | $R^4$ | $R^5$ |
|---|---|---|---|---|---|---|
| A-1036 | I.1A | $SCF_3$ | #-thiazol-2-yl | Cl | H | H |
| A-1037 | I.1A | $SCF_3$ | #-thiazol-2-yl | $CF_3$ | H | H |
| A-1038 | I.1A | $SCF_3$ | #-thiazol-2-yl | $CHF_2$ | H | H |
| A-1039 | I.1A | $SCF_3$ | #-thiazol-2-yl | F | H | H |
| A-1040 | I.1A | $SCF_3$ | #-thiazol-2-yl | $OCHF_2$ | H | H |
| A-1041 | I.1A | $SCF_3$ | #-thiazol-2-yl | $SO_2CH_3$ | H | H |
| A-1042 | I.1A | $SCF_3$ | #-(1-methyl-5-oxo-tetrazol-4-yl) | H | H | H |

TABLE A-continued
Compounds of the formula I which correspond to the formulae I.1A and I.2A
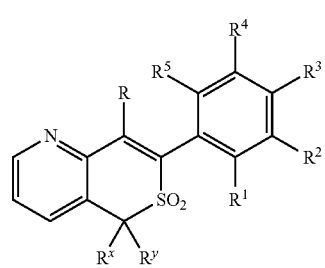
I.1A
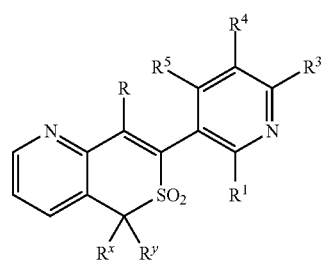
I.2A
| No. | Formula | R¹ | R² | R³ | R⁴ | R⁵ |
|---|---|---|---|---|---|---|
| A-1043 | I.1A | SCF₃ | 1-methyl-5-oxo-tetrazol-4-yl | Cl | H | H |
| A-1044 | I.1A | SCF₃ | 1-methyl-5-oxo-tetrazol-4-yl | CF₃ | H | H |
| A-1045 | I.1A | SCF₃ | 1-methyl-5-oxo-tetrazol-4-yl | CHF₂ | H | H |
| A-1046 | I.1A | SCF₃ | 1-methyl-5-oxo-tetrazol-4-yl | F | H | H |
| A-1047 | I.1A | SCF₃ | 1-methyl-5-oxo-tetrazol-4-yl | OCHF₂ | H | H |
| A-1048 | I.1A | SCF₃ | 1-methyl-5-oxo-tetrazol-4-yl | SO₂CH₃ | H | H |

TABLE A-continued
Compounds of the formula I which correspond to the formulae I.1A and I.2A
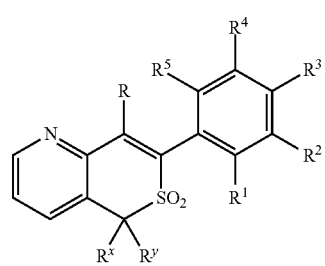
I.1A
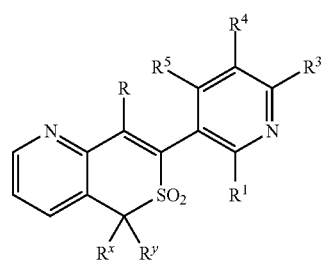
I.2A
| No. | Formula | R¹ | R² | R³ | R⁴ | R⁵ |
|---|---|---|---|---|---|---|
| A-1049 | I.1A | SCF₃ | #-N-tetrazolone-N-CH₃ | H | H | H |
| A-1050 | I.1A | SCF₃ | #-N-tetrazolone-N-CH₃ | Cl | H | H |
| A-1051 | I.1A | SCF₃ | #-N-tetrazolone-N-CH₃ | CF₃ | H | H |
| A-1052 | I.1A | SCF₃ | #-N-tetrazolone-N-CH₃ | CHF₂ | H | H |
| A-1053 | I.1A | SCF₃ | #-N-tetrazolone-N-CH₃ | F | H | H |
| A-1054 | I.1A | SCF₃ | #-N-tetrazolone-N-CH₃ | OCHF₂ | H | H |

TABLE A-continued
Compounds of the formula I which correspond to the formulae I.1A and I.2A
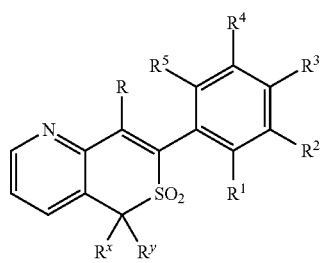
I.1A
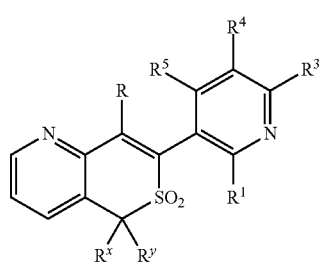
I.2A
| No. | Formula | R¹ | R² | R³ | R⁴ | R⁵ |
|---|---|---|---|---|---|---|
| A-1055 | I.1A | SCF$_3$ | # —N(tetrazolinone with N—CH$_3$, =O) | SO$_2$CH$_3$ | H | H |
| A-1056 | I.1A | SCF$_3$ | # —N-morpholino | H | H | H |
| A-1057 | I.1A | SCF$_3$ | # —N-morpholino | Cl | H | H |
| A-1058 | I.1A | SCF$_3$ | # —N-morpholino | CF$_3$ | H | H |
| A-1059 | I.1A | SCF$_3$ | # —N-morpholino | CHF$_2$ | H | H |
| A-1060 | I.1A | SCF$_3$ | # —N-morpholino | F | H | H |
| A-1061 | I.1A | SCF$_3$ | # —N-morpholino | OCHF$_2$ | H | H |

TABLE A-continued

Compounds of the formula I which correspond to the formulae I.1A and I.2A

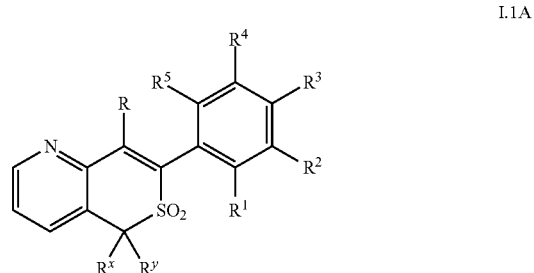

I.1A

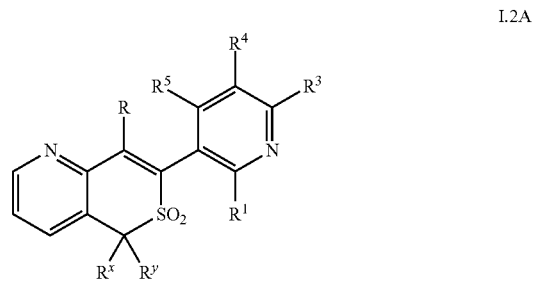

I.2A

| No. | Formula | $R^1$ | $R^2$ | $R^3$ | $R^4$ | $R^5$ |
|---|---|---|---|---|---|---|
| A-1062 | I.1A | $SCF_3$ | 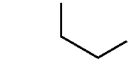 (morpholin-4-yl) | $SO_2CH_3$ | H | H |
| A-1063 | I.1A | $SCF_3$ | $C_6H_5$ | H | H | H |
| A-1064 | I.1A | $SCF_3$ | $C_6H_5$ | Cl | H | H |
| A-1065 | I.1A | $SCF_3$ | $C_6H_5$ | $CF_3$ | H | H |
| A-1066 | I.1A | $SCF_3$ | $C_6H_5$ | $CHF_2$ | H | H |
| A-1067 | I.1A | $SCF_3$ | $C_6H_5$ | F | H | H |
| A-1068 | I.1A | $SCF_3$ | $C_6H_5$ | $OCHF_2$ | H | H |
| A-1069 | I.1A | $SCF_3$ | $C_6H_5$ | $SO_2CH_3$ | H | H |
| A-1070 | I.1A | $SCF_3$ | 4-$OCH_3$—$C_6H_4$ | H | H | H |
| A-1071 | I.1A | $SCF_3$ | 4-$OCH_3$—$C_6H_4$ | Cl | H | H |
| A-1072 | I.1A | $SCF_3$ | 4-$OCH_3$—$C_6H_4$ | $CF_3$ | H | H |
| A-1073 | I.1A | $SCF_3$ | 4-$OCH_3$—$C_6H_4$ | $CHF_2$ | H | H |
| A-1074 | I.1A | $SCF_3$ | 4-$OCH_3$—$C_6H_4$ | F | H | H |
| A-1075 | I.1A | $SCF_3$ | 4-$OCH_3$—$C_6H_4$ | $OCHF_2$ | H | H |
| A-1076 | I.1A | $SCF_3$ | 4-$OCH_3$—$C_6H_4$ | $SO_2CH_3$ | H | H |
| A-1077 | I.1A | $SCF_3$ | $CH=CH_2$ | H | H | H |
| A-1078 | I.1A | $SCF_3$ | $CH=CH_2$ | Cl | H | H |
| A-1079 | I.1A | $SCF_3$ | $CH=CH_2$ | $CF_3$ | H | H |
| A-1080 | I.1A | $SCF_3$ | $CH=CH_2$ | $CHF_2$ | H | H |
| A-1081 | I.1A | $SCF_3$ | $CH=CH_2$ | F | H | H |
| A-1082 | I.1A | $SCF_3$ | $CH=CH_2$ | $OCHF_2$ | H | H |
| A-1083 | I.1A | $SCF_3$ | $CH=CH_2$ | $SO_2CH_3$ | H | H |
| A-1084 | I.1A | $SCF_3$ | $CH=CH$—$CH_3$ | H | H | H |
| A-1085 | I.1A | $SCF_3$ | $CH=CH$—$CH_3$ | Cl | H | H |
| A-1086 | I.1A | $SCF_3$ | $CH=CH$—$CH_3$ | $CF_3$ | H | H |
| A-1087 | I.1A | $SCF_3$ | $CH=CH$—$CH_3$ | $CHF_2$ | H | H |
| A-1088 | I.1A | $SCF_3$ | $CH=CH$—$CH_3$ | F | H | H |
| A-1089 | I.1A | $SCF_3$ | $CH=CH$—$CH_3$ | $OCHF_2$ | H | H |
| A-1090 | I.1A | $SCF_3$ | $CH=CH$—$CH_3$ | $SO_2CH_3$ | H | H |
| A-1091 | I.1A | $SCF_3$ | $CH_2CH=CH_2$ | H | H | H |
| A-1092 | I.1A | $SCF_3$ | $CH_2CH=CH_2$ | Cl | H | H |
| A-1093 | I.1A | $SCF_3$ | $CH_2CH=CH_2$ | $CF_3$ | H | H |
| A-1094 | I.1A | $SCF_3$ | $CH_2CH=CH_2$ | $CHF_2$ | H | H |
| A-1095 | I.1A | $SCF_3$ | $CH_2CH=CH_2$ | F | H | H |
| A-1096 | I.1A | $SCF_3$ | $CH_2CH=CH_2$ | $OCHF_2$ | H | H |
| A-1097 | I.1A | $SCF_3$ | $CH_2CH=CH_2$ | $SO_2CH_3$ | H | H |
| A-1098 | I.1A | $SCF_3$ | $CH_2C\equiv CH$ | H | H | H |
| A-1099 | I.1A | $SCF_3$ | $CH_2C\equiv CH$ | Cl | H | H |
| A-1100 | I.1A | $SCF_3$ | $CH_2C\equiv CH$ | $CF_3$ | H | H |
| A-1101 | I.1A | $SCF_3$ | $CH_2C\equiv CH$ | $CHF_2$ | H | H |
| A-1102 | I.1A | $SCF_3$ | $CH_2C\equiv CH$ | F | H | H |
| A-1103 | I.1A | $SCF_3$ | $CH_2C\equiv CH$ | $OCHF_2$ | H | H |

TABLE A-continued

Compounds of the formula I which correspond to the formulae I.1A and I.2A

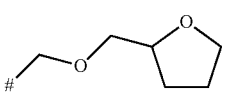
I.1A

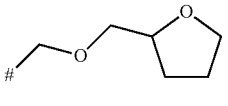
I.2A

| No. | Formula | R¹ | R² | R³ | R⁴ | R⁵ |
|---|---|---|---|---|---|---|
| A-1104 | I.1A | SCF$_3$ | CH$_2$C≡CH | SO$_2$CH$_3$ | H | H |
| A-1105 | I.1A | SCF$_3$ | CH$_2$OCH$_2$CF$_3$ | H | H | H |
| A-1106 | I.1A | SCF$_3$ | CH$_2$OCH$_2$CF$_3$ | Cl | H | H |
| A-1107 | I.1A | SCF$_3$ | CH$_2$OCH$_2$CF$_3$ | CF$_3$ | H | H |
| A-1108 | I.1A | SCF$_3$ | CH$_2$OCH$_2$CF$_3$ | CHF$_2$ | H | H |
| A-1109 | I.1A | SCF$_3$ | CH$_2$OCH$_2$CF$_3$ | F | H | H |
| A-1110 | I.1A | SCF$_3$ | CH$_2$OCH$_2$CF$_3$ | OCHF$_2$ | H | H |
| A-1111 | I.1A | SCF$_3$ | CH$_2$OCH$_2$CF$_3$ | SO$_2$CH$_3$ | H | H |
| A-1112 | I.1A | SCF$_3$ | 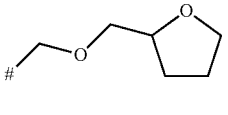 | H | H | H |
| A-1113 | I.1A | SCF$_3$ | 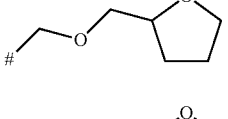 | Cl | H | H |
| A-1114 | I.1A | SCF$_3$ | (same group) | CF$_3$ | H | H |
| A-1115 | I.1A | SCF$_3$ | 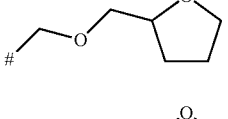 | CHF$_2$ | H | H |
| A-1116 | I.1A | SCF$_3$ | 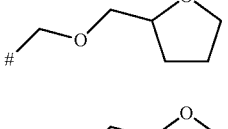 | F | H | H |
| A-1117 | I.1A | SCF$_3$ | (same group) | OCHF$_2$ | H | H |
| A-1118 | I.1A | SCF$_3$ | 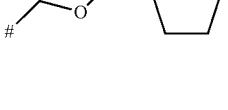 | SO$_2$CH$_3$ | H | H |

TABLE A-continued

Compounds of the formula I which correspond to the formulae I.1A and I.2A

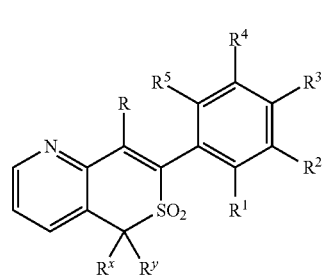

I.1A

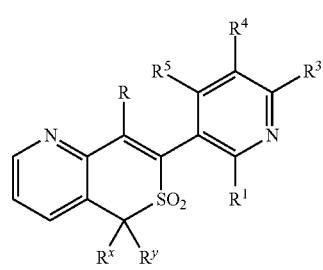

I.2A

| No. | Formula | $R^1$ | $R^2$ | $R^3$ | $R^4$ | $R^5$ |
|---|---|---|---|---|---|---|
| A-1119 | I.1A | $SCF_3$ | $OCH_2CH_3$ | H | H | H |
| A-1120 | I.1A | $SCF_3$ | $OCH_2CH_3$ | Cl | H | H |
| A-1121 | I.1A | $SCF_3$ | $OCH_2CH_3$ | $CF_3$ | H | H |
| A-1122 | I.1A | $SCF_3$ | $OCH_2CH_3$ | $CHF_2$ | H | H |
| A-1123 | I.1A | $SCF_3$ | $OCH_2CH_3$ | F | H | H |
| A-1124 | I.1A | $SCF_3$ | $OCH_2CH_3$ | $OCHF_2$ | H | H |
| A-1125 | I.1A | $SCF_3$ | $OCH_2CH_3$ | $SO_2CH_3$ | H | H |
| A-1126 | I.1A | $SCF_3$ | $OCH_2CH_2OCH_3$ | H | H | H |
| A-1127 | I.1A | $SCF_3$ | $OCH_2CH_2OCH_3$ | Cl | H | H |
| A-1128 | I.1A | $SCF_3$ | $OCH_2CH_2OCH_3$ | $CF_3$ | H | H |
| A-1129 | I.1A | $SCF_3$ | $OCH_2CH_2OCH_3$ | $CHF_2$ | H | H |
| A-1130 | I.1A | $SCF_3$ | $OCH_2CH_2OCH_3$ | F | H | H |
| A-1131 | I.1A | $SCF_3$ | $OCH_2CH_2OCH_3$ | $OCHF_2$ | H | H |
| A-1132 | I.1A | $SCF_3$ | $OCH_2CH_2OCH_3$ | $SO_2CH_3$ | H | H |
| A-1133 | I.1A | $SCF_3$ | $SO_2CH_3$ | H | H | H |
| A-1134 | I.1A | $SCF_3$ | $SO_2CH_3$ | Cl | H | H |
| A-1135 | I.1A | $SCF_3$ | $SO_2CH_3$ | $CF_3$ | H | H |
| A-1136 | I.1A | $SCF_3$ | $SO_2CH_3$ | $CHF_2$ | H | H |
| A-1137 | I.1A | $SCF_3$ | $SO_2CH_3$ | F | H | H |
| A-1138 | I.1A | $SCF_3$ | $SO_2CH_3$ | $OCHF_2$ | H | H |
| A-1139 | I.1A | $SCF_3$ | $SO_2CH_3$ | $SO_2CH_3$ | H | H |
| A-1140 | I.1A | $SCF_3$ | $SO_2CH_2CH_3$ | H | H | H |
| A-1141 | I.1A | $SCF_3$ | $SO_2CH_2CH_3$ | Cl | H | H |
| A-1142 | I.1A | $SCF_3$ | $SO_2CH_2CH_3$ | $CF_3$ | H | H |
| A-1143 | I.1A | $SCF_3$ | $SO_2CH_2CH_3$ | $CHF_2$ | H | H |
| A-1144 | I.1A | $SCF_3$ | $SO_2CH_2CH_3$ | F | H | H |
| A-1145 | I.1A | $SCF_3$ | $SO_2CH_2CH_3$ | $OCHF_2$ | H | H |
| A-1146 | I.1A | $SCF_3$ | $SO_2CH_2CH_3$ | $SO_2CH_3$ | H | H |
| A-1147 | I.1A | $SCF_3$ | $SO_2CH(CH_3)_2$ | H | H | H |
| A-1148 | I.1A | $SCF_3$ | $SO_2CH(CH_3)_2$ | Cl | H | H |
| A-1149 | I.1A | $SCF_3$ | $SO_2CH(CH_3)_2$ | $CF_3$ | H | H |
| A-1150 | I.1A | $SCF_3$ | $SO_2CH(CH_3)_2$ | $CHF_2$ | H | H |
| A-1151 | I.1A | $SCF_3$ | $SO_2CH(CH_3)_2$ | F | H | H |
| A-1152 | I.1A | $SCF_3$ | $SO_2CH(CH_3)_2$ | $OCHF_2$ | H | H |
| A-1153 | I.1A | $SCF_3$ | $SO_2CH(CH_3)_2$ | $SO_2CH_3$ | H | H |
| A-1154 | I.1A | $SCF_3$ | $COOCH_3$ | H | H | H |
| A-1155 | I.1A | $SCF_3$ | $COOCH_3$ | Cl | H | H |
| A-1156 | I.1A | $SCF_3$ | $COOCH_3$ | $CF_3$ | H | H |
| A-1157 | I.1A | $SCF_3$ | $COOCH_3$ | $CHF_2$ | H | H |
| A-1158 | I.1A | $SCF_3$ | $COOCH_3$ | F | H | H |
| A-1159 | I.1A | $SCF_3$ | $COOCH_3$ | $OCHF_2$ | H | H |
| A-1160 | I.1A | $SCF_3$ | $COOCH_3$ | $SO_2CH_3$ | H | H |
| A-1161 | I.1A | $SCF_3$ | $COOCH_2CH_3$ | H | H | H |
| A-1162 | I.1A | $SCF_3$ | $COOCH_2CH_3$ | Cl | H | H |
| A-1163 | I.1A | $SCF_3$ | $COOCH_2CH_3$ | $CF_3$ | H | H |
| A-1164 | I.1A | $SCF_3$ | $COOCH_2CH_3$ | $CHF_2$ | H | H |
| A-1165 | I.1A | $SCF_3$ | $COOCH_2CH_3$ | F | H | H |

TABLE A-continued

Compounds of the formula I which correspond to the formulae I.1A and I.2A

I.1A

I.2A

| No. | Formula | R¹ | R² | R³ | R⁴ | R⁵ |
|---|---|---|---|---|---|---|
| A-1166 | I.1A | SCF$_3$ | COOCH$_2$CH$_3$ | OCHF$_2$ | H | H |
| A-1167 | I.1A | SCF$_3$ | COOCH$_2$CH$_3$ | SO$_2$CH$_3$ | H | H |
| A-1168 | I.1A | SCF$_3$ | #²—CH$_2$CH$_2$SO$_2$—#³ | | H | H |
| A-1169 | I.1A | SCF$_3$ | #²—CH(CH$_3$)CH$_2$SO$_2$—#³ | | H | H |
| A-1170 | I.1A | SCF$_3$ | #²—C(CH$_3$)$_2$CH$_2$SO$_2$—#³ | | H | H |
| A-1171 | I.1A | SCF$_3$ | #²—SO$_2$CH$_2$CH$_2$SO$_2$—#³ | | H | H |
| A-1172 | I.1A | SCF$_3$ | #²—CH(OCH$_2$CH$_2$F)CH$_2$CH$_2$SO$_2$—#³ | | H | H |
| A-1173 | I.1A | SCF$_3$ | #²—C(=NOCH$_3$)CH$_2$CH$_2$SO$_2$—#³ | | H | H |
| A-1174 | I.1A | SCF$_3$ | #²—SO$_2$CH$_2$CH$_2$C(CH$_3$)$_2$—#³ | | H | H |
| A-1175 | I.1A | SCF$_3$ | #²—N(CH$_3$)C(=O)S—#³ | | H | H |
| A-1176 | I.1A | SCF$_3$ | #²—C(=O)N(CH$_3$)SO$_2$—#³ | | H | H |
| A-1177 | I.2A | CH$_2$OCH$_2$CH$_2$OCH$_3$ | — | CF$_3$ | H | H |
| A-1178 | I.1A | #¹—CH=CH—CH=N—#² | | F | H | H |
| A-1179 | I.1A | #¹—CH=CH—CH=N—#² | | Cl | H | H |
| A-1180 | I.1A | #¹—CH=CH—CH=N—#² | | CF$_3$ | H | H |
| A-1181 | I.1A | Cl | — | H | H | H |
| A-1182 | I.1A | CF$_3$ | — | H | H | H |
| A-1183 | I.1A | Br | — | H | H | H |
| A-1184 | I.2A | CH$_3$ | — | H | H | H |
| A-1185 | I.2A | Cl | — | Cl | H | H |
| A-1186 | I.2A | CF$_3$ | — | Cl | H | H |
| A-1187 | I.2A | Br | — | Cl | H | H |
| A-1188 | I.2A | CH$_3$ | — | Cl | H | H |
| A-1189 | I.2A | Cl | — | CN | H | H |
| A-1190 | I.2A | CF$_3$ | — | CN | H | H |
| A-1191 | I.2A | Br | — | CN | H | H |
| A-1192 | I.2A | CH$_3$ | — | CN | H | H |
| A-1193 | I.2A | Cl | — | H | H | Cl |
| A-1194 | I.2A | CF$_3$ | — | H | H | Cl |
| A-1195 | I.2A | Br | — | H | H | Cl |
| A-1196 | I.2A | CH$_3$ | — | H | H | Cl |
| A-1197 | I.2A | Cl | — | Cl | H | Cl |
| A-1198 | I.2A | CF$_3$ | — | Cl | H | Cl |
| A-1199 | I.2A | Br | — | Cl | H | Cl |
| A-1200 | I.2A | CH$_3$ | — | Cl | H | Cl |
| A-1201 | I.2A | Cl | — | CN | H | Cl |
| A-1202 | I.2A | CF$_3$ | — | CN | H | Cl |
| A-1203 | I.2A | Br | — | CN | H | Cl |
| A-1204 | I.2A | CH$_3$ | — | CN | H | Cl |

Wherein #¹ characterizes the bond in position 2 (group R¹),
² characterizes the bond in position 3 (group R²) and
³ characterizes the bond in position 4 (group R³).

Table A.1

Also especially preferred are compounds A.1-1 to A.1-247, A.1-257 to A.1-431, A.1-441 to A.1-615, A.1-625 to A.1-799, A.1-809 to A.1-983 and A.1-993 to A.1-1167 which differ from the corresponding compounds A-1 to A-247, A-257 to A-431, A-441 to A-615, A-625 to A-799, A-809 to A-983 and A-993 to A-1167 as indicated in Table A hereinabove only in that $R^3$ is CN.

Table A.2

Also especially preferred are compounds A.2-7 to A.2-12, A.2-19 to A.2-54, A.2-73 to A.2-1180 which differ from the corresponding compounds A-7 to A-12, A-19 to A-54, A-73 to A-1180 as indicated in Table A hereinabove only in that $R^5$ is F.

Table A.3

Also especially preferred are compounds A.3-7 to A.3-54 and A.3-73 to A.3-1180 which differ from the corresponding compounds A-7 to A-54 and A-73 to A-1180 as indicated in Table A hereinabove only in that $R^5$ is Cl.

Table A.4

Also especially preferred are compounds A.4-7 to A.4-12, A.4-19 to A.4-54, A.4-73 to A.4-247, A.2-257 to A.4-431, A.4-441 to A.4-615, A.4-625 to A.4-799, A.4-809 to A.4-983 and A.4-993 to A.4-1167 which differ from the corresponding compounds A.2-7 to A.2-12, A.2-19 to A.2-54, A.2-73 to A.2-247, A.2-257 to A.2-431, A.2-441 to A.2-615, A.2-625 to A.2-799, A.2-809 to A.2-983 and A.2-993 to A.2-1167 as indicated in Table A.2 hereinabove only in that $R^3$ is CN.

Table A.5

Also especially preferred are compounds A.5-7 to A.5-54, A.5-73 to A.5-247, A.5-257 to A.5-431, A.5-441 to A.5-615, A.5-625 to A.5-799, A.5-809 to A.5-983 and A.5-993 to A.5-1167 which differ from the corresponding compounds A.3-7 to A.3-54, A.3-73 to A.3-247, A.3-257 to A.3-431, A.3-441 to A.3-615, A.3-625 to A.3-799, A.3-809 to A.3-983 and A.3-993 to A.3-1167 as indicated in Table A.3 hereinabove only in that $R^3$ is CN.

The substituted pyridine compounds of formula I according to the invention can be prepared by standard processes of organic chemistry, for example by the following processes:

Picolinic acid derivatives of the formula II can be reacted with a thiol compound of the formula III to yield thioether compounds of the formula III. In the formulae II and III, the variables have the meaning given for the compounds of formula I. The group X is a halogen atom, in particular Cl or Br. Y is a methyl or ethyl group.

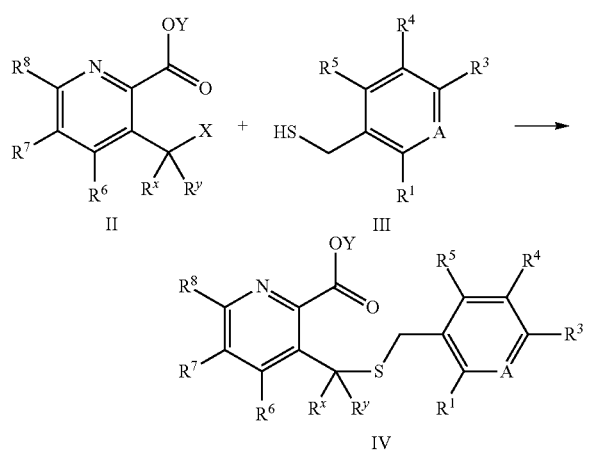

The reaction of the picolinic acid derivative II with the thiol compound III can be carried out according to literature procedures [cf. Journal of the Chemical Society, Perkin Transactions 1: Organic and Bio-Organic Chemistry (1972-1999) (1984), (7), 1501-1505] in an organic solvent, such as, for example acetonitrile or dimethylformamide (DMF), at temperatures between −78° C. and reflux of the solvent, preferably in a temperature range of from 10° C. to 50° C. It is also possible to use mixtures of the solvents mentioned. The starting materials II and III are generally reacted with one another in equimolar amounts.

The picolinic acid derivatives II can be prepared according to literature procedures (cf. Journal of Medicinal Chemistry, 32(4), 827-33; 1989).

The thiol compound III can be prepared from e.g. the corresponding thioacetate by cleavage with an alkali metal hydroxide like sodium hydroxide, potassium hydroxide or lithium hydroxide in water at a temperature of from 0° C. to 100° C., preferably at a temperature of from 10° C. to 30° C. Many benzylthiols can also be acquired from commercial sources. The thioacetate can be prepared from correspondingly substituted benzoic acids or halobenzenes on the basis of syntheses known in the literature [cf. Journal of Medicinal Chemistry 49(12), 3563-3580 (2006); Journal of Medicinal Chemistry 28(10), 1533-6 (1985); US 2004/077901; US 2004/068141; Chemistry-A European Journal 14(26), 7969-7977 (2008); Journal of Enzyme Inhibition and Medicinal Chemistry 17(3), 187-196 (2002)]. Suitably substituted benzoic acids and halobenzenes are known, for example from: WO 2002/006211, WO 2009/058237, WO 98/52926, WO 96/26193, EP-A 352 543, WO 98/52926, WO 97/30986, WO 98/12180.

The thioether compound IV can be reacted with an oxidizing agent to give the sulfone compound V.

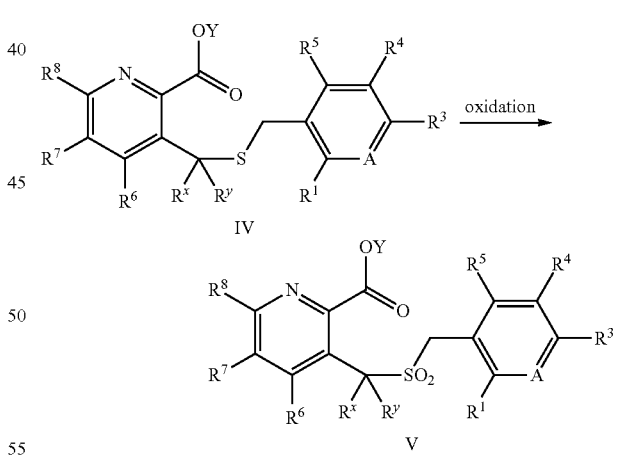

Suitable oxidizing agents include, for example, 3-chloroperoxybenzoic acid or hydrogen peroxide. The oxidation of the thioether compound IV to the sulfone compound V is usually carried out in an organic solvent, such as, for example methylene chloride, at a temperature of from 0° C. to reflux of the solvent, preferably at a temperature of from 10° C. to 25° C. The amount of the oxidizing agent is generally at least 2 molar equivalents relative to the thioether compound IV.

The sulfone compound V can be reacted with a base to give compounds of the formula VI.

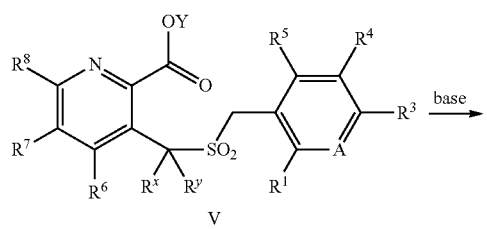

V

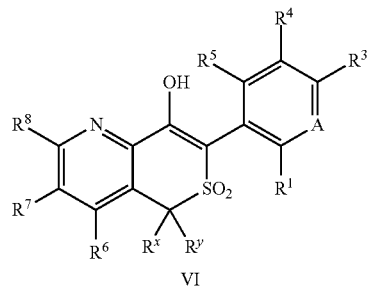

VI

The cyclization reaction is usually carried out at a temperature of from −78° C. to 0° C., preferably at a temperature of from −60° C. to 0° C. in an inert organic solvent in the presence of a base (analogous to the procedure as described in WO 2010/000892). Suitable inert organic solvents are tetrahydrofurane (THF), diethyl ether, diisopropyl ether and tert-butyl methyl ether, preferably tetrahydrofurane. It is also possible to use mixtures of the solvents mentioned. Suitable bases are lithiumdiisopropylamide, sodium tert-butoxide, potassium tert-butoxide, lithium tert-butoxide, sodium methoxide, potassium methoxide, lithium methoxide, triethylamine and tributylamine, preferably lithiumdiisopropylamide. The bases are generally employed in equimolar amounts; however, they can also be used in excess or, if appropriate, as solvents.

The compound VI can be reacted with a halogenating agent to give the compound of formula VII. The group Hal in the compound of formula VII means a halogen atom, in particular chlorine.

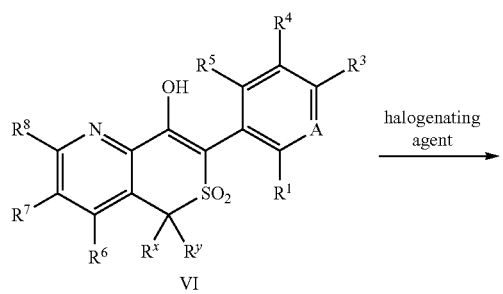

VI

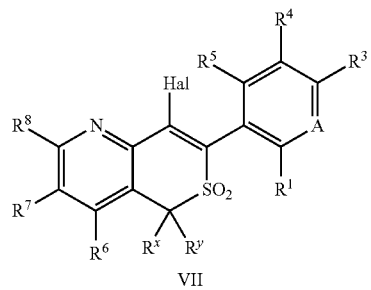

VII

Suitable halogenating agents include, for example, phosphoryl chloride, phosphorus pentachloride, thionyl chloride and phosgene. This reaction is usually carried out at a temperature of from 0° C. to 150° C., preferably at a temperature of from 20° C. to 59° C. in an organic solvent. Suitable organic solvents are chlorobenzene, methylenehloride and chloroform, preferably chlorobenzene. It is also possible to use mixtures of the solvents mentioned. The compound VI and the halogenating agent are generally reacted with one another in equimolar amounts. The halogenating agent can also be used in excess relative to the compound VI.

The compounds of formula VII can subsequently be reacted with a nucleophile (such as, for example a thiol of the formula R—SH wherein R has the same meaning given for the compound of formula I) to give the compounds of formula I.

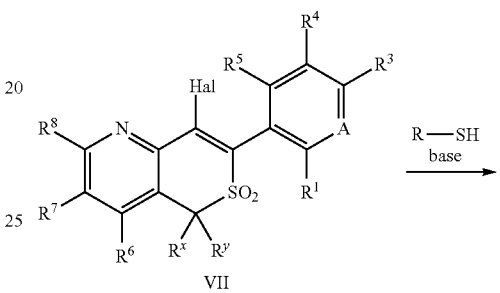

VII

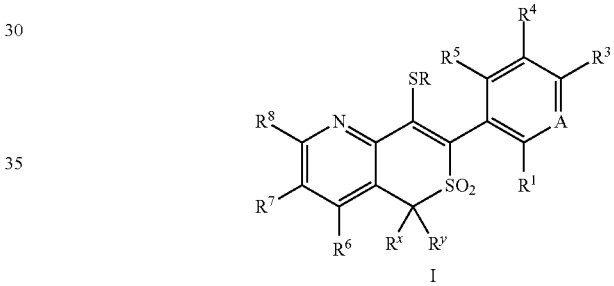

I

This reaction is usually carried out at a temperature of from in an organic solvent in the presence of a base at temperatures of 0° C. to reflux of the solvent, preferably at a temperature of from 0° C. to 100° C. Suitable organic solvents are dimethylformamide (DMF), acetonitrile and dimethyl sulfoxide, preferably dimethylformamide. It is also possible to use mixtures of the solvents mentioned. Suitable bases are triethylamine, tributylamine, sodium carbonate and potassium carbonate, preferably triethylamine. The compound VII and the nucleophile, e.g. the thiol of the formula R—SH, are generally reacted with one another in equimolar amounts. The bases are generally employed in equimolar amounts; however, they can also be used in catalytic amounts, in excess or, if appropriate, as solvents.

Alternatively, the compound of formula VI can be reacted with a sulfonylhalide of the formula $X^1$—$SO_2$—R (wherein R has the same meaning given for the compound of formula I and $X^1$ is halogen, in particular chlorine) or an acylhalide of the formula $X^2$—C(O)—R (wherein R has the same meaning given for the compound of formula I and $X^2$ is halogen, in particular chlorine) to give the compounds of formula I. Such reactions are usually carried out in an organic solvent in the presence of a base at temperatures of 0° C. to reflux of the solvent, preferably at a temperature of from 0° C. to 30° C. Suitable organic solvents are tetrahydrofurane, dichloromethane, dimethylformamide and acetonitrile, preferably dichloromethane. It is also possible to use mixtures of the solvents mentioned. Suitable bases are triethylamine, tributylamine, sodium carbonate and potassium carbonate, preferably triethylamine. The compound VI is generally reacted with the sulfonylhalide of the formula $X^1$—$SO_2$—R or with the acylhalide of the formula $X^2$—C(O)—R in equimolar amounts. The bases are generally employed in equimolar amounts; however, they can also be used in catalytic amounts, in excess or, if appropriate, as solvents.

In case the preparation of compounds I with $R^x$ and/or $R^y$=halogen is desired, any of the intermediates VI, VII and VII which are substituted by hydrogen in the $R^x$ and/or $R^y$ positions can be deprotonated with a base, preferably lithiumdiisopropylamide, in an organic solvent like tetrahydrofurane, methyl-tert-butylether or diethylether at a temperature of from −78° C. to 0° C., preferably at a temperature of from −60° C. to 0° C., and subsequently reacted with a halogenating agent like N-bromosuccinimide or N-fluorodi(benzenesulfonyl)amine at a temperature of from −78° C. to 0° C., preferably at a temperature or from −60° C. to 0° C.

In case the preparation of compounds I with $R^x$ and/or $R^y$=alkyl or cycloalkyl is desired, any of the intermediates VI, VII and VII which are substituted by hydrogen in the $R^x$ and/or $R^y$ positions can be deprotonated with a base, preferably potassium-tertbutanolate, in an organic solvent like tetrahydrofurane, methyl-tert-butylether or di-ethylether at a temperature of from −78° C. to 0° C., preferably at a temperature of from −60° C. to 0° C., and subsequently reacted with an alkylating agent like bromomethane or dibromoethane at a temperature of from −78° C. to 0° C., preferably at a temperature or from −60° C. to 0° C.

With respect to the variables, preferred embodiments of the intermediates II, III, IV, V, VI and VII correspond to those described above for the variables of the compound of formula I.

The reaction mixtures are worked up in a customary manner, for example by mixing with water, separating the phases and, if appropriate, chromatographic purification of the crude products. Some of the intermediates and end products are obtained in the form of colorless or slightly brownish viscous oils which are purified or freed from volatile components under reduced pressure and at moderately elevated temperature. If the intermediates and end products are obtained as solids, the purification can also be carried out by recrystallization or digestion.

If individual compounds I cannot be obtained by the routes described above, they can be prepared by derivatization of other compounds I.

If the synthesis yields mixtures of isomers, a separation is generally however not necessarily required since in some cases the individual isomers can be interconverted during work-up for use or during application (for example under the action of light, acids or bases). Such conversions may also take place after application, for example in the case of the treatment of plants in the treated plant or in the harmful plant to be controlled.

As shown above the thioether compounds of formula IV are novel compounds and suitable intermediates for the preparation of the compounds of formula I according to the present invention.

Therefore the present invention also provides novel thioether compounds of formula IV

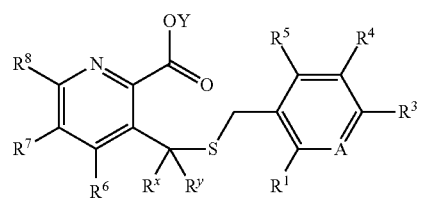

wherein the variables $R^1$, $R^3$, $R^4$, $R^5$, $R^6$, $R^7$, $R^8$, $R^x$, $R^y$ and A have the same meaning given for the compound of formula I and Y is methyl or ethyl.

With respect to the variables $R^1$, $R^3$, $R^4$, $R^5$, $R^6$, $R^7$, $R^8$, $R^x$, $R^y$ and A, preferred embodiments of the intermediate IV correspond to those described above for the variables of the compound of formula I.

As shown above the sulfone compounds of formula V are novel compounds and suitable intermediates for the preparation of the compounds of formula I according to the present invention.

Therefore the present invention also provides novel sulfone compounds of formula V

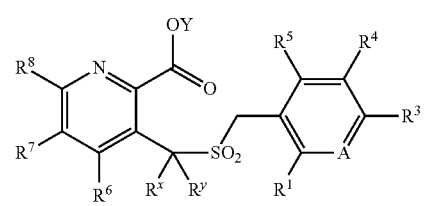

wherein the variables $R^1$, $R^3$, $R^4$, $R^5$, $R^6$, $R^7$, $R^8$, $R^x$, $R^y$ and A have the same meaning given for the compound of formula I and Y is methyl or ethyl.

With respect to the variables $R^1$, $R^3$, $R^4$, $R^5$, $R^6$, $R^7$, $R^8$, $R^x$, $R^y$ and A, preferred embodiments of the intermediate V correspond to those described above for the variables of the compound of formula I.

As shown above the compounds of formula VI are novel compounds and suitable intermediates for the preparation of the compounds of formula I according to the present invention.

Therefore the present invention also provides novel compounds of formula VI

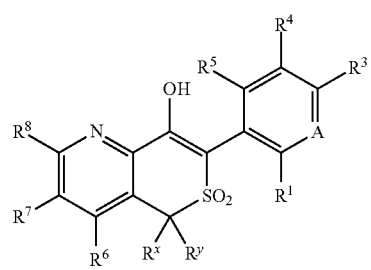

wherein the variables $R^1$, $R^3$, $R^4$, $R^5$, $R^6$, $R^7$, $R^8$, $R^x$, $R^y$ and A have the same meaning given for the compound of formula I.

With respect to the variables $R^1$, $R^3$, $R^4$, $R^5$, $R^6$, $R^7$, $R^8$, $R^x$, $R^y$ and A, preferred embodiments of the intermediate VI correspond to those described above for the variables of the compound of formula I.

As shown above the compounds of formula VII are novel compounds and suitable intermediates for the preparation of the compounds of formula I according to the present invention.

Therefore the present invention also provides novel compounds of formula VII

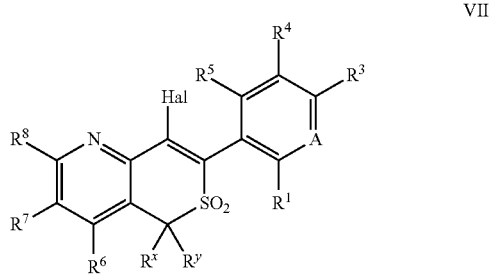

VII wherein the variables $R^1$, $R^3$, $R^4$, $R^5$, $R^6$, $R^7$, $R^8$, $R^x$, $R^y$ and A have the same meaning given for the compound of formula I and Hal is halogen, in particular chlorine.

With respect to the variables $R^1$, $R^3$, $R^4$, $R^5$, $R^6$, $R^7$, $R^8$, $R^x$, $R^y$ and A, preferred embodiments of the intermediate VII correspond to those described above for the variables of the compound of formula I.

The compounds I are suitable as herbicides. They are suitable as such or as an appropriately formulated composition (herbicidal composition). As used in this application, the terms "formulated composition" and "herbicidal composition" are synonyms.

The herbicidal compositions comprising the compounds of formula I control vegetation on non-crop areas very efficiently, especially at high rates of application. They act against broad-leaved weeds and grass weeds in crops such as wheat, rice, maize, soya and cotton without causing any significant damage to the crop plants. This effect is mainly observed at low rates of application.

Depending on the application method in question, the compounds I or compositions comprising them can additionally be employed in a further number of crop plants for eliminating undesirable plants. Examples of suitable crops are the following:

*Allium cepa, Ananas comosus, Arachis hypogaea, Asparagus officinalis, Avena sativa, Beta vulgaris* spec. *altissima, Beta vulgaris* spec. *rapa, Brassica napus* var. *napus, Brassica napus* var. *napobrassica, Brassica rapa* var. *silvestris, Brassica oleracea, Brassica nigra, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum* (*N. rustica*), *Olea europaea, Oryza sativa, Phaseolus lunatus, Phaseolus vulgaris, Picea abies, Pinus* spec., *Pistacia vera, Pisum sativum, Prunus avium, Prunus persica, Pyrus communis, Prunus armeniaca, Prunus cerasus, Prunus dulcis* and *Prunus domestica, Ribes sylvestre, Ricinus communis, Saccharum officinarum, Secale cereale, Sinapis alba, Solanum tuberosum, Sorghum bicolor* (*s. vulgare*), *Theobroma cacao, Trifolium pratense, Triticum aestivum, Triticale, Triticum durum, Vicia faba, Vitis vinifera* and *Zea mays.*

Preferred crops are the following: *Arachis hypogaea, Beta vulgaris* spec. *altissima, Brassica napus* var. *napus, Brassica oleracea, Citrus limon, Citrus sinensis, Coffea arabica* (*Coffea canephora, Coffea liberica*), *Cynodon dactylon, Glycine max, Gossypium hirsutum,* (*Gossypium arboreum, Gossypium herbaceum, Gossypium vitifolium*), *Helianthus annuus, Hordeum vulgare, Juglans regia, Lens culinaris, Linum usitatissimum, Lycopersicon lycopersicum, Malus* spec., *Medicago sativa, Nicotiana tabacum* (*N. rustica*), *Olea europaea, Oryza sativa, Phaseolus lunatus, Phaseolus vulgaris, Pistacia vera, Pisum sativum, Prunus dulcis, Saccharum officinarum, Secale cereale, Solanum tuberosum, Sorghum bicolor* (*s. vulgare*), *Triticale, Triticum aestivum, Triticum durum, Vicia faba, Vitis vinifera* and *Zea mays.*

The compositions/compounds of formula I according to the invention can also be used in genetically modified plants. The term "genetically modified plants" is to be understood as plants whose genetic material has been modified by the use of recombinant DNA techniques to include an inserted sequence of DNA that is not native to that plant species' genome or to exhibit a deletion of DNA that was native to that species' genome, wherein the modification(s) cannot readily be obtained by cross breeding, mutagenesis or natural recombination alone. Often, a particular genetically modified plant will be one that has obtained its genetic modification(s) by inheritance through a natural breeding or propagation process from an ancestral plant whose genome was the one directly treated by use of a recombinant DNA technique. Typically, one or more genes have been integrated into the genetic material of a genetically modified plant in order to improve certain properties of the plant. Such genetic modifications also include but are not limited to targeted post-translational modification of protein(s), oligo- or polypeptides. e.g., by inclusion therein of amino acid mutation(s) that permit, decrease, or promote glycosylation or polymer additions such as prenylation, acetylation farnesylation, or PEG moiety attachment.

Plants that have been modified by breeding, mutagenesis or genetic engineering, e.g. have been rendered tolerant to applications of specific classes of herbicides, such as auxin herbicides such as dicamba or 2,4-D; bleacher herbicides such as hydroxyphenylpyruvate dioxygenase (HPPD) inhibitors or phytoene desaturase (PDS) inhibitors; acetolactate synthase (ALS) inhibitors such as sulfonyl ureas or imidazolinones; enolpyruvyl shikimate 3-phosphate synthase (EPSP) inhibitors such as glyphosate; glutamine synthetase (GS) inhibitors such as glufosinate; protoporphyrinogen-IX oxidase inhibitors; lipid biosynthesis inhibitors such as acetyl CoA carboxylase (ACCase) inhibitors; or oxynil (i.e. bromoxynil or ioxynil) herbicides as a result of conventional methods of breeding or genetic engineering; furthermore, plants have been made resistant to multiple classes of herbicides through multiple genetic modifications, such as resistance to both glyphosate and glufosinate or to both glyphosate and a herbicide from another class such as ALS inhibitors, HPPD inhibitors, auxin herbicides, or ACCase inhibitors. These herbicide resistance technologies are, for example, described in Pest Management Science 61, 2005, 246; 61, 2005, 258; 61, 2005, 277; 61, 2005, 269; 61, 2005, 286; 64, 2008, 326; 64, 2008, 332; Weed Science 57, 2009, 108; Australian Journal of Agricultural Research 58, 2007, 708; Science 316, 2007, 1185; and references quoted therein. Several cultivated plants have been rendered tolerant to herbicides by mutagenesis and conventional methods of breeding, e.g., Clearfield® summer rape (Canola, BASF SE, Germany) being tolerant to imidazolinones, e.g., imazamox, or ExpressSun® sunflowers (DuPont, USA) being tolerant to sulfonyl ureas, e.g., tribenuron. Genetic engineering methods have been used to render cultivated plants such as soybean, cotton, corn, beets and rape, tolerant to herbicides such as glyphosate, imidazolinones and glufosinate, some of which are under development or commercially available under the brands or trade names RoundupReady® (glyphosate tolerant, Monsanto, USA), Cultivance® (imidazolinone tolerant, BASF SE, Germany) and LibertyLink® (glufosinate tolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringiensis*, such as delta-endotoxins, e.g., CryIA(b), CryIA(c), CryIF, CryIF(a2), CryIIA(b), CryIIIA, CryIIIB(b1) or Cry9c; vegetative insecticidal proteins (VIP), e.g., VIP1, VIP2, VIP3 or VIP3A; insecticidal proteins of bacteria colonizing nematodes, e.g., *Photorhabdus* spp. or *Xenorhabdus* spp.; toxins produced by animals, such as scorpion toxins, arachnid toxins, wasp toxins, or other insect-specific neurotoxins; toxins produced by fungi, such as Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxy-steroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilbene synthase, bibenzyl synthase, chitinases or glucanases. In the context of the present invention these insecticidal proteins or toxins are to be understood expressly also as including pre-toxins, hybrid proteins, truncated or otherwise modified proteins. Hybrid proteins are characterized by a new combination of protein domains, (see, e.g., WO 02/015701). Further examples of such toxins or genetically modified plants capable of synthesizing such toxins are disclosed, e.g., in EP-A 374 753, WO 93/007278, WO 95/34656, EP-A 427 529, EP-A 451 878, WO 03/18810 and WO 03/52073. The methods for producing such genetically modified plants are generally known to the person skilled in the art and are described, e.g., in the publications mentioned above. These insecticidal proteins contained in the genetically modified plants impart to the plants producing these proteins tolerance to harmful pests from all taxonomic groups of arthropods, especially to beetles (Coeloptera), two-winged insects (Diptera), and moths (Lepidoptera) and to nematodes (Nematoda). Genetically modified plants capable to synthesize one or more insecticidal proteins are, e.g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e.g., Agrisure® CB) and Bt176 from Syngenta Seeds SAS, France, (corn cultivars producing the Cry1Ab toxin and PAT enzyme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the CryIF toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e.g., EP-A 392 225), plant disease resistance genes (e.g., potato culti-vars, which express resistance genes acting against *Phytophthora infestans* derived from the Mexican wild potato, *Solanum bulbocastanum*) or T4-lyso-zym (e.g., potato cultivars capable of synthesizing these proteins with increased resistance against bacteria such as *Erwinia amylovora*). The methods for producing such genetically modi-fied plants are generally known to the person skilled in the art and are described, e.g., in the publications mentioned above.

Furthermore, plants are also covered that are by the use of recombinant DNA techniques capable to synthesize one or more proteins to increase the productivity (e.g., bio-mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of ingredients or new ingredients, specifically to improve human or animal nutrition, e.g., oil crops that produce health-promoting long-chain omega-3 fatty acids or unsaturated omega-9 fatty acids (e.g., Nexera® rape, Dow AgroSciences, Canada).

Furthermore, plants are also covered that contain by the use of recombinant DNA techniques a modified amount of ingredients or new ingredients, specifically to improve raw material production, e.g., potatoes that produce increased amounts of amylopectin (e.g. Amflora® potato, BASF SE, Germany).

Furthermore, it has been found that the compounds of the formula I are also suitable for the defoliation and/or desiccation of plant parts, for which crop plants such as cotton, potato, oilseed rape, sunflower, soybean or field beans, in particular cotton, are suitable. In this regard, compositions for the desiccation and/or defoliation of plants, processes for preparing these compositions and methods for desiccating and/or defoliating plants using the compounds of the formula I have been found.

As desiccants, the compounds of the formula I are particularly suitable for desiccating the above-ground parts of crop plants such as potato, oilseed rape, sunflower and soybean, but also cereals. This makes possible the fully mechanical harvesting of these important crop plants.

Also of economic interest is to facilitate harvesting, which is made possible by concentrating within a certain period of time the dehiscence, or reduction of adhesion to the tree, in citrus fruit, olives and other species and varieties of pernicious fruit, stone fruit and nuts. The same mechanism, i.e. the promotion of the development of abscission tissue between fruit part or leaf part and shoot part of the plants is also essential for the controlled defoliation of useful plants, in particular cotton.

Moreover, a shortening of the time interval in which the individual cotton plants mature leads to an increased fiber quality after harvesting.

The compounds I, or the herbicidal compositions comprising the compounds I, can be used, for example, in the form of ready-to-spray aqueous solutions, powders, suspensions, also highly concentrated aqueous, oily or other suspensions or dispersions, emulsions, oil dispersions, pastes, dusts, materials for broadcasting, or granules, by means of spraying, atomizing, dusting, spreading, watering or treatment of the seed or mixing with the seed. The use forms depend on the intended purpose; in any case, they should ensure the finest possible distribution of the active ingredients according to the invention.

The herbicidal compositions comprise an herbicidal effective amount of at least one compound of the formula I and auxiliaries which are customary for the formulation of crop protection agents.

Examples of auxiliaries customary for the formulation of crop protection agents are inert auxiliaries, solid carriers, surfactants (such as dispersants, protective colloids, emulsifiers, wetting agents and tackifiers), organic and inorganic thickeners, bactericides, antifreeze agents, antifoams, optionally colorants and, for seed formulations, adhesives.

The person skilled in the art is sufficiently familiar with the recipes for such formulations.

Examples of thickeners (i.e. compounds which impart to the formulation modified flow properties, i.e. high viscosity in the state of rest and low viscosity in motion) are polysaccharides, such as xanthan gum (Kelzan® from Kelco), Rhodopol® 23 (Rhone Poulenc) or Veegum® (from R.T. Vanderbilt), and also organic and inorganic sheet minerals, such as Attaclay® (from Engelhardt).

Examples of antifoams are silicone emulsions (such as, for example, Silikon® SRE, Wacker or Rhodorsil® from Rhodia), long-chain alcohols, fatty acids, salts of fatty acids, organofluorine compounds and mixtures thereof.

Bactericides can be added for stabilizing the aqueous herbicidal formulations.

Examples of bactericides are bactericides based on dichlorophen and benzyl alcohol hemiformal (Proxel® from ICI or Acticide® RS from Thor Chemie and Kathon® MK from Rohm & Haas), and also isothiazolinone derivates, such as alkylisothiazolinones and benzisothiazolinones (Acticide MBS from Thor Chemie).

Examples of antifreeze agents are ethylene glycol, propylene glycol, urea or glycerol.

Examples of colorants are both sparingly water-soluble pigments and water-soluble dyes. Examples which may be mentioned are the dyes known under the names Rhodamin B, C.I. Pigment Red 112 and C.I. Solvent Red 1, and also pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples of adhesives are polyvinylpyrrolidone, polyvinyl acetate, polyvinyl alcohol and tylose.

Suitable inert auxiliaries are, for example, the following:
mineral oil fractions of medium to high boiling point, such as kerosene and diesel oil, furthermore coal tar oils and oils of vegetable or animal origin, aliphatic, cyclic and aromatic hydrocarbons, for example paraffin, tetrahydronaphthalene, alkylated naphthalenes and their derivatives, alkylated benzenes and their derivatives, alcohols such as methanol, ethanol, propanol, butanol and cyclohexanol, ketones such as cyclohexanone or strongly polar solvents, for example amines such as N-methylpyrrolidone, and water.

Suitable carriers include liquid and solid carriers.

Liquid carriers include e.g. non-aqueous solvents such as cyclic and aromatic hydrocarbons, e.g. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, e.g. amines such as N-methylpyrrolidone, and water as well as mixtures thereof.

Solid carriers include e.g. mineral earths such as silicas, silica gels, silicates, talc, kaolin, limestone, lime, chalk, bole, loess, clay, dolomite, diatomaceous earth, calcium sulfate, magnesium sulfate and magnesium oxide, ground synthetic materials, fertilizers such as ammonium sulfate, ammonium phosphate, ammonium nitrate and ureas, and products of vegetable origin, such as cereal meal, tree bark meal, wood meal and nutshell meal, cellulose powders, or other solid carriers.

Suitable surfactants (adjuvants, wetting agents, tackifiers, dispersants and also emulsifiers) are the alkali metal salts, alkaline earth metal salts and ammonium salts of aromatic sulfonic acids, for example lignosulfonic acids (e.g. Borrespers-types, Borregaard), phenolsulfonic acids, naphthalenesulfonic acids (Morwet types, Akzo Nobel) and dibutylnaphthalenesulfonic acid (Nekal types, BASF AG), and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors and proteins, denaturated proteins, polysaccharides (e.g. methylcellulose), hydrophobically modified starches, polyvinyl alcohol (Mowiol types Clariant), polycarboxylates (BASF AG, Sokalan types), polyalkoxylates, polyvinylamine (BASF AG, Lupamine types), polyethyleneimine (BASF AG, Lupasol types), polyvinylpyrrolidone and copolymers thereof.

Powders, materials for broadcasting and dusts can be prepared by mixing or concomitant grinding the active ingredients together with a solid carrier.

Granules, for example coated granules, impregnated granules and homogeneous granules, can be prepared by binding the active ingredients to solid carriers.

Aqueous use forms can be prepared from emulsion concentrates, suspensions, pastes, wettable powders or water-dispersible granules by adding water.

To prepare emulsions, pastes or oil dispersions, the compounds of the formula I, either as such or dissolved in an oil or solvent, can be homogenized in water by means of a wetting agent, tackifier, dispersant or emulsifier. Alternatively, it is also possible to prepare concentrates comprising active compound, wetting agent, tackifier, dispersant or emulsifier and, if desired, solvent or oil, which are suitable for dilution with water.

The concentrations of the compounds of the formula I in the ready-to-use preparations (formulations) can be varied within wide ranges. In general, the formulations comprise approximately from 0.001 to 98% by weight, preferably 0.01 to 95% by weight of at least one active ingredient. The active ingredients are employed in a purity of from 90% to 100%, preferably 95% to 100% (according to NMR spectrum).

In the formulation of the compound of formula I according to the present invention the active ingredients, e.g. the compounds of formula I, are present in suspended, emulsified or dissolved form. The formulation according to the invention can be in the form of aqueous solutions, powders, suspensions, also highly-concentrated aqueous, oily or other suspensions or dispersions, aqueous emulsions, aqueous microemulsions, aqueous suspo-emulsions, oil dispersions, pastes, dusts, materials for spreading or granules.

The compounds of formula I according to the present invention can, for example, be formulated as follows:

1. Products for Dilution with Water

A Water-Soluble Concentrates 10 parts by weight of active compound are dissolved in 90 parts by weight of water or a water-soluble solvent. As an alternative, wetters or other adjuvants are added. The active compound dissolves upon dilution with water. This gives a formulation with an active compound content of 10% by weight.

B Dispersible Concentrates 20 parts by weight of active compound are dissolved in 70 parts by weight of cyclohexanone with addition of 10 parts by weight of a dispersant, for example polyvinylpyrrolidone. Dilution with water gives a dispersion. The active compound content is 20% by weight.

C Emulsifiable Concentrates 15 parts by weight of active compound are dissolved in 75 parts by weight of an organic solvent (eg. alkylaromatics) with addition of calcium dodecylbenzenesulfonate and castor oil ethoxylate (in each case 5 parts by weight). Dilution with water gives an emulsion. The formulation has an active compound content of 15% by weight.

D Emulsions 25 parts by weight of active compound are dissolved in 35 parts by weight of an organic solvent (eg. alkylaromatics) with addition of calcium dodecylbenzenesulfonate and castor oil ethoxylate (in each case 5 parts by weight). This mixture is introduced into 30 parts by weight of water by means of an emulsifier (Ultraturrax) and made into a homogeneous emulsion. Dilution with water gives an emulsion. The formulation has an active compound content of 25% by weight.

E Suspensions

In an agitated ball mill, 20 parts by weight of active compound are comminuted with addition of 10 parts by weight of dispersants and wetters and 70 parts by weight of water or an organic solvent to give a fine active compound suspension. Dilution with water gives a stable suspension of the active compound. The active compound content in the formulation is 20% by weight.

F Water-Dispersible Granules and Water-Soluble Granules 50 parts by weight of active compound are ground finely with addition of 50 parts by weight of dispersants and wetters and made into water-dispersible or water-soluble granules by means of technical appliances (for example extrusion, spray tower, fluidized bed). Dilution with water gives a stable dispersion or solution of the active compound. The formulation has an active compound content of 50% by weight.

G Water-Dispersible Powders and Water-Soluble Powders 75 parts by weight of active compound are ground in a rotor-stator mill with addition of 25 parts by weight of dispersants, wetters and silica gel. Dilution with water gives a stable dispersion or solution of the active compound. The active compound content of the formulation is 75% by weight.

H Gel Formulations

In a ball mill, 20 parts by weight of active compound, 10 parts by weight of dispersant, 1 part by weight of gelling agent and 70 parts by weight of water or of an organic solvent are mixed to give a fine suspension.ABuilder with water gives a stable suspension with active compound content of 20% by weight.

2. Products to be Applied Undiluted

I Dusts 5 parts by weight of active compound are ground finely and mixed intimately with 95 parts by weight of finely divided kaolin. This gives a dusting powder with an active compound content of 5% by weight.

J Granules (GR, FG, GG, MG)

0.5 parts by weight of active compound are ground finely and associated with 99.5 parts by weight of carriers. Current methods here are extrusion, spray-drying or the fluidized bed. This gives granules to be applied undiluted with an active compound content of 0.5% by weight.

K ULV Solutions (UL)

10 parts by weight of active compound are dissolved in 90 parts by weight of an organic solvent, for example xylene. This gives a product to be applied undiluted with an active compound content of 10% by weight.

Aqueous use forms can be prepared from emulsion concentrates, suspensions, pastes, wettable powders or water-dispersible granules by adding water.

The compounds of the formula I or the herbicidal compositions comprising them can be applied pre-, post-emergence or pre-plant, or together with the seed of a crop plant. It is also possible to apply the herbicidal composition or active compounds by applying seed, pretreated with the herbicidal compositions or active compounds, of a crop plant. If the active ingredients are less well tolerated by certain crop plants, application techniques may be used in which the herbicidal compositions are sprayed, with the aid of the spraying equipment, in such a way that as far as possible they do not come into contact with the leaves of the sensitive crop plants, while the active ingredients reach the leaves of undesirable plants growing underneath, or the bare soil surface (post-directed, lay-by).

In a further embodiment, the compounds of the formula I or the herbicidal compositions can be applied by treating seed. The treatment of seeds comprises essentially all procedures familiar to the person skilled in the art (seed dressing, seed coating, seed dusting, seed soaking, seed film coating, seed multilayer coating, seed encrusting, seed dripping and seed pelleting) based on the compounds of the formula I according to the invention or the compositions prepared therefrom. Here, the herbicidal compositions can be applied diluted or undiluted.

The term "seed" comprises seed of all types, such as, for example, corns, seeds, fruits, tubers, seedlings and similar forms. Here, preferably, the term seed describes corns and seeds.

The seed used can be seed of the useful plants mentioned above, but also the seed of transgenic plants or plants obtained by customary breeding methods.

The rates of application of the active compounds of formula I according to the present invention (total amount of compounds I) are from 0.1 g/ha to 3000 g/ha, preferably 10 g/ha to 1000 g/ha of active substance (a.s.), depending on the control target, the season, the target plants and the growth stage.

In another preferred embodiment of the invention, the application rates of the compounds of formula I are in the range from 0.1 g/ha to 5000 g/ha and preferably in the range from 1 g/ha to 2500 g/ha or from 5 g/ha to 2000 g/ha of active substance (a.s.).

In another preferred embodiment of the invention, the application rate of the compounds of formula I is 0.1 to 1000 g/ha, preferably 1 to 750 g/ha, more preferably 5 to 500 g/ha, of active substance.

To treat the seed, the compounds I are generally employed in amounts of from 0.001 to 10 kg per 100 kg of seed.

To widen the spectrum of action and to achieve synergistic effects, the compounds of the formula I may be mixed with a large number of representatives of other herbicidal or growth-regulating active ingredient groups and then applied concomitantly. Suitable components for mixtures are, for example, 1,2,4-thiadiazoles, 1,3,4-thiadiazoles, amides, aminophosphoric acid and its derivatives, aminotriazoles, anilides, (het)aryloxyalkanoic acids and their derivatives, benzoic acid and its derivatives, benzothiadiazinones, 2-aroyl-1,3-cyclohexanediones, 2-hetaroyl-1,3-cyclohexane-diones, hetaryl aryl ketones, benzylisoxazolidinones, meta-$CF_3$-phenyl derivatives, carbamates, quinolinecarboxylic acid and its derivatives, chloroacetanilides, cyclohexenone oxime ether derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetaryloxyphenoxypropionic esters, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides, uracils, phenyl pyrazolines and isoxazolines and derivatives thereof.

It may furthermore be beneficial to apply the compounds of the formula I alone or in combination with other herbicides, or else in the form of a mixture with other crop protection agents, for example together with agents for controlling pests or phytopathogenic fungi or bacteria. Also of interest is the miscibility with mineral salt solutions, which are employed for treating nutritional and trace element deficiencies. Other additives such as non-phytotoxic oils and oil concentrates may also be added.

The further herbicidal active compound B is preferably selected from the herbicides of class b1) to b15):
b1) lipid biosynthesis inhibitors;
b2) acetolactate synthase inhibitors (ALS inhibitors);
b3) photosynthesis inhibitors;
b4) protoporphyrinogen-IX oxidase inhibitors,
b5) bleacher herbicides;
b6) enolpyruvyl shikimate 3-phosphate synthase inhibitors (EPSP inhibitors);
b7) glutamine synthetase inhibitors;
b8) 7,8-dihydropteroate synthase inhibitors (DHP inhibitors);
b9) mitosis inhibitors;
b10) inhibitors of the synthesis of very long chain fatty acids (VLCFA inhibitors);
b11) cellulose biosynthesis inhibitors;
b12) decoupler herbicides;
b13) auxinic herbicides;
b14) auxin transport inhibitors; and
b15) other herbicides selected from the group consisting of bromobutide, chlorflurenol, chlorflurenol-methyl, cinmethylin, cumyluron, dalapon, dazomet, difenzoquat, difenzoquat-metilsulfate, dimethipin, DSMA, dymron, endothal and its salts, etobenzanid, flamprop, flamprop-isopropyl, flamprop-methyl, flamprop-M-isopropyl, flamprop-M-methyl, flurenol, flurenol-butyl, flurprimidol, fosamine, fosamine-ammonium, indanofan, indaziflam, maleic hydrazide, mefluidide, metam, methiozolin (CAS 403640-27-7), methyl azide, methyl bromide, methyldymron, methyl iodide, MSMA, oleic acid, oxaziclomefone, pelargonic acid, pyributicarb, quinoclamine, triaziflam, tridiphane and 6-chloro-3-(2-cyclopropyl-6-methylphenoxy)-4-pyridazinol (CAS 499223-49-3) and its salts and esters.

Preference is given to those compositions according to the present invention comprising at least one herbicide B selected from herbicides of class b1, b2, b3, b4, b5, b6, b9 and b10.

Specific preference is given to those compositions according to the present invention which comprise at least one herbicide B selected from the herbicides of class b1, b2, b6, b9 and b10.

Particular preference is given to those compositions according to the present invention which comprise at least one herbicide B selected from the herbicides of class b2, b6 and b10.

Examples of herbicides B which can be used in combination with the compounds of the formula I according to the present invention are:
b1) from the group of the lipid biosynthesis inhibitors:
ACC-herbicides such as alloxydim, alloxydim-sodium, butroxydim, clethodim, clodinafop, clodinafop-propargyl, cycloxydim, cyhalofop, cyhalofop-butyl, diclofop, diclofop-methyl, fenoxaprop, fenoxaprop-ethyl, fenoxaprop-P, fenoxaprop-P-ethyl, fluazifop, fluazifop-butyl, fluazifop-P, fluazifop-P-butyl, haloxyfop, haloxyfop-methyl, haloxyfop-P, haloxyfop-P-methyl, metamifop, pinoxaden, profoxydim, propaquizafop, quizalofop, quizalofop-ethyl, quizalofop-tefuryl, quizalofop-P, quizalofop-P-ethyl, quizalofop-P-tefuryl, sethoxydim, tepraloxydim and tralkoxydim, and non ACC herbicides such as benfuresate, butylate, cycloate, dalapon, dimepiperate, EPTC, esprocarb, ethofumesate, flupropanate, molinate, orbencarb, pebulate, prosulfocarb, TCA, thiobencarb, tiocarbazil, triallate and vernolate;
b2) from the group of the ALS inhibitors:
sulfonylureas such as amidosulfuron, azimsulfuron, bensulfuron, bensulfuron-methyl, chlorimuron, chlorimuron-ethyl, chlorsulfuron, cinosulfuron, cyclosulfamuron, ethametsulfuron, ethametsulfuron-methyl, ethoxysulfuron, flazasulfuron, flucetosulfuron, flupyrsulfuron, flupyrsulfuron-methyl-sodium, foramsulfuron, halosulfuron, halosulfuronmethyl, imazosulfuron, iodosulfuron, iodosulfuron-methyl-sodium, mesosulfuron, metazosulfuron, metsulfuron, metsulfuron-methyl, nicosulfuron, orthosulfamuron, oxasulfuron, primisulfuron, primisulfuron-methyl, propyrisulfuron, prosulfuron, pyrazosulfuron, pyrazosulfuron-ethyl, rimsulfuron, sulfometuron, sulfometuron-methyl, sulfosulfuron, thifensulfuron, thifensulfuron-methyl, triasulfuron, tribenuron, tribenuron-methyl, trifloxysulfuron, triflusulfuron, triflusulfuron-methyl and tritosulfuron,
imidazolinones such as imazamethabenz, imazamethabenz-methyl, imazamox, imazapic, imazapyr, imazaquin and imazethapyr, triazolopyrimidine herbicides and sulfonanilides such as cloransulam, cloransulam-methyl, diclosulam, flumetsulam, florasulam, metosulam, penoxsulam, pyrimisulfan and pyroxsulam, pyrimidinylbenzoates such as bispyribac, bispyribac-sodium, pyribenzoxim, pyriftalid, pyriminobac, pyriminobac-methyl, pyrithiobac, pyrithiobac-sodium, 4-[[[2-[(4,6-dimethoxy-2-pyrimidinyl)oxy]phenyl]methyl]amino]-benzoic acid-1-methylethyl ester (CAS 420138-41-6), 4-[[[2-[(4,6-dimethoxy-2-pyrimidinyl)oxy]phenyl]methyl]amino]-benzoic acid propyl ester (CAS 420138-40-5), N-(4-bromophenyl)-2-[(4,6-dimethoxy-2-pyrimidinyl)oxy]benzenemethanamine (CAS 420138-01-8), sulfonylaminocarbonyl-triazolinone herbicides such as flucarbazone, flucarbazone-sodium, propoxycarbazone, propoxycarbazone-sodium, thiencarbazone and thiencarbazone-methyl, and triafamone.

Among these, a preferred embodiment of the invention relates to those compositions comprising at least one imidazolinone herbicide;

b3) from the group of the photosynthesis inhibitors:
amicarbazone, inhibitors of the photosystem II, e.g. triazine herbicides, including of chlorotriazine, triazinones, triazindiones, methylthiotriazines and pyridazinones such as ametryn, atrazine, chloridazon, cyanazine, desmetryn, dimethametryn, hexazinone, metribuzin, prometon, prometryn, propazine, simazine, simetryn, terbumeton, terbuthylazin, terbutryn and trietazin, aryl urea such as chlorobromuron, chlorotoluron, chloroxuron, dimefuron, diuron, fluometuron, isoproturon, isouron, linuron, metamitron, methabenzthiazuron, metobenzuron, metoxuron, monolinuron, neburon, siduron, tebuthiuron and thiadiazuron, phenyl carbamates such as desmedipham, karbutilat, phenmedipham, phenmedipham-ethyl, nitrile herbicides such as bromofenoxim, bromoxynil and its salts and esters, ioxynil and its salts and esters, uraciles such as bromacil, lenacil and terbacil, and bentazon and bentazon-sodium, pyridate, pyridafol, pentanochlor and propanil and inhibitors of the photosystem I such as diquat, diquatdibromide, paraquat, paraquat-dichloride and paraquat-dimetilsulfate. Among these, a preferred embodiment of the invention relates to those compositions comprising at least one aryl urea herbicide. Among these, likewise a preferred embodiment of the invention relates to those compositions comprising at least one triazine herbicide. Among these, likewise a preferred embodiment of the invention relates to those compositions comprising at least one nitrile herbicide;

b4) from the group of the protoporphyrinogen-IX oxidase inhibitors:
acifluorfen, acifluorfen-sodium, azafenidin, bencarbazone, benzfendizone, bifenox, butafenacil, carfentrazone, carfentrazone-ethyl, chlomethoxyfen, cinidon-ethyl, fluazolate, flufenpyr, flufenpyr-ethyl, flumiclorac, flumiclorac-pentyl, flumioxazin, fluoroglycofen, fluoroglycofen-ethyl, fluthiacet, fluthiacet-methyl, fomesafen, halosafen, lactofen, oxadiargyl, oxadiazon, oxyfluorfen, pentoxazone, profluazol, pyraclonil, pyraflufen, pyraflufen-ethyl, saflufenacil, sulfentrazone, thidiazimin, ethyl[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), N-ethyl-3-(2,6-dichloro-4-trifluoro-methylphenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1-pyrazole-1-carboxamide (CAS 915396-43-9), N-ethyl-3-(2-chloro-6-fluoro-4-trifluoromethyl-phenoxy)-5-methyl-1H-pyrazole-1-carboxamide (CAS 452099-05-7), N-tetrahydro-furfuryl-3-(2-chloro-6-fluoro-4-trifluoromethylphenoxy)-5-methyl-1-pyrazole-1-carboxamide (CAS 45100-03-7), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione, 2-(2,2,7-Trifluoro-3-oxo-4-prop-2-ynyl-3,4-dihydro-2H-benzo[1,4]oxazin-6-yl)-4,5,6,7-tetrahydro-isoindole-1,3-dione, and 1-Methyl-6-trifluoro-methyl-3-(2,2,7-trifluoro-3-oxo-4-prop-2-ynyl-3,4-dihydro-2H-benzo[1,4]oxazin-6-yl)-1H-pyrimidine-2,4-dione;

b5) from the group of the bleacher herbicides:
PDS inhibitors: beflubutamid, diflufenican, fluridone, fluorochloridone, flurtamone, norflurazon, picolinafen, and 4-(3-trifluoromethylphenoxy)-2-(4-trifluoromethylphenyl)pyrimidine (CAS 180608-33-7), HPPD inhibitors: benzobicyclon, benzofenap, clomazone, isoxaflutole, mesotrione, pyrasulfotole, pyrazolynate, pyrazoxyfen, sulcotrione, tefuryltrione, tembotrione, topramezone and bicyclopyrone, bleacher, unknown target: aclonifen, amitrole and flumeturon;

b6) from the group of the EPSP synthase inhibitors:
glyphosate, glyphosate-isopropylammonium, glyposate-potassium and glyphosate-trimesium (sulfosate);

b7) from the group of the glutamine synthase inhibitors:
bilanaphos (bialaphos), bilanaphos-sodium, glufosinate, glufosinate-P and glufosinate-ammonium;

b8) from the group of the DHP synthase inhibitors:
asulam;

b9) from the group of the mitosis inhibitors:
compounds of group K1: dinitroanilines such as benfluralin, butralin, dinitramine, ethalfluralin, fluchloralin, oryzalin, pendimethalin, prodiamine and trifluralin, phosphoramidates such as amiprophos, amiprophos-methyl, and butamiphos, benzoic acid herbicides such as chlorthal, chlorthal-dimethyl, pyridines such as dithiopyr and thiazopyr, benzamides such as propyzamide and tebutam; compounds of group K2: chlorpropham, propham and carbetamide, among these, compounds of group K1, in particular dinitroanilines are preferred;

b10) from the group of the VLCFA inhibitors:
chloroacetamides such as acetochlor, alachlor, butachlor, dimethachlor, dimethenamid, dimethenamid-P, metazachlor, metolachlor, metolachlor-S, pethoxamid, pretilachlor, propachlor, propisochlor and thenylchlor, oxyacetanilides such as flufenacet and mefenacet, acetanilides such as diphenamid, naproanilide and napropamide, tetrazolinones such fentrazamide, and other herbicides such as anilofos, cafenstrole, fenoxasulfone, ipfencarbazone, piperophos, pyroxasulfone and isoxazoline compounds of the formula II,

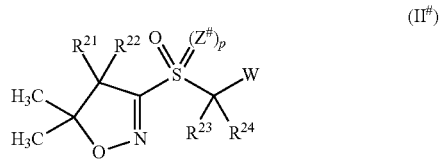

(II#)

wherein $R^{21}$, $R^{22}$, $R^{23}$, $R^{24}$, W, Z and n have the following meanings:
$R^{21}$, $R^{22}$, $R^{23}$, $R^{24}$ independently of one another hydrogen, halogen or $C_1$-$C_4$-alkyl;
W phenyl or monocyclic 5-, 6-, 7-, 8-, 9- or 10-membered heterocyclyl containing, in addition to carbon ring members one, two or three same or different heteroatoms selected from oxygen, nitrogen and sulfur as ring members, wherein phenyl and heterocyclyl are unsubstituted or carry 1, 2 or 3 substituents $R^{yy}$ selected from halogen, $C_1$-$C_4$-alkyl, $C_1$-$C_4$-alkoxy, $C_1$-$C_4$-haloalkyl and $C_1$-$C_4$-haloalkoxy;
preferably phenyl or 5- or 6-membered aromatic heterocyclyl (hetaryl) which contains, in addition to carbon ring members, one, two or three nitrogen atoms as ring members, wherein phenyl and hetaryl are unsubstituted or carry 1, 2 or 3 substituents $R^{yy}$;
Z# oxygen or NH; and
p zero or one;
among the isoxazoline compounds of the formula II, preference is given to isoxazoline compounds of the formula II, wherein
$R^{21}$, $R^{22}$, $R^{23}$, $R^{24}$ independently of one another are H, F, Cl or methyl;
Z is oxygen;
n is 0 or 1; and
W is phenyl, pyrazolyl or 1,2,3-triazolyl, wherein the three last-mentioned radicals are unsubstituted or carry one, two or three substituents $R^{yy}$, especially one of the following radicals

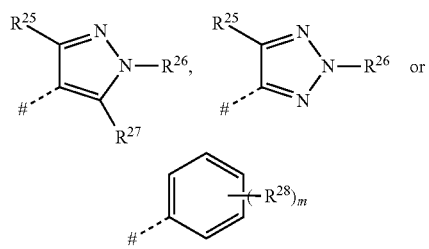

wherein
$R^{25}$ is halogen, $C_1$-$C_4$-alkyl or $C_1$-$C_4$-haloalkyl;
$R^{26}$ is $C_1$-$C_4$-alkyl;
$R^{27}$ is halogen, $C_1$-$C_4$-alkoxy or $C_1$-$C_4$-haloalkoxy;
$R^{28}$ is halogen, $C_1$-$C_4$-alkyl, $C_1$-$C_4$-haloalkyl or $C_1$-$C_4$-haloalkoxy;
m is 0, 1, 2 or 3; and
# denotes the point of attachment to the group $CR^{23}R^{24}$;
among the isoxazoline compounds of the formula II, particular preference is given to those isoxazoline compounds of the formula II, wherein
$R^{21}$ is hydrogen;
$R^{22}$ is fluorine;
$R^{23}$ is hydrogen or fluorine;
$R^{24}$ is hydrogen or fluorine;
W is one of the radicals of the formulae $W^1$, $W^2$, $W^3$ or $W^4$ W¹
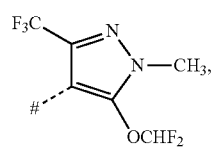

W²
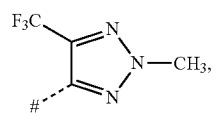

W³
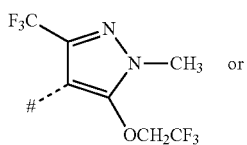
or

W⁴
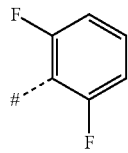

wherein # denotes the point of attachment to the group $CR^{23}R^{24}$;
Z is oxygen;
n is zero or 1, in particular 1; and
among these, especially preferred are the isoxazoline compounds of the formulae II.1, II.2, II.3, II.4, II.5, II.6, II.7, II.8 and II.9

II.1
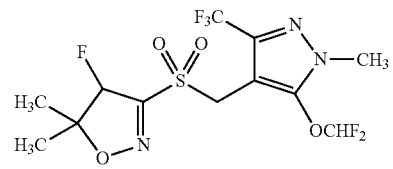

II.2
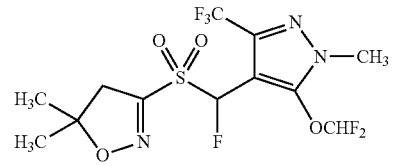

II.3
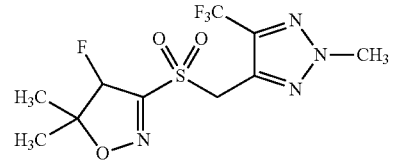

II.4
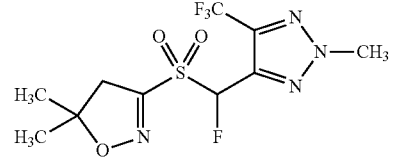

II.5
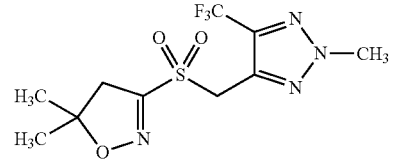

II.6
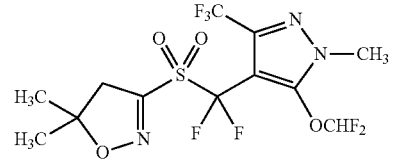

-continued

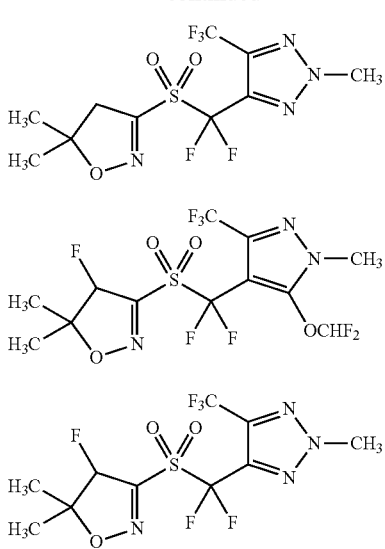

II.7

II.8

II.9 the isoxazoline compounds of the formula II are known in the art, e.g. from WO 2006/024820, WO 2006/037945, WO 2007/071900 and WO 2007/096576;

among the VLCFA inhibitors, preference is given to chloroacetamides and oxyacetamides;

b11) from the group of the cellulose biosynthesis inhibitors: chlorthiamid, dichlobenil, flupoxam, isoxaben, 1-Cyclohexyl-5-pentafluorphenyloxy-1$^4$-[1,2,4,6]thiatriazin-3-ylamine and piperazine compounds of formula III$^\#$,

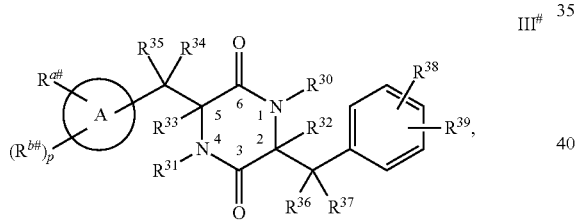

III$^\#$ in which

A is phenyl or pyridyl where $R^a$ is attached in the ortho-position to the point of attachment of A to a carbon atom;

$R^{a\#}$ is CN, NO$_2$, C$_1$-C$_4$-alkyl, D-C$_3$-C$_6$-cycloalkyl, C$_1$-C$_4$-haloalkyl, C$_1$-C$_4$-alkoxy, C$_1$-C$_4$-haloalkoxy, O-D-C$_3$-C$_6$-cycloalkyl, S(O)$_q$R$^{y\#}$, C$_2$-C$_6$-alkenyl, D-C$_3$-C$_6$-cycloalkenyl, C$_3$-C$_6$-alkenyloxy, C$_2$-C$_6$-alkynyl, C$_3$-C$_6$-alkynyloxy, NR$^{A\#}$R$^{B\#}$, tri-C$_1$-C$_4$-alkylsilyl, D-C(=O)—R$^{a\#1}$, D-P(=O)(R$^{a\#1}$)$_2$, phenyl, naphthyl, a 3- to 7-membered monocyclic or 9- or 10-membered bicyclic saturated, unsaturated or aromatic heterocycle which is attached via carbon or nitrogen, which contains 1, 2, 3 or 4 heteroatoms selected from the group consisting of O, N and S, and which may be partially or fully substituted by groups R$^{aa\#}$ and/or R$^{a\#1}$, and, if R$^{a\#}$ is attached to a carbon atom, additionally halogen;

$R^{y\#}$ is C$_1$-C$_6$-alkyl, C$_3$-C$_4$-alkenyl, C$_3$-C$_4$-alkynyl, NR$^{A\#}$R$^{B\#}$ or C$_1$-C$_4$-haloalkyl and q is 0, 1 or 2;

$R^{A\#}$, $R^{B\#}$ independently of one another are hydrogen, C$_1$-C$_6$-alkyl, C$_3$-C$_6$-alkenyl and C$_3$-C$_6$-alkynyl; together with the nitrogen atom to which they are attached, R$^{A\#}$, R$^{B\#}$ may also form a five- or six-membered saturated, partially or fully unsaturated ring which, in addition to carbon atoms, may contain 1, 2 or 3 heteroatoms selected from the group consisting of O, N and S, which ring may be substituted by 1 to 3 groups R$^{aa\#}$;

D is a covalent bond, C$_1$-C$_4$-alkylene, C$_2$-C$_6$-alkenyl or C$_2$-C$_6$-alkynyl;

$R^{a\#1}$ is hydrogen, OH, C$_1$-C$_8$-Alkyl, C$_1$-C$_4$-haloalkyl, C$_3$-C$_6$-cycloalkyl, C$_2$-C$_8$-alkenyl, C$_5$-C$_6$-cycloalkenyl, C$_2$-C$_8$-alkynyl, C$_1$-C$_6$-alkoxy, C$_1$-C$_4$-haloalkoxy, C$_3$-C$_8$-alkenyloxy, C$_3$-C$_8$-alkynyloxy, NR$^{A\#}$R$^{B\#}$, C$_1$-C$_6$-alkoxyamino, C$_1$-C$_6$-alkylsulfonylamino, C$_1$-C$_6$-alkylaminosulfonylamino, [di-(C$_1$-C$_6$)alkylamino]sulfonylamino, C$_3$-C$_6$-alkenylamino, C$_3$-C$_6$-alkynylamino, N—(C$_2$-C$_6$-alkenyl)-N—(C$_1$-C$_6$-alkyl)amino, N—(C$_2$-C$_6$-alkynyl)-N—(C$_1$-C$_6$-alkyl)amino, N—(C$_1$-C$_6$-alkoxy)-N—(C$_1$-C$_6$-alkyl)amino, N—(C$_2$-C$_6$-alkenyl)-N—(C$_1$-C$_6$-alkoxy)amino, N—(C$_2$-C$_6$-alkynyl)-N—(C$_1$-C$_6$-alkoxy)-amino, C$_1$-C$_6$-alkylsulfonyl, tri-C$_1$-C$_4$-alkylsilyl, phenyl, phenoxy, phenylamino or a 5- or 6-membered monocyclic or 9- or 10-membered bicyclic heterocycle which contains 1, 2, 3 or 4 heteroatoms selected from the group consisting of O, N and S, where the cyclic groups are unsubstituted or substituted by 1, 2, 3 or 4 groups R$^{aa\#}$;

$R^{aa\#}$ is halogen, OH, CN, NO$_2$, C$_1$-C$_4$-alkyl, C$_1$-C$_4$-haloalkyl, C$_1$-C$_4$-alkoxy, C$_1$-C$_4$-haloalkoxy, S(O)$_q$R$^{y\#}$, D-C(=O)—R$^{a\#1}$ and tri-C$_1$-C$_4$-alkylsilyl;

$R^{b\#}$ independently of one another are hydrogen, CN, NO$_2$, halogen, C$_1$-C$_4$-alkyl, C$_1$-C$_4$-haloalkyl, C$_2$-C$_4$-alkenyl, C$_3$-C$_6$-alkynyl, C$_1$-C$_4$-alkoxy, C$_1$-C$_4$-haloalkoxy, benzyl or S(O)$_q$R$^{y\#}$, $R^{b\#}$ together with the group R$^{a\#}$ or R$^{b\#}$ attached to the adjacent ring atom may also form a five- or six-membered saturated or partially or fully unsaturated ring which, in addition to carbon atoms, may contain 1, 2 or 3 heteroatoms selected from the group consisting of O, N and S, which ring may be partially or fully substituted by R$^{aa\#}$;

p is 0, 1, 2 or 3;

$R^{30}$ is hydrogen, OH, CN, C$_1$-C$_{12}$-alkyl, C$_3$-C$_{12}$-alkenyl, C$_3$-C$_{12}$-alkynyl, C$_1$-C$_4$-alkoxy, C$_3$-C$_6$-cycloalkyl, C$_5$-C$_6$-cycloalkenyl, NR$^{A\#}$R$^{B\#}$, S(O)$_n$R$^{y\#}$, S(O)$_n$NR$^{A\#}$R$^{B\#}$, C(=O)R$^{40}$, CONR$^{A\#}$R$^{B\#}$, phenyl or a 5- or 6-membered monocyclic or 9- or 10- membered bicyclic aromatic heterocycly which contains 1, 2, 3 or 4 heteroatoms selected from the group consisting of O, N and S, where the cyclic groups are attached via D$^1$ and are unsubstituted or substituted by 1, 2, 3 or 4 groups R$^{aa\#}$, and also the following partially or fully R$^{aa\#}$-substituted groups: C$_1$-C$_4$-alkyl, C$_3$-C$_4$-alkenyl, C$_3$-C$_4$-alkynyl, C$_1$-C$_4$-alkoxy, C$_3$-C$_6$-cycloalkyl, C$_5$-C$_6$-cycloalkenyl, NR$^{A\#}$R$^{B\#}$, S(O)$_n$R$_y$, S(O)$_n$R$^{A\#}$R$^{B\#}$, C(=O)R$^{40}$ and CONR$^{A\#}$R$^{B\#}$;

$R^{40}$ is hydrogen, C$_1$-C$_4$-alkyl, C$_1$-C$_4$-haloalkyl, C$_1$-C$_4$-alkoxy or C$_1$-C$_4$-halo-alkoxy;

$D^1$ is carbonyl or a group D;

where in groups R$^{15}$, R$^{a\#}$ and their sub-substituents the carbon chains and/or the cyclic groups may carry 1, 2, 3 or 4 substituents R$^{aa\#}$ and/or R$^{a\#1}$;

$R^{31}$ is C$_1$-C$_4$-alkyl, C$_3$-C$_4$-alkenyl or C$_3$-C$_4$-alkynyl;

$R^{32}$ is OH, NH$_2$, C$_1$-C$_4$-alkyl, C$_3$-C$_6$-cycloalkyl, C$_3$-C$_6$-alkenyl, C$_3$-C$_6$-alkynyl, C$_1$-C$_4$-hydroxyalkyl, C$_1$-C$_4$-cyanoalkyl, C$_1$-C$_4$-haloalkyl, C$_1$-C$_4$-alkoxy-C$_1$-C$_4$-alkyl or C(=O)R$^{40}$;

$R^{33}$ is hydrogen, halogen, C$_1$-C$_4$-alkyl or C$_1$-C$_4$-haloalkyl, or R$^{33}$ and R$^{34}$ together are a covalent bond;

$R^{34}$, $R^{35}$, $R^{36}$, $R^{37}$ independently of one another are hydrogen, halogen, OH, CN, NO$_2$, C$_1$-C$_4$-alkyl, C$_1$-C$_4$-haloalkyl, C$_2$-C$_6$-alkenyl, C$_2$-C$_6$-alkynyl, C$_1$-C$_4$-alkoxy, C$_1$-C$_4$-haloalkoxy, C$_3$-C$_6$-cycloalkyl, C$_3$-C$_6$-cycloalkenyl and C$_3$-C$_6$-cycloalkynyl;

$R^{38}$, $R^{39}$ independently of one another are hydrogen, halogen, OH, haloalkyl, NR$^{A\#}$R$^{B\#}$, NR$^{A\#}$C(O)R$^{41}$, CN, NO$_2$, C$_1$-C$_4$-alkyl, C$_1$-C$_4$-haloalkyl, C$_2$-C$_4$-alkenyl, C$_3$-C$_6$-alkynyl, C$_1$-C$_4$-alkoxy, C$_1$-C$_4$-haloalkoxy, O—C(O)R$^{41}$, phenoxy or benzyloxy, where in groups R$^{38}$ and R$^{39}$ the carbon chains and/or the cyclic groups may carry 1, 2, 3 or 4 substituents R$^{aa\#}$;

$R^{41}$ is C$_1$-C$_4$-alkyl or NR$^{A\#}$R$^{B\#}$;

among the piperazine compounds of formula III, preference is given to the piperazine compounds of the formula III, wherein A is phenyl or pyridyl where R$^{a\#}$ is attached in the ortho-position to the point of attachment of A to a carbon atom;

$R^{a\#}$ is CN, NO$_2$, C$_1$-C$_4$-alkyl, C$_1$-C$_4$-haloalkyl, C$_1$-C$_4$-alkoxy, C$_1$-C$_4$-haloalkoxy or D-C(=O)—R$^{a\#1}$;

$R^{y\#}$ is C$_1$-C$_6$-alkyl, C$_3$-C$_4$-alkenyl, C$_3$-C$_4$-alkynyl, NR$^{A\#}$R$^{B\#}$ or C$_1$-C$_4$-haloalkyl and q is 0, 1 or 2;

$R^{A\#}$, $R^{B\#}$ independently of one another are hydrogen, C$_1$-C$_6$-alkyl, C$_3$-C$_6$-alkenyl and C$_3$-C$_6$-alkynyl; together with the nitrogen atom to which they are attached, R$^{A\#}$, R$^{B\#}$ may also form a five- or six-membered saturated, partially or fully unsaturated ring which, in addition to carbon atoms, may contain 1, 2 or 3 heteroatoms selected from the group consisting of O, N and S, which ring may be substituted by 1 to 3 groups R$^{aa\#}$;

D is a covalent bond or C$_1$-C$_4$-alkylene;

$R^{a\#1}$ is hydrogen, OH, C$_1$-C$_8$-Alkyl, C$_1$-C$_4$-haloalkyl, C$_3$-C$_6$-cycloalkyl;

$R^{aa\#}$ is halogen, OH, CN, NO$_2$, C$_1$-C$_4$-alkyl, C$_1$-C$_4$-haloalkyl, C$_1$-C$_4$-alkoxy, C$_1$-C$_4$-haloalkoxy, S(O)$_q$R$^{y\#}$, D-C(=O)—R$^{a1}$ and tri-C$_1$-C$_4$-alkylsilyl;

$R^{b\#}$ independently of one another is CN, NO$_2$, halogen, C$_1$-C$_4$-alkyl, C$_1$-C$_4$-haloalkyl, C$_2$-C$_4$-alkenyl, C$_3$-C$_6$-alkynyl, C$_1$-C$_4$-alkoxy, C$_1$-C$_4$-haloalkoxy, benzyl or S(O)$_q$R$^{y\#}$, $R^{b\#}$ together with the group R$^{a\#}$ or R$^{b\#}$ attached to the adjacent ring atom may also form a five- or six-membered saturated or partially or fully unsaturated ring which, in addition to carbon atoms, may contain 1, 2 or 3 heteroatoms selected from the group consisting of O, N and S, which ring may be partially or fully substituted by R$^{aa\#}$;

p is 0 or 1;

$R^{30}$ is hydrogen, C$_1$-C$_{12}$-alkyl, C$_3$-C$_{12}$-alkenyl, C$_3$-C$_{12}$-alkynyl, C$_1$-C$_4$-alkoxy or C(=O)R$^{40}$, which can be partially or fully be substituted by R$^{aa\#}$ groups;

$R^{40}$ is hydrogen, C$_1$-C$_4$-alkyl, C$_1$-C$_4$-haloalkyl, C$_1$-C$_4$-alkoxy or C$_1$-C$_4$-halo-alkoxy;

where in groups R$^{30}$, R$^a$ and their sub-substituents the carbon chains and/or the cyclic groups may carry 1, 2, 3 or 4 substituents R$^{aa\#}$ and/or R$^{a1\#}$;

$R^{31}$ is C$_1$-C$_4$-alkyl;

$R^{32}$ is OH, NH$_2$, C$_1$-C$_4$-alkyl, C$_3$-C$_6$-cycloalkyl, C$_1$-C$_4$-haloalkyl or C(=O)R$^{25}$;

$R^{33}$ is hydrogen, or R$^{33}$ and R$^{34}$ together are a covalent bond;

$R^{34}$, $R^{35}$, $R^{36}$, $R^{37}$ independently of one another are hydrogen;

$R^{38}$, $R^{39}$ independently of one another are hydrogen, halogen or OH;

b12) from the group of the decoupler herbicides: dinoseb, dinoterb and DNOC and its salts;

b13) from the group of the auxinic herbicides: 2,4-D and its salts and esters, 2,4-DB and its salts and esters, aminopyralid and its salts such as aminopyralid-tris(2-hydroxypropyl)ammonium and its esters, benazolin, benazolin-ethyl, chloramben and its salts and esters, clomeprop, clopyralid and its salts and esters, dicamba and its salts and esters, dichlorprop and its salts and esters, di-chlorprop-P and its salts and esters, fluoroxypyr, fluoroxypyr-butomethyl, fluoroxypyr-meptyl, MCPA and its salts and esters, MCPA-thioethyl, MCPB and its salts and esters, mecoprop and its salts and esters, mecoprop-P and its salts and esters, picloram and its salts and esters, quinclorac, quinmerac, TBA (2,3,6) and its salts and esters, triclopyr and its salts and esters, and aminocyclopyrachlor and its salts and esters;

b14) from the group of the auxin transport inhibitors: diflufenzopyr, diflufenzopyr-sodium, naptalam and naptalam-sodium;

b15) from the group of the other herbicides: bromobutide, chlorflurenol, chlorflurenolmethyl, cinmethylin, cumyluron, dalapon, dazomet, difenzoquat, difenzoquatmetilsulfate, dimethipin, DSMA, dymron, endothal and its salts, etobenzanid, flamprop, flamprop-isopropyl, flamprop-methyl, flamprop-M-isopropyl, flamprop-M-methyl, flurenol, flurenol-butyl, flurprimidol, fosamine, fosamine-ammonium, indanofan, indaziflam, maleic hydrazide, mefluidide, metam, methiozolin (CAS 403640-27-7), methyl azide, methyl bromide, methyl-dymron, methyl iodide, MSMA, oleic acid, oxaziclomefone, pelargonic acid, pyributicarb, quinoclamine, triaziflam, tridiphane and 6-chloro-3-(2-cyclopropyl-6-methylphenoxy)-4-pyridazinol (CAS 499223-49-3) and its salts and esters.

Moreover, it may be useful to apply the compounds of the formula I in combination with safeners. Safeners are chemical compounds which prevent or reduce damage on useful plants without having a major impact on the herbicidal action of the compounds of the formula I towards unwanted plants. They can be applied either before sowings (e.g. on seed treatments, shoots or seedlings) or in the pre-emergence application or post-emergence application of the useful plant. The safeners and the compounds of the formula I can be applied simultaneously or in succession.

Suitable safeners are e.g. (quinolin-8-oxy)acetic acids, 1-phenyl-5-haloalkyl-1H-1,2,4-triazol-3-carboxylic acids, 1-phenyl-4,5-dihydro-5-alkyl-1H-pyrazol-3,5-dicarboxylic acids, 4,5-dihydro-5,5-diaryl-3-isoxazol carboxylic acids, dichloroacetamides, alpha-oximinophenylacetonitriles, acetophenonoximes, 4,6-dihalo-2-phenylpyrimidines, N—[[4-(aminocarbonyl)phenyl]sulfonyl]-2-benzoic amides, 1,8-naphthalic anhydride, 2-halo-4-(haloalkyl)-5-thiazol carboxylic acids, phosphorthiolates and N-alkyl-O-phenyl-carbamates and their agriculturally acceptable salts and their agriculturally acceptable derivatives such amides, esters, and thioesters, provided they have an acid group.

Examples of preferred safeners C are benoxacor, cloquintocet, cyometrinil, cyprosulfamide, dichlormid, dicyclonon, dietholate, fenchlorazole, fenclorim, flurazole, fluxofenim, furilazole, isoxadifen, mefenpyr, mephenate, naphthalic anhydride, oxabetrinil, 4-(dichloroacetyl)-1-oxa-4-azaspiro[4.5]decane (MON4660, CAS 71526-07-3), 2,2,5-trimethyl-3-(dichloroacetyl)-1,3-oxazolidine (R-29148, CAS 52836-31-4) and N-(2-Methoxybenzoyl)-4-[(methylaminocarbonyl)amino]benzenesulfonamide (CAS 129531-12-0).

Especially preferred safeners C are benoxacor, cloquintocet, cyprosulfamide, dichlor-mid, fenchlorazole, fenclorim, flurazole, fluxofenim, furilazole, isoxadifen, mefenpyr, naphthalic anhydride, oxabetrinil, 4-(dichloroacetyl)-1-oxa-4-azaspiro[4.5]decane (MON4660, CAS 71526-07-3), 2,2,5-trimethyl-3-(dichloroacetyl)-1,3-oxazolidine (R-29148, CAS 52836-31-4) and N-(2-Methoxybenzoyl)-4-[(methylaminocarbonyl)amino]benzenesulfonamide (CAS 129531-12-0).

Particularly preferred safeners C are benoxacor, cloquintocet, cyprosulfamide, dichlor-mid, fenchlorazole, fenclorim, furilazole, isoxadifen, mefenpyr, naphtalic anhydride, 4-(dichloroacetyl)-1-oxa-4-azaspiro[4.5]decane (MON4660, CAS 71526-07-3), 2,2,5-trimethyl-3-(dichloroacetyl)-1,3-oxazolidine (R-29148, CAS 52836-31-4) and N-(2-Methoxybenzoyl)-4-[(methylaminocarbonyl)amino] benzenesulfonamide (CAS 129531-12-0).

The active compounds B of groups b1) to b15) and the active compounds C are known herbicides and safeners, see, for example, The Compendium of Pesticide Common Names (http://www.alanwood.net/pesticides/); Farm Chemicals Handbook 2000 volume 86, Meister Publishing Company, 2000; B. Hock, C. Fedtke, R. R. Schmidt, Herbizide [Herbicides], Georg Thieme Verlag, Stuttgart 1995; W. H. Ahrens, Herbicide Handbook, 7th edition, Weed Science Society of America, 1994; and K. K. Hatzios, Herbicide Handbook, Supplement for the 7th edition, Weed Science Society of America, 1998. 2,2,5-Trimethyl-3-(dichloroacetyl)-1,3-oxazolidine [CAS No. 52836-31-4] is also referred to as R-29148. 4-(Dichloroacetyl)-1-oxa-4-azaspiro[4.5]decane [CAS No. 71526-07-3] is also referred to as AD-67 and MON 4660.

The piperazine compounds of formula III# as defined above (hereinafter also referred to as "compound III#") as well as its pesticidal action and methods for preparation are de-scribed in WO 2010/049369, WO 2010/037727 und WO 2010/012649.

The invention also relates to compositions in the form of a crop protection composition formulated as a 1-component composition comprising an active compound combination comprising at least one benzoxazinone of the formula I and at least one further active compound, preferably selected from the active compounds of groups b1 to b15, and at least one solid or liquid carrier and/or one or more surfactants and, if desired, one or more further auxiliaries customary for crop protection compositions.

The invention also relates to compositions in the form of a crop protection composition formulated as a 2-component composition comprising a first component comprising at least one benzoxazinone of the formula I, a solid or liquid carrier and/or one or more surfactants and a second component comprising at least one further active compound selected from the active compounds of groups b1 to b15, a solid or liquid carrier and/or one or more surfactants, where additionally both components may also comprise further auxiliaries customary for crop protection compositions.

In binary compositions comprising at least one compound of the formula I as component A and at least one herbicide B, the weight ratio of the active compounds A:B is generally in the range of from 1:1000 to 1000:1, preferably in the range of from 1:500 to 500:1, in particular in the range of from 1:250 to 250:1 and particularly preferably in the range of from 1:75 to 75:1.

In binary compositions comprising at least one compound of the formula I as component A and at least one safener C, the weight ratio of the active compounds A:C is generally in the range of from 1:1000 to 1000:1, preferably in the range of from 1:500 to 500:1, in particular in the range of from 1:250 to 250:1 and particularly preferably in the range of from 1:75 to 75:1.

In ternary compositions comprising both at least one compound of the formula I as component A, at least one herbicide B and at least one safener C, the relative parts by weight of the components A:B are generally in the range of from 1:1000 to 1000:1, preferably in the range of from 1:500 to 500:1, in particular in the range of from 1:250 to 250:1 and particularly preferably in the range of from 1:75 to 75:1; the weight ratio of the components A:C is generally in the range of from 1:1000 to 1000:1, preferably in the range of from 1:500 to 500:1, in particular in the range of from 1:250 to 250:1 and particularly preferably in the range of from 1:75 to 75:1; and the weight ratio of the components B:C is generally in the range of from 1:1000 to 1000:1, preferably in the range of from 1:500 to 500:1, in particular in the range of from 1:250 to 250:1 and particularly preferably in the range of from 1:75 to 75:1. Preferably, the weight ratio of the components A+B to the component C is in the range of from 1:500 to 500:1, in particular in the range of from 1:250 to 250:1 and particularly preferably in the range of from 1:75 to 75:1.
1.

Particularly preferred herbicides B are the herbicides B as defined above; in particular the herbicides B.1-B.144 listed below in table B:

TABLE B

| | Herbicide B |
|---|---|
| B.1 | clethodim |
| B.2 | clodinafop-propargyl |
| B.3 | cycloxydim |
| B.4 | cyhalofop-butyl |
| B.5 | fenoxaprop-P-ethyl |
| B.6 | metamifop |
| B.7 | pinoxaden |
| B.8 | profoxydim |
| B.9 | sethoxydim |
| B.10 | tepraloxydim |
| B.11 | tralkoxydim |
| B.12 | esprocarb |
| B.13 | ethofumesate |
| B.14 | molinate |
| B.15 | prosulfocarb |
| B.16 | thiobencarb |
| B.17 | triallate |
| B.18 | bensulfuron-methyl |
| B.19 | bispyribac-sodium |
| B.20 | cloransulam |
| B.21 | chlorsulfuron |
| B.22 | clorimuron |
| B.23 | cyclosulfamuron |
| B.24 | diclosulam |
| B.25 | florasulam |
| B.26 | flumetsulam |
| B.27 | flupyrsulfuron-methyl-sodium |
| B.28 | foramsulfuron |
| B.29 | imazamox |
| B.30 | imazapic |
| B.31 | imazapyr |
| B.32 | imazaquin |
| B.33 | imazethapyr |
| B.34 | imazosulfuron |
| B.35 | iodosulfuron-methyl-sodium |
| B.36 | mesosulfuron |
| B.37 | metazosulfuron |
| B.38 | metsulfuron |
| B.39 | metosulam |
| B.40 | nicosulfuron |
| B.41 | penoxsulam |
| B.42 | propoxycarbazon-sodium |
| B.43 | pyrazosulfuron-ethyl |
| B.44 | pyribenzoxim |

TABLE B-continued

| | Herbicide B |
|---|---|
| B.45 | pyriftalid |
| B.46 | pyroxsulam |
| B.47 | rimsulfuron |
| B.48 | sulfosulfuron |
| B.49 | thiencarbazone-methyl |
| B.50 | thifensulfuron |
| B.51 | tribenuron |
| B.52 | tritosulfuron |
| B.53 | ametryne |
| B.54 | atrazine |
| B.55 | bentazon |
| B.56 | bromoxynil |
| B.57 | diuron |
| B.58 | fluometuron |
| B.59 | hexazinone |
| B.60 | isoproturon |
| B.61 | linuron |
| B.62 | metamitron |
| B.63 | metribuzin |
| B.64 | propanil |
| B.65 | simazin |
| B.66 | terbuthylazine |
| B.67 | terbutryn |
| B.68 | paraquat-dichloride |
| B.69 | acifluorfen |
| B.70 | butafenacil |
| B.71 | carfentrazone-ethyl |
| B.72 | flumioxazin |
| B.73 | fomesafen |
| B.74 | oxadiargyl |
| B.75 | oxyfluorfen |
| B.76 | saflufenacil |
| B.77 | sulfentrazone |
| B.78 | ethyl [3-[2-chloro-4-fluoro-5-(1-methyl-6-trifluoromethyl-2,4-di-oxo-1,2,3,4-tetrahydropyrimidin-3-yl)phenoxy]-2-pyridyl-oxy]acetate (CAS 353292-31-6) |
| B.79 | 3-[7-fluoro-3-oxo-4-(prop-2-ynyl)-3,4-dihydro-2H-benzo[1,4]-oxazin-6-yl]-1,5-dimethyl-6-thi-oxo-[1,3,5]triazinan-2,4-dione |
| B.80 | 1,5-dimethyl-6-thioxo-3-(2,2,7-trifluoro-3-oxo-4-(prop-2-ynyl)-3,4-dihydro-2H-benzo[b][1,4]-oxazin-6-yl)-1,3,5-triazinane-2,4-dione |
| B.81 | 2-(2,2,7-Trifluoro-3-oxo-4-prop-2-ynyl-3,4-dihydro-2H-benzo[1,4]oxazin-6-yl)-4,5,6,7-tetrahydro-isoindole-1,3-dione |
| B.82 | 1-Methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione |
| B.83 | benzobicyclon |
| B.84 | clomazone |
| B.85 | diflufenican |
| B.86 | flurochloridone |
| B.87 | isoxaflutole |
| B.88 | mesotrione |
| B.89 | norflurazone |
| B.90 | picolinafen |
| B.91 | sulcotrione |
| B.92 | tefuryltrione |
| B.93 | tembotrione |
| B.94 | topramezone |
| B.95 | bicyclopyrone |
| B.96 | amitrole |
| B.97 | fluometuron |
| B.98 | glyphosate |
| B.99 | glyphosate-isopropylammonium |
| B.100 | glyphosate-trimesium (sulfosate) |
| B.101 | glufosinate |
| B.102 | glufosinate-P |
| B.103 | glufosinate-ammonium |
| B.104 | pendimethalin |
| B.105 | trifluralin |
| B.106 | acetochlor |
| B.107 | butachlor |
| B.108 | cafenstrole |
| B.109 | dimethenamid-P |
| B.110 | fentrazamide |
| B.111 | flufenacet |
| B.112 | mefenacet |
| B.113 | metazachlor |
| B.114 | metolachlor |
| B.115 | S-metolachlor |
| B.116 | pretilachlor |
| B.117 | fenoxasulfone |
| B.118 | isoxaben |
| B.119 | pyroxasulfone |
| B.120 | 2,4-D |
| B.121 | aminopyralid |
| B.122 | clopyralid |
| B.123 | dicamba |
| B.124 | fluroxypyr-meptyl |
| B.125 | MCPA |
| B.126 | quinclorac |
| B.127 | quinmerac |
| B.128 | aminocyclopyrachlor |
| B.129 | diflufenzopyr |
| B.130 | diflufenzopyr-sodium |
| B.131 | dymron |
| B.132 | indanofan |
| B.133 | indaziflam |
| B.134 | oxaziclomefone |
| B.135 | triaziflam |
| B.136 | II.1 |
| B.137 | II.2 |
| B.138 | II.3 |
| B.139 | II.4 |
| B.140 | II.5 |
| B.141 | II.6 |
| B.142 | II.7 |
| B.143 | II.8 |
| B.144 | II.9 |

Particularly preferred safeners C, which, as component C, are constituent of the PP-51 composition according to the invention are the safeners C as defined above; in particular the safeners C.1-C.13 listed below in table C:

TABLE C

| | Safener C |
|---|---|
| C.1 | benoxacor |
| C.2 | cloquintocet |
| C.3 | cyprosulfamide |
| C.4 | dichlormid |
| C.5 | fenchlorazole |
| C.6 | fenclorim |
| C.7 | furilazole |
| C.8 | isoxadifen |
| C.9 | mefenpyr |
| C.10 | naphtalic acid anhydride |
| C.11 | 4-(dichloroacetyl)-1-oxa-4-azaspiro[4.5]decane (MON4660, CAS 71526-07-3) |
| C.12 | 2,2,5-trimethyl-3-(dichloroacetyl)-1,3-oxazolidine (R-29148, CAS 52836-31-4) |
| C.13 | N-(2-Methoxybenzoyl)-4-[(methylaminocarbonyl)-amino]benzenesulfonamide (CAS 129531-12-0) |

The weight ratios of the individual components in the preferred mixtures mentioned below are within the limits given above, in particular within the preferred limits.

Particularly preferred are the compositions mentioned below comprising the compounds of formula I as defined and the substance(s) as defined in the respective row of table 1;

especially preferred comprising as only herbicidal active compounds the compounds of formula I as defined and the substance(s) as defined in the respective row of table 1;

most preferably comprising as only active compounds the compounds of formula I as defined and the substance(s) as defined in the respective row of table 1.

Particularly preferred are compositions 1.1 to 1.2029, comprising the compound I and the substance(s) as defined in the respective row of table 2:

TABLE 2

(compositions 1.1 to 1.2029):

| comp. no. | herbicide B | safener C |
|---|---|---|
| 1.1 | B.1 | — |
| 1.2 | B.2 | — |
| 1.3 | B.3 | — |
| 1.4 | B.4 | — |
| 1.5 | B.5 | — |
| 1.6 | B.6 | — |
| 1.7 | B.7 | — |
| 1.8 | B.8 | — |
| 1.9 | B.9 | — |
| 1.10 | B.10 | — |
| 1.11 | B.11 | — |
| 1.12 | B.12 | — |
| 1.13 | B.13 | — |
| 1.14 | B.14 | — |
| 1.15 | B.15 | — |
| 1.16 | B.16 | — |
| 1.17 | B.17 | — |
| 1.18 | B.18 | — |
| 1.19 | B.19 | — |
| 1.20 | B.20 | — |
| 1.21 | B.21 | — |
| 1.22 | B.22 | — |
| 1.23 | B.23 | — |
| 1.24 | B.24 | — |
| 1.25 | B.25 | — |
| 1.26 | B.26 | — |
| 1.27 | B.27 | — |
| 1.28 | B.28 | — |
| 1.29 | B.29 | — |
| 1.30 | B.30 | — |
| 1.31 | B.31 | — |
| 1.32 | B.32 | — |
| 1.33 | B.33 | — |
| 1.34 | B.34 | — |
| 1.35 | B.35 | — |
| 1.36 | B.36 | — |
| 1.37 | B.37 | — |
| 1.38 | B.38 | — |
| 1.39 | B.39 | — |
| 1.40 | B.40 | — |
| 1.41 | B.41 | — |
| 1.42 | B.42 | — |
| 1.43 | B.43 | — |
| 1.44 | B.44 | — |
| 1.45 | B.45 | — |
| 1.46 | B.46 | — |
| 1.47 | B.47 | — |
| 1.48 | B.48 | — |
| 1.49 | B.49 | — |
| 1.50 | B.50 | — |
| 1.51 | B.51 | — |
| 1.52 | B.52 | — |
| 1.53 | B.53 | — |
| 1.54 | B.54 | — |
| 1.55 | B.55 | — |
| 1.56 | B.56 | — |
| 1.57 | B.57 | — |
| 1.58 | B.58. | — |
| 1.59 | B.59 | — |
| 1.60 | B.60 | — |
| 1.61 | B.61 | — |
| 1.62 | B.62 | — |
| 1.63 | B.63 | — |
| 1.64 | B.64 | — |
| 1.65 | B.65 | — |
| 1.66 | B.66 | — |
| 1.67 | B.67 | — |
| 1.68 | B.68 | — |
| 1.69 | B.69 | — |
| 1.70 | B.70 | — |
| 1.71 | B.71 | — |
| 1.72 | B.72 | — |
| 1.73 | B.73 | — |
| 1.74 | B.74 | — |
| 1.75 | B.75 | — |
| 1.76 | B.76 | — |
| 1.77 | B.77 | — |
| 1.78 | B.78 | — |
| 1.79 | B.79 | — |
| 1.80 | B.80 | — |
| 1.81 | B.81 | — |
| 1.82 | B.82 | — |
| 1.83 | B.83 | — |
| 1.84 | B.84 | — |
| 1.85 | B.85 | — |
| 1.86 | B.86 | — |
| 1.87 | B.87 | — |
| 1.88 | B.88 | — |
| 1.89 | B.89 | — |
| 1.90 | B.90 | — |
| 1.91 | B.91 | — |
| 1.92 | B.92 | — |
| 1.93 | B.93 | — |
| 1.94 | B.94 | — |
| 1.95 | B.95 | — |
| 1.96 | B.96 | — |
| 1.97 | B.97 | — |
| 1.98 | B.98 | — |
| 1.99 | B.99 | — |
| 1.100 | B.100 | — |
| 1.101 | B.101 | — |
| 1.102 | B.102 | — |
| 1.103 | B.103 | — |
| 1.104 | B.104 | — |
| 1.105 | B.105 | — |
| 1.106 | B.106 | — |
| 1.107 | B.107 | — |
| 1.108 | B.108 | — |
| 1.109 | B.109 | — |
| 1.110 | B.110 | — |
| 1.111 | B.111 | — |
| 1.112 | B.112 | — |
| 1.113 | B.113 | — |
| 1.114 | B.114 | — |
| 1.115 | B.115 | — |
| 1.116 | B.116 | — |
| 1.117 | B.117 | — |
| 1.118 | B.118 | — |
| 1.119 | B.119 | — |
| 1.120 | B.120 | — |
| 1.121 | B.121 | — |
| 1.122 | B.122 | — |
| 1.123 | B.123 | — |
| 1.124 | B.124 | — |
| 1.125 | B.125 | — |
| 1.126 | B.126 | — |
| 1.127 | B.127 | — |
| 1.128 | B.128 | — |
| 1.129 | B.129 | — |
| 1.130 | B.130 | — |
| 1.131 | B.131 | — |
| 1.132 | B.132 | — |
| 1.133 | B.133 | — |
| 1.134 | B.134 | — |
| 1.135 | B.135 | — |
| 1.136 | B.136 | — |
| 1.137 | B.137 | — |
| 1.138 | B.138 | — |
| 1.139 | B.139 | — |

TABLE 2-continued (compositions 1.1 to 1.2029):

| comp. no. | herbicide B | safener C |
|---|---|---|
| 1.140 | B.140 | — |
| 1.141 | B.141 | — |
| 1.142 | B.142 | — |
| 1.143 | B.143 | — |
| 1.144 | B.144 | — |
| 1.145 | B.1 | C.1 |
| 1.146 | B.2 | C.1 |
| 1.147 | B.3 | C.1 |
| 1.148 | B.4 | C.1 |
| 1.149 | B.5 | C.1 |
| 1.150 | B.6 | C.1 |
| 1.151 | B.7 | C.1 |
| 1.152 | B.8 | C.1 |
| 1.153 | B.9 | C.1 |
| 1.154 | B.10 | C.1 |
| 1.155 | B.11 | C.1 |
| 1.156 | B.12 | C.1 |
| 1.157 | B.13 | C.1 |
| 1.158 | B.14 | C.1 |
| 1.159 | B.15 | C.1 |
| 1.160 | B.16 | C.1 |
| 1.161 | B.17 | C.1 |
| 1.162 | B.18 | C.1 |
| 1.163 | B.19 | C.1 |
| 1.164 | B.20 | C.1 |
| 1.165 | B.21 | C.1 |
| 1.166 | B.22 | C.1 |
| 1.167 | B.23 | C.1 |
| 1.168 | B.24 | C.1 |
| 1.169 | B.25 | C.1 |
| 1.170 | B.26 | C.1 |
| 1.171 | B.27 | C.1 |
| 1.172 | B.28 | C.1 |
| 1.173 | B.29 | C.1 |
| 1.174 | B.30 | C.1 |
| 1.175 | B.31 | C.1 |
| 1.176 | B.32 | C.1 |
| 1.177 | B.33 | C.1 |
| 1.178 | B.34 | C.1 |
| 1.179 | B.35 | C.1 |
| 1.180 | B.36 | C.1 |
| 1.181 | B.37 | C.1 |
| 1.182 | B.38 | C.1 |
| 1.183 | B.39 | C.1 |
| 1.184 | B.40 | C.1 |
| 1.185 | B.41 | C.1 |
| 1.186 | B.42 | C.1 |
| 1.187 | B.43 | C.1 |
| 1.188 | B.44 | C.1 |
| 1.189 | B.45 | C.1 |
| 1.190 | B.46 | C.1 |
| 1.191 | B.47 | C.1 |
| 1.192 | B.48 | C.1 |
| 1.193 | B.49 | C.1 |
| 1.194 | B.50 | C.1 |
| 1.195 | B.51 | C.1 |
| 1.196 | B.52 | C.1 |
| 1.197 | B.53 | C.1 |
| 1.198 | B.54 | C.1 |
| 1.199 | B.55 | C.1 |
| 1.200 | B.56 | C.1 |
| 1.201 | B.57 | C.1 |
| 1.202 | B.58. | C.1 |
| 1.203 | B.59 | C.1 |
| 1.204 | B.60 | C.1 |
| 1.205 | B.61 | C.1 |
| 1.206 | B.62 | C.1 |
| 1.207 | B.63 | C.1 |
| 1.208 | B.64 | C.1 |
| 1.209 | B.65 | C.1 |
| 1.210 | B.66 | C.1 |
| 1.211 | B.67 | C.1 |
| 1.212 | B.68 | C.1 |
| 1.213 | B.69 | C.1 |
| 1.214 | B.70 | C.1 |
| 1.215 | B.71 | C.1 |
| 1.216 | B.72 | C.1 |
| 1.217 | B.73 | C.1 |
| 1.218 | B.74 | C.1 |
| 1.219 | B.75 | C.1 |
| 1.220 | B.76 | C.1 |
| 1.221 | B.77 | C.1 |
| 1.222 | B.78 | C.1 |
| 1.223 | B.79 | C.1 |
| 1.224 | B.80 | C.1 |
| 1.225 | B.81 | C.1 |
| 1.226 | B.82 | C.1 |
| 1.227 | B.83 | C.1 |
| 1.228 | B.84 | C.1 |
| 1.229 | B.85 | C.1 |
| 1.230 | B.86 | C.1 |
| 1.231 | B.87 | C.1 |
| 1.232 | B.88 | C.1 |
| 1.233 | B.89 | C.1 |
| 1.234 | B.90 | C.1 |
| 1.235 | B.91 | C.1 |
| 1.236 | B.92 | C.1 |
| 1.237 | B.93 | C.1 |
| 1.238 | B.94 | C.1 |
| 1.239 | B.95 | C.1 |
| 1.240 | B.96 | C.1 |
| 1.241 | B.97 | C.1 |
| 1.242 | B.98 | C.1 |
| 1.243 | B.99 | C.1 |
| 1.244 | B.100 | C.1 |
| 1.245 | B.101 | C.1 |
| 1.246 | B.102 | C.1 |
| 1.247 | B.103 | C.1 |
| 1.248 | B.104 | C.1 |
| 1.249 | B.105 | C.1 |
| 1.250 | B.106 | C.1 |
| 1.251 | B.107 | C.1 |
| 1.252 | B.108 | C.1 |
| 1.253 | B.109 | C.1 |
| 1.254 | B.110 | C.1 |
| 1.255 | B.111 | C.1 |
| 1.256 | B.112 | C.1 |
| 1.257 | B.113 | C.1 |
| 1.258 | B.114 | C.1 |
| 1.259 | B.115 | C.1 |
| 1.260 | B.116 | C.1 |
| 1.261 | B.117 | C.1 |
| 1.262 | B.118 | C.1 |
| 1.263 | B.119 | C.1 |
| 1.264 | B.120 | C.1 |
| 1.265 | B.121 | C.1 |
| 1.266 | B.122 | C.1 |
| 1.267 | B.123 | C.1 |
| 1.268 | B.124 | C.1 |
| 1.269 | B.125 | C.1 |
| 1.270 | B.126 | C.1 |
| 1.271 | B.127 | C.1 |
| 1.272 | B.128 | C.1 |
| 1.273 | B.129 | C.1 |
| 1.274 | B.130 | C.1 |
| 1.275 | B.131 | C.1 |
| 1.276 | B.132 | C.1 |
| 1.277 | B.133 | C.1 |
| 1.278 | B.134 | C.1 |
| 1.279 | B.135 | C.1 |
| 1.280 | B.136 | C.1 |
| 1.281 | B.137 | C.1 |
| 1.282 | B.138 | C.1 |
| 1.283 | B.139 | C.1 |
| 1.284 | B.140 | C.1 |
| 1.285 | B.141 | C.1 |
| 1.286 | B.142 | C.1 |
| 1.287 | B.143 | C.1 |
| 1.288 | B.144 | C.1 |
| 1.289 | B.1 | C.2 |
| 1.290 | B.2 | C.2 |
| 1.291 | B.3 | C.2 |

TABLE 2-continued (compositions 1.1 to 1.2029):

| comp. no. | herbicide B | safener C |
|---|---|---|
| 1.292 | B.4 | C.2 |
| 1.293 | B.5 | C.2 |
| 1.294 | B.6 | C.2 |
| 1.295 | B.7 | C.2 |
| 1.296 | B.8 | C.2 |
| 1.297 | B.9 | C.2 |
| 1.298 | B.10 | C.2 |
| 1.299 | B.11 | C.2 |
| 1.300 | B.12 | C.2 |
| 1.301 | B.13 | C.2 |
| 1.302 | B.14 | C.2 |
| 1.303 | B.15 | C.2 |
| 1.304 | B.16 | C.2 |
| 1.305 | B.17 | C.2 |
| 1.306 | B.18 | C.2 |
| 1.307 | B.19 | C.2 |
| 1.308 | B.20 | C.2 |
| 1.309 | B.21 | C.2 |
| 1.310 | B.22 | C.2 |
| 1.311 | B.23 | C.2 |
| 1.312 | B.24 | C.2 |
| 1.313 | B.25 | C.2 |
| 1.314 | B.26 | C.2 |
| 1.315 | B.27 | C.2 |
| 1.316 | B.28 | C.2 |
| 1.317 | B.29 | C.2 |
| 1.318 | B.30 | C.2 |
| 1.319 | B.31 | C.2 |
| 1.320 | B.32 | C.2 |
| 1.321 | B.33 | C.2 |
| 1.322 | B.34 | C.2 |
| 1.323 | B.35 | C.2 |
| 1.324 | B.36 | C.2 |
| 1.325 | B.37 | C.2 |
| 1.326 | B.38 | C.2 |
| 1.327 | B.39 | C.2 |
| 1.328 | B.40 | C.2 |
| 1.329 | B.41 | C.2 |
| 1.330 | B.42 | C.2 |
| 1.331 | B.43 | C.2 |
| 1.332 | B.44 | C.2 |
| 1.333 | B.45 | C.2 |
| 1.334 | B.46 | C.2 |
| 1.335 | B.47 | C.2 |
| 1.336 | B.48 | C.2 |
| 1.337 | B.49 | C.2 |
| 1.338 | B.50 | C.2 |
| 1.339 | B.51 | C.2 |
| 1.340 | B.52 | C.2 |
| 1.341 | B.53 | C.2 |
| 1.342 | B.54 | C.2 |
| 1.343 | B.55 | C.2 |
| 1.344 | B.56 | C.2 |
| 1.345 | B.57 | C.2 |
| 1.346 | B.58. | C.2 |
| 1.347 | B.59 | C.2 |
| 1.348 | B.60 | C.2 |
| 1.349 | B.61 | C.2 |
| 1.350 | B.62 | C.2 |
| 1.351 | B.63 | C.2 |
| 1.352 | B.64 | C.2 |
| 1.353 | B.65 | C.2 |
| 1.354 | B.66 | C.2 |
| 1.355 | B.67 | C.2 |
| 1.356 | B.68 | C.2 |
| 1.357 | B.69 | C.2 |
| 1.358 | B.70 | C.2 |
| 1.359 | B.71 | C.2 |
| 1.360 | B.72 | C.2 |
| 1.361 | B.73 | C.2 |
| 1.362 | B.74 | C.2 |
| 1.363 | B.75 | C.2 |
| 1.364 | B.76 | C.2 |
| 1.365 | B.77 | C.2 |
| 1.366 | B.78 | C.2 |
| 1.367 | B.79 | C.2 |
| 1.368 | B.80 | C.2 |
| 1.369 | B.81 | C.2 |
| 1.370 | B.82 | C.2 |
| 1.371 | B.83 | C.2 |
| 1.372 | B.84 | C.2 |
| 1.373 | B.85 | C.2 |
| 1.374 | B.86 | C.2 |
| 1.375 | B.87 | C.2 |
| 1.376 | B.88 | C.2 |
| 1.377 | B.89 | C.2 |
| 1.378 | B.90 | C.2 |
| 1.379 | B.91 | C.2 |
| 1.380 | B.92 | C.2 |
| 1.381 | B.93 | C.2 |
| 1.382 | B.94 | C.2 |
| 1.383 | B.95 | C.2 |
| 1.384 | B.96 | C.2 |
| 1.385 | B.97 | C.2 |
| 1.386 | B.98 | C.2 |
| 1.387 | B.99 | C.2 |
| 1.388 | B.100 | C.2 |
| 1.389 | B.101 | C.2 |
| 1.390 | B.102 | C.2 |
| 1.391 | B.103 | C.2 |
| 1.392 | B.104 | C.2 |
| 1.393 | B.105 | C.2 |
| 1.394 | B.106 | C.2 |
| 1.395 | B.107 | C.2 |
| 1.396 | B.108 | C.2 |
| 1.397 | B.109 | C.2 |
| 1.398 | B.110 | C.2 |
| 1.399 | B.111 | C.2 |
| 1.400 | B.112 | C.2 |
| 1.401 | B.113 | C.2 |
| 1.402 | B.114 | C.2 |
| 1.403 | B.115 | C.2 |
| 1.404 | B.116 | C.2 |
| 1.405 | B.117 | C.2 |
| 1.406 | B.118 | C.2 |
| 1.407 | B.119 | C.2 |
| 1.408 | B.120 | C.2 |
| 1.409 | B.121 | C.2 |
| 1.410 | B.122 | C.2 |
| 1.411 | B.123 | C.2 |
| 1.412 | B.124 | C.2 |
| 1.413 | B.125 | C.2 |
| 1.414 | B.126 | C.2 |
| 1.415 | B.127 | C.2 |
| 1.416 | B.128 | C.2 |
| 1.417 | B.129 | C.2 |
| 1.418 | B.130 | C.2 |
| 1.419 | B.131 | C.2 |
| 1.420 | B.132 | C.2 |
| 1.421 | B.133 | C.2 |
| 1.422 | B.134 | C.2 |
| 1.423 | B.135 | C.2 |
| 1.424 | B.136 | C.2 |
| 1.425 | B.137 | C.2 |
| 1.426 | B.138 | C.2 |
| 1.427 | B.139 | C.2 |
| 1.428 | B.140 | C.2 |
| 1.429 | B.141 | C.2 |
| 1.430 | B.142 | C.2 |
| 1.431 | B.143 | C.2 |
| 1.432 | B.144 | C.2 |
| 1.433 | B.1 | C.3 |
| 1.434 | B.2 | C.3 |
| 1.435 | B.3 | C.3 |
| 1.436 | B.4 | C.3 |
| 1.437 | B.5 | C.3 |
| 1.438 | B.6 | C.3 |
| 1.439 | B.7 | C.3 |
| 1.440 | B.8 | C.3 |
| 1.441 | B.9 | C.3 |
| 1.442 | B.10 | C.3 |
| 1.443 | B.11 | C.3 |

TABLE 2-continued (compositions 1.1 to 1.2029):

| comp. no. | herbicide B | safener C |
|---|---|---|
| 1.444 | B.12 | C.3 |
| 1.445 | B.13 | C.3 |
| 1.446 | B.14 | C.3 |
| 1.447 | B.15 | C.3 |
| 1.448 | B.16 | C.3 |
| 1.449 | B.17 | C.3 |
| 1.450 | B.18 | C.3 |
| 1.451 | B.19 | C.3 |
| 1.452 | B.20 | C.3 |
| 1.453 | B.21 | C.3 |
| 1.454 | B.22 | C.3 |
| 1.455 | B.23 | C.3 |
| 1.456 | B.24 | C.3 |
| 1.457 | B.25 | C.3 |
| 1.458 | B.26 | C.3 |
| 1.459 | B.27 | C.3 |
| 1.460 | B.28 | C.3 |
| 1.461 | B.29 | C.3 |
| 1.462 | B.30 | C.3 |
| 1.463 | B.31 | C.3 |
| 1.464 | B.32 | C.3 |
| 1.465 | B.33 | C.3 |
| 1.466 | B.34 | C.3 |
| 1.467 | B.35 | C.3 |
| 1.468 | B.36 | C.3 |
| 1.469 | B.37 | C.3 |
| 1.470 | B.38 | C.3 |
| 1.471 | B.39 | C.3 |
| 1.472 | B.40 | C.3 |
| 1.473 | B.41 | C.3 |
| 1.474 | B.42 | C.3 |
| 1.475 | B.43 | C.3 |
| 1.476 | B.44 | C.3 |
| 1.477 | B.45 | C.3 |
| 1.478 | B.46 | C.3 |
| 1.479 | B.47 | C.3 |
| 1.480 | B.48 | C.3 |
| 1.481 | B.49 | C.3 |
| 1.482 | B.50 | C.3 |
| 1.483 | B.51 | C.3 |
| 1.484 | B.52 | C.3 |
| 1.485 | B.53 | C.3 |
| 1.486 | B.54 | C.3 |
| 1.487 | B.55 | C.3 |
| 1.488 | B.56 | C.3 |
| 1.489 | B.57 | C.3 |
| 1.490 | B.58. | C.3 |
| 1.491 | B.59 | C.3 |
| 1.492 | B.60 | C.3 |
| 1.493 | B.61 | C.3 |
| 1.494 | B.62 | C.3 |
| 1.495 | B.63 | C.3 |
| 1.496 | B.64 | C.3 |
| 1.497 | B.65 | C.3 |
| 1.498 | B.66 | C.3 |
| 1.499 | B.67 | C.3 |
| 1.500 | B.68 | C.3 |
| 1.501 | B.69 | C.3 |
| 1.502 | B.70 | C.3 |
| 1.503 | B.71 | C.3 |
| 1.504 | B.72 | C.3 |
| 1.505 | B.73 | C.3 |
| 1.506 | B.74 | C.3 |
| 1.507 | B.75 | C.3 |
| 1.508 | B.76 | C.3 |
| 1.509 | B.77 | C.3 |
| 1.510 | B.78 | C.3 |
| 1.511 | B.79 | C.3 |
| 1.512 | B.80 | C.3 |
| 1.513 | B.81 | C.3 |
| 1.514 | B.82 | C.3 |
| 1.515 | B.83 | C.3 |
| 1.516 | B.84 | C.3 |
| 1.517 | B.85 | C.3 |
| 1.518 | B.86 | C.3 |
| 1.519 | B.87 | C.3 |
| 1.520 | B.88 | C.3 |
| 1.521 | B.89 | C.3 |
| 1.522 | B.90 | C.3 |
| 1.523 | B.91 | C.3 |
| 1.524 | B.92 | C.3 |
| 1.525 | B.93 | C.3 |
| 1.526 | B.94 | C.3 |
| 1.527 | B.95 | C.3 |
| 1.528 | B.96 | C.3 |
| 1.529 | B.97 | C.3 |
| 1.530 | B.98 | C.3 |
| 1.531 | B.99 | C.3 |
| 1.532 | B.100 | C.3 |
| 1.533 | B.101 | C.3 |
| 1.534 | B.102 | C.3 |
| 1.535 | B.103 | C.3 |
| 1.536 | B.104 | C.3 |
| 1.537 | B.105 | C.3 |
| 1.538 | B.106 | C.3 |
| 1.539 | B.107 | C.3 |
| 1.540 | B.108 | C.3 |
| 1.541 | B.109 | C.3 |
| 1.542 | B.110 | C.3 |
| 1.543 | B.111 | C.3 |
| 1.544 | B.112 | C.3 |
| 1.545 | B.113 | C.3 |
| 1.546 | B.114 | C.3 |
| 1.547 | B.115 | C.3 |
| 1.548 | B.116 | C.3 |
| 1.549 | B.117 | C.3 |
| 1.550 | B.118 | C.3 |
| 1.551 | B.119 | C.3 |
| 1.552 | B.120 | C.3 |
| 1.553 | B.121 | C.3 |
| 1.554 | B.122 | C.3 |
| 1.555 | B.123 | C.3 |
| 1.556 | B.124 | C.3 |
| 1.557 | B.125 | C.3 |
| 1.558 | B.126 | C.3 |
| 1.559 | B.127 | C.3 |
| 1.560 | B.128 | C.3 |
| 1.561 | B.129 | C.3 |
| 1.562 | B.130 | C.3 |
| 1.563 | B.131 | C.3 |
| 1.564 | B.132 | C.3 |
| 1.565 | B.133 | C.3 |
| 1.566 | B.134 | C.3 |
| 1.567 | B.135 | C.3 |
| 1.568 | B.136 | C.3 |
| 1.569 | B.137 | C.3 |
| 1.570 | B.138 | C.3 |
| 1.571 | B.139 | C.3 |
| 1.572 | B.140 | C.3 |
| 1.573 | B.141 | C.3 |
| 1.574 | B.142 | C.3 |
| 1.575 | B.143 | C.3 |
| 1.576 | B.144 | C.3 |
| 1.577 | B.1 | C.4 |
| 1.578 | B.2 | C.4 |
| 1.579 | B.3 | C.4 |
| 1.580 | B.4 | C.4 |
| 1.581 | B.5 | C.4 |
| 1.582 | B.6 | C.4 |
| 1.583 | B.7 | C.4 |
| 1.584 | B.8 | C.4 |
| 1.585 | B.9 | C.4 |
| 1.586 | B.10 | C.4 |
| 1.587 | B.11 | C.4 |
| 1.588 | B.12 | C.4 |
| 1.589 | B.13 | C.4 |
| 1.590 | B.14 | C.4 |
| 1.591 | B.15 | C.4 |
| 1.592 | B.16 | C.4 |
| 1.593 | B.17 | C.4 |
| 1.594 | B.18 | C.4 |
| 1.595 | B.19 | C.4 |

TABLE 2-continued (compositions 1.1 to 1.2029):

| comp. no. | herbicide B | safener C |
|---|---|---|
| 1.596 | B.20 | C.4 |
| 1.597 | B.21 | C.4 |
| 1.598 | B.22 | C.4 |
| 1.599 | B.23 | C.4 |
| 1.600 | B.24 | C.4 |
| 1.601 | B.25 | C.4 |
| 1.602 | B.26 | C.4 |
| 1.603 | B.27 | C.4 |
| 1.604 | B.28 | C.4 |
| 1.605 | B.29 | C.4 |
| 1.606 | B.30 | C.4 |
| 1.607 | B.31 | C.4 |
| 1.608 | B.32 | C.4 |
| 1.609 | B.33 | C.4 |
| 1.610 | B.34 | C.4 |
| 1.611 | B.35 | C.4 |
| 1.612 | B.36 | C.4 |
| 1.613 | B.37 | C.4 |
| 1.614 | B.38 | C.4 |
| 1.615 | B.39 | C.4 |
| 1.616 | B.40 | C.4 |
| 1.617 | B.41 | C.4 |
| 1.618 | B.42 | C.4 |
| 1.619 | B.43 | C.4 |
| 1.620 | B.44 | C.4 |
| 1.621 | B.45 | C.4 |
| 1.622 | B.46 | C.4 |
| 1.623 | B.47 | C.4 |
| 1.624 | B.48 | C.4 |
| 1.625 | B.49 | C.4 |
| 1.626 | B.50 | C.4 |
| 1.627 | B.51 | C.4 |
| 1.628 | B.52 | C.4 |
| 1.629 | B.53 | C.4 |
| 1.630 | B.54 | C.4 |
| 1.631 | B.55 | C.4 |
| 1.632 | B.56 | C.4 |
| 1.633 | B.57 | C.4 |
| 1.634 | B.58. | C.4 |
| 1.635 | B.59 | C.4 |
| 1.636 | B.60 | C.4 |
| 1.637 | B.61 | C.4 |
| 1.638 | B.62 | C.4 |
| 1.639 | B.63 | C.4 |
| 1.640 | B.64 | C.4 |
| 1.641 | B.65 | C.4 |
| 1.642 | B.66 | C.4 |
| 1.643 | B.67 | C.4 |
| 1.644 | B.68 | C.4 |
| 1.645 | B.69 | C.4 |
| 1.646 | B.70 | C.4 |
| 1.647 | B.71 | C.4 |
| 1.648 | B.72 | C.4 |
| 1.649 | B.73 | C.4 |
| 1.650 | B.74 | C.4 |
| 1.651 | B.75 | C.4 |
| 1.652 | B.76 | C.4 |
| 1.653 | B.77 | C.4 |
| 1.654 | B.78 | C.4 |
| 1.655 | B.79 | C.4 |
| 1.656 | B.80 | C.4 |
| 1.657 | B.81 | C.4 |
| 1.658 | B.82 | C.4 |
| 1.659 | B.83 | C.4 |
| 1.660 | B.84 | C.4 |
| 1.661 | B.85 | C.4 |
| 1.662 | B.86 | C.4 |
| 1.663 | B.87 | C.4 |
| 1.664 | B.88 | C.4 |
| 1.665 | B.89 | C.4 |
| 1.666 | B.90 | C.4 |
| 1.667 | B.91 | C.4 |
| 1.668 | B.92 | C.4 |
| 1.669 | B.93 | C.4 |
| 1.670 | B.94 | C.4 |
| 1.671 | B.95 | C.4 |
| 1.672 | B.96 | C.4 |
| 1.673 | B.97 | C.4 |
| 1.674 | B.98 | C.4 |
| 1.675 | B.99 | C.4 |
| 1.676 | B.100 | C.4 |
| 1.677 | B.101 | C.4 |
| 1.678 | B.102 | C.4 |
| 1.679 | B.103 | C.4 |
| 1.680 | B.104 | C.4 |
| 1.681 | B.105 | C.4 |
| 1.682 | B.106 | C.4 |
| 1.683 | B.107 | C.4 |
| 1.684 | B.108 | C.4 |
| 1.685 | B.109 | C.4 |
| 1.686 | B.110 | C.4 |
| 1.687 | B.111 | C.4 |
| 1.688 | B.112 | C.4 |
| 1.689 | B.113 | C.4 |
| 1.690 | B.114 | C.4 |
| 1.691 | B.115 | C.4 |
| 1.692 | B.116 | C.4 |
| 1.693 | B.117 | C.4 |
| 1.694 | B.118 | C.4 |
| 1.695 | B.119 | C.4 |
| 1.696 | B.120 | C.4 |
| 1.697 | B.121 | C.4 |
| 1.698 | B.122 | C.4 |
| 1.699 | B.123 | C.4 |
| 1.700 | B.124 | C.4 |
| 1.701 | B.125 | C.4 |
| 1.702 | B.126 | C.4 |
| 1.703 | B.127 | C.4 |
| 1.704 | B.128 | C.4 |
| 1.705 | B.129 | C.4 |
| 1.706 | B.130 | C.4 |
| 1.707 | B.131 | C.4 |
| 1.708 | B.132 | C.4 |
| 1.709 | B.133 | C.4 |
| 1.710 | B.134 | C.4 |
| 1.711 | B.135 | C.4 |
| 1.712 | B.136 | C.4 |
| 1.713 | B.137 | C.4 |
| 1.714 | B.138 | C.4 |
| 1.715 | B.139 | C.4 |
| 1.716 | B.140 | C.4 |
| 1.717 | B.141 | C.4 |
| 1.718 | B.142 | C.4 |
| 1.719 | B.143 | C.4 |
| 1.720 | B.144 | C.4 |
| 1.721 | B.1 | C.5 |
| 1.722 | B.2 | C.5 |
| 1.723 | B.3 | C.5 |
| 1.724 | B.4 | C.5 |
| 1.725 | B.5 | C.5 |
| 1.726 | B.6 | C.5 |
| 1.727 | B.7 | C.5 |
| 1.728 | B.8 | C.5 |
| 1.729 | B.9 | C.5 |
| 1.730 | B.10 | C.5 |
| 1.731 | B.11 | C.5 |
| 1.732 | B.12 | C.5 |
| 1.733 | B.13 | C.5 |
| 1.734 | B.14 | C.5 |
| 1.735 | B.15 | C.5 |
| 1.736 | B.16 | C.5 |
| 1.737 | B.17 | C.5 |
| 1.738 | B.18 | C.5 |
| 1.739 | B.19 | C.5 |
| 1.740 | B.20 | C.5 |
| 1.741 | B.21 | C.5 |
| 1.742 | B.22 | C.5 |
| 1.743 | B.23 | C.5 |
| 1.744 | B.24 | C.5 |
| 1.745 | B.25 | C.5 |
| 1.746 | B.26 | C.5 |
| 1.747 | B.27 | C.5 |

TABLE 2-continued (compositions 1.1 to 1.2029):

| comp. no. | herbicide B | safener C |
|---|---|---|
| 1.748 | B.28 | C.5 |
| 1.749 | B.29 | C.5 |
| 1.750 | B.30 | C.5 |
| 1.751 | B.31 | C.5 |
| 1.752 | B.32 | C.5 |
| 1.753 | B.33 | C.5 |
| 1.754 | B.34 | C.5 |
| 1.755 | B.35 | C.5 |
| 1.756 | B.36 | C.5 |
| 1.757 | B.37 | C.5 |
| 1.758 | B.38 | C.5 |
| 1.759 | B.39 | C.5 |
| 1.760 | B.40 | C.5 |
| 1.761 | B.41 | C.5 |
| 1.762 | B.42 | C.5 |
| 1.763 | B.43 | C.5 |
| 1.764 | B.44 | C.5 |
| 1.765 | B.45 | C.5 |
| 1.766 | B.46 | C.5 |
| 1.767 | B.47 | C.5 |
| 1.768 | B.48 | C.5 |
| 1.769 | B.49 | C.5 |
| 1.770 | B.50 | C.5 |
| 1.771 | B.51 | C.5 |
| 1.772 | B.52 | C.5 |
| 1.773 | B.53 | C.5 |
| 1.774 | B.54 | C.5 |
| 1.775 | B.55 | C.5 |
| 1.776 | B.56 | C.5 |
| 1.777 | B.57 | C.5 |
| 1.778 | B.58. | C.5 |
| 1.779 | B.59 | C.5 |
| 1.780 | B.60 | C.5 |
| 1.781 | B.61 | C.5 |
| 1.782 | B.62 | C.5 |
| 1.783 | B.63 | C.5 |
| 1.784 | B.64 | C.5 |
| 1.785 | B.65 | C.5 |
| 1.786 | B.66 | C.5 |
| 1.787 | B.67 | C.5 |
| 1.788 | B.68 | C.5 |
| 1.789 | B.69 | C.5 |
| 1.790 | B.70 | C.5 |
| 1.791 | B.71 | C.5 |
| 1.792 | B.72 | C.5 |
| 1.793 | B.73 | C.5 |
| 1.794 | B.74 | C.5 |
| 1.795 | B.75 | C.5 |
| 1.796 | B.76 | C.5 |
| 1.797 | B.77 | C.5 |
| 1.798 | B.78 | C.5 |
| 1.799 | B.79 | C.5 |
| 1.800 | B.80 | C.5 |
| 1.801 | B.81 | C.5 |
| 1.802 | B.82 | C.5 |
| 1.803 | B.83 | C.5 |
| 1.804 | B.84 | C.5 |
| 1.805 | B.85 | C.5 |
| 1.806 | B.86 | C.5 |
| 1.807 | B.87 | C.5 |
| 1.808 | B.88 | C.5 |
| 1.809 | B.89 | C.5 |
| 1.810 | B.90 | C.5 |
| 1.811 | B.91 | C.5 |
| 1.812 | B.92 | C.5 |
| 1.813 | B.93 | C.5 |
| 1.814 | B.94 | C.5 |
| 1.815 | B.95 | C.5 |
| 1.816 | B.96 | C.5 |
| 1.817 | B.97 | C.5 |
| 1.818 | B.98 | C.5 |
| 1.819 | B.99 | C.5 |
| 1.820 | B.100 | C.5 |
| 1.821 | B.101 | C.5 |
| 1.822 | B.102 | C.5 |
| 1.823 | B.103 | C.5 |
| 1.824 | B.104 | C.5 |
| 1.825 | B.105 | C.5 |
| 1.826 | B.106 | C.5 |
| 1.827 | B.107 | C.5 |
| 1.828 | B.108 | C.5 |
| 1.829 | B.109 | C.5 |
| 1.830 | B.110 | C.5 |
| 1.831 | B.111 | C.5 |
| 1.832 | B.112 | C.5 |
| 1.833 | B.113 | C.5 |
| 1.834 | B.114 | C.5 |
| 1.835 | B.115 | C.5 |
| 1.836 | B.116 | C.5 |
| 1.837 | B.117 | C.5 |
| 1.838 | B.118 | C.5 |
| 1.839 | B.119 | C.5 |
| 1.840 | B.120 | C.5 |
| 1.841 | B.121 | C.5 |
| 1.842 | B.122 | C.5 |
| 1.843 | B.123 | C.5 |
| 1.844 | B.124 | C.5 |
| 1.845 | B.125 | C.5 |
| 1.846 | B.126 | C.5 |
| 1.847 | B.127 | C.5 |
| 1.848 | B.128 | C.5 |
| 1.849 | B.129 | C.5 |
| 1.850 | B.130 | C.5 |
| 1.851 | B.131 | C.5 |
| 1.852 | B.132 | C.5 |
| 1.853 | B.133 | C.5 |
| 1.854 | B.134 | C.5 |
| 1.855 | B.135 | C.5 |
| 1.856 | B.136 | C.5 |
| 1.857 | B.137 | C.5 |
| 1.858 | B.138 | C.5 |
| 1.859 | B.139 | C.5 |
| 1.860 | B.140 | C.5 |
| 1.861 | B.141 | C.5 |
| 1.862 | B.142 | C.5 |
| 1.863 | B.143 | C.5 |
| 1.864 | B.144 | C.5 |
| 1.865 | B.1 | C.6 |
| 1.866 | B.2 | C.6 |
| 1.867 | B.3 | C.6 |
| 1.868 | B.4 | C.6 |
| 1.869 | B.5 | C.6 |
| 1.870 | B.6 | C.6 |
| 1.871 | B.7 | C.6 |
| 1.872 | B.8 | C.6 |
| 1.873 | B.9 | C.6 |
| 1.874 | B.10 | C.6 |
| 1.875 | B.11 | C.6 |
| 1.876 | B.12 | C.6 |
| 1.877 | B.13 | C.6 |
| 1.878 | B.14 | C.6 |
| 1.879 | B.15 | C.6 |
| 1.880 | B.16 | C.6 |
| 1.881 | B.17 | C.6 |
| 1.882 | B.18 | C.6 |
| 1.883 | B.19 | C.6 |
| 1.884 | B.20 | C.6 |
| 1.885 | B.21 | C.6 |
| 1.886 | B.22 | C.6 |
| 1.887 | B.23 | C.6 |
| 1.888 | B.24 | C.6 |
| 1.889 | B.25 | C.6 |
| 1.890 | B.26 | C.6 |
| 1.891 | B.27 | C.6 |
| 1.892 | B.28 | C.6 |
| 1.893 | B.29 | C.6 |
| 1.894 | B.30 | C.6 |
| 1.895 | B.31 | C.6 |
| 1.896 | B.32 | C.6 |
| 1.897 | B.33 | C.6 |
| 1.898 | B.34 | C.6 |
| 1.899 | B.35 | C.6 |

TABLE 2-continued (compositions 1.1 to 1.2029):

| comp. no. | herbicide B | safener C |
|---|---|---|
| 1.900 | B.36 | C.6 |
| 1.901 | B.37 | C.6 |
| 1.902 | B.38 | C.6 |
| 1.903 | B.39 | C.6 |
| 1.904 | B.40 | C.6 |
| 1.905 | B.41 | C.6 |
| 1.906 | B.42 | C.6 |
| 1.907 | B.43 | C.6 |
| 1.908 | B.44 | C.6 |
| 1.909 | B.45 | C.6 |
| 1.910 | B.46 | C.6 |
| 1.911 | B.47 | C.6 |
| 1.912 | B.48 | C.6 |
| 1.913 | B.49 | C.6 |
| 1.914 | B.50 | C.6 |
| 1.915 | B.51 | C.6 |
| 1.916 | B.52 | C.6 |
| 1.917 | B.53 | C.6 |
| 1.918 | B.54 | C.6 |
| 1.919 | B.55 | C.6 |
| 1.920 | B.56 | C.6 |
| 1.921 | B.57 | C.6 |
| 1.922 | B.58. | C.6 |
| 1.923 | B.59 | C.6 |
| 1.924 | B.60 | C.6 |
| 1.925 | B.61 | C.6 |
| 1.926 | B.62 | C.6 |
| 1.927 | B.63 | C.6 |
| 1.928 | B.64 | C.6 |
| 1.929 | B.65 | C.6 |
| 1.930 | B.66 | C.6 |
| 1.931 | B.67 | C.6 |
| 1.932 | B.68 | C.6 |
| 1.933 | B.69 | C.6 |
| 1.934 | B.70 | C.6 |
| 1.935 | B.71 | C.6 |
| 1.936 | B.72 | C.6 |
| 1.937 | B.73 | C.6 |
| 1.938 | B.74 | C.6 |
| 1.939 | B.75 | C.6 |
| 1.940 | B.76 | C.6 |
| 1.941 | B.77 | C.6 |
| 1.942 | B.78 | C.6 |
| 1.943 | B.79 | C.6 |
| 1.944 | B.80 | C.6 |
| 1.945 | B.81 | C.6 |
| 1.946 | B.82 | C.6 |
| 1.947 | B.83 | C.6 |
| 1.948 | B.84 | C.6 |
| 1.949 | B.85 | C.6 |
| 1.950 | B.86 | C.6 |
| 1.951 | B.87 | C.6 |
| 1.952 | B.88 | C.6 |
| 1.953 | B.89 | C.6 |
| 1.954 | B.90 | C.6 |
| 1.955 | B.91 | C.6 |
| 1.956 | B.92 | C.6 |
| 1.957 | B.93 | C.6 |
| 1.958 | B.94 | C.6 |
| 1.959 | B.95 | C.6 |
| 1.960 | B.96 | C.6 |
| 1.961 | B.97 | C.6 |
| 1.962 | B.98 | C.6 |
| 1.963 | B.99 | C.6 |
| 1.964 | B.100 | C.6 |
| 1.965 | B.101 | C.6 |
| 1.966 | B.102 | C.6 |
| 1.967 | B.103 | C.6 |
| 1.968 | B.104 | C.6 |
| 1.969 | B.105 | C.6 |
| 1.970 | B.106 | C.6 |
| 1.971 | B.107 | C.6 |
| 1.972 | B.108 | C.6 |
| 1.973 | B.109 | C.6 |
| 1.974 | B.110 | C.6 |
| 1.975 | B.111 | C.6 |
| 1.976 | B.112 | C.6 |
| 1.977 | B.113 | C.6 |
| 1.978 | B.114 | C.6 |
| 1.979 | B.115 | C.6 |
| 1.980 | B.116 | C.6 |
| 1.981 | B.117 | C.6 |
| 1.982 | B.118 | C.6 |
| 1.983 | B.119 | C.6 |
| 1.984 | B.120 | C.6 |
| 1.985 | B.121 | C.6 |
| 1.986 | B.122 | C.6 |
| 1.987 | B.123 | C.6 |
| 1.988 | B.124 | C.6 |
| 1.989 | B.125 | C.6 |
| 1.990 | B.126 | C.6 |
| 1.991 | B.127 | C.6 |
| 1.992 | B.128 | C.6 |
| 1.993 | B.129 | C.6 |
| 1.994 | B.130 | C.6 |
| 1.995 | B.131 | C.6 |
| 1.996 | B.132 | C.6 |
| 1.997 | B.133 | C.6 |
| 1.998 | B.134 | C.6 |
| 1.999 | B.135 | C.6 |
| 1.1000 | B.136 | C.6 |
| 1.1001 | B.137 | C.6 |
| 1.1002 | B.138 | C.6 |
| 1.1003 | B.139 | C.6 |
| 1.1004 | B.140 | C.6 |
| 1.1005 | B.141 | C.6 |
| 1.1006 | B.142 | C.6 |
| 1.1007 | B.143 | C.6 |
| 1.1008 | B.144 | C.6 |
| 1.1009 | B.1 | C.7 |
| 1.1010 | B.2 | C.7 |
| 1.1011 | B.3 | C.7 |
| 1.1012 | B.4 | C.7 |
| 1.1013 | B.5 | C.7 |
| 1.1014 | B.6 | C.7 |
| 1.1015 | B.7 | C.7 |
| 1.1016 | B.8 | C.7 |
| 1.1017 | B.9 | C.7 |
| 1.1018 | B.10 | C.7 |
| 1.1019 | B.11 | C.7 |
| 1.1020 | B.12 | C.7 |
| 1.1021 | B.13 | C.7 |
| 1.1022 | B.14 | C.7 |
| 1.1023 | B.15 | C.7 |
| 1.1024 | B.16 | C.7 |
| 1.1025 | B.17 | C.7 |
| 1.1026 | B.18 | C.7 |
| 1.1027 | B.19 | C.7 |
| 1.1028 | B.20 | C.7 |
| 1.1029 | B.21 | C.7 |
| 1.1030 | B.22 | C.7 |
| 1.1031 | B.23 | C.7 |
| 1.1032 | B.24 | C.7 |
| 1.1033 | B.25 | C.7 |
| 1.1034 | B.26 | C.7 |
| 1.1035 | B.27 | C.7 |
| 1.1036 | B.28 | C.7 |
| 1.1037 | B.29 | C.7 |
| 1.1038 | B.30 | C.7 |
| 1.1039 | B.31 | C.7 |
| 1.1040 | B.32 | C.7 |
| 1.1041 | B.33 | C.7 |
| 1.1042 | B.34 | C.7 |
| 1.1043 | B.35 | C.7 |
| 1.1044 | B.36 | C.7 |
| 1.1045 | B.37 | C.7 |
| 1.1046 | B.38 | C.7 |
| 1.1047 | B.39 | C.7 |
| 1.1048 | B.40 | C.7 |
| 1.1049 | B.41 | C.7 |
| 1.1050 | B.42 | C.7 |
| 1.1051 | B.43 | C.7 |

TABLE 2-continued (compositions 1.1 to 1.2029):

| comp. no. | herbicide B | safener C |
|---|---|---|
| 1.1052 | B.44 | C.7 |
| 1.1053 | B.45 | C.7 |
| 1.1054 | B.46 | C.7 |
| 1.1055 | B.47 | C.7 |
| 1.1056 | B.48 | C.7 |
| 1.1057 | B.49 | C.7 |
| 1.1058 | B.50 | C.7 |
| 1.1059 | B.51 | C.7 |
| 1.1060 | B.52 | C.7 |
| 1.1061 | B.53 | C.7 |
| 1.1062 | B.54 | C.7 |
| 1.1063 | B.55 | C.7 |
| 1.1064 | B.56 | C.7 |
| 1.1065 | B.57 | C.7 |
| 1.1066 | B.58. | C.7 |
| 1.1067 | B.59 | C.7 |
| 1.1068 | B.60 | C.7 |
| 1.1069 | B.61 | C.7 |
| 1.1070 | B.62 | C.7 |
| 1.1071 | B.63 | C.7 |
| 1.1072 | B.64 | C.7 |
| 1.1073 | B.65 | C.7 |
| 1.1074 | B.66 | C.7 |
| 1.1075 | B.67 | C.7 |
| 1.1076 | B.68 | C.7 |
| 1.1077 | B.69 | C.7 |
| 1.1078 | B.70 | C.7 |
| 1.1079 | B.71 | C.7 |
| 1.1080 | B.72 | C.7 |
| 1.1081 | B.73 | C.7 |
| 1.1082 | B.74 | C.7 |
| 1.1083 | B.75 | C.7 |
| 1.1084 | B.76 | C.7 |
| 1.1085 | B.77 | C.7 |
| 1.1086 | B.78 | C.7 |
| 1.1087 | B.79 | C.7 |
| 1.1088 | B.80 | C.7 |
| 1.1089 | B.81 | C.7 |
| 1.1090 | B.82 | C.7 |
| 1.1091 | B.83 | C.7 |
| 1.1092 | B.84 | C.7 |
| 1.1093 | B.85 | C.7 |
| 1.1094 | B.86 | C.7 |
| 1.1095 | B.87 | C.7 |
| 1.1096 | B.88 | C.7 |
| 1.1097 | B.89 | C.7 |
| 1.1098 | B.90 | C.7 |
| 1.1099 | B.91 | C.7 |
| 1.1100 | B.92 | C.7 |
| 1.1101 | B.93 | C.7 |
| 1.1102 | B.94 | C.7 |
| 1.1103 | B.95 | C.7 |
| 1.1104 | B.96 | C.7 |
| 1.1105 | B.97 | C.7 |
| 1.1106 | B.98 | C.7 |
| 1.1107 | B.99 | C.7 |
| 1.1108 | B.100 | C.7 |
| 1.1109 | B.101 | C.7 |
| 1.1110 | B.102 | C.7 |
| 1.1111 | B.103 | C.7 |
| 1.1112 | B.104 | C.7 |
| 1.1113 | B.105 | C.7 |
| 1.1114 | B.106 | C.7 |
| 1.1115 | B.107 | C.7 |
| 1.1116 | B.108 | C.7 |
| 1.1117 | B.109 | C.7 |
| 1.1118 | B.110 | C.7 |
| 1.1119 | B.111 | C.7 |
| 1.1120 | B.112 | C.7 |
| 1.1121 | B.113 | C.7 |
| 1.1122 | B.114 | C.7 |
| 1.1123 | B.115 | C.7 |
| 1.1124 | B.116 | C.7 |
| 1.1125 | B.117 | C.7 |
| 1.1126 | B.118 | C.7 |
| 1.1127 | B.119 | C.7 |
| 1.1128 | B.120 | C.7 |
| 1.1129 | B.121 | C.7 |
| 1.1130 | B.122 | C.7 |
| 1.1131 | B.123 | C.7 |
| 1.1132 | B.124 | C.7 |
| 1.1133 | B.125 | C.7 |
| 1.1134 | B.126 | C.7 |
| 1.1135 | B.127 | C.7 |
| 1.1136 | B.128 | C.7 |
| 1.1137 | B.129 | C.7 |
| 1.1138 | B.130 | C.7 |
| 1.1139 | B.131 | C.7 |
| 1.1140 | B.132 | C.7 |
| 1.1141 | B.133 | C.7 |
| 1.1142 | B.134 | C.7 |
| 1.1143 | B.135 | C.7 |
| 1.1144 | B.136 | C.7 |
| 1.1145 | B.137 | C.7 |
| 1.1146 | B.138 | C.7 |
| 1.1147 | B.139 | C.7 |
| 1.1148 | B.140 | C.7 |
| 1.1149 | B.141 | C.7 |
| 1.1150 | B.142 | C.7 |
| 1.1151 | B.143 | C.7 |
| 1.1152 | B.144 | C.7 |
| 1.1153 | B.1 | C.8 |
| 1.1154 | B.2 | C.8 |
| 1.1155 | B.3 | C.8 |
| 1.1156 | B.4 | C.8 |
| 1.1157 | B.5 | C.8 |
| 1.1158 | B.6 | C.8 |
| 1.1159 | B.7 | C.8 |
| 1.1160 | B.8 | C.8 |
| 1.1161 | B.9 | C.8 |
| 1.1162 | B.10 | C.8 |
| 1.1163 | B.11 | C.8 |
| 1.1164 | B.12 | C.8 |
| 1.1165 | B.13 | C.8 |
| 1.1166 | B.14 | C.8 |
| 1.1167 | B.15 | C.8 |
| 1.1168 | B.16 | C.8 |
| 1.1169 | B.17 | C.8 |
| 1.1170 | B.18 | C.8 |
| 1.1171 | B.19 | C.8 |
| 1.1172 | B.20 | C.8 |
| 1.1173 | B.21 | C.8 |
| 1.1174 | B.22 | C.8 |
| 1.1175 | B.23 | C.8 |
| 1.1176 | B.24 | C.8 |
| 1.1177 | B.25 | C.8 |
| 1.1178 | B.26 | C.8 |
| 1.1179 | B.27 | C.8 |
| 1.1180 | B.28 | C.8 |
| 1.1181 | B.29 | C.8 |
| 1.1182 | B.30 | C.8 |
| 1.1183 | B.31 | C.8 |
| 1.1184 | B.32 | C.8 |
| 1.1185 | B.33 | C.8 |
| 1.1186 | B.34 | C.8 |
| 1.1187 | B.35 | C.8 |
| 1.1188 | B.36 | C.8 |
| 1.1189 | B.37 | C.8 |
| 1.1190 | B.38 | C.8 |
| 1.1191 | B.39 | C.8 |
| 1.1192 | B.40 | C.8 |
| 1.1193 | B.41 | C.8 |
| 1.1194 | B.42 | C.8 |
| 1.1195 | B.43 | C.8 |
| 1.1196 | B.44 | C.8 |
| 1.1197 | B.45 | C.8 |
| 1.1198 | B.46 | C.8 |
| 1.1199 | B.47 | C.8 |
| 1.1200 | B.48 | C.8 |
| 1.1201 | B.49 | C.8 |
| 1.1202 | B.50 | C.8 |
| 1.1203 | B.51 | C.8 |

TABLE 2-continued (compositions 1.1 to 1.2029):

| comp. no. | herbicide B | safener C |
|---|---|---|
| 1.1204 | B.52 | C.8 |
| 1.1205 | B.53 | C.8 |
| 1.1206 | B.54 | C.8 |
| 1.1207 | B.55 | C.8 |
| 1.1208 | B.56 | C.8 |
| 1.1209 | B.57 | C.8 |
| 1.1210 | B.58. | C.8 |
| 1.1211 | B.59 | C.8 |
| 1.1212 | B.60 | C.8 |
| 1.1213 | B.61 | C.8 |
| 1.1214 | B.62 | C.8 |
| 1.1215 | B.63 | C.8 |
| 1.1216 | B.64 | C.8 |
| 1.1217 | B.65 | C.8 |
| 1.1218 | B.66 | C.8 |
| 1.1219 | B.67 | C.8 |
| 1.1220 | B.68 | C.8 |
| 1.1221 | B.69 | C.8 |
| 1.1222 | B.70 | C.8 |
| 1.1223 | B.71 | C.8 |
| 1.1224 | B.72 | C.8 |
| 1.1225 | B.73 | C.8 |
| 1.1226 | B.74 | C.8 |
| 1.1227 | B.75 | C.8 |
| 1.1228 | B.76 | C.8 |
| 1.1229 | B.77 | C.8 |
| 1.1230 | B.78 | C.8 |
| 1.1231 | B.79 | C.8 |
| 1.1232 | B.80 | C.8 |
| 1.1233 | B.81 | C.8 |
| 1.1234 | B.82 | C.8 |
| 1.1235 | B.83 | C.8 |
| 1.1236 | B.84 | C.8 |
| 1.1237 | B.85 | C.8 |
| 1.1238 | B.86 | C.8 |
| 1.1239 | B.87 | C.8 |
| 1.1240 | B.88 | C.8 |
| 1.1241 | B.89 | C.8 |
| 1.1242 | B.90 | C.8 |
| 1.1243 | B.91 | C.8 |
| 1.1244 | B.92 | C.8 |
| 1.1245 | B.93 | C.8 |
| 1.1246 | B.94 | C.8 |
| 1.1247 | B.95 | C.8 |
| 1.1248 | B.96 | C.8 |
| 1.1249 | B.97 | C.8 |
| 1.1250 | B.98 | C.8 |
| 1.1251 | B.99 | C.8 |
| 1.1252 | B.100 | C.8 |
| 1.1253 | B.101 | C.8 |
| 1.1254 | B.102 | C.8 |
| 1.1255 | B.103 | C.8 |
| 1.1256 | B.104 | C.8 |
| 1.1257 | B.105 | C.8 |
| 1.1258 | B.106 | C.8 |
| 1.1259 | B.107 | C.8 |
| 1.1260 | B.108 | C.8 |
| 1.1261 | B.109 | C.8 |
| 1.1262 | B.110 | C.8 |
| 1.1263 | B.111 | C.8 |
| 1.1264 | B.112 | C.8 |
| 1.1265 | B.113 | C.8 |
| 1.1266 | B.114 | C.8 |
| 1.1267 | B.115 | C.8 |
| 1.1268 | B.116 | C.8 |
| 1.1269 | B.117 | C.8 |
| 1.1270 | B.118 | C.8 |
| 1.1271 | B.119 | C.8 |
| 1.1272 | B.120 | C.8 |
| 1.1273 | B.121 | C.8 |
| 1.1274 | B.122 | C.8 |
| 1.1275 | B.123 | C.8 |
| 1.1276 | B.124 | C.8 |
| 1.1277 | B.125 | C.8 |
| 1.1278 | B.126 | C.8 |
| 1.1279 | B.127 | C.8 |
| 1.1280 | B.128 | C.8 |
| 1.1281 | B.129 | C.8 |
| 1.1282 | B.130 | C.8 |
| 1.1283 | B.131 | C.8 |
| 1.1284 | B.132 | C.8 |
| 1.1285 | B.133 | C.8 |
| 1.1286 | B.134 | C.8 |
| 1.1287 | B.135 | C.8 |
| 1.1288 | B.136 | C.8 |
| 1.1289 | B.137 | C.8 |
| 1.1290 | B.138 | C.8 |
| 1.1291 | B.139 | C.8 |
| 1.1292 | B.140 | C.8 |
| 1.1293 | B.141 | C.8 |
| 1.1294 | B.142 | C.8 |
| 1.1295 | B.143 | C.8 |
| 1.1296 | B.144 | C.8 |
| 1.1297 | B.1 | C.9 |
| 1.1298 | B.2 | C.9 |
| 1.1299 | B.3 | C.9 |
| 1.1300 | B.4 | C.9 |
| 1.1301 | B.5 | C.9 |
| 1.1302 | B.6 | C.9 |
| 1.1303 | B.7 | C.9 |
| 1.1304 | B.8 | C.9 |
| 1.1305 | B.9 | C.9 |
| 1.1306 | B.10 | C.9 |
| 1.1307 | B.11 | C.9 |
| 1.1308 | B.12 | C.9 |
| 1.1309 | B.13 | C.9 |
| 1.1310 | B.14 | C.9 |
| 1.1311 | B.15 | C.9 |
| 1.1312 | B.16 | C.9 |
| 1.1313 | B.17 | C.9 |
| 1.1314 | B.18 | C.9 |
| 1.1315 | B.19 | C.9 |
| 1.1316 | B.20 | C.9 |
| 1.1317 | B.21 | C.9 |
| 1.1318 | B.22 | C.9 |
| 1.1319 | B.23 | C.9 |
| 1.1320 | B.24 | C.9 |
| 1.1321 | B.25 | C.9 |
| 1.1322 | B.26 | C.9 |
| 1.1323 | B.27 | C.9 |
| 1.1324 | B.28 | C.9 |
| 1.1325 | B.29 | C.9 |
| 1.1326 | B.30 | C.9 |
| 1.1327 | B.31 | C.9 |
| 1.1328 | B.32 | C.9 |
| 1.1329 | B.33 | C.9 |
| 1.1330 | B.34 | C.9 |
| 1.1331 | B.35 | C.9 |
| 1.1332 | B.36 | C.9 |
| 1.1333 | B.37 | C.9 |
| 1.1334 | B.38 | C.9 |
| 1.1335 | B.39 | C.9 |
| 1.1336 | B.40 | C.9 |
| 1.1337 | B.41 | C.9 |
| 1.1338 | B.42 | C.9 |
| 1.1339 | B.43 | C.9 |
| 1.1340 | B.44 | C.9 |
| 1.1341 | B.45 | C.9 |
| 1.1342 | B.46 | C.9 |
| 1.1343 | B.47 | C.9 |
| 1.1344 | B.48 | C.9 |
| 1.1345 | B.49 | C.9 |
| 1.1346 | B.50 | C.9 |
| 1.1347 | B.51 | C.9 |
| 1.1348 | B.52 | C.9 |
| 1.1349 | B.53 | C.9 |
| 1.1350 | B.54 | C.9 |
| 1.1351 | B.55 | C.9 |
| 1.1352 | B.56 | C.9 |
| 1.1353 | B.57 | C.9 |
| 1.1354 | B.58. | C.9 |
| 1.1355 | B.59 | C.9 |

TABLE 2-continued (compositions 1.1 to 1.2029):

| comp. no. | herbicide B | safener C |
|---|---|---|
| 1.1356 | B.60 | C.9 |
| 1.1357 | B.61 | C.9 |
| 1.1358 | B.62 | C.9 |
| 1.1359 | B.63 | C.9 |
| 1.1360 | B.64 | C.9 |
| 1.1361 | B.65 | C.9 |
| 1.1362 | B.66 | C.9 |
| 1.1363 | B.67 | C.9 |
| 1.1364 | B.68 | C.9 |
| 1.1365 | B.69 | C.9 |
| 1.1366 | B.70 | C.9 |
| 1.1367 | B.71 | C.9 |
| 1.1368 | B.72 | C.9 |
| 1.1369 | B.73 | C.9 |
| 1.1370 | B.74 | C.9 |
| 1.1371 | B.75 | C.9 |
| 1.1372 | B.76 | C.9 |
| 1.1373 | B.77 | C.9 |
| 1.1374 | B.78 | C.9 |
| 1.1375 | B.79 | C.9 |
| 1.1376 | B.80 | C.9 |
| 1.1377 | B.81 | C.9 |
| 1.1378 | B.82 | C.9 |
| 1.1379 | B.83 | C.9 |
| 1.1380 | B.84 | C.9 |
| 1.1381 | B.85 | C.9 |
| 1.1382 | B.86 | C.9 |
| 1.1383 | B.87 | C.9 |
| 1.1384 | B.88 | C.9 |
| 1.1385 | B.89 | C.9 |
| 1.1386 | B.90 | C.9 |
| 1.1387 | B.91 | C.9 |
| 1.1388 | B.92 | C.9 |
| 1.1389 | B.93 | C.9 |
| 1.1390 | B.94 | C.9 |
| 1.1391 | B.95 | C.9 |
| 1.1392 | B.96 | C.9 |
| 1.1393 | B.97 | C.9 |
| 1.1394 | B.98 | C.9 |
| 1.1395 | B.99 | C.9 |
| 1.1396 | B.100 | C.9 |
| 1.1397 | B.101 | C.9 |
| 1.1398 | B.102 | C.9 |
| 1.1399 | B.103 | C.9 |
| 1.1400 | B.104 | C.9 |
| 1.1401 | B.105 | C.9 |
| 1.1402 | B.106 | C.9 |
| 1.1403 | B.107 | C.9 |
| 1.1404 | B.108 | C.9 |
| 1.1405 | B.109 | C.9 |
| 1.1406 | B.110 | C.9 |
| 1.1407 | B.111 | C.9 |
| 1.1408 | B.112 | C.9 |
| 1.1409 | B.113 | C.9 |
| 1.1410 | B.114 | C.9 |
| 1.1411 | B.115 | C.9 |
| 1.1412 | B.116 | C.9 |
| 1.1413 | B.117 | C.9 |
| 1.1414 | B.118 | C.9 |
| 1.1415 | B.119 | C.9 |
| 1.1416 | B.120 | C.9 |
| 1.1417 | B.121 | C.9 |
| 1.1418 | B.122 | C.9 |
| 1.1419 | B.123 | C.9 |
| 1.1420 | B.124 | C.9 |
| 1.1421 | B.125 | C.9 |
| 1.1422 | B.126 | C.9 |
| 1.1423 | B.127 | C.9 |
| 1.1424 | B.128 | C.9 |
| 1.1425 | B.129 | C.9 |
| 1.1426 | B.130 | C.9 |
| 1.1427 | B.131 | C.9 |
| 1.1428 | B.132 | C.9 |
| 1.1429 | B.133 | C.9 |
| 1.1430 | B.134 | C.9 |
| 1.1431 | B.135 | C.9 |
| 1.1432 | B.136 | C.9 |
| 1.1433 | B.137 | C.9 |
| 1.1434 | B.138 | C.9 |
| 1.1435 | B.139 | C.9 |
| 1.1436 | B.140 | C.9 |
| 1.1437 | B.141 | C.9 |
| 1.1438 | B.142 | C.9 |
| 1.1439 | B.143 | C.9 |
| 1.1440 | B.144 | C.9 |
| 1.1441 | B.1 | C.10 |
| 1.1442 | B.2 | C.10 |
| 1.1443 | B.3 | C.10 |
| 1.1444 | B.4 | C.10 |
| 1.1445 | B.5 | C.10 |
| 1.1446 | B.6 | C.10 |
| 1.1447 | B.7 | C.10 |
| 1.1448 | B.8 | C.10 |
| 1.1449 | B.9 | C.10 |
| 1.1450 | B.10 | C.10 |
| 1.1451 | B.11 | C.10 |
| 1.1452 | B.12 | C.10 |
| 1.1453 | B.13 | C.10 |
| 1.1454 | B.14 | C.10 |
| 1.1455 | B.15 | C.10 |
| 1.1456 | B.16 | C.10 |
| 1.1457 | B.17 | C.10 |
| 1.1458 | B.18 | C.10 |
| 1.1459 | B.19 | C.10 |
| 1.1460 | B.20 | C.10 |
| 1.1461 | B.21 | C.10 |
| 1.1462 | B.22 | C.10 |
| 1.1463 | B.23 | C.10 |
| 1.1464 | B.24 | C.10 |
| 1.1465 | B.25 | C.10 |
| 1.1466 | B.26 | C.10 |
| 1.1467 | B.27 | C.10 |
| 1.1468 | B.28 | C.10 |
| 1.1469 | B.29 | C.10 |
| 1.1470 | B.30 | C.10 |
| 1.1471 | B.31 | C.10 |
| 1.1472 | B.32 | C.10 |
| 1.1473 | B.33 | C.10 |
| 1.1474 | B.34 | C.10 |
| 1.1475 | B.35 | C.10 |
| 1.1476 | B.36 | C.10 |
| 1.1477 | B.37 | C.10 |
| 1.1478 | B.38 | C.10 |
| 1.1479 | B.39 | C.10 |
| 1.1480 | B.40 | C.10 |
| 1.1481 | B.41 | C.10 |
| 1.1482 | B.42 | C.10 |
| 1.1483 | B.43 | C.10 |
| 1.1484 | B.44 | C.10 |
| 1.1485 | B.45 | C.10 |
| 1.1486 | B.46 | C.10 |
| 1.1487 | B.47 | C.10 |
| 1.1488 | B.48 | C.10 |
| 1.1489 | B.49 | C.10 |
| 1.1490 | B.50 | C.10 |
| 1.1491 | B.51 | C.10 |
| 1.1492 | B.52 | C.10 |
| 1.1493 | B.53 | C.10 |
| 1.1494 | B.54 | C.10 |
| 1.1495 | B.55 | C.10 |
| 1.1496 | B.56 | C.10 |
| 1.1497 | B.57 | C.10 |
| 1.1498 | B.58. | C.10 |
| 1.1499 | B.59 | C.10 |
| 1.1500 | B.60 | C.10 |
| 1.1501 | B.61 | C.10 |
| 1.1502 | B.62 | C.10 |
| 1.1503 | B.63 | C.10 |
| 1.1504 | B.64 | C.10 |
| 1.1505 | B.65 | C.10 |
| 1.1506 | B.66 | C.10 |
| 1.1507 | B.67 | C.10 |

TABLE 2-continued (compositions 1.1 to 1.2029):

| comp. no. | herbicide B | safener C |
|---|---|---|
| 1.1508 | B.68 | C.10 |
| 1.1509 | B.69 | C.10 |
| 1.1510 | B.70 | C.10 |
| 1.1511 | B.71 | C.10 |
| 1.1512 | B.72 | C.10 |
| 1.1513 | B.73 | C.10 |
| 1.1514 | B.74 | C.10 |
| 1.1515 | B.75 | C.10 |
| 1.1516 | B.76 | C.10 |
| 1.1517 | B.77 | C.10 |
| 1.1518 | B.78 | C.10 |
| 1.1519 | B.79 | C.10 |
| 1.1520 | B.80 | C.10 |
| 1.1521 | B.81 | C.10 |
| 1.1522 | B.82 | C.10 |
| 1.1523 | B.83 | C.10 |
| 1.1524 | B.84 | C.10 |
| 1.1525 | B.85 | C.10 |
| 1.1526 | B.86 | C.10 |
| 1.1527 | B.87 | C.10 |
| 1.1528 | B.88 | C.10 |
| 1.1529 | B.89 | C.10 |
| 1.1530 | B.90 | C.10 |
| 1.1531 | B.91 | C.10 |
| 1.1532 | B.92 | C.10 |
| 1.1533 | B.93 | C.10 |
| 1.1534 | B.94 | C.10 |
| 1.1535 | B.95 | C.10 |
| 1.1536 | B.96 | C.10 |
| 1.1537 | B.97 | C.10 |
| 1.1538 | B.98 | C.10 |
| 1.1539 | B.99 | C.10 |
| 1.1540 | B.100 | C.10 |
| 1.1541 | B.101 | C.10 |
| 1.1542 | B.102 | C.10 |
| 1.1543 | B.103 | C.10 |
| 1.1544 | B.104 | C.10 |
| 1.1545 | B.105 | C.10 |
| 1.1546 | B.106 | C.10 |
| 1.1547 | B.107 | C.10 |
| 1.1548 | B.108 | C.10 |
| 1.1549 | B.109 | C.10 |
| 1.1550 | B.110 | C.10 |
| 1.1551 | B.111 | C.10 |
| 1.1552 | B.112 | C.10 |
| 1.1553 | B.113 | C.10 |
| 1.1554 | B.114 | C.10 |
| 1.1555 | B.115 | C.10 |
| 1.1556 | B.116 | C.10 |
| 1.1557 | B.117 | C.10 |
| 1.1558 | B.118 | C.10 |
| 1.1559 | B.119 | C.10 |
| 1.1560 | B.120 | C.10 |
| 1.1561 | B.121 | C.10 |
| 1.1562 | B.122 | C.10 |
| 1.1563 | B.123 | C.10 |
| 1.1564 | B.124 | C.10 |
| 1.1565 | B.125 | C.10 |
| 1.1566 | B.126 | C.10 |
| 1.1567 | B.127 | C.10 |
| 1.1568 | B.128 | C.10 |
| 1.1569 | B.129 | C.10 |
| 1.1570 | B.130 | C.10 |
| 1.1571 | B.131 | C.10 |
| 1.1572 | B.132 | C.10 |
| 1.1573 | B.133 | C.10 |
| 1.1574 | B.134 | C.10 |
| 1.1575 | B.135 | C.10 |
| 1.1576 | B.136 | C.10 |
| 1.1577 | B.137 | C.10 |
| 1.1578 | B.138 | C.10 |
| 1.1579 | B.139 | C.10 |
| 1.1580 | B.140 | C.10 |
| 1.1581 | B.141 | C.10 |
| 1.1582 | B.142 | C.10 |
| 1.1583 | B.143 | C.10 |
| 1.1584 | B.144 | C.10 |
| 1.1585 | B.1 | C.11 |
| 1.1586 | B.2 | C.11 |
| 1.1587 | B.3 | C.11 |
| 1.1588 | B.4 | C.11 |
| 1.1589 | B.5 | C.11 |
| 1.1590 | B.6 | C.11 |
| 1.1591 | B.7 | C.11 |
| 1.1592 | B.8 | C.11 |
| 1.1593 | B.9 | C.11 |
| 1.1594 | B.10 | C.11 |
| 1.1595 | B.11 | C.11 |
| 1.1596 | B.12 | C.11 |
| 1.1597 | B.13 | C.11 |
| 1.1598 | B.14 | C.11 |
| 1.1599 | B.15 | C.11 |
| 1.1600 | B.16 | C.11 |
| 1.1601 | B.17 | C.11 |
| 1.1602 | B.18 | C.11 |
| 1.1603 | B.19 | C.11 |
| 1.1604 | B.20 | C.11 |
| 1.1605 | B.21 | C.11 |
| 1.1606 | B.22 | C.11 |
| 1.1607 | B.23 | C.11 |
| 1.1608 | B.24 | C.11 |
| 1.1609 | B.25 | C.11 |
| 1.1610 | B.26 | C.11 |
| 1.1611 | B.27 | C.11 |
| 1.1612 | B.28 | C.11 |
| 1.1613 | B.29 | C.11 |
| 1.1614 | B.30 | C.11 |
| 1.1615 | B.31 | C.11 |
| 1.1616 | B.32 | C.11 |
| 1.1617 | B.33 | C.11 |
| 1.1618 | B.34 | C.11 |
| 1.1619 | B.35 | C.11 |
| 1.1620 | B.36 | C.11 |
| 1.1621 | B.37 | C.11 |
| 1.1622 | B.38 | C.11 |
| 1.1623 | B.39 | C.11 |
| 1.1624 | B.40 | C.11 |
| 1.1625 | B.41 | C.11 |
| 1.1626 | B.42 | C.11 |
| 1.1627 | B.43 | C.11 |
| 1.1628 | B.44 | C.11 |
| 1.1629 | B.45 | C.11 |
| 1.1630 | B.46 | C.11 |
| 1.1631 | B.47 | C.11 |
| 1.1632 | B.48 | C.11 |
| 1.1633 | B.49 | C.11 |
| 1.1634 | B.50 | C.11 |
| 1.1635 | B.51 | C.11 |
| 1.1636 | B.52 | C.11 |
| 1.1637 | B.53 | C.11 |
| 1.1638 | B.54 | C.11 |
| 1.1639 | B.55 | C.11 |
| 1.1640 | B.56 | C.11 |
| 1.1641 | B.57 | C.11 |
| 1.1642 | B.58. | C.11 |
| 1.1643 | B.59 | C.11 |
| 1.1644 | B.60 | C.11 |
| 1.1645 | B.61 | C.11 |
| 1.1646 | B.62 | C.11 |
| 1.1647 | B.63 | C.11 |
| 1.1648 | B.64 | C.11 |
| 1.1649 | B.65 | C.11 |
| 1.1650 | B.66 | C.11 |
| 1.1651 | B.67 | C.11 |
| 1.1652 | B.68 | C.11 |
| 1.1653 | B.69 | C.11 |
| 1.1654 | B.70 | C.11 |
| 1.1655 | B.71 | C.11 |
| 1.1656 | B.72 | C.11 |
| 1.1657 | B.73 | C.11 |
| 1.1658 | B.74 | C.11 |
| 1.1659 | B.75 | C.11 |

TABLE 2-continued (compositions 1.1 to 1.2029):

| comp. no. | herbicide B | safener C |
|---|---|---|
| 1.1660 | B.76 | C.11 |
| 1.1661 | B.77 | C.11 |
| 1.1662 | B.78 | C.11 |
| 1.1663 | B.79 | C.11 |
| 1.1664 | B.80 | C.11 |
| 1.1665 | B.81 | C.11 |
| 1.1666 | B.82 | C.11 |
| 1.1667 | B.83 | C.11 |
| 1.1668 | B.84 | C.11 |
| 1.1669 | B.85 | C.11 |
| 1.1670 | B.86 | C.11 |
| 1.1671 | B.87 | C.11 |
| 1.1672 | B.88 | C.11 |
| 1.1673 | B.89 | C.11 |
| 1.1674 | B.90 | C.11 |
| 1.1675 | B.91 | C.11 |
| 1.1676 | B.92 | C.11 |
| 1.1677 | B.93 | C.11 |
| 1.1678 | B.94 | C.11 |
| 1.1679 | B.95 | C.11 |
| 1.1680 | B.96 | C.11 |
| 1.1681 | B.97 | C.11 |
| 1.1682 | B.98 | C.11 |
| 1.1683 | B.99 | C.11 |
| 1.1684 | B.100 | C.11 |
| 1.1685 | B.101 | C.11 |
| 1.1686 | B.102 | C.11 |
| 1.1687 | B.103 | C.11 |
| 1.1688 | B.104 | C.11 |
| 1.1689 | B.105 | C.11 |
| 1.1690 | B.106 | C.11 |
| 1.1691 | B.107 | C.11 |
| 1.1692 | B.108 | C.11 |
| 1.1693 | B.109 | C.11 |
| 1.1694 | B.110 | C.11 |
| 1.1695 | B.111 | C.11 |
| 1.1696 | B.112 | C.11 |
| 1.1697 | B.113 | C.11 |
| 1.1698 | B.114 | C.11 |
| 1.1699 | B.115 | C.11 |
| 1.1700 | B.116 | C.11 |
| 1.1701 | B.117 | C.11 |
| 1.1702 | B.118 | C.11 |
| 1.1703 | B.119 | C.11 |
| 1.1704 | B.120 | C.11 |
| 1.1705 | B.121 | C.11 |
| 1.1706 | B.122 | C.11 |
| 1.1707 | B.123 | C.11 |
| 1.1708 | B.124 | C.11 |
| 1.1709 | B.125 | C.11 |
| 1.1710 | B.126 | C.11 |
| 1.1711 | B.127 | C.11 |
| 1.1712 | B.128 | C.11 |
| 1.1713 | B.129 | C.11 |
| 1.1714 | B.130 | C.11 |
| 1.1715 | B.131 | C.11 |
| 1.1716 | B.132 | C.11 |
| 1.1717 | B.133 | C.11 |
| 1.1718 | B.134 | C.11 |
| 1.1719 | B.135 | C.11 |
| 1.1720 | B.136 | C.11 |
| 1.1721 | B.137 | C.11 |
| 1.1722 | B.138 | C.11 |
| 1.1723 | B.139 | C.11 |
| 1.1724 | B.140 | C.11 |
| 1.1725 | B.141 | C.11 |
| 1.1726 | B.142 | C.11 |
| 1.1727 | B.143 | C.11 |
| 1.1728 | B.144 | C.11 |
| 1.1729 | B.1 | C.12 |
| 1.1730 | B.2 | C.12 |
| 1.1731 | B.3 | C.12 |
| 1.1732 | B.4 | C.12 |
| 1.1733 | B.5 | C.12 |
| 1.1734 | B.6 | C.12 |
| 1.1735 | B.7 | C.12 |
| 1.1736 | B.8 | C.12 |
| 1.1737 | B.9 | C.12 |
| 1.1738 | B.10 | C.12 |
| 1.1739 | B.11 | C.12 |
| 1.1740 | B.12 | C.12 |
| 1.1741 | B.13 | C.12 |
| 1.1742 | B.14 | C.12 |
| 1.1743 | B.15 | C.12 |
| 1.1744 | B.16 | C.12 |
| 1.1745 | B.17 | C.12 |
| 1.1746 | B.18 | C.12 |
| 1.1747 | B.19 | C.12 |
| 1.1748 | B.20 | C.12 |
| 1.1749 | B.21 | C.12 |
| 1.1750 | B.22 | C.12 |
| 1.1751 | B.23 | C.12 |
| 1.1752 | B.24 | C.12 |
| 1.1753 | B.25 | C.12 |
| 1.1754 | B.26 | C.12 |
| 1.1755 | B.27 | C.12 |
| 1.1756 | B.28 | C.12 |
| 1.1757 | B.29 | C.12 |
| 1.1758 | B.30 | C.12 |
| 1.1759 | B.31 | C.12 |
| 1.1760 | B.32 | C.12 |
| 1.1761 | B.33 | C.12 |
| 1.1762 | B.34 | C.12 |
| 1.1763 | B.35 | C.12 |
| 1.1764 | B.36 | C.12 |
| 1.1765 | B.37 | C.12 |
| 1.1766 | B.38 | C.12 |
| 1.1767 | B.39 | C.12 |
| 1.1768 | B.40 | C.12 |
| 1.1769 | B.41 | C.12 |
| 1.1770 | B.42 | C.12 |
| 1.1771 | B.43 | C.12 |
| 1.1772 | B.44 | C.12 |
| 1.1773 | B.45 | C.12 |
| 1.1774 | B.46 | C.12 |
| 1.1775 | B.47 | C.12 |
| 1.1776 | B.48 | C.12 |
| 1.1777 | B.49 | C.12 |
| 1.1778 | B.50 | C.12 |
| 1.1779 | B.51 | C.12 |
| 1.1780 | B.52 | C.12 |
| 1.1781 | B.53 | C.12 |
| 1.1782 | B.54 | C.12 |
| 1.1783 | B.55 | C.12 |
| 1.1784 | B.56 | C.12 |
| 1.1785 | B.57 | C.12 |
| 1.1786 | B.58. | C.12 |
| 1.1787 | B.59 | C.12 |
| 1.1788 | B.60 | C.12 |
| 1.1789 | B.61 | C.12 |
| 1.1790 | B.62 | C.12 |
| 1.1791 | B.63 | C.12 |
| 1.1792 | B.64 | C.12 |
| 1.1793 | B.65 | C.12 |
| 1.1794 | B.66 | C.12 |
| 1.1795 | B.67 | C.12 |
| 1.1796 | B.68 | C.12 |
| 1.1797 | B.69 | C.12 |
| 1.1798 | B.70 | C.12 |
| 1.1799 | B.71 | C.12 |
| 1.1800 | B.72 | C.12 |
| 1.1801 | B.73 | C.12 |
| 1.1802 | B.74 | C.12 |
| 1.1803 | B.75 | C.12 |
| 1.1804 | B.76 | C.12 |
| 1.1805 | B.77 | C.12 |
| 1.1806 | B.78 | C.12 |
| 1.1807 | B.79 | C.12 |
| 1.1808 | B.80 | C.12 |
| 1.1809 | B.81 | C.12 |
| 1.1810 | B.82 | C.12 |
| 1.1811 | B.83 | C.12 |

TABLE 2-continued (compositions 1.1 to 1.2029):

| comp. no. | herbicide B | safener C |
|---|---|---|
| 1.1812 | B.84 | C.12 |
| 1.1813 | B.85 | C.12 |
| 1.1814 | B.86 | C.12 |
| 1.1815 | B.87 | C.12 |
| 1.1816 | B.88 | C.12 |
| 1.1817 | B.89 | C.12 |
| 1.1818 | B.90 | C.12 |
| 1.1819 | B.91 | C.12 |
| 1.1820 | B.92 | C.12 |
| 1.1821 | B.93 | C.12 |
| 1.1822 | B.94 | C.12 |
| 1.1823 | B.95 | C.12 |
| 1.1824 | B.96 | C.12 |
| 1.1825 | B.97 | C.12 |
| 1.1826 | B.98 | C.12 |
| 1.1827 | B.99 | C.12 |
| 1.1828 | B.100 | C.12 |
| 1.1829 | B.101 | C.12 |
| 1.1830 | B.102 | C.12 |
| 1.1831 | B.103 | C.12 |
| 1.1832 | B.104 | C.12 |
| 1.1833 | B.105 | C.12 |
| 1.1834 | B.106 | C.12 |
| 1.1835 | B.107 | C.12 |
| 1.1836 | B.108 | C.12 |
| 1.1837 | B.109 | C.12 |
| 1.1838 | B.110 | C.12 |
| 1.1839 | B.111 | C.12 |
| 1.1840 | B.112 | C.12 |
| 1.1841 | B.113 | C.12 |
| 1.1842 | B.114 | C.12 |
| 1.1843 | B.115 | C.12 |
| 1.1844 | B.116 | C.12 |
| 1.1845 | B.117 | C.12 |
| 1.1846 | B.118 | C.12 |
| 1.1847 | B.119 | C.12 |
| 1.1848 | B.120 | C.12 |
| 1.1849 | B.121 | C.12 |
| 1.1850 | B.122 | C.12 |
| 1.1851 | B.123 | C.12 |
| 1.1852 | B.124 | C.12 |
| 1.1853 | B.125 | C.12 |
| 1.1854 | B.126 | C.12 |
| 1.1855 | B.127 | C.12 |
| 1.1856 | B.128 | C.12 |
| 1.1857 | B.129 | C.12 |
| 1.1858 | B.130 | C.12 |
| 1.1859 | B.131 | C.12 |
| 1.1860 | B.132 | C.12 |
| 1.1861 | B.133 | C.12 |
| 1.1862 | B.134 | C.12 |
| 1.1863 | B.135 | C.12 |
| 1.1864 | B.136 | C.12 |
| 1.1865 | B.137 | C.12 |
| 1.1866 | B.138 | C.12 |
| 1.1867 | B.139 | C.12 |
| 1.1868 | B.140 | C.12 |
| 1.1869 | B.141 | C.12 |
| 1.1870 | B.142 | C.12 |
| 1.1871 | B.143 | C.12 |
| 1.1872 | B.144 | C.12 |
| 1.1873 | B.1 | C.13 |
| 1.1874 | B.2 | C.13 |
| 1.1875 | B.3 | C.13 |
| 1.1876 | B.4 | C.13 |
| 1.1877 | B.5 | C.13 |
| 1.1878 | B.6 | C.13 |
| 1.1879 | B.7 | C.13 |
| 1.1880 | B.8 | C.13 |
| 1.1881 | B.9 | C.13 |
| 1.1882 | B.10 | C.13 |
| 1.1883 | B.11 | C.13 |
| 1.1884 | B.12 | C.13 |
| 1.1885 | B.13 | C.13 |
| 1.1886 | B.14 | C.13 |
| 1.1887 | B.15 | C.13 |
| 1.1888 | B.16 | C.13 |
| 1.1889 | B.17 | C.13 |
| 1.1890 | B.18 | C.13 |
| 1.1891 | B.19 | C.13 |
| 1.1892 | B.20 | C.13 |
| 1.1893 | B.21 | C.13 |
| 1.1894 | B.22 | C.13 |
| 1.1895 | B.23 | C.13 |
| 1.1896 | B.24 | C.13 |
| 1.1897 | B.25 | C.13 |
| 1.1898 | B.26 | C.13 |
| 1.1899 | B.27 | C.13 |
| 1.1900 | B.28 | C.13 |
| 1.1901 | B.29 | C.13 |
| 1.1902 | B.30 | C.13 |
| 1.1903 | B.31 | C.13 |
| 1.1904 | B.32 | C.13 |
| 1.1905 | B.33 | C.13 |
| 1.1906 | B.34 | C.13 |
| 1.1907 | B.35 | C.13 |
| 1.1908 | B.36 | C.13 |
| 1.1909 | B.37 | C.13 |
| 1.1910 | B.38 | C.13 |
| 1.1911 | B.39 | C.13 |
| 1.1912 | B.40 | C.13 |
| 1.1913 | B.41 | C.13 |
| 1.1914 | B.42 | C.13 |
| 1.1915 | B.43 | C.13 |
| 1.1916 | B.44 | C.13 |
| 1.1917 | B.45 | C.13 |
| 1.1918 | B.46 | C.13 |
| 1.1919 | B.47 | C.13 |
| 1.1920 | B.48 | C.13 |
| 1.1921 | B.49 | C.13 |
| 1.1922 | B.50 | C.13 |
| 1.1923 | B.51 | C.13 |
| 1.1924 | B.52 | C.13 |
| 1.1925 | B.53 | C.13 |
| 1.1926 | B.54 | C.13 |
| 1.1927 | B.55 | C.13 |
| 1.1928 | B.56 | C.13 |
| 1.1929 | B.57 | C.13 |
| 1.1930 | B.58. | C.13 |
| 1.1931 | B.59 | C.13 |
| 1.1932 | B.60 | C.13 |
| 1.1933 | B.61 | C.13 |
| 1.1934 | B.62 | C.13 |
| 1.1935 | B.63 | C.13 |
| 1.1936 | B.64 | C.13 |
| 1.1937 | B.65 | C.13 |
| 1.1938 | B.66 | C.13 |
| 1.1939 | B.67 | C.13 |
| 1.1940 | B.68 | C.13 |
| 1.1941 | B.69 | C.13 |
| 1.1942 | B.70 | C.13 |
| 1.1943 | B.71 | C.13 |
| 1.1944 | B.72 | C.13 |
| 1.1945 | B.73 | C.13 |
| 1.1946 | B.74 | C.13 |
| 1.1947 | B.75 | C.13 |
| 1.1948 | B.76 | C.13 |
| 1.1949 | B.77 | C.13 |
| 1.1950 | B.78 | C.13 |
| 1.1951 | B.79 | C.13 |
| 1.1952 | B.80 | C.13 |
| 1.1953 | B.81 | C.13 |
| 1.1954 | B.82 | C.13 |
| 1.1955 | B.83 | C.13 |
| 1.1956 | B.84 | C.13 |
| 1.1957 | B.85 | C.13 |
| 1.1958 | B.86 | C.13 |
| 1.1959 | B.87 | C.13 |
| 1.1960 | B.88 | C.13 |
| 1.1961 | B.89 | C.13 |
| 1.1962 | B.90 | C.13 |
| 1.1963 | B.91 | C.13 |

TABLE 2-continued (compositions 1.1 to 1.2029):

| comp. no. | herbicide B | safener C |
|---|---|---|
| 1.1964 | B.92 | C.13 |
| 1.1965 | B.93 | C.13 |
| 1.1966 | B.94 | C.13 |
| 1.1967 | B.95 | C.13 |
| 1.1968 | B.96 | C.13 |
| 1.1969 | B.97 | C.13 |
| 1.1970 | B.98 | C.13 |
| 1.1971 | B.99 | C.13 |
| 1.1972 | B.100 | C.13 |
| 1.1973 | B.101 | C.13 |
| 1.1974 | B.102 | C.13 |
| 1.1975 | B.103 | C.13 |
| 1.1976 | B.104 | C.13 |
| 1.1977 | B.105 | C.13 |
| 1.1978 | B.106 | C.13 |
| 1.1979 | B.107 | C.13 |
| 1.1980 | B.108 | C.13 |
| 1.1981 | B.109 | C.13 |
| 1.1982 | B.110 | C.13 |
| 1.1983 | B.111 | C.13 |
| 1.1984 | B.112 | C.13 |
| 1.1985 | B.113 | C.13 |
| 1.1986 | B.114 | C.13 |
| 1.1987 | B.115 | C.13 |
| 1.1988 | B.116 | C.13 |
| 1.1989 | B.117 | C.13 |
| 1.1990 | B.118 | C.13 |
| 1.1991 | B.119 | C.13 |
| 1.1992 | B.120 | C.13 |
| 1.1993 | B.121 | C.13 |
| 1.1994 | B.122 | C.13 |
| 1.1995 | B.123 | C.13 |
| 1.1996 | B.124 | C.13 |
| 1.1997 | B.125 | C.13 |
| 1.1998 | B.126 | C.13 |
| 1.1999 | B.127 | C.13 |
| 1.2000 | B.128 | C.13 |
| 1.2001 | B.129 | C.13 |
| 1.2002 | B.130 | C.13 |
| 1.2003 | B.131 | C.13 |
| 1.2004 | B.132 | C.13 |
| 1.2005 | B.133 | C.13 |
| 1.2006 | B.134 | C.13 |
| 1.2007 | B.135 | C.13 |
| 1.2008 | B.136 | C.13 |
| 1.2009 | B.137 | C.13 |
| 1.2010 | B.138 | C.13 |
| 1.2011 | B.139 | C.13 |
| 1.2012 | B.140 | C.13 |
| 1.2013 | B.141 | C.13 |
| 1.2014 | B.142 | C.13 |
| 1.2015 | B.143 | C.13 |
| 1.2016 | B.144 | C.13 |
| 1.2017 | — | C.1 |
| 1.2018 | — | C.2 |
| 1.2019 | — | C.3 |
| 1.2020 | — | C.4 |
| 1.2021 | — | C.5 |
| 1.2022 | — | C.6 |
| 1.2023 | — | C.7 |
| 1.2024 | — | C.8 |
| 1.2025 | — | C.9 |
| 1.2026 | — | C.10 |
| 1.2027 | — | C.11 |
| 1.2028 | — | C.12 |
| 1.2029 | — | C.13 |

The specific number for each single composition is deductible as follows:
Composition 1.777 for example comprises the compound I, terbutryn (B.67) and fenchlorazole (C.5) (see table 1, entry 1.777; as well as table B, entry B.67 and table C, entry C.5).
Composition 7.777 for example comprises imazapyr (B31) (see the definition for compositions 7.1 to 7.2029 below), and the compound Ia . . . , terbutryn (B.67) and fenchlorazole (C.5) (see table 1, entry 1.777-; as well as table B, entry B.67 and table C, entry C.5).

Also especially preferred are compositions 3.1. to 3.2029 which differ from the corresponding compositions 1.1 to 1.2029 only in that they additionally comprise B.2 as further herbicide B.

Also especially preferred are compositions 4.1. to 4.2029 which differ from the corresponding compositions 1.1 to 1.2029 only in that they additionally comprise B.7 as further herbicide B.

Also especially preferred are compositions 5.1. to 5.2029 which differ from the corresponding compositions 1.1 to 1.2029 only in that they additionally comprise B.29 as further herbicide B.

Also especially preferred are compositions 6.1. to 6.2029 which differ from the corresponding compositions 1.1 to 1.2029 only in that they additionally comprise B.30 as further herbicide B.

Also especially preferred are compositions 7.1. to 7.2029 which differ from the corresponding compositions 1.1 to 1.2029 only in that they additionally comprise B.31 as further herbicide B.

Also especially preferred are compositions 8.1. to 8.2029 which differ from the corresponding compositions 1.1 to 1.2029 only in that they additionally comprise B.32 as further herbicide B.

Also especially preferred are compositions 9.1. to 9.2029 which differ from the corresponding compositions 1.1 to 1.2029 only in that they additionally comprise B.33 as further herbicide B.

Also especially preferred are compositions 10.1. to 10.2029 which differ from the corresponding compositions 1.1 to 1.2029 only in that they additionally comprise B.40 as further herbicide B.

Also especially preferred are compositions 11.1. to 11.2029 which differ from the corresponding compositions 1.1 to 1.2029 only in that they additionally comprise B.44 as further herbicide B.

Also especially preferred are compositions 12.1. to 12.2029 which differ from the corresponding compositions 1.1 to 1.2029 only in that they additionally comprise B.45 as further herbicide B.

Also especially preferred are compositions 13.1. to 13.2029 which differ from the corresponding compositions 1.1 to 1.2029 only in that they additionally comprise B.52 as further herbicide B.

Also especially preferred are compositions 14.1. to 14.2029 which differ from the corresponding compositions 1.1 to 1.2029 only in that they additionally comprise B.53 as further herbicide B.

Also especially preferred are compositions 15.1. to 15.2029 which differ from the corresponding compositions 1.1 to 1.2029 only in that they additionally comprise B.54 as further herbicide B.

Also especially preferred are compositions 16.1. to 16.2029 which differ from the corresponding compositions 1.1 to 1.2029 only in that they additionally comprise B.55 as further herbicide B.

Also especially preferred are compositions 17.1. to 17.2029 which differ from the corresponding compositions 1.1 to 1.2029 only in that they additionally comprise B.56 as further herbicide B.

Also especially preferred are compositions 18.1. to 18.2029 which differ from the corresponding compositions 1.1 to 1.2029 only in that they additionally comprise B.57 as further herbicide B.

Also especially preferred are compositions 19.1. to 19.2029 which differ from the corresponding compositions 1.1 to 1.2029 only in that they additionally comprise B.60 as further herbicide B.

Also especially preferred are compositions 20.1. to 20.2029 which differ from the corresponding compositions 1.1 to 1.2029 only in that they additionally comprise B.65 as further herbicide B.

Also especially preferred are compositions 21.1. to 21.2029 which differ from the corresponding compositions 1.1 to 1.2029 only in that they additionally comprise B.66 as further herbicide B.

Also especially preferred are compositions 22.1. to 22.2029 which differ from the corresponding compositions 1.1 to 1.2029 only in that they additionally comprise B.69 as further herbicide B.

Also especially preferred are compositions 23.1. to 23.2029 which differ from the corresponding compositions 1.1 to 1.2029 only in that they additionally comprise B.72 as further herbicide B.

Also especially preferred are compositions 24.1. to 24.2029 which differ from the corresponding compositions 1.1 to 1.2029 only in that they additionally comprise B.73 as further herbicide B.

Also especially preferred are compositions 25.1. to 25.2029 which differ from the corresponding compositions 1.1 to 1.2029 only in that they additionally comprise B.76 as further herbicide B.

Also especially preferred are compositions 26.1. to 26.2029 which differ from the corresponding compositions 1.1 to 1.2029 only in that they additionally comprise B.77 as further herbicide B.

Also especially preferred are compositions 27.1. to 27.2029 which differ from the corresponding compositions 1.1 to 1.2029 only in that they additionally comprise B.81 as further herbicide B.

Also especially preferred are compositions 28.1. to 28.2029 which differ from the corresponding compositions 1.1 to 1.2029 only in that they additionally comprise B.82 as further herbicide B.

Also especially preferred are compositions 29.1. to 29.2029 which differ from the corresponding compositions 1.1 to 1.2029 only in that they additionally comprise B.85 as further herbicide B.

Also especially preferred are compositions 30.1. to 30.2029 which differ from the corresponding compositions 1.1 to 1.2029 only in that they additionally comprise B.85 and B.54 as further herbicides B.

Also especially preferred are compositions 31.1. to 31.2029 which differ from the corresponding compositions 1.1 to 1.2029 only in that they additionally comprise B.85 and B.60 as further herbicides B.

Also especially preferred are compositions 32.1. to 32.2029 which differ from the corresponding compositions 1.1 to 1.2029 only in that they additionally comprise B.85 and B.66 as further herbicides B.

Also especially preferred are compositions 33.1. to 33.2029 which differ from the corresponding compositions 1.1 to 1.2029 only in that they additionally comprise B.86 as further herbicide B.

Also especially preferred are compositions 34.1. to 34.2029 which differ from the corresponding compositions 1.1 to 1.2029 only in that they additionally comprise B.86 and B.54 as further herbicides B.

Also especially preferred are compositions 35.1. to 35.2029 which differ from the corresponding compositions 1.1 to 1.2029 only in that they additionally comprise B.86 and B.60 as further herbicides B.

Also especially preferred are compositions 36.1. to 36.2029 which differ from the corresponding compositions 1.1 to 1.2029 only in that they additionally comprise B.86 and B.66 as further herbicides B.

Also especially preferred are compositions 37.1. to 37.2029 which differ from the corresponding compositions 1.1 to 1.2029 only in that they additionally comprise B.88 as further herbicide B.

Also especially preferred are compositions 38.1. to 38.2029 which differ from the corresponding compositions 1.1 to 1.2029 only in that they additionally comprise B.89 as further herbicide B.

Also especially preferred are compositions 39.1. to 39.2029 which differ from the corresponding compositions 1.1 to 1.2029 only in that they additionally comprise B.89 and B.54 as further herbicides B.

Also especially preferred are compositions 40.1. to 40.2029 which differ from the corresponding compositions 1.1 to 1.2029 only in that they additionally comprise B.89 and B.60 as further herbicides B.

Also especially preferred are compositions 41.1. to 41.2029 which differ from the corresponding compositions 1.1 to 1.2029 only in that they additionally comprise B.89 and B.66 as further herbicides B.

Also especially preferred are compositions 42.1. to 42.2029 which differ from the corresponding compositions 1.1 to 1.2029 only in that they additionally comprise B.91 as further herbicide B.

Also especially preferred are compositions 43.1. to 43.2029 which differ from the corresponding compositions 1.1 to 1.2029 only in that they additionally comprise B.92 as further herbicide B.

Also especially preferred are compositions 44.1. to 44.2029 which differ from the corresponding compositions 1.1 to 1.2029 only in that they additionally comprise B.92 and B.54 as further herbicides B.

Also especially preferred are compositions 45.1. to 45.2029 which differ from the corresponding compositions 1.1 to 1.2029 only in that they additionally comprise B.92 and B.60 as further herbicides B.

Also especially preferred are compositions 46.1. to 46.2029 which differ from the corresponding compositions 1.1 to 1.2029 only in that they additionally comprise B.92 and B.66 as further herbicides B.

Also especially preferred are compositions 47.1. to 47.2029 which differ from the corresponding compositions 1.1 to 1.2029 only in that they additionally comprise B.96 as further herbicide B.

Also especially preferred are compositions 48.1. to 48.2029 which differ from the corresponding compositions 1.1 to 1.2029 only in that they additionally comprise B.96 and B.54 as further herbicides B.

Also especially preferred are compositions 49.1. to 49.2029 which differ from the corresponding compositions 1.1 to 1.2029 only in that they additionally comprise B.96 and B.76 as further herbicides B.

Also especially preferred are compositions 50.1. to 50.2029 which differ from the corresponding compositions 1.1 to 1.2029 only in that they additionally comprise B.96 and B.85 as further herbicides B.

Also especially preferred are compositions 51.1. to 51.2029 which differ from the corresponding compositions 1.1 to 1.2029 only in that they additionally comprise B.96 and B.104 as further herbicides B.

Also especially preferred are compositions 52.1. to 52.2029 which differ from the corresponding compositions 1.1 to 1.2029 only in that they additionally comprise B.96 and B.86 as further herbicides B.

Also especially preferred are compositions 53.1. to 53.2029 which differ from the corresponding compositions 1.1 to 1.2029 only in that they additionally comprise B.96 and B.89 as further herbicides B.

Also especially preferred are compositions 54.1. to 54.2029 which differ from the corresponding compositions 1.1 to 1.2029 only in that they additionally comprise B.96 and B.92 as further herbicides B.

Also especially preferred are compositions 55.1. to 55.2029 which differ from the corresponding compositions 1.1 to 1.2029 only in that they additionally comprise B.99 as further herbicide B.

Also especially preferred are compositions 56.1. to 56.2029 which differ from the corresponding compositions 1.1 to 1.2029 only in that they additionally comprise B.102 as further herbicide B.

Also especially preferred are compositions 57.1. to 57.2029 which differ from the corresponding compositions 1.1 to 1.2029 only in that they additionally comprise B.104 as further herbicide B.

Also especially preferred are compositions 58.1. to 58.2029 which differ from the corresponding compositions 1.1 to 1.2029 only in that they additionally comprise B.107 as further herbicide B.

Also especially preferred are compositions 59.1. to 59.2029 which differ from the corresponding compositions 1.1 to 1.2029 only in that they additionally comprise B.108 as further herbicide B.

Also especially preferred are compositions 60.1. to 60.2029 which differ from the corresponding compositions 1.1 to 1.2029 only in that they additionally comprise B.109 as further herbicide B.

Also especially preferred are compositions 61.1. to 61.2029 which differ from the corresponding compositions 1.1 to 1.2029 only in that they additionally comprise B.111 as further herbicide B.

Also especially preferred are compositions 62.1. to 62.2029 which differ from the corresponding compositions 1.1 to 1.2029 only in that they additionally comprise B.113 as further herbicide B.

Also especially preferred are compositions 63.1. to 63.2029 which differ from the corresponding compositions 11.1 to 1.2029 only in that they additionally comprise B.114 as further herbicide B.

Also especially preferred are compositions 64.1. to 64.2029 which differ from the corresponding compositions 1.1 to 1.2029 only in that they additionally comprise B.118 as further herbicide B.

Also especially preferred are compositions 65.1. to 65.2029 which differ from the corresponding compositions 1.1 to 1.2029 only in that they additionally comprise B.120 as further herbicide B.

Also especially preferred are compositions 66.1. to 66.2029 which differ from the corresponding compositions 1.1 to 1.2029 only in that they additionally comprise B.121 as further herbicide B.

Also especially preferred are compositions 67.1. to 67.2029 which differ from the corresponding compositions 1.1 to 1.2029 only in that they additionally comprise B.123 as further herbicide B.

Also especially preferred are compositions 68.1. to 68.2029 which differ from the corresponding compositions 1.1 to 1.2029 only in that they additionally comprise B.124 as further herbicide B.

Also especially preferred are compositions 69.1. to 69.2029 which differ from the corresponding compositions 1.1 to 1.2029 only in that they additionally comprise B.131 as further herbicide B.

Hereinbelow, the compounds of the formula I are illustrated by way of examples, without limiting the subject matter of the present invention to the examples shown.

I. SYNTHESIS EXAMPLES

With appropriate modification of the starting materials, the procedures given in the synthesis examples below were used to obtain further compounds I. The compounds obtained in this manner are listed in the table that follows, together with physical data. The products shown below were characterized by determination of the melting point, by NMR spectroscopy or by the masses ([m/z]) or retention time (RT; [min.]) determined by HPLC-MS spectrometry.

HPLC-MS=high performance liquid chromatography coupled with mass spectrometry; HPLC column: RP-18 column (Chromolith Speed ROD from Merck KgaA, Germany), 50*4.6 mm; mobile phase: acetonitrile+0.1% trifluoroacetic acid (TFA)/water+0.1% TFA, using a gradient from 5:95 to 100:0 over 5 minutes at 40° C., flow rate 1.8 ml/min. MS: quadrupole electrospray ionization, 80 V (positive mode).

Example 1

Preparation of 6,6-Dioxo-7-(2-trifluoromethyl-phenyl)-5,6-dihydro-thiopyrano[4,3-b]pyridin-8-ol (compound I-2 in Table I below)

Step 1: Preparation of 3-(2-Trifluoromethyl-benzylsulfanylmethyl)-pyridine-2-carboxylic acid methyl ester

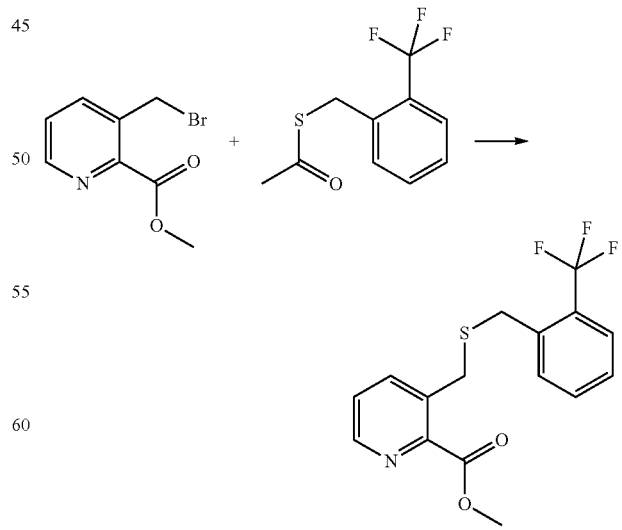

To a solution of thioacetic acid S-(2-trifluoromethyl-benzyl)ester (10.2 g, 37.5 mmol) in methanol (130 ml) potassium carbonate (5.18 g, 37.5 mmol) was added at room temperature and it was stirred for 30 min. 3-Bromomethyl-pyridine-2-carboxylic acid methyl ester (4.40 g, 18.7 mmol) was added and after refluxing for 150 min the solution was diluted with water, extracted with ethylacetate, the organic phase dried with sodium sulfate and concentrated. Chromatography over silica with ethylacetate/cyclohexane gave 7.82 g colorless crystals (18.7 mmol).

$^1$H-NMR (CDCl$_3$): 8.60 (d, 1H); 7.75 (d, 1H); 7.3-7.7 (m, 5H); 4.15 (s, 2H); 4.00 (s, 3H); 3.90 (s, 2H).

Step 2: Preparation of 3-(2-Trifluoromethyl-phenyl-methanesulfonylmethyl)-pyridine-2-carboxylic acid methyl ester

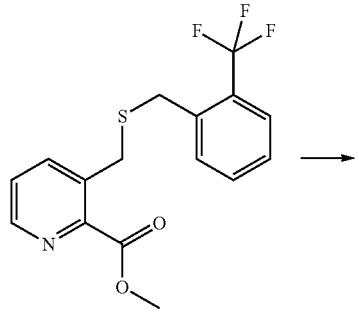

To a solution of 3-(2-Trifluoromethyl-benzylsulfanylmethyl)-pyridine-2-carboxylic acid methyl ester (0.262 g, 0.77 mmol) in methylenehloride (10 ml) and 3-chloroperbenzoicacid (0.516 g, 2.30 mmol) was added over 4.5 h at room temperature. After further 6.5 h saturated sodiumbicarbonatesolution and sodium thiosulfate solution was added, extracted with methylenehloride, the organic phase dried with sodiumsulfate and concentrated, resulting in colorless crystals (281 mg, 0.75 mmol).

$^1$H-NMR (CDCl$_3$): 8.75 (d, 1H); 7.90 (d, 1H); 7.5-7.8 (m, 5H); 4.85 (s, 2H); 4.55 (s, 2H); 4.00 (s, 3H).

Step 3: Preparation of Compound I-2

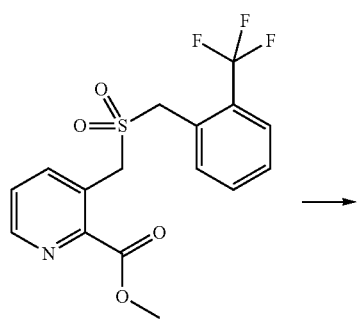

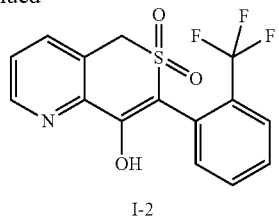

I-2

To a solution of 3-(2-Trifluoromethyl-phenylmethanesulfonylmethyl)-pyridine-2-carboxylic acid methyl ester (7.58 g, 19.6 mmol) in tetrahydrofurane (160 ml) potassium tert-butoxide (2.20 g, 19.57 mmol) was added at room temperature and stirring was continued for 3.5 h. 1M HCl was added, diluted with methylenehloride and extracted. The organic phase was dried with sodiumsulfate and concentrated. Chromatography over silica with ethylacetate/cyclohexane gave 2.50 g colourless crystals (7.32 mmol).

$^1$H-NMR (CDCl$_3$): 8.75 (d, 1H); 7.85 (d, 1H); 7.75 (d, 1H); 7.5-7.7 (m, 4H); 4.75 (d, 1H); 4.55 (d, 1H).

Example 2

Preparation of 2,2-Dimethyl-propionic acid 6,6-dioxo-7-(2-trifluoromethyl-phenyl)-5,6-dihydro-thiopyrano[4,3-b]pyridin-8-yl ester (compound I-8 in Table I below)

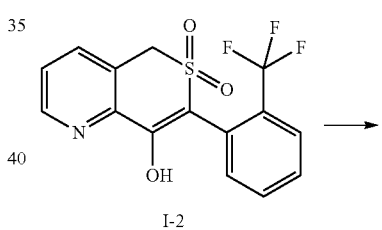

I-2

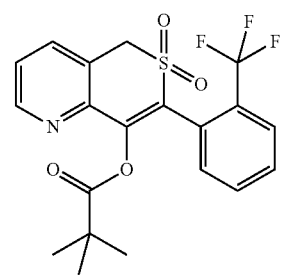

I-8

To a solution of 6,6-Dioxo-7-(2-trifluoromethyl-phenyl)-5,6-dihydro-thiopyrano[4,3-b]pyridin-8-ol (1.92 g, 5.61 mmol) prepared according to the above Example 1 in methylenehloride (70 ml) was added at 0° C. pyridine (1.77 g, 22.4 mmol), followed by pivaloylchloride (0.744 g, 6.17 mmol). After stirring at room temperature for 16 h methylenehloride and water was added, the organic phase separated and concentrated. Chromatography over silica with ethylacetate/cyclohexane gave 380 mg colourless crystals (0.88 mmol).

$^1$H-NMR (CDCl$_3$): 8.70 (d, 1H); 7.80 (d, 1H); 7.4-7.7 (m, 5H); 4.75 (d, 1H, 4.50 (d, 1H); 1.05 (s, 9H).

Example 3

Preparation of 2,2-Dimethyl-propionic acid 5,5-dimethyl-6,6-dioxo-7-(2-trifluoromethyl-phenyl)-5,6-dihydro-thiopyrano[4,3-b]pyridin-8-yl ester (compound I-18 in Table I below)

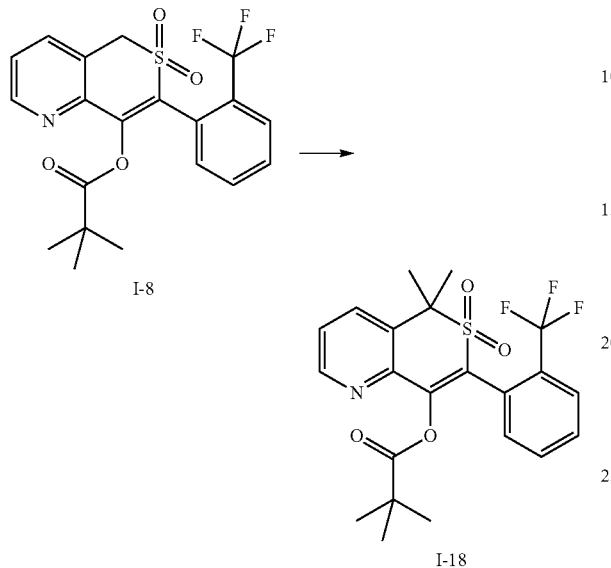

To a solution of 2,2-Dimethyl-propionic acid 6,6-dioxo-7-(2-trifluoromethyl-phenyl)-5,6-dihydro-thiopyrano[4,3-b]pyridin-8-yl ester (0.215 g, 0.51 mmol) prepared according to the above Example 2 in tetrahydrofurane (10 ml) was added 1-t-butyl-2,2,4,4,4-pentakis(dimethylamino)-catenadi(phosphazene) (0.279 g, 0.76 mmol) and methyliodide (0.215 g, 1.52 mmol) at room temperature. After 18 h 1M HCl and dichloromethane was added, the organic phase dried with sodiumsulfate and concentrated. Chromatography over silica with ethylacetate/cyclohexane gave 201 mg colourless crystals (0.44 mmol).

$^1$H-NMR (CDCl$_3$): 8.60 (d, 1H); 7.3-7.9 (m, 6H); 1.95 (s, 3H); 1.90 (s, 3H); 1.05 (s, 9H).

Example 4

Preparation of [6',6'-dioxo-7'-[2-(trifluoromethyl)phenyl]spiro[cyclopropane-1,5'-thiopyrano[4,3-b]pyridine]-8'-yl]2,2-dimethylpropanoate (compound I-24 in Table I below)

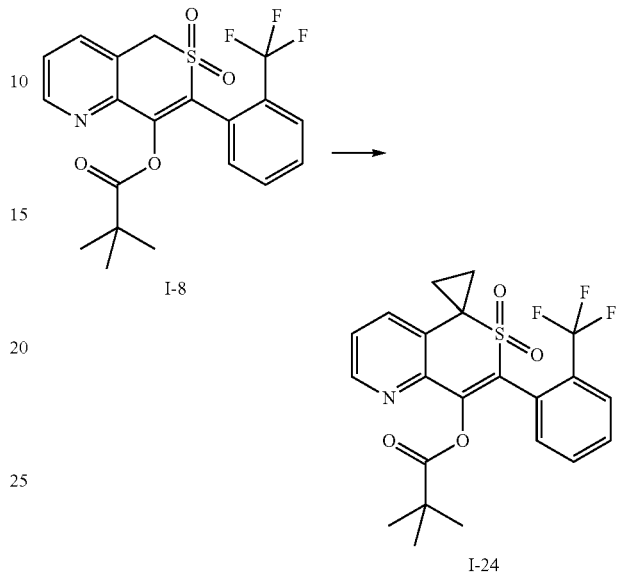

To a solution if 2,2-Dimethyl-propionic acid 6,6-dioxo-7-(2-trifluoromethyl-phenyl)-5,6-dihydro-thiopyrano[4,3-b]pyridin-8-yl ester (0.215 g, 0.51 mmol) prepared according to the above Example 2 in tetrahydrofurane (10 ml) was added 1-t-butyl-2,2,4,4,4-pentakis(dimethylamino)-catenadi(phosphazene) (0.557 g, 1.52 mmol) and 1-bromo-2-chloroethane (0.174 g, 1.21 mmol) at room temperature. After 21 h 1M HCl and dichloromethane was added, the organic phase dried with sodiumsulfate and concentrated. Chromatography over silica with ethylacetate/cyclohexane gave 93 mg colourless crystals (0.21 mmol).

$^1$H-NMR (CDCl$_3$): 8.60 (d, 1H); 7.3-7.9 (m, 6H); 2.0-2.3 (, 2H); 1.9-2.0 (m, 1H, 1.3-1.5 (m, 1H); 1.05 (s, 9H).

TABLE I

Compounds of the formula I.A

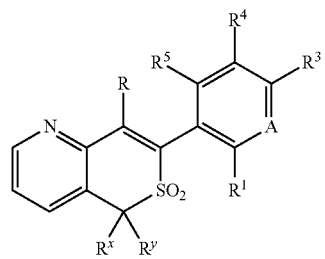

I.A

| No. | R | A | R$^1$ | R$^2$ | R$^3$ | R$^4$ | R$^5$ | R$^x$ | R$^y$ | LCMS (M + H) |
|---|---|---|---|---|---|---|---|---|---|---|
| I-1 | OH | CR$^2$ | Cl | H | Cl | H | H | H | H | 342.0 |
| I-2 | OH | CR$^2$ | CF$_3$ | H | H | H | H | H | H | 342.0 |
| I-3 | OCOiPr | CR$^2$ | CF$_3$ | H | H | H | H | H | H | 412.1 |
| I-4 | OCOiPr | CR$^2$ | Cl | H | Cl | H | H | Me | Me | 439.0 |
| I-5 | OH | CR$^2$ | Cl | H | Cl | H | H | Me | Me | 370.0 |
| I-6 | OH | CR$^2$ | CF$_3$ | H | H | H | F | H | H | 360.0 |
| I-7 | OH | CR$^2$ | Cl | H | Cl | H | H | Et | H | 370.0 |

TABLE I-continued

Compounds of the formula I.A

I.A

| No. | R | A | $R^1$ | $R^2$ | $R^3$ | $R^4$ | $R^5$ | $R^x$ | $R^y$ | LCMS (M + H) |
|---|---|---|---|---|---|---|---|---|---|---|
| I-8 | OCOtBu | $CR^2$ | $CF_3$ | H | H | H | H | H | H | 426.1 |
| I-9 | OCOtBu | $CR^2$ | $CF_3$ | H | H | H | F | H | H | 444.1 |
| I-10 | OCOtBu | $CR^2$ | Br | H | F | H | H | H | H | 456.0 |
| I-11 | OCOtBu | $CR^2$ | Cl | 5-Methyl-3-Isoxazolinyl | Cl | H | H | H | H | 509.1 |
| I-12 | OCOtBu | $CR^2$ | Cl | H | H | H | Cl | H | H | 426.0 |
| I-13 | OH | $CR^2$ | Cl | H | H | H | Cl | H | H | 342.0 |
| I-14 | OH | $CR^2$ | Br | H | F | H | H | H | H | 371.9 |
| I-15 | OH | $CR^2$ | Cl | 5-Methyl-3-Isoxazolinyl | Cl | H | H | H | H | 425.0 |
| I-16 | OH | $CR^2$ | I | H | F | H | H | H | H | 417.9 |
| I-17 | OH | $CR^2$ | Cl | H | F | H | H | H | H | 326.0 |
| I-18 | OCOtBu | $CR^2$ | $CF_3$ | H | H | H | H | Me | Me | 454.1 |
| I-19 | OCOtBu | $CR^2$ | Cl | H | H | H | Cl | Me | Me | 454.1 |
| I-20 | OCOtBu | $CR^2$ | Br | H | F | H | H | Me | Me | 484.0 |
| I-21 | OCOt Bu | $CR^2$ | $CF_3$ | H | H | H | F | Me | Me | 472.1 |
| I-22 | OCOtBu | N | Cl | — | H | H | Cl | H | H | 427.0 |
| I-23 | OCOtBu | N | Cl | — | Cl | H | H | H | H | 427.0 |
| I-24 | OCOtBu | $CR^2$ | $CF_3$ | H | H | H | H | $CH_2CH_2$ | | 452.1 |
| I-25 | OCOtBu | $CR^2$ | $CF_3$ | H | H | H | H | Et | H | 454.1 |
| I-26 | OH | $CR^2$ | $CF_3$ | H | H | H | H | Et | Et | 482.2 |
| I-27 | OH | $CR^2$ | $CF_3$ | H | H | Cl | H | H | H | 376.0 |
| I-28 | OH | $CR^2$ | $CF_3$ | H | H | F | H | H | H | 360.0 |
| I-29 | OCOtBu | N | Cl | — | Cl | H | H | Me | Me | 455.1 |
| I-30 | OH | $CR^2$ | Cl | H | H | H | F | H | H | 326.0 |
| I-31 | OH | $CR^2$ | $CF_3$ | H | H | H | Cl | H | H | 376.0 |
| I-32 | OH | $CR^2$ | Cl | Cl | H | H | F | H | H | 360.0 |
| I-33 | OH | $CR^2$ | Cl | Cl | H | H | Cl | H | H | 377.9 |
| I-34 | OH | $CR^2$ | $CF_3$ | H | Br | H | H | H | H | 421.9 |
| I-35 | OH | $CR^2$ | Cl | Br | H | H | F | H | H | 405.9 |
| I-36 | OH | N | $CF_3$ | — | H | H | H | H | H | 343.0 |
| I-37 | OH | N | $CF_3$ | — | H | H | H | Me | Me | 371.1 |
| I-38 | OH | $CR^2$ | Cl | 3-Methyl-5-Isoxazolinyl | Cl | H | H | H | H | 425.0 |
| I-39 | OH | $CR^2$ | Cl | 3-Methyl-5-Isoxazolinyl | Cl | H | H | Me | Me | 453.0 |
| I-40 | OCOtBu | $CR^2$ | Cl | H | Cl | H | Cl | H | H | 462.0 |
| I-41 | OCOtBu | $CR^2$ | I | H | H | H | F | H | H | 502.0 |
| I-42 | OH | $CR^2$ | Cl | 5-Methyl-3-Isoxazolinyl | Cl | H | H | Me | Me | 453.0 |
| I-43 | OH | $CR^2$ | $CF_3$ | H | CN | H | H | H | H | 367.0 |
| I-44 | OCOtBu | $CR^2$ | Cl | H | Cl | H | H | Me | Me | 490.0 |
| I-45 | OH | $CR^2$ | $SO_2Me$ | H | Cl | H | H | H | H | 386.0 |
| I-46 | OH | $CR^2$ | $CF_3$ | H | Cl | H | H | H | H | 376.0 |
| I-47 | OH | $CR^2$ | | $CHNN(CH_3)$ | H | H | H | H | H | 328.1 |
| I-48 | OCOtBu | $CR^2$ | $CF_3$ | H | H | H | H | Me | Me | 488.1 |
| I-49 | OH | N | Cl | — | Cl | H | H | Me | Me | 371.0 |
| I-50 | OCOtBu | $CR^2$ | | $CHNN(CH_3)$ | H | H | H | H | H | 440.2 |
| I-51 | OH | $CR^2$ | Cl | H | I | H | H | H | H | 433.9 |
| I-52 | OCOtBu | $CR^2$ | $SO_2Me$ | H | Cl | H | H | Me | Me | 498.1 |
| I-53 | OH | $CR^2$ | Cl | H | Br | H | H | H | H | 385.9 |
| I-54 | OH | $CR^2$ | Cl | H | Cl | H | H | Me | H | 356.0 |
| I-55 | OH | $CR^2$ | $CF_3$ | H | F | H | H | Me | Me | 388.1 |
| I-56 | OH | $CR^2$ | $CF_3$ | H | H | Cl | H | Me | Me | 404.0 |
| I-57 | OH | $CR^2$ | Cl | H | Br | H | H | Me | Me | 413.9 |
| I-58 | OH | $CR^2$ | Cl | H | I | H | H | H | H | 462.7 |
| I-59 | OH | $CR^2$ | Cl | $CH_2OCH_3$ | Cl | H | H | H | H | 386.0 |
| I-60 | OH | $CR^2$ | Cl | $CH_2OCH_2$—$CH_2OCH_3$ | Cl | H | H | H | H | 430.0 |
| I-61 | OH | $CR^2$ | Cl | $CH_2OH$ | Cl | H | H | H | H | 372.0 |
| I-62 | OH | $CR^2$ | Cl | $C(CH_3)_2OH$ | H | H | Cl | H | H | 400.0 |

TABLE I-continued

Compounds of the formula I.A

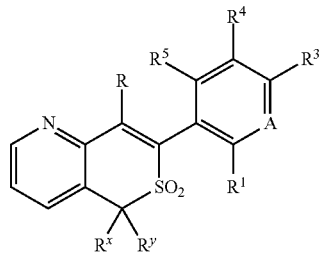

I.A

| No. | R | A | $R^1$ | $R^2$ | $R^3$ | $R^4$ | $R^5$ | $R^x$ | $R^y$ | LCMS (M + H) |
|---|---|---|---|---|---|---|---|---|---|---|
| I-63 | OH | $CR^2$ | $CF_3$ | H | Br | H | H | Me | Me | 448.0 |
| I-64 | OH | $CR^2$ | $CF_3$ | H | CN | H | H | H | H | 367.0 |
| I-65 | OH | $CR^2$ | $CF_3$ | H | CN | H | H | Me | Me | 395.1 |
| I-66 | OH | N | $CF_3$ | H | Cl | H | H | H | H | 377.0 |

Wherein Me denotes methyl, Et denotes ethyl, iPr denotes iso-propyl and t-Bu denotes tert.-butyl.

II. USE EXAMPLES

The herbicidal activity of the compounds of the formula I was demonstrated by the following greenhouse experiments:

The culture containers used were plastic flowerpots containing loamy sand with approximately 3.0% of humus as the substrate. The seeds of the test plants were sown separately for each species.

For the pre-emergence treatment, the active ingredients, which had been suspended or emulsified in water, were applied directly after sowing by means of finely distributing nozzles. The containers were irrigated gently to promote germination and growth and subsequently covered with transparent plastic hoods until the plants had rooted. This cover caused uniform germination of the test plants, unless this has been impaired by the active ingredients.

For the post-emergence treatment, the test plants were first grown to a height of 3 to 15 cm, depending on the plant habit, and only then treated with the active ingredients which had been suspended or emulsified in water. For this purpose, the test plants were either sown directly and grown in the same containers, or they were first grown separately as seedlings and transplanted into the test containers a few days prior to treatment.

Depending on the species, the plants were kept at 10-25° C. or 20-35° C. The test period extended over 2 to 4 weeks. During this time, the plants were tended, and their response to the individual treatments was evaluated.

Evaluation was carried out using a scale from 0 to 100. 100 means no emergence of the plants, or complete destruction of at least the aerial moieties, and 0 means no damage, or normal course of growth. A good herbicidal activity is given at values of at least 70 and a very good herbicidal activity is given at values of at least 85.

The plants used in the greenhouse experiments belonged to the following species:

| Bayer code | Scientific name | English name |
|---|---|---|
| ABUTH | Abutilon theophrasti | velvetleaf |
| ALOMY | Alopercurus myosuroides | blackgrass |
| AMARE | Amaranthus retroflexus | common amaranth |
| AVEFA | Avena fatua | wild oat |
| BRSNW | Brassica napus (winter) | winter rape |
| CHEAL | Chenopodium album | lampsquaters |
| ECHCG | Echinocloa crus-galli | comon barnyardgrass |
| SETFA | Setaria faberi | Faber's foxtail |
| SETVI | Setaria viridis | green foxtail |

At an application rate of 0.25 kg/ha, the compound I-12, applied by the post-emergence method, showed very good herbicidal activity against ABUTH.

At an application rate of 0.25 kg/ha, the compound I-2, applied by the post-emergence method, showed very good herbicidal activity against ALOMY.

At an application rate of 0.25 kg/ha, the compound I-8, applied by the post-emergence method, showed good herbicidal activity against ALOMY.

At an application rate of 0.5 kg/ha, the compounds I-27 and I-28, applied by the post-emergence method, showed very good herbicidal activity against ALOMY.

At an application rate of 3 kg/ha, the compound I-6, applied by the post-emergence method, showed very good herbicidal activity against ALOMY.

At an application rate of 0.25 kg/ha, the compound I-12, applied by the post-emergence method, showed very good herbicidal activity against AMARE.

At an application rate of 0.275 kg/ha, the compound I-4, applied by the post-emergence method, showed very good herbicidal activity against AMARE.

At an application rate of 0.302 kg/ha, the compound I-7, applied by the post-emergence method, showed very good herbicidal activity against AMARE.

At an application rate of 0.398 kg/ha, the compound I-5, applied by the post-emergence method, showed very good herbicidal activity against AMARE.

At an application rate of 0.5 kg/ha, the compounds I-1, I-2, I-3, I-18, I-19, I-20, I-21, I-27 and I-28, applied by the post-emergence method, showed very good herbicidal activity against AMARE.

At an application rate of 0.25 kg/ha, the compound I-2, applied by the post-emergence method, showed very good herbicidal activity against AVEFA.

At an application rate of 3 kg/ha, the compound I-6, applied by the post-emergence method, showed very good herbicidal activity against AVEFA.

At an application rate of 0.25 kg/ha, the compound I-13, applied by the post-emergence method, showed very good herbicidal activity against BRSNW.

At an application rate of 0.25 kg/ha, the compounds I-9, I-11, I-13, I-14 and I-15, applied by the post-emergence method, showed very good herbicidal activity against CHEAL.

At an application rate of 0.275 kg/ha, the compound I-4, applied by the post-emergence method, showed very good herbicidal activity against CHEAL.

At an application rate of 0.302 kg/ha, the compound I-7, applied by the post-emergence method, showed very good herbicidal activity against CHEAL.

At an application rate of 0.398 kg/ha, the compound I-5, applied by the post-emergence method, showed very good herbicidal activity against CHEAL At an application rate of 0.5 kg/ha, the compounds I-1, I-2, I-18, I-19, I-20 and I-21, applied by the post-emergence method, showed very good herbicidal activity against CHEAL.

At an application rate of 0.25 kg/ha, the compounds I-2 and I-13, applied by the post-emergence method, showed very good herbicidal activity against ECHGG.

At an application rate of 0.275 kg/ha, the compound I-4, applied by the post-emergence method, showed very good herbicidal activity against ECHGG.

At an application rate of 0.398 kg/ha, the compound I-5, applied by the post-emergence method, showed very good herbicidal activity against ECHGG.

At an application rate of 0.5 kg/ha, the compounds I-1, I-2 and I-3, applied by the post-emergence method, showed very good herbicidal activity against ECHGG.

At an application rate of 0.25 kg/ha, the compound I-14, applied by the post-emergence method, showed very good herbicidal activity against SETFA.

At an application rate of 0.302 kg/ha, the compound I-7, applied by the post-emergence method, showed very good herbicidal activity against SETFA.

At an application rate of 3 kg/ha, the compound I-6, applied by the post-emergence method, showed very good herbicidal activity against SETFA.

At an application rate of 0.25 kg/ha, the compounds I-9, I-11, I-13 and I-15, applied by the post-emergence method, showed very good herbicidal activity against SETVI.

III. COMPARATIVE EXAMPLES

The herbicidal activity of the substituted pyridine compounds I-2 and I-13 according to this invention was tested in comparison with the corresponding pyrazine compounds Nos. C-11 and C-19 disclosed on page 48 of WO 2010/130970 (not of the invention). These comparative experiments were performed at an application rate of 0.25 kg/ha in a post-emergence treatment by following the same procedure as described above in the Use Examples. The results of Comparative Examples 1 and 2 are indicated below in Tables II and III.

TABLE II

Results of Comparative Example 1

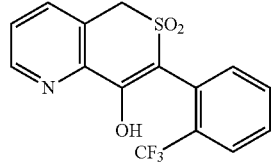

Compound I-2
(according to the invention)

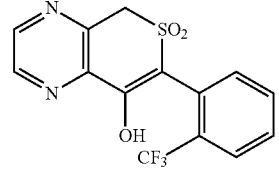

Compound No. C11 of
WO 2010/130970)
(not of the invention)

| Tested species | Evaluation of herbicidal activity | |
| --- | --- | --- |
| ALOMY | very good | good |
| AVEFA | very good | less than good |
| ECHCG | very good | less than good |

TABLE III

Results of Comparative Example 2

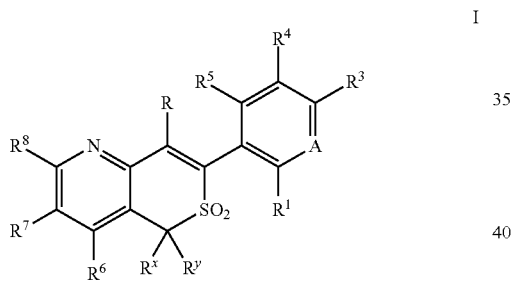

| | |
|---|---|
| Compound I-13 (according to the invention) | Compound No. C19 of WO 2010/130970 (not of the invention) |

| Tested species | Evaluation of herbicidal activity | |
|---|---|---|
| BRSNW | very good | good |
| CHEAL | very good | less than good |
| ECHCG | very good | less than good |

The results of Comparative Examples 1 and 2 indicate that the pyridine compounds I of the present invention surprisingly exhibit superior herbicidal activity in comparison to the corresponding pyrazine compounds which are not of the invention.

The invention claimed is:
1. A compound of formula I wherein:
R is O—$R^A$, S(O)$_n$—$R^A$ or O—S(O)$_n$—$R^A$;
$R^A$ is hydrogen, $C_1$-$C_4$-alkyl, Z—$C_3$-$C_6$-cycloalkyl, $C_1$-$C_4$-haloalkyl, $C_2$-$C_6$-alkenyl, Z—$C_3$-$C_6$-cycloalkenyl, $C_2$-$C_6$-alkynyl, Z-(tri-$C_1$-$C_4$-alkyl)silyl, Z—C(=O)—$R^a$, Z—$NR^i$—C(O)—$NR^iR^{ii}$, Z—P(=O)($R^a$)$_2$, $NR^iR^{ii}$ or a 3- to 7-membered monocyclic or 9- or 10-membered bicyclic saturated, unsaturated or aromatic heterocycle which contains 1, 2, 3 or 4 heteroatoms selected from the group consisting of O, N and S and which may be partially or fully substituted by groups $R^a$ and/or $R^b$,
$R^a$ is independently hydrogen, OH, $C_1$-$C_8$-alkyl, $C_1$-$C_4$-haloalkyl, Z—$C_3$-$C_6$-cycloalkyl, $C_2$-$C_8$-alkenyl, Z—$C_5$-$C_6$-cycloalkenyl, $C_2$-$C_8$-alkynyl, Z—$C_1$-$C_6$-alkoxy, Z—$C_1$-$C_4$-haloalkoxy, Z—$C_3$-$C_8$-alkenyloxy, Z—$C_3$-$C_8$-alkynyloxy, $NR^iR^{ii}$, $C_1$-$C_6$-alkylsulfonyl, Z-(tri-$C_1$-$C_4$-alkyl)silyl, Z-phenyl, Z-phenoxy, Z-phenylamino or a 5- or 6-membered monocyclic or 9- or 10-membered bicyclic heterocycle which contains 1, 2, 3 or 4 heteroatoms selected from the group consisting of O, N and S, where the cyclic groups are unsubstituted or substituted by 1, 2, 3 or 4 groups $R^b$;

$R^i$, $R^{ii}$ independently of one another are hydrogen, $C_1$-$C_8$-alkyl, $C_1$-$C_4$-halo-alkyl, $C_3$-$C_8$-alkenyl, $C_3$-$C_8$-alkynyl, Z—$C_3$-$C_6$-cycloalkyl, Z—$C_1$-$C_8$-alkoxy, Z—$C_1$-$C_8$-haloalkoxy, Z—C(=O)—$R^a$, Z-phenyl, a 3- to 7-membered monocyclic or 9- or 10-membered bicyclic saturated, unsaturated or aromatic heterocycle which contains 1, 2, 3 or 4 heteroatoms selected from the group consisting of O, N and S and which is attached via Z; or $R^i$ and $R^{ii}$ together with the nitrogen atom to which they are attached may form a 5- or 6-membered monocyclic or 9- or 10-membered bicyclic heterocycle which contains 1, 2, 3 or 4 heteroatoms selected from the group consisting of O, N and S;

$R^b$ independently of one another are Z—CN, Z—OH, Z—$NO_2$, Z-halogen, oxo (=O), =N—$R^a$, $C_1$-$C_8$-alkyl, $C_1$-$C_4$-haloalkyl, $C_2$-$C_8$-alkenyl, $C_2$-$C_8$-alkynyl, Z—$C_1$-$C_8$-alkoxy, Z—$C_1$-$C_8$-haloalkoxy, Z—$C_3$-$C_{10}$-cycloalkyl, O—Z—$C_3$-$C_{10}$-cycloalkyl, Z—C(=O)—$R^a$, $NR^iR^{ii}$, Z-(tri-$C_1$-$C_4$-alkyl)silyl, Z-phenyl or S(O)$_n R^{bb}$; or two groups $R^b$ may together form a ring which has 3 to 6 ring members and, in addition to carbon atoms, may contain heteroatoms selected from the group consisting of O, N and S and may be unsubstituted or substituted by further groups $R^b$;

$R^{bb}$ is $C_1$-$C_8$-alkyl, $C_2$-$C_6$-alkenyl, $C_2$-$C_6$-alkynyl, $C_2$-$C_6$-haloalkenyl, $C_2$-$C_6$-haloalkynyl or $C_1$-$C_6$-haloalkyl;

Z is a covalent bond or $C_1$-$C_4$-alkylene;

n is 0, 1 or 2;

$R^1$ is cyano, halogen, nitro, $C_1$-$C_6$-alkyl, $C_2$-$C_6$-alkenyl, $C_2$-$C_6$-alkynyl, $C_1$-$C_6$-haloalkyl, Z—$C_1$-$C_6$-alkoxy, Z—$C_1$-$C_4$-alkoxy-$C_1$-$C_4$-alkoxy, Z—$C_1$-$C_4$-alkylthio, Z—$C_1$-$C_4$-alkylthio-$C_1$-$C_4$-alkylthio, $C_2$-$C_6$-alkenyloxy, $C_2$-$C_6$-alkynyloxy, $C_1$-$C_6$-haloalkoxy, $C_1$-$C_4$-haloalkoxy-$C_1$-$C_4$-alkoxy, S(O)$_n R^{bb}$, Z-phenoxy or Z-heterocyclyloxy, where heterocyclyl is a 5- or 6-membered monocyclic or 9- or 10-membered bicyclic saturated, partially unsaturated or aromatic heterocycle which contains 1, 2, 3 or 4 heteroatoms selected from the group consisting of O, N and S, where cyclic groups are unsubstituted or partially or fully substituted by $R^b$;

A is N or C—$R^2$;

$R^2$, $R^3$, $R^4$, $R^5$ independently of one another are hydrogen, Z-halogen, Z—CN, Z—OH, Z—$NO_2$, $C_1$-$C_8$-alkyl, $C_1$-$C_4$-haloalkyl, $C_2$-$C_8$-alkenyl, $C_2$-$C_8$-alkynyl, $C_2$-$C_8$-halo-alkenyl, $C_2$-$C_8$-haloalkynyl, Z—$C_1$-$C_8$-alkoxy, Z—$C_1$-$C_8$-haloalkoxy, Z—$C_1$-$C_4$-alkoxy-$C_1$-$C_4$-alkoxy, Z—$C_1$-$C_4$-alkylthio, Z—$C_1$-$C_4$-alkylthio-$C_1$-$C_4$-alkylthio, Z—$C_1$-$C_6$-haloalkylthio, $C_2$-$C_6$-alkenyloxy, $C_2$-$C_6$-alkynyloxy, $C_1$-$C_6$-haloalkoxy, $C_1$-$C_4$-haloalkoxy-$C_1$-$C_4$-alkoxy, Z—$C_3$-$C_{10}$-cycloalkyl, O—Z—$C_3$-$C_{10}$-cycloalkyl, Z—C(=O)—$R^a$, $NR^iR^{ii}$, Z-(tri-$C_1$-$C_4$-alkyl)silyl, $S(O)_n R^{bb}$, Z-phenyl, $Z^1$-phenyl, Z-heterocyclyl or $Z^1$-heterocyclyl, where heterocyclyl is a 5- or 6-membered monocyclic or 9- or 10-membered bicyclic saturated, partially unsaturated or aromatic heterocycle which contains 1, 2, 3 or 4 heteroatoms selected from the group consisting of O, N and S, where cyclic groups are unsubstituted or partially or fully substituted by $R^b$; or $R^2$ together with the group attached to the adjacent carbon atom may also form a 5- to 10-membered saturated or partially or fully unsaturated mono- or bicyclic ring which, in addition to carbon atoms, may contain 1, 2 or 3 heteroatoms selected from the group consisting of O, N and S and may be substituted by further groups $R^b$;

$Z^1$ is a covalent bond, $C_1$-$C_4$-alkyleneoxy, $C_1$-$C_4$-oxyalkylene or $C_1$-$C_4$-alkyleneoxy-$C_1$-$C_4$-alkylene;

$R^6$ is hydrogen, $C_1$-$C_4$-alkyl, $C_1$-$C_4$-haloalkyl, $C_1$-$C_4$-alkoxy, $C_1$-$C_4$-alkylthio, $C_1$-$C_4$-haloalkoxy or $C_1$-$C_4$-haloalkylthio;

$R^7$, $R^8$ independently of one another are hydrogen, halogen or $C_1$-$C_4$-alkyl;

$R^x$, $R^y$ independently of one another are hydrogen, $C_1$-$C_5$-alkyl, $C_2$-$C_5$-alkenyl, $C_2$-$C_5$-alkynyl, $C_1$-$C_5$-haloalkyl, $C_1$-$C_2$-alkoxy-$C_1$-$C_2$-alkyl or halogen; or $R^x$ and $R^y$ are together a $C_2$-$C_5$-alkylene or $C_2$-$C_5$-alkenylene chain and form a 3-, 4-, 5- or 6-membered saturated, partially unsaturated or fully unsaturated monocyclic ring together with the carbon atom they are bonded to, wherein 1 or 2 of any of the $CH_2$ or CH groups in the $C_2$-$C_5$-alkylene or $C_2$-$C_5$-alkenylene chain may be replaced by 1 or 2 heteroatoms independently selected from the groups consisting of O and S;

where in the groups $R^A$, and $R^1$, $R^2$, $R^3$, $R^4$ and $R^5$ and their substituents, the carbon chains and/or the cyclic groups may be partially or fully substituted by groups $R^b$, or an N-oxide or an agriculturally suitable salt thereof.

2. The compound of claim 1 wherein A is $CR^2$.

3. The compound of claim 2 wherein $R^2$ is an optionally substituted 5- or 6-membered saturated, partially unsaturated or aromatic heterocycle which contains 1, 2, 3 or 4 heteroatoms selected from the group consisting of O, N and S.

4. The compound of claim 2 wherein $R^2$ is a group of the formula

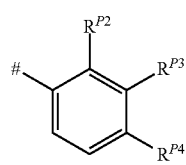

wherein # denotes the bond through which the group $R^2$ is attached and $R^{P2}$ is H or F;

$R^{P3}$ is H, F, Cl or $OCH_3$; and $R^{P4}$ is H, F, Cl, $CH_3$, $CF_3$, $OCH_3$, $OCH_2OCH_3$ or $OCH_2CH_2OCH_3$.

5. The compound of claim 3 wherein $R^2$ is a heterocycle selected from the group consisting of isoxazoline, tetrazolone, 1,2-dihydrotetrazolone, 1,4-dihydrotetrazolone, tetrahydrofuran, dioxolane, piperidine, morpholine, piperazine, isoxazole, pyrazole, thiazole, oxazole, furyl, pyridine and pyrazine, said heterocycle optionally being substituted with $R^b$, where $R^b$ selected from the group consisting of $C_1$-$C_4$-alkyl, $C_1$-$C_4$-haloalkyl, $C_1$-$C_4$-alkoxy, $C_1$-$C_4$-alkoxy-$C_1$-$C_4$-alkyl, $C_1$-$C_4$-alkylthio-$C_1$-$C_4$-alkyl, halogen and oxo.

6. The compound of claim 2 wherein $R^2$ is an aliphatic group selected from the group consisting of $C_1$-$C_6$-alkyl, $C_1$-$C_4$-alkoxy-$C_1$-$C_4$-alkyl, $C_1$-$C_4$-haloalkoxy-$C_1$-$C_4$-alkyl, $C_2$-$C_6$-alkenyl, $C_2$-$C_6$-alkynyl, $C_2$-$C_4$-alkoxy, $C_2$-$C_4$-haloalkoxy, $C_3$-$C_6$-alkenyloxy, $C_3$-$C_6$-alkynyloxy, $C_3$-$C_6$-haloalkenyloxy, $C_3$-$C_6$-haloalkynyloxy, $C_1$-$C_4$-alkoxycarbonyl, $S(O)_2$—$C_1$-$C_4$-alkyl and $S(O)_2$—$C_1$-$C_6$-haloalkyl.

7. The compound of claim 1 wherein $R^1$ is halogen, $C_1$-$C_4$-alkyl, $C_1$-$C_4$-haloalkyl, $C_1$-$C_4$-alkoxy-$C_1$-$C_4$-alkyl, $C_1$-$C_4$-alkoxy-$C_1$-$C_4$-alkoxy-$C_1$-$C_4$-alkyl, $C_1$-$C_4$-alkoxy, $C_1$-$C_4$-haloalkoxy, $C_1$-$C_4$-alkylthio, $C_1$-$C_4$-haloalkylthio or $C_1$-$C_4$-alkylsulfonyl; and $R^3$ is H, halogen, CN, $NO_2$, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio or $C_1$-$C_4$-alkylsulfonyl.

8. The compound of claim 2 wherein $R^2$ together with $R^1$ or $R^3$ forms a 5- to 10-membered mono- or bicyclic, partially unsaturated ring which contains 1, 2, 3 or 4 heteroatoms selected from the group consisting of O, N and S, said ring optionally being substituted with $R^b$.

9. The compound of claim 8 wherein the ring substituted by groups $R^1$, $R^2$, $R^3$ and $R^4$ corresponds to one of groups A to L

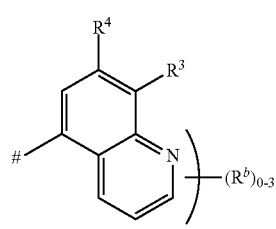

A

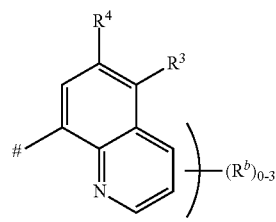

B

C 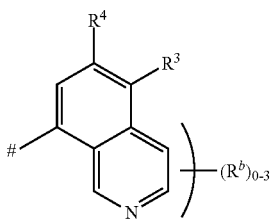

D 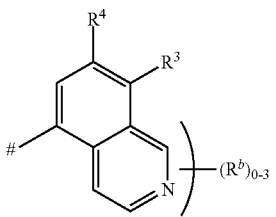

E 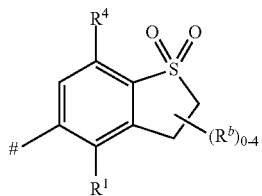

F 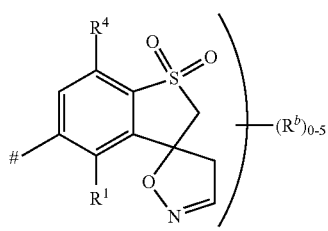

G 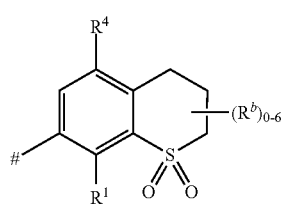

H 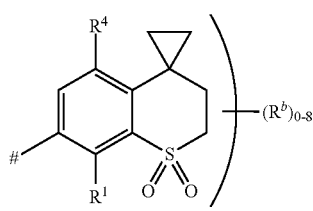

I 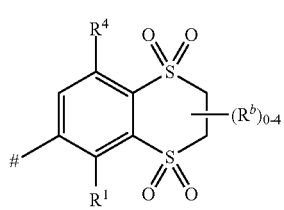

J 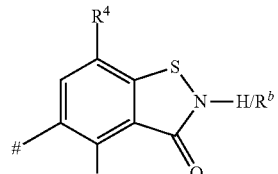

K 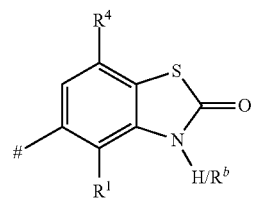

L 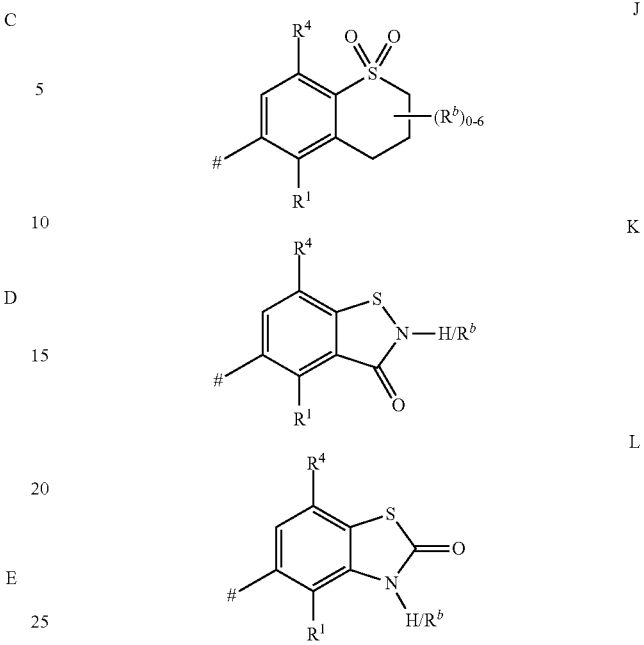

10. The compound of claim 1 wherein A is N and $R^1$ is nitro, $C_1$-$C_4$-alkyl, $C_1$-$C_4$-haloalkyl, $C_1$-$C_4$-alkoxy-$C_1$-$C_4$-alkyl, $C_1$-$C_4$-alkoxy-$C_1$-$C_4$-alkoxy-$C_1$-$C_4$-alkyl, $C_1$-$C_4$-alkoxy, $C_1$-$C_4$-haloalkoxy, $C_1$-$C_4$-alkylthio, $C_1$-$C_4$-haloalkylthio or $C_1$-$C_4$-alkylsulfonyl; and $R^3$ is H, CN, $NO_2$, $C_1$-$C_4$-alkyl, $C_1$-$C_4$-haloalkyl, $C_1$-$C_4$-alkoxy, $C_1$-$C_4$-alkylthio or $C_1$-$C_4$-alkylsulfonyl.

11. The compound of claim 1 wherein $R^4$, $R^5$ independently of one another are H, Cl or F; and $R^6$, $R^7$ are H.

12. The compound of claim 3 wherein $R^4$ and $R^5$ are hydrogen.

13. The compound of claim 2 wherein at least one of the groups $R^1$, $R^2$, $R^3$, $R^4$ and $R^5$ form a substitution pattern selected from the group consisting of 2-Br, 2-Cl, 2,4-$Cl_2$, 2-Cl-4-F, 2-Cl-5-F, 2-Cl-6-F, 2-Cl-4-$CF_3$, 2-Cl-5-$CF_3$, 2-Cl-6-$CF_3$, 2-Cl-3,6-$F_2$, 2-F, 2,4-$F_2$, 2,5-$F_2$, 2,6-$F_2$, 2-F-4-$CF_3$, 2-F-5-$CF_3$, 2-F-6-$CF_3$, 2,3,6-$F_3$, 2-$NO_2$, 2-$NO_2$-4-F, 2-$NO_2$-5-F, 2-$NO_2$-6-F, 2-$NO_2$-4-$CF_3$, 2-$NO_2$-5-$CF_3$, 2-$NO_2$-6-$CF_3$, 2-$NO_2$-3,6-$F_2$, 2-CN, 2-$CH_3$, 2-$CH_3$-4-F, 2-$CH_3$-5-F, 2-$CH_3$-6-F, 2-$CH_3$-4-$CF_3$, 2-$CH_3$-5-$CF_3$, 2-$CH_3$-6-$CF_3$, 2-$CH_3$-3,6-$F_2$, 2-$OCH_3$, 2-$OCH_3$-4-F, 2-$OCH_3$-5-F, 2-$OCH_3$-6-F, 2-$OCH_3$-4-$CF_3$, 2-$OCH_3$-5-$CF_3$, 2-$OCH_3$-6-$CF_3$, 2-$OCH_3$-3,6-$F_2$, 2-$CHF_2$, 2-$CHF_2$-4-F, 2-$CHF_2$-5-F, 2-$CHF_2$-6-F, 2-$CHF_2$-4-$CF_3$, 2-$CHF_2$-5-$CF_3$, 2-$CHF_2$-6-$CF_3$, 2-$CHF_2$-3,6-$F_2$, 2-$CF_3$, 2-$CF_3$-4-F, 2-$CF_3$-5-F, 2-$CF_3$-6-F, 2-$CF_3$-4-$CF_3$, 2-$CF_3$-5-$CF_3$, 2-$CF_3$-6-$CF_3$, 2-$CF_3$-3,6-$F_2$, 2-$OCHF_2$, 2-$OCHF_2$-4-F, 2-$OCHF_2$-5-F, 2-$OCHF_2$-6-F, 2-$OCHF_2$-4-$CF_3$, 2-$OCHF_2$-5-$CF_3$, 2-$OCHF_2$-6-$CF_3$, 2-$OCHF_2$-3,6-$F_2$, 2-$OCF_3$, 2-$OCF_3$-4-F, 2-$OCF_3$-5-F, 2-$OCF_3$-6-F, 2-$OCF_3$-4-$CF_3$, 2-$OCF_3$-5-$CF_3$, 2-$OCF_3$-6-$CF_3$, 2-$OCF_3$-3,6-$F_2$, 2-Cl-3-Br-6-F, 2-Cl-5-$CF_3$, 2,5,6-$Cl_3$ 2,6-$Cl_2$, 2-$CF_3$-4,6-$Cl_2$, 2,4,5-$Cl_3$, 2,4,6-$Cl_3$ and 2-$CF_3$-5-Cl.

14. A composition comprising a herbicidally effective amount of at least one compound of claim 1 and auxiliaries customary for formulating crop protection agents.

15. A method for controlling unwanted vegetation which comprises allowing a herbicidally effective amount of at least one compound of claim 1 to act on plants, their seed and/or their habitat.

16. The method of claim 15 wherein A is $CR^2$.

17. The method of claim 16 wherein
$R^2$ is an optionally substituted 5- or 6-membered saturated, partially unsaturated or aromatic heterocycle which contains 1, 2, 3 or 4 heteroatoms selected from the group consisting of O, N and S.

18. The method of claim 16 wherein $R^2$ is a group of the formula

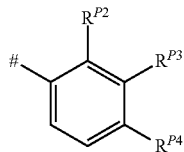

wherein # denotes the bond through which the group $R^2$ is attached and
$R^{P2}$ is H or F;
$R^{P3}$ is H, F, Cl or $OCH_3$; and
$R^{P4}$ is H, F, Cl, $CH_3$, $CF_3$, $OCH_3$, $OCH_2OCH_3$ or $OCH_2CH_2OCH_3$.

19. The method of claim 17 wherein $R^2$ is a heterocycle selected from the group consisting of isoxazoline, tetrazolone, 1,2-dihydrotetrazolone, 1,4-dihydrotetrazolone, tetrahydrofuran, dioxolane, piperidine, morpholine, piperazine, isoxazole, pyrazole, thiazole, oxazole, furyl, pyridine and pyrazine, said heterocycle optionally being substituted with $R^b$, where $R^b$ selected from the group consisting of $C_1$-$C_4$-alkyl, $C_1$-$C_4$-haloalkyl, $C_1$-$C_4$-alkoxy, $C_1$-$C_4$-alkoxy-$C_1$-$C_4$-alkyl, $C_1$-$C_4$-alkylthio-$C_1$-$C_4$-alkyl, halogen and oxo.

20. The method of claim 16 wherein
$R^2$ is an aliphatic group selected from the group consisting of $C_1$-$C_6$-alkyl, $C_1$-$C_4$-alkoxy-$C_1$-$C_4$-alkyl, $C_1$-$C_4$-haloalkoxy-$C_1$-$C_4$-alkyl, $C_2$-$C_6$-alkenyl, $C_2$-$C_6$-alkynyl, $C_2$-$C_4$-alkoxy, $C_2$-$C_4$-haloalkoxy, $C_3$-$C_6$-alkenyloxy, $C_3$-$C_6$-alkynyloxy, $C_3$-$C_6$-haloalkenyloxy, $C_3$-$C_6$-haloalkynyloxy, $C_1$-$C_4$-alkoxycarbonyl, $S(O)_2$—$C_1$-$C_4$-alkyl and $S(O)_2$—$C_1$-$C_6$-haloalkyl.

* * * * *